(12) United States Patent
Rao et al.

(10) Patent No.: US 10,875,851 B2
(45) Date of Patent: Dec. 29, 2020

(54) FACTOR XIIA INHIBITORS

(71) Applicants: Merck Sharp & Dohme Corp., Rahway, NJ (US); Ashwin U. Rao, Morganville, NJ (US); Brian Alexander McKittrick, New Vernon, NJ (US); Matthew Lombardo, Flemington, NJ (US); Jacqueline D. Hicks, Watchung, NJ (US); Amy Bittner McCracken, Berkeley Heights, NJ (US); Hong Dong Chu, Livingston, NJ (US); Sung-Sau So, Verona, NJ (US); Peter Orth, Pittstown, NJ (US); Zhicai Wu, Montvale, NJ (US); Ping Lan, Plainsboro, NJ (US); John S. Debenham, Scotch Plains, NJ (US); Brent R. Whitehead, Morristown, NJ (US); Jerry A. Taylor, Trenton, NJ (US); Zhongxiang Sun, Princeton, NJ (US); Revathi Reddy Katipally, Monmouth Junction, NJ (US); Jonathan E. Gable, Jersey City, NJ (US); Markus K. Dahlgren, Shelton, CT (US); Sathesh P. Bhat, Jersey City, NJ (US)

(72) Inventors: Ashwin U. Rao, Morganville, NJ (US); Brian Alexander McKittrick, New Vernon, NJ (US); Matthew Lombardo, Flemington, NJ (US); Jacqueline D. Hicks, Watchung, NJ (US); Amy Bittner McCracken, Berkeley Heights, NJ (US); Hong Dong Chu, Livingston, NJ (US); Sung-Sau So, Verona, NJ (US); Peter Orth, Pittstown, NJ (US); Zhicai Wu, Montvale, NJ (US); Ping Lan, Plainsboro, NJ (US); John S. Debenham, Scotch Plains, NJ (US); Brent R. Whitehead, Morristown, NJ (US); Jerry A. Taylor, Trenton, NJ (US); Zhongxiang Sun, Princeton, NJ (US); Revathi Reddy Katipally, Monmouth Junction, NJ (US); Jonathan E. Gable, Jersey City, NJ (US); Markus K. Dahlgren, Shelton, CT (US); Sathesh P. Bhat, Jersey City, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 16/461,849

(22) PCT Filed: Nov. 13, 2017

(86) PCT No.: PCT/US2017/061222
§ 371 (c)(1),
(2) Date: May 17, 2019

(87) PCT Pub. No.: WO2018/093695
PCT Pub. Date: May 24, 2018

(65) Prior Publication Data
US 2019/0352294 A1 Nov. 21, 2019

Related U.S. Application Data

(60) Provisional application No. 62/423,844, filed on Nov. 18, 2016.

(51) Int. Cl.
*C07D 413/14* (2006.01)
*A61P 7/02* (2006.01)
*C07D 495/04* (2006.01)

(52) U.S. Cl.
CPC .............. *C07D 413/14* (2013.01); *A61P 7/02* (2018.01); *C07D 495/04* (2013.01)

(58) Field of Classification Search
CPC .. C07D 241/00; C07D 241/02; C07D 241/04; A61K 31/395; A61K 31/495; A61K 31/4965
See application file for complete search history.

(56) References Cited

U.S. PATENT DOCUMENTS 8,017,612 B2 * 9/2011 Abe ...................... C07D 241/04
514/252.12
2008/0003214 A1 1/2008 Cezanne et al.
(Continued)

FOREIGN PATENT DOCUMENTS

WO 1998057960 A1 12/1998
WO 2006113376 A1 10/2006
(Continued)

OTHER PUBLICATIONS

International Search Report for PCT/US2017/061222, dated Feb. 15, 2018, 13 pages.
(Continued)

*Primary Examiner* — Deepak R Rao
(74) *Attorney, Agent, or Firm* — Nicole M. Beeler; John C. Todaro

(57) ABSTRACT

The present invention provides a compound of Formula (I) and pharmaceutical compositions comprising one or more said compounds, and methods for using said compounds for treating or preventing thromboses, embolisms, hypercoagulability or fibrotic changes. The compounds are selective Factor XIIa inhibitors.

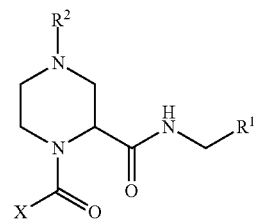

13 Claims, No Drawings

(56) References Cited

U.S. PATENT DOCUMENTS

2008/0287453 A1 11/2008 Bower et al.
2011/0033459 A1 2/2011 Conley et al.

FOREIGN PATENT DOCUMENTS

WO     WO 2008/016676 A2 * 2/2008
WO         2018093716 A1    5/2018

OTHER PUBLICATIONS

Invitation to Pay Additional Fees for PCT/US2017/061222, dated Dec. 22, 2017. 3 pages.
Supplementary European Search Report for 17872824.2, dated Apr. 14, 2020, 7 pages.

* cited by examiner

FACTOR XIIA INHIBITORS

CROSS REFERENCE TO RELATED APPLICATIONS

This application is a U.S. National Phase application under 35 U.S.C. § 371 of PCT Application No. PCT/US2017/061222 filed Nov. 13, 2017, which claims priority from U.S. Ser. No. 62/423,844 filed Nov. 18, 2016.

BACKGROUND OF THE INVENTION

Factor XIIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel, blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)).

Patients undergoing coronary pulmonary bypass (CPB), excorporeal membrane oxygenation (ECMO) or hemodialysis are at risk for thrombotic events and complications due to increased inflammatory responses. FXIIa plays a unique dual role in initiating both the intrinsic coagulation pathway leading to thrombin mediated clot formation and also activating the Kallirein-Kinin pathway leading to increased levels of the inflammatory mediator, bradykinin, see Kenne, E.; Renne, T. Factor XII: a drug target for safe interference with thrombosis and inflammation. *Drug DISCOvery Today* 2014, 19, 1459-146. Inhibitors of FXIIa seem ideally suited for the prevention of this device mediated thrombosis while lowering the incidence of complications during these procedures[7-9]. See, Renne, T., et al. In vivo roles of factor XII. *Blood* 2012, 120, 4296-4303; Kleinschnitz, C. et al., Targeting coagulation factor XII provides protection from pathological thrombosis in cerebral ischemia without interfering with hemostasis. *Journal of Experimental Medicine* 2006, 203, 513-518.

There is emerging evidence to show that in preclinical settings the inactivation of FXIIa by mAbs (see, Gruber, A., et al., Therapeutic antibodies against factor XII. In *Vanderbilt University, USA; Aronora, Inc.; Oregon Health & Science University.* 2014; pp 91), infestin 4 (see, Worm, M., et al., The factor XIIa blocking antibody 3F7: a safe anticoagulant with anti-inflammatory activities. *Annals of Translational Medicine* 2015, 3, 247/241-247/245), the knockout or knockdown of FXII (see, Cheng, Q.; Tucker, E. I.; Pine, M. S.; Sisler, I.; Matafonov, A.; Sun, M.-f.; White-Adams, T. C.; Smith, S. A.; Hanson, S. R.; McCarty, O. J. T.; Renne, T.; Gruber, A.; Gailani, D. A role for factor XIIa-mediated factor XI activation in thrombus formation in vivo. *Blood* 2010, 116, 3981-3989), leads to a selective prolongation of aPTT over PT, and reduced thrombosis formation. In some cases this has been shown to occur without increased bleeding. This feature distinguishes FXIIa from FIIa, FXa and FXIa and suggests that FXIIa inhibitors will have an improved safety profile with regard to bleeding (see, Gailani, D., et al., Factor XI and contact activation as targets for antithrombotic therapy. *Journal of Thrombosis and Haemostasis* 2015, 13, 1383-1395).

SUMMARY OF THE INVENTION

The present invention relates to compounds of Formula I:

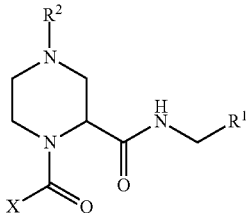

I and pharmaceutically acceptable salts thereof. The compounds of Formula I are selective Factor XIIa inhibitors, and as such may be useful in the treatment, inhibition or amelioration of one or more disease states that could benefit from inhibition of Factor XIIa, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

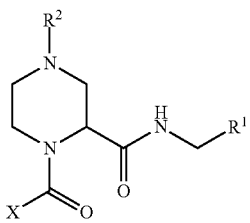

I wherein X is

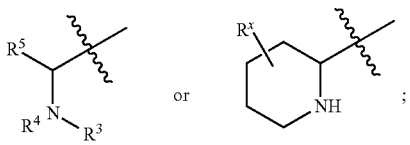

$R^1$ is aryl or heteroaryl, wherein said aryl and heteroaryl groups are optionally substituted with one to three substituents independently selected from the group consisting of hydroxyl, cyano, halo, $C_{1-3}$ alkyl, $O(C_{1-3}$ alkyl), $NR^{10}R^{11}$, $CH_2NR^{10}R^{11}$, $(C=O)NR^{10}R^{11}$ or heteroaryl;

$R^2$ is $(C=O)OR^6$, $(C=O)NHR^6$, $(C=O)CH_2R^6$, $(C=O)R^6$, $SO_2R^6$, $CH_2R^6$, or

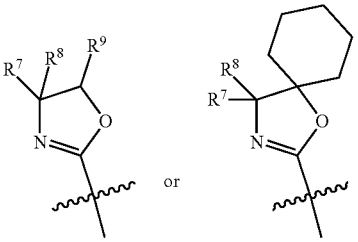

$R^3$ is hydrogen, $C_{1-3}$ alkyl

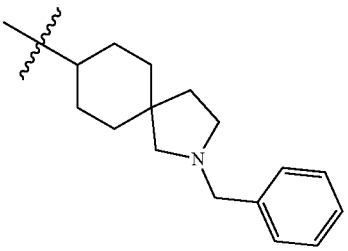 [SMILES: *C1CCC2(CC1)CCN(Cc1ccccc1)C2]

or $C_{3-7}$ cycloalkyl, which is optionally substituted with one or two substituents independently selected from the group consisting of $R^6$, $R^{11}$, $NR^{10}R^{11}$, $(C=O)NR^{10}R^{11}$ and $CH_2NR^{10}R^{11}$;

$R^4$ is hydrogen or $C_{1-4}$ alkyl;

$R^5$ is
(a) hydrogen,
(b) $(CH_2)_m$-cyclohexyl, which is optionally substituted with $NR^{10}R^{11}$ or heterocyclyl,
(c) $(CH_2)_n$-piperidinyl, which is optionally substituted with benzyl, $R^{11}$, $SO_2R^{10}$, $SO_2R^6$, $(C=O)R^6$, $R^6$ or $(C=O)R^{10}$,
(d) $C_{1-4}$ alkyl which is optionally substituted with $R^6$, $NR^{10}R^{11}$ or $NHSO_2CH_3$;

each $R^6$ is independently aryl, heteroaryl, heterocyclyl or $C_{3-6}$ cycloalkyl, wherein said aryl and heteroaryl groups are optionally substituted with one to three substituents independently selected from the group consisting of hydroxyl, oxo, cyano, halo, $C_{1-3}$ alkyl, $C_{1-3}$ haloalkyl, $O(C_{1-3}$ alkyl), $NR^{10}R^{11}$, $CH_2NR^{10}R^{11}$, $CH_2CN$, $(C=O)NR^{10}R^{11}$ and $CH(NH_2)(OCH_3)$;

$R^7$ is hydrogen or $C_{1-3}$ alkyl;
$R^8$ is hydrogen or $C_{1-3}$ alkyl;
$R^9$ is hydrogen, $C_{1-3}$ alkyl, $C_{1-3}$ haloalkyl or phenyl, wherein said phenyl group is optionally substituted with halo, cyano, methyl or $CH_2NR^{10}R^{11}$;

each $R^{10}$ is independently hydrogen or $C_{1-5}$ alkyl;
each $R^{11}$ is independently hydrogen or $C_{1-3}$ alkyl, which is optionally substituted with one to three substituents independently selected from the group consisting of halo and hydroxyl;

$R^x$ is hydrogen or $C_{1-4}$ alkyl, which is optionally substituted with one to three substituents independently selected from the group consisting of halo, hydroxyl $N+CH_3R^{10}R^{11}$ and $NR^{10}R^{11}$;

m is zero or one;
n is zero or one;
or a pharmaceutically acceptable salt thereof.

In an embodiment of the invention, is a compound of the following formula:

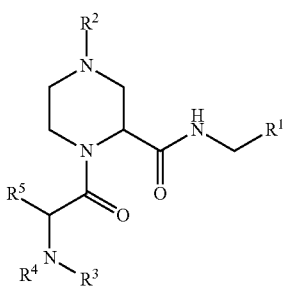

wherein $R^1$ is aryl or heteroaryl, wherein said aryl and heteroaryl groups are optionally substituted with one to three substituents independently selected from the group consisting of hydroxyl, cyano, halo, $C_{1-3}$ alkyl, $O(C_{1-3}$ alkyl), $NR^{10}R^{11}$, $CH_2NR^{10}R^{11}$, $(C=O)NR^{10}R^{11}$ or heteroaryl;

$R^2$ is $(C=O)OR^6$, $(C=O)NHR^6$, $(C=O)CH_2R^6$, $(C=O)R^6$, $SO_2R^6$, $CH_2R^6$,

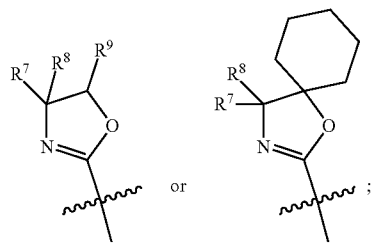

$R^3$ is hydrogen, $C_{1-3}$ alkyl,

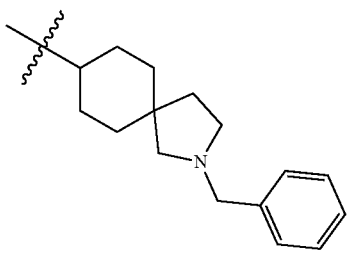 [SMILES: *C1CCC2(CC1)CCN(Cc1ccccc1)C2]

or $C_{3-7}$ cycloalkyl, which is optionally substituted with one or two substituents independently selected from the group consisting of $R^6$, $R^{11}$, $NR^{10}R^{11}$, $(C=O)NR^{10}R^{11}$ and $CH_2NR^{10}R^{11}$;

$R^4$ is hydrogen or $C_{1-4}$ alkyl;

$R^5$ is
(a) hydrogen,
(b) $(CH_2)_m$-cyclohexyl, which is optionally substituted with $NR^{10}R^{11}$ or heterocyclyl,
(c) $(CH_2)_n$-piperidinyl, which is optionally substituted with benzyl, $R^{11}$, $SO_2R^{10}$, $SO_2R^6$, $(C=O)R^6$, $R^6$ or $(C=O)R^{10}$,
(d) $C_{1-4}$ alkyl which is optionally substituted with $R^6$, $NR^{10}R^{11}$ or $NHSO_2CH_3$;

each $R^6$ is independently aryl, heteroaryl, heterocyclyl or $C_{3-6}$ cycloalkyl, wherein said aryl and heteroaryl groups are optionally substituted with one to three substituents independently selected from the group consisting of hydroxyl, oxo, cyano, halo, $C_{1-3}$ alkyl, $C_{1-3}$ haloalkyl, $O(C_{1-3}$ alkyl), $NR^{10}R^{11}$, $CH_2NR^{10}R^{11}$, $CH_2CN$, $(C=O)NR^{10}R^{11}$ and $CH(NH_2)(OCH_3)$;

$R^7$ is hydrogen or $C_{1-3}$ alkyl;
$R^8$ is hydrogen or $C_{1-3}$ alkyl;
$R^9$ is hydrogen or phenyl, which is optionally substituted with halo, cyano, methyl or $CH_2NR^{10}R^{11}$;
each $R^{10}$ is independently hydrogen or $C_{1-5}$ alkyl;
each $R^{11}$ is independently hydrogen or $C_{1-3}$ alkyl, which is optionally substituted with one to three substituents independently selected from the group consisting of halo and hydroxyl; m is zero or one;
n is zero or one
or a pharmaceutically acceptable salt thereof.

In an embodiment of the invention, $R^1$ is phenyl, thiophenyl, indolyl or thienopyridinyl, wherein said phenyl, thiophenyl, indolyl or thienopyridinyl groups are optionally substituted with one to three substituents independently selected from the group consisting of halo, $O(C_{1-3}$ alkyl), $CH_2NR^{10}R^{11}$, $(C=O)NR^{10}R^{11}$ or tetrazolyl. In a class of the embodiment, $R^1$ is thiophenyl.

In an embodiment of the invention, $R^2$ is $(C=O)OR^6$, $(C=O)CH_2R^6$, or

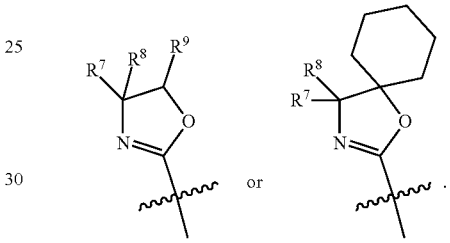

In a class of the invention $R^2$ is $(C=O)OR^6$.

In an embodiment of the invention, $R^3$ is hydrogen, $C_{1-3}$ alkyl,

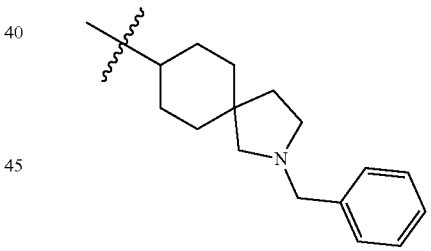

or $C_{5-6}$ cycloalkyl, which is optionally substituted with one or two substituents independently selected from the group consisting of $R^6$, $R^{11}$, $NR^{10}R^{11}$, $(C=O)NR^{10}R^{11}$ and $CH_2NR^{10}R^{11}$. In a class of the invention, $R^3$ is

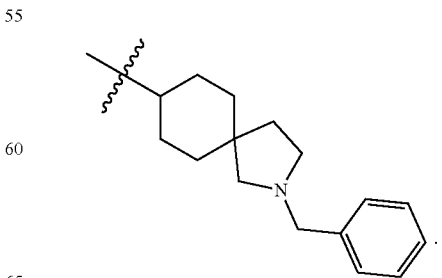

In another class of the invention, $R^3$ is cyclohexyl.

In an embodiment of the invention, $R^4$ is hydrogen or methyl. In a class of the invention, $R^4$ is hydrogen. In another class of the invention, $R^4$ is methyl.

In an embodiment of the invention, $R^5$ is $C_{1-4}$ alkyl which is optionally substituted with $R^6$, $NR^{10}R^{11}$ or $NHSO_2CH_3$. In another embodiment of the invention, $R^5$ is $CH_2$-cyclohexyl, which is optionally substituted with $NR^{10}R^{11}$ or heterocyclyl. In another embodiment of the invention, $R^5$ is piperidinyl, which is optionally substituted with benzyl, $R^{11}$, $SO_2R^{10}$, $SO_2R^6$, $(C=O)R^6$, $R^6$ or $(C=O)R^{10}$. In another embodiment of the invention, $R^5$ is (a) $CH_2$-cyclohexyl, or (b) $C_{1-4}$ alkyl which is optionally substituted with $R^6$, $R^{11}$, $NR^{10}R^{11}$ or $NHSO_2CH_3$.

In an embodiment of the invention, m is zero. In another embodiment of the invention, m is one.

In an embodiment of the invention, n is zero. In another embodiment of the invention, n is one.

Reference to the preferred classes and subclasses set forth above is meant to include all combinations of particular and preferred groups unless stated otherwise.

Specific embodiments of the present invention include, but are not limited to the compounds identified herein as Examples 1 to 183, or pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIIa inhibitors and may have therapeutic value in, for example, preventing coronary artery disease. The compounds are selective Factor XIIa inhibitors.

It will be understood that, the present invention includes compounds of structural Formula I and also the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I simultaneously contain acidic and basic groups in the molecule the invention also includes, in addition to the salt forms mentioned, inner salts or betaines (zwitterions).

The present invention encompasses all stereoisomeric forms of the compounds of Formula I. Unless a specific stereochemistry is indicated, the present invention is meant to comprehend all such isomeric forms of these compounds. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enationmer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^6$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the terms "alkyl" and "alkylene" are intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

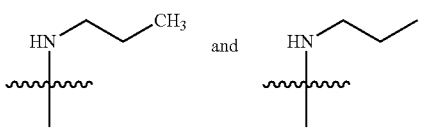

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted, the term "haloalkyl" means an alkyl radical as defined above, unless otherwise specified, that is substituted with one to five, preferably one to three halogen. Representative examples include, but are not limited to trifluoromethyl, dichloroethyl, and the like.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetrahydroquinoline and 3-oxo-3,4dihydro-2N-benzo[b][1,4]thiazine. If the heteroaryl contains nitrogen atoms, it is understood that the corresponding N-oxides thereof are also encompassed by this definition.

Except where noted, the term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, $SO$, or $SO_2$. Bicyclic heterocyclic ring systems include fused ring systems, where two rings share two atoms, and spiro ring systems, where two rings share one atom. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

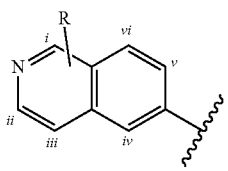

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also relates to medicaments containing at least one compound of the Formula I and/or of a pharmaceutically acceptable salt of the compound of the Formula I and/or an optionally stereoisomeric form of the compound of the Formula I or a pharmaceutically acceptable salt of the stereoisomeric form of the compound of Formula I, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIIa inhibition may be useful not only in the anticoagulant therapy of individuals having thrombotic conditions, but may be useful whenever inhibition of blood coagulation is required such as to prevent coagulation of stored whole blood and to prevent coagulation in other biological samples for testing or storage. Thus, the Factor XIIa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula I and other surfaces which come into contact with blood in the body is possible.

The invention also relates to a process for the production of a medicament, which comprises bringing at least one compound of the Formula I into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIIa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIIa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably between 8 mg and 40 mg, e.g., 8 mg, 10 mg, 20 mg and 40 mg. Advantageously, the Factor XIIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIIa inhibitors can also be co-administered with suitable anticoagulants, including, but not limited to, other Factor XIIa inhibitors, thrombin inhibitors, thrombin receptor antagonists, factor VIIa inhibitors, factor Xa inhibitors, factor IXa inhibitors, factor XIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin, remogliflozin and sotagliflozin), and SGLT-3; or with other drugs beneficial for the prevention or the treatment of the abovementioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIIa inhibitors of the invention in combination with other suitable anti-platelet agents, anticoagulation agents, or thrombolytic agents may be the same as those doses of Factor XIIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

For purposes of this specification, the following abbreviations have the indicated meanings:

Ac acetyl
ACN acetonitrile
AcOH or HOAc acetic acid
aq aqueous
Bn benzyl
Boc or BOC tert-butoxycarbonyl
Bu butyl
Bz benzoyl
cBu cyclobutyl
Cbz benyzloxycarbonyl
CDI 1,1'-carbonyldiimidazole
cPr cyclopropyl
DCM dichloromethane
DIPEA, DIEA or Hünig's base N,N-diisopropylethylamine
DMA dimethylacetamide
DMF dimethylformamide
DMSO dimethyl sulfoxide
EDC 1-ethyl-3-(3-dimethylaminopropyl)carbodiimide
Et ethyl
EtOAc ethyl acetate
FMOC fluorenylmethyloxycarbonyl
g grams
h hour HATU N,N,N',N'-tetramethyl-O-(7-azabenzotriazol-1-yl) uronium hexafluorophosphate
HOBT hydroxybenzotriazole
HPLC high-performance liquid chromatography
iPr isopropyl
LAH lithium aluminium hydride
LCMS liquid chromatography mass spectrometry
Me methyl
MeOH methanol
mg milligrams
min minute
μL microliters
mL milliliters
mmol millimoles
MP macroporous
MS mass spectrometry
Ms methanesulfonyl (mesyl)
NMR nuclear magnetic resonance spectroscopy
Ph phenyl
Pr propyl
rac racemic mixture
RT or rt room temperature (ambient, about 25° C.)
SFC supercritical fluid chromatography
TBAF tetra-n-butylammonium fluoride
tBu tert-butyl
TEA triethylamine (Et$_3$N)
TFA trifluoroacetic acid
TFAA trifluoroacetic anhydride
THF tetrahydrofuran
TLC thin layer chromatography
TMS trimethylsilyl
XPHOS 2-dicyclohexylphosphino-2',4',6'-triisopropylbiphenyl Also, UV is ultraviolet; W is watts; wt. % is percentage by weight; x g is times gravity; $α_D$ is the specific rotation of polarized light at 589 nm; ° C. is degrees Celsius; % w/v is percentage in weight of the former agent relative to the volume of the latter agent; Hz is hertz; cpm is counts per minute; $δ_H$ is chemical shift; d is doublet; dd is doublet of doublets; MHz is megahertz; MS is mass spectrum, and a mass spectrum obtained by ES-MS may be denoted herein by "LC-MS"; m/z is mass to charge ratio; n is normal; N is normal; nm is nanometer; nM is nanomolar.

"FXIIa IC50 (nm)" is Human Factor XIIa IC50 (nm).

LCMS conditions: Waters Acquity UPLC/SQD MS system, Electrospray positive ionization mode; Column: Waters BEH C18 column, 1.0×50 mm, 1.7 um; MP: A:B/(H$_2$O/ 0.05% TFA: ACN/0.05% TFA); Gradient: 0-2 min, (10-99)% B; Flow: 0.3 min/mL.

General Methods

Compounds of the present invention may be prepared using conventional techniques or according to the methodology outlined in the following general synthetic schemes.

The compounds described can be prepared by functionalization of 4-(((9H-fluoren-9-yl)methoxy)carbonyl)-1-(tert-butoxycarbonyl)piperazine-2-carboxylic acid at C2 using standard amide bond forming techniques, e.g. HATU. FMOC-deprotection followed by standard amide bond forming technique or carbamate (or urea) formation using CDI and desired phenol (or amine) installs R$^2$. Alternatively, a dihydrooxazole can be installed using desired 2-methoxy-4,5-dihydrooxazole. Boc-deprotection and amide bond formation with Boc protected alpha-amino acid provides the functionalized core. Boc-deprotection followed by reductive amination installs $R^3$ and $R^4$.

INTERMEDIATES

Intermediate 1c

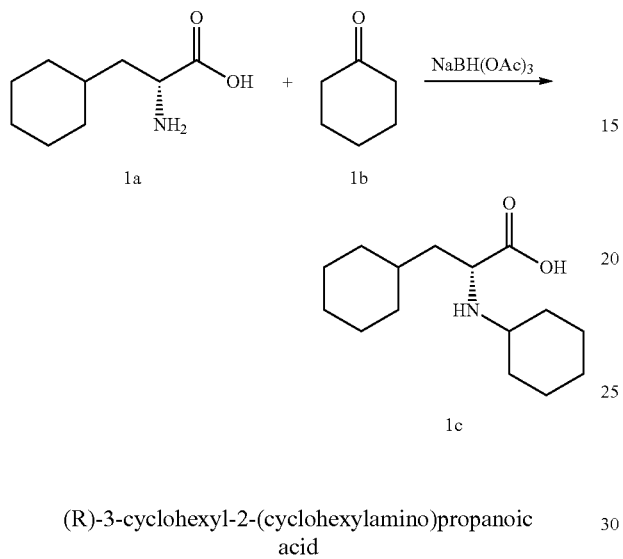

(R)-3-cyclohexyl-2-(cyclohexylamino)propanoic acid

Sodium triacetoxyborohydride (2.475 g, 11.68 mmol) was added to a stirred mixture of (R)-2-amino-3-cyclohexylpropanoic acid 1a (1.00 g, 5.84 mmol), cyclohexanone 1b (0.908 mL, 8.76 mmol) and AcOH (0.435 mL, 7.59 mmol) in a mixture of THF (10 mL)/MeOH (0.5 mL) and the reaction was allowed to stir at room temperature for 1 h. After 1 h, water was added, upon which some solids precipitated out and were filtered. The solid was triturated with water followed by $CH_2Cl_2$ and dried overnight to yield the product, which was used as such without further purification.

Intermediate 3b

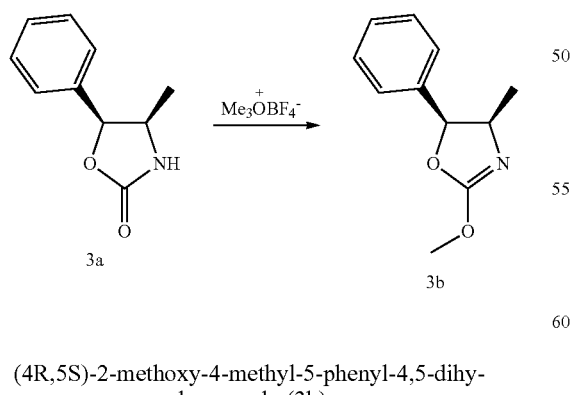

(4R,5S)-2-methoxy-4-methyl-5-phenyl-4,5-dihydrooxazole (3b)

Trimethyloxonium tetrafluoroborate (250 mg, 1.693 mmol) was added to a stirred mixture of (4R,5S)-(+)-4-methyl-5-phenyl-2-oxazolidinone 3a (200 mg, 1.129 mmol) in $CH_2Cl_2$ (5 mL) and the mixture was stirred at room temperature for 1 h. The reaction was monitored by LCMS. After completion, the reaction mixture was quenched by the addition of sat. $NaHCO_3$, extracted with $CH_2Cl_2$, dried over $Na_2SO_4$, filtered and concentrated in vacuo to yield 3b. The product was used as such without further purification.

Intermediate 4b

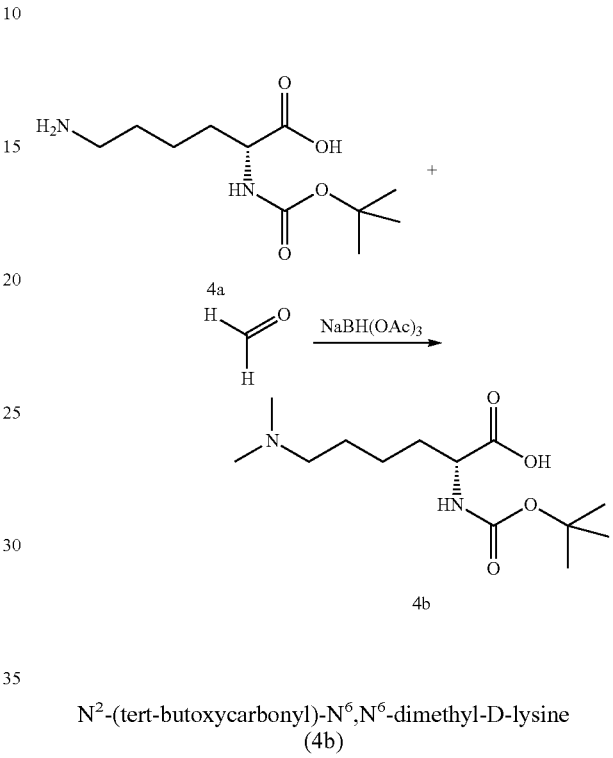

$N^2$-(tert-butoxycarbonyl)-$N^6,N^6$-dimethyl-D-lysine (4b)

Sodium triacetoxyborohydride (7.74 g, 36.5 mmol) was added to a stirred mixture of BOC-D-LYS-OH 4a (3.0 g, 12.18 mmol), formaldehyde (1.814 mL, 24.36 mmol) and acetic acid (0.837 mL, 14.62 mmol) in THF (40 mL)/MeOH (5 mL), and the mixture was stirred at room temperature overnight. LCMS showed product peak. To the mixture was added water, and it was extracted with EtOAc. The product was in the water layer. The water layer was concentrated and dried overnight. To the solid mixture was added DCM and it was filtered through celite. The filtrate was concentrated and dried overnight to yield 4b. The product was used as such without further purification.

Intermediate 5c

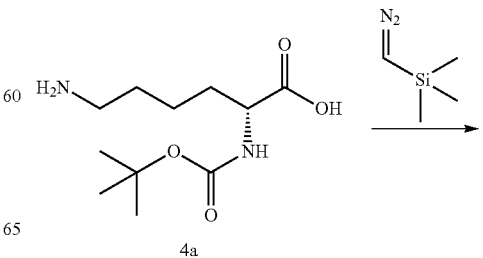

4a

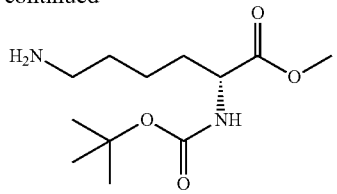

5a

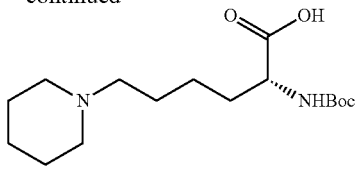

5c

Methyl (tert-butoxycarbonyl)-D-lysinate (5a)

BOC-D-LYS-OH 4a (8 g, 32.5 mmol) was dissolved in dichloromethane/methanol (10:1, 110 mL). TMS-Diazomethane (2M in hexanes, 20 mL, 40 mmol) was added dropwise and the reaction mixture was stirred for 50 minutes at room temperature. The reaction was quenched with dropwise addition of acetic acid until the reaction mixture became colorless. The reaction was then concentrated and carried forward without purification.

(R)-2-((tert-butoxycarbonyl)amino)-6-(piperidin-1-yl)hexanoic acid (5c)

Methyl (R)-2-((tert-butoxycarbonyl)amino)-6-(piperidin-1-yl)hexanoate 5b (11.07 g, 33.7 mmol) was dissolved in methanol/water (1:1, 150 mL). Potassium trimethylsilanoate (12.97 g 101 mmol) was added, and the reaction mixture was stirred at room temperature for 6 hours. The reaction was then neutralized with 6 N HCl in water and concentrated. The crude reaction mixture was purified by reverse phase flash chromatography 10-100% MeCN/H$_2$O. Product containing fractions were combined to obtain 5c.

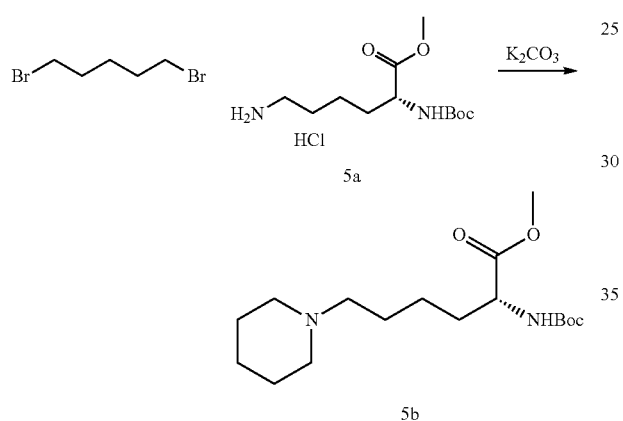

Intermediate 6e

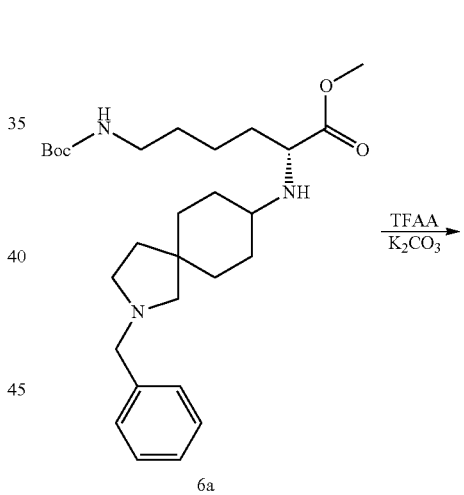

6a

Methyl (R)-2-((tert-butoxycarbonyl)amino)-6-(piperidin-1-yl)hexanoate (5b)

Methyl (tert-butoxycarbonyl)-D-lysinate hydrochloride 5a (250 mg, 0.960 mmol) was dissolved in DMF (4 mL). Potassium carbonate (465 mg, 3.36 mmol) was added, followed by 1,5-dibromopentane (0.157 mL, 1.152 mmol). The reaction mixture was stirred at 60° C. overnight. DMF was removed by concentration. Water was then added, and the organics were extracted with ethyl acetate (3×). The combined organic layers were dried over Na$_2$SO$_4$, filtered and concentrated. The crude product was carried forward without purification.

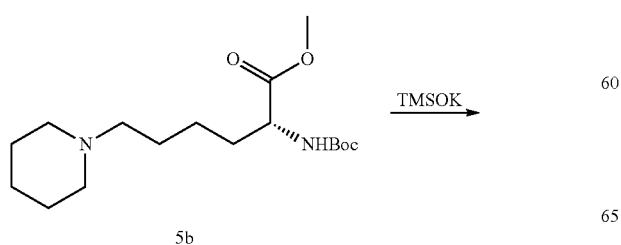

5b

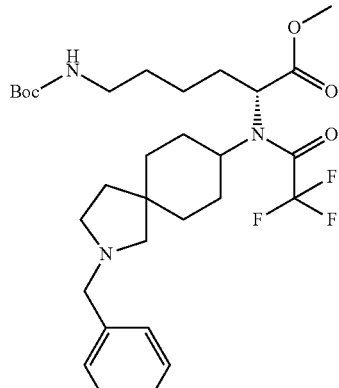

6b

Step A.:

To a flask containing Intermediate 6a (5 g, 10.25 mmol) in CH$_2$Cl$_2$ (10 mL) was added K$_2$CO$_3$ (4.25 g, 30.8 mmol). Then TFAA (4.34 mL, 30.8 mmol) was added to the mixture slowly and the mixture was stirred for 48 hours at room temperature, filtered and concentrated under reduced pressure. 100 mL of water was added to the mixture and it was concentrated under reduced pressure; this was repeated 3 times. The crude mixture was purified by reverse phase chromatography (ISCO Gold C18, 270 g; Water/Acetonitrile with a 0.1% Formic Acid additive; 0-80%) to give (R)-methyl 2-(N-(2-benzyl-2-azaspiro[4.5]decan-8-yl)-2,2,2-trifluoroacetamido)-6-((tert-butoxycarbonyl)amino)hexanoate Formic Acid 6b. LCMS m/z 585-08.

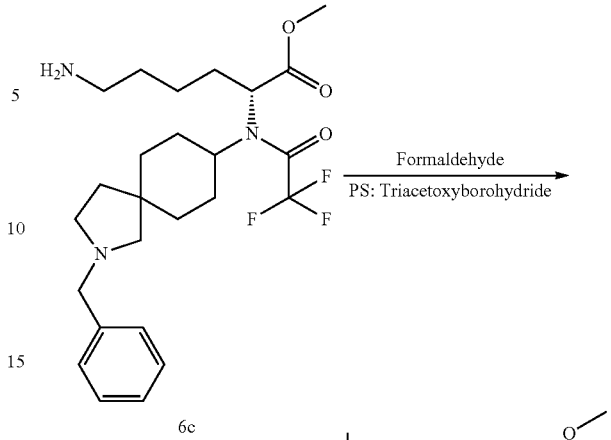

6c

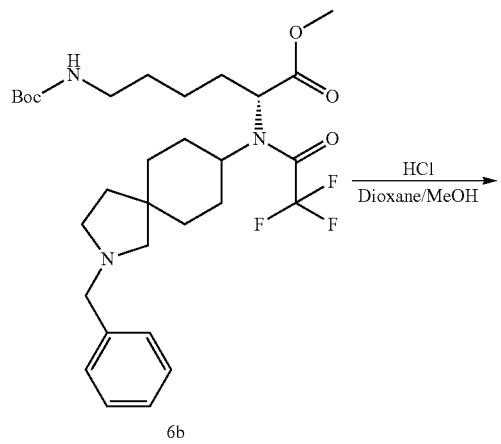

6b

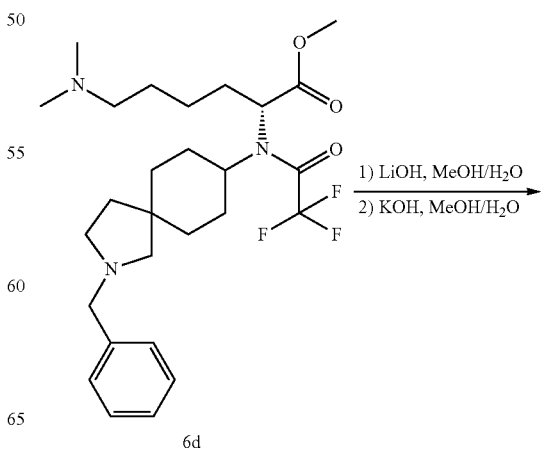

6d

Step C.:

To a flask containing (R)-methyl 6-amino-2-(N-(2-benzyl-2-azaspiro[4.5]decan-8-yl)-2,2,2-trifluoroacetamido)hexanoate, HCl 6c (5 g, 9.61 mmol) in DCM (10 mL) was added formaldehyde (3.58 mL, 48.1 mmol). The mixture was stirred at room temperature for 5 minutes at room temperature and then polymer supported triacetoxyborohydride (8.36 g, 19.23 mmol) was added. The mixture was stirred at room temperature for 18 hours and then filtered and concentrated under reduced pressure to give (R)-methyl 2-(N-(2-benzyl-2-azaspiro[4.5]decan-8-yl)-2,2,2-trifluoroacetamido)-6-(dimethylamino)hexanoate 6d: LCMS m/z 512.30 [M+H].

6c

Step B.:

To a flask containing (R)-methyl 2-(N-(2-benzyl-2-azaspiro[4.5]decan-8-yl)-2,2,2-trifluoroacetamido)-6-((tert-butoxycarbonyl)amino)hexanoate, formic acid 6b (6.06 g, 9.62 mmol) in MeOH (5 mL) was added a 4.0 N solution of HCl (12.03 mL, 48.1 mmol) in dioxane. The mixture was stirred at room temperature for 4 hours and then concentrated under reduced pressure to give (R)-methyl 6-amino-2-(N-(2-benzyl-2-azaspiro[4.5]decan-8-yl)-2,2,2-trifluoroacetamido)hexanoate, HCl 6c. LCMS m/z 484.47.

6d

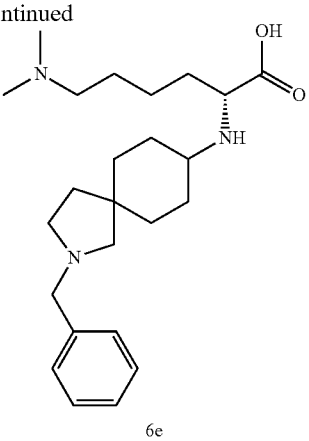

6e

Step D.:
To a flask containing (R)-methyl 2-(N-(2-benzyl-2-azaspiro[4.5]decan-8-yl)-2,2,2-trifluoroacetamido)-6-(dimethylamino)hexanoate 6d (5 g, 9.77 mmol) in MeOH (5 mL) and water (5.00 mL) was added LiOH (1.170 g, 48.9 mmol). The mixture was stirred at room temperature for 4 hours. Then KOH (3.29 g, 58.6 mmol) was added to the mixture and it was heated to 60° C. for 6 hours, acidified with 1.0 N HCl and concentrated under reduced pressure. The reaction mixture was purified by reverse phase chromatography (ISCO Gold C18 120 g; Water; 100%) to give (R)-2-((2-benzyl-2-azaspiro[4.5]decan-8-yl)amino)-6-(dimethylamino)hexanoic acid, HCl 6e: LCMS m/z 402.31 [M+2+H].

Intermediate 8a

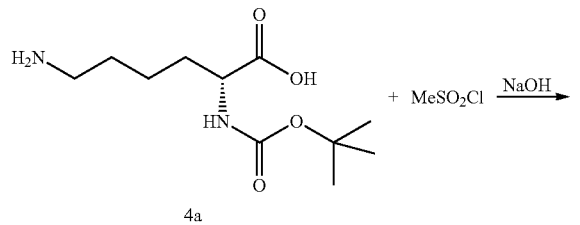

8a

N-(tert-butoxycarbonyl)-N⁶-(methylsulfonyl)-D-lysine (8a)

Mesyl-Cl (3.16 mL, 40.6 mmol) was added to a stirred mixture of BOC-D-LYS-OH 4a (5.0 g, 20.30 mmol) and NaOH (60.9 mL, 60.9 mmol) in THF (50 mL) and the mixture was stirred at room temperature for 3 h. The reaction was monitored by LCMS. After the reaction was complete, the reaction was neutralized by the addition of 1 N HCl until slightly acidic and extracted with EtOAc. The organic layer was dried over $Na_2SO_4$, filtered and concentrated in vacuo to yield 8a.

Intermediate 9b

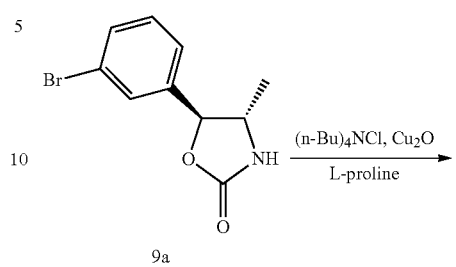

9a

9b (4S,5S)-5-(3-chlorophenyl)-4-methyloxazolidin-2-one (9b)

A mixture of (4S,5S)-5-(3-bromophenyl)-4-methyloxazolidin-2-one 9a (100 mg, 0.390 mmol), tetrabutylammonium chloride (217 mg, 0.781 mmol), copper(I) oxide (5.59 mg, 0.039 mmol) and L-proline (8.99 mg, 0.078 mmol) in ethanol (2 mL) was stirred at 110° C. overnight. LCMS showed some product formation along with starting material. The reaction mixture was cooled and filtered. The excess solvent was concentrated in vacuo and purified by reverse phase HPLC system using 0.05% TFA in ACN/$H_2O$ to yield 9b.

Intermediate 9c

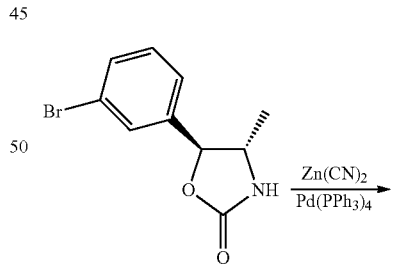

9a

9c

3-((4S,5S)-4-methyl-2-oxooxazolidin-5-yl)benzonitrile (9c)

A mixture of (4S,5S)-5-(3-bromophenyl)-4-methyloxazolidin-2-one 9a (100 mg, 0.390 mmol), zinc cyanide (45.8 mg, 0.390 mmol) and tetrakis(triphenylphosphine)palladium(0) (45.1 mg, 0.039 mmol) in DMF (1 mL) was stirred at 120° C. for 1 h. in a microwave. The reaction was monitored by LCMS. Upon completion, the reaction mixture was diluted with water, extracted with EtOAc, washed with brine, dried over Na$_2$SO$_4$, filtered and concentrated in vacuo. The residue was purified by column chromatography on silica gel Teledyne ISCO REDISEP [4 g prepacked] eluting with 0-30-40% EtOAc/isohexane to give 9c.

Intermediate 9d

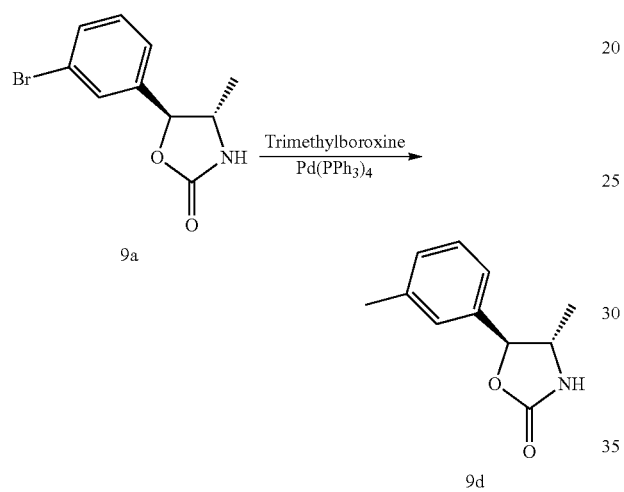

(4S,5S)-4-methyl-5-(m-tolyl)oxazolidin-2-one (9d)

A mixture of (4S,5S)-5-(3-bromophenyl)-4-methyloxazolidin-2-one 9a (500 mg, 1.952 mmol), trimethylboroxine (368 mg, 2.93 mmol), tetrakis(triphenylphosphine)palladium(0) (226 mg, 0.195 mmol) and Na$_2$CO$_3$ (621 mg, 5.86 mmol) in 1,4-dioxane (3 mL)/water (3.00 mL) was stirred at 100° C. for 1 h in a microwave. The reaction was monitored by LCMS. Upon completion, the reaction was diluted with water and filtered. The filtrate was extracted with EtOAc, dried over Na$_2$SO$_4$, filtered and concentrated in vacuo to yield 9d. The product was used as such without further purification.

Intermediate 10c

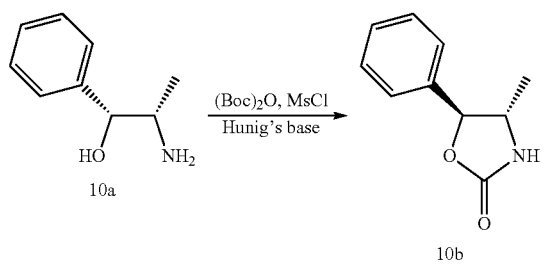

(4S,5S)-4-methyl-5-phenyloxazolidin-2-one (10b)

Methylene chloride was added to (1R,2S)-norephedrine (5 g, 33.1 mmol) to afford approximately a 0.3 M solution. To this solution, was added triethylamine (5.07 mL, 36.4 mmol) and the reaction was cooled in an ice bath. Upon sufficient cooling, di-tert-butyl dicarbonate (7.79 g, 35.7 mmol) was added and the ice removed after the di-tert-butyl dicarbonate was dissolved approximately (5 min). The reaction was allowed to proceed for 2 h at ambient temperature. The reaction was again cooled in an ice bath and an additional portion of triethylamine (5.07 mL, 36.4 mmol) was added followed by an addition of methanesulfonyl chloride (3.87 mL, 49.6 mmol) and the ice was removed after 5 min. The reaction was then refluxed for 3 h at which time the reaction was allowed to cool to room temperature. Oxazolidinone 10b was washed with bicarbonate and brine solutions and the solvents removed. The resulting orange crystals were triturated in diethyl ether to afford 10b.

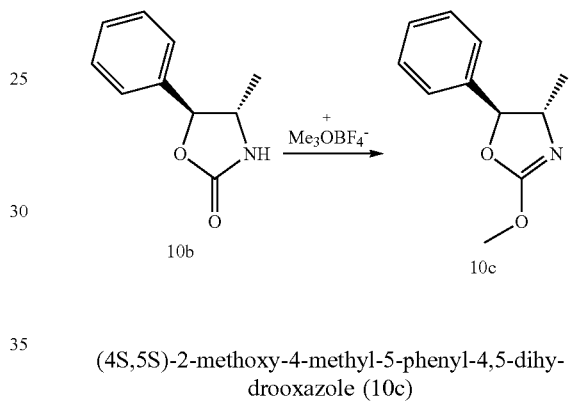

(4S,5S)-2-methoxy-4-methyl-5-phenyl-4,5-dihydrooxazole (10c)

Compound 10c was prepared by using procedures analogous to those described for Compound 3b.

Intermediate 13

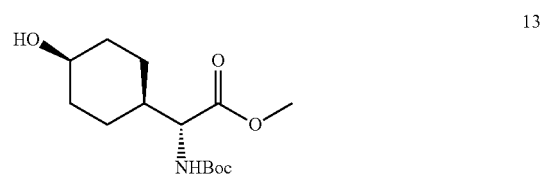 [SMILES: COC(=O)[C@H](NC(=O)OC(C)(C)C)[C@H]1CC[C@@H](O)CC1]

(R)-methyl 2-((tert-butoxycarbonyl)amino)-2-((1s,4S)-4-hydroxycyclohexyl)acetate (13)

A solution of (R)-methyl 2-((tert-butoxycarbonyl)amino)-2-(4-hydroxyphenyl)acetate 13a (3 g, 10.66 mmol) in MeOH (100 mL) was thoroughly degassed with nitrogen, then platinum(IV) oxide (0.387 g, 1.706 mmol) was added and degassed thoroughly. The reaction was performed using a Parr shaker using H$_2$ gas at 32 psi for 2 h. LCMS showed two product peaks. NMR showed the mixture contains cis/trans in a ratio of 3:1. The reaction was filtered and concentrated. The reaction was purified by flash column chromatography (REDISEP gold, 80 g), and the products were eluted by 20%-40% EtOAc in hexanes to yield 'cis' which eluted first followed by 'trans'.

Intermediate 14

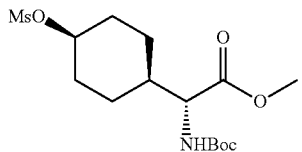

(R)-methyl 2-((tert-butoxycarbonyl)amino)-2-((1s,4S)-4-((methylsulfonyl)oxy)cyclohexyl)acetate (14)

To a solution of (R)-methyl 2-((tert-butoxycarbonyl)amino)-2-((1s,4S)-4-hydroxycyclohexyl)acetate 13 (1 g, 3.48 mmol) in DCM (10 mL), $Et_3N$ was added. The reaction was cooled to 0° C. Methanesulfonyl chloride (0.325 mL, 4.18 mmol) was added dropwise at 0° C. and the reaction was stirred for 1 h. LCMS showed a product peak and no starting materials. The reaction was diluted with DCM (50 mL), washed with water, brine, dried over $Na_2SO_4$, filtered and concentrated. The reaction was purified by flash column chromatography and the compound was eluted by 20%-50% EtOAc in hexanes.

Intermediate 15

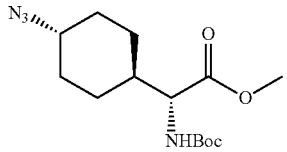

(R)-methyl 2-((1r,4R)-4-azidocyclohexyl)-2-((tert-butoxycarbonyl)amino)acetate (15)

A solution of (R)-methyl 2-((tert-butoxycarbonyl)amino)-2-((1s,4S)-4-((methylsulfonyl)oxy)cyclohexyl)acetate 14 (1 g, 2.74 mmol), sodium azide (0.356 g, 5.47 mmol) in DMF (10 mL) was stirred at 80° C. for overnight. LCMS showed the product peak. Water (10 mL)/EtOAc (40 mL) were added. The EtOAc layer was washed with brine, dried over $Na_2SO_4$, filtered and concentrated. The reaction was purified normal phase column chromatography (REDISEP column, 25 g) and the compound was eluted by 20% EtOAc to 50% EtOAc in hexane.

Intermediate 16

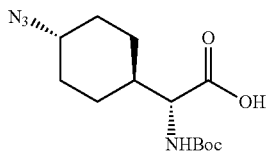

(R)-2-((1r,4R)-4-azidocyclohexyl)-2-((tert-butoxycarbonyl)amino)acetic acid (16)

A solution of (R)-methyl 2-((1r,4R)-4-azidocyclohexyl)-2-((tert-butoxycarbonyl)amino)acetate 15 (0.9 g, 2.88 mmol) in THF (2.00 mL)/MeOH (4 mL) was added LiOH (2.88 mL, 5.76 mmol) dropwise. The resulting mixture was stirred at r.t. for 4 h. LCMS showed complete conversion to the hydrolyzed product. The reaction was cooled to 0° C. and HCl (2.88 mL, 2.88 mmol) was added to adjust the pH to 5.0. The solvent was removed and DCM (80 mL) was added followed by water. The water layer was washed with DCM (2×). The combined DCM layer was dried over $Na_2SO_4$, filtered and concentrated. The crude product was used as such.

Example 1

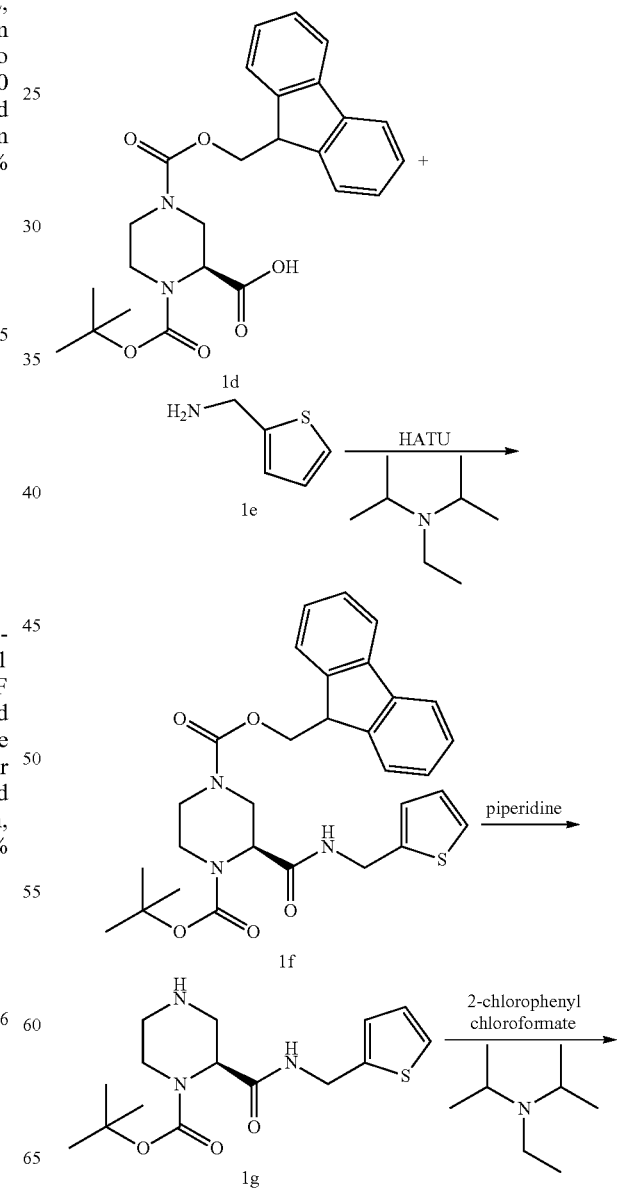

33
-continued

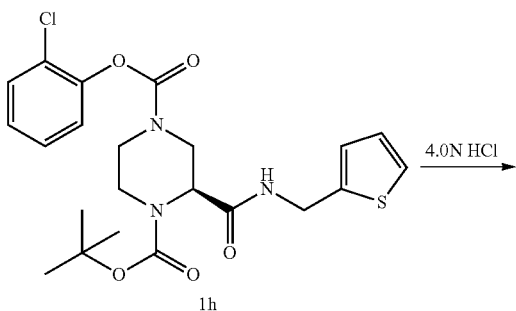

1h

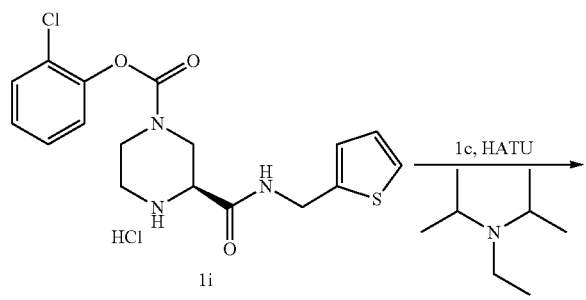

1i

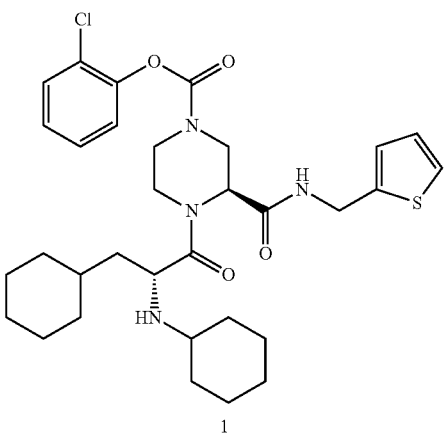

1

4-((9H-fluoren-9-yl)methyl) 1-(tert-butyl) (S)-2-((thiophen-2-ylmethyl)carbamoyl)piperazine-1,4-dicarboxylate (1f)

HATU (16.81 g, 44.2 mmol) was added to a stirred mixture of (S)-1-N-Boc-4-N-fmoc-piperazine-2-carboxylic acid (10.00 g, 22.10 mmol), 2-thiophenemethylamine (2.83 mL, 27.6 mmol) and Hunig's base (11.58 mL, 66.3 mmol) in CH$_2$Cl$_2$ (30 mL) and the mixture was stirred at room temperature for 2 h. The reaction was monitored by LCMS. After LCMS showed the product peak, the reaction mixture was diluted with water, extracted with CH$_2$Cl$_2$, washed with brine, dried over Na$_2$SO$_4$, filtered and concentrated in vacuo. The residue was purified by column chromatography on silica gel Teledyne ISCO REDISEP[330 g prepacked] eluting with 0-80% EtOAc/isohexane to give 1f.

34 tert-butyl (S)-2-((thiophen-2-ylmethyl)carbamoyl)piperazine-1-carboxylate (1g)

Piperidine (13.13 mL, 133 mmol) was added to a stirred mixture of (S)-4-((9H-fluoren-9-yl)methyl) 1-tert-butyl 2-((thiophen-2-ylmethyl)carbamoyl)piperazine-1,4-dicarboxylate if (12.10 g, 22.09 mmol) in DMF (25 mL) and the mixture was stirred at room temperature for 2 h. Upon completion by LCMS, the reaction was diluted with water, extracted with EtOAc, washed with brine, dried over Na$_2$SO$_4$, filtered and concentrated in vacuo. The residue was purified by column chromatography on silica gel Teledyne ISCO REDISEP[220 g prepacked] eluting with 0-20% MeOH/DCM to give 1g.

1-(tert-butyl) 4-(2-chlorophenyl) (S)-2-((thiophen-2-ylmethyl)carbamoyl)piperazine-1,4-dicarboxylate (1h)

2-Chlorophenyl chloroformate (0.129 mL, 0.922 mmol) was added to a stirred mixture of (S)-tert-butyl 2-((thiophen-2-ylmethyl)carbamoyl)piperazine-1-carboxylate 1g (250 mg, 0.768 mmol) and Hunig's Base (0.268 mL, 1.536 mmol) in CH$_2$Cl$_2$ (3 mL), and the mixture was stirred at room temperature for 90 min. Upon completion by LCMS, the residue was purified by column chromatography on silica gel Teledyne ISCO REDISEP[12 g prepacked] eluting with 0-40-50% EtOAc/isohexane to give 1h.

2-Chlorophenyl (S)-3-((thiophen-2-ylmethyl)carbamoyl)piperazine-1-carboxylate hydrochloride (1i)

HCl (1.729 mL, 6.92 mmol, 4.0 M) in 1,4-dioxane was added to a stirred mixture of (S)-1-tert-butyl 4-(2-chlorophenyl) 2-((thiophen-2-ylmethyl)carbamoyl)piperazine-1,4-dicarboxylate 1h (332 mg, 0.692 mmol) in CH$_2$Cl$_2$ (5 mL) and the mixture was stirred at room temperature for 2 h. The reaction was monitored by LCMS. Upon completion the excess solvent was concentrated and dried to yield 1i. The product was used without further purification.

2-chlorophenyl (S)-4-((R)-3-cyclohexyl-2-(cyclohexylamino)propanoyl)-3-((thiophen-2-ylmethyl)carbamoyl)piperazine-1-carboxylate (1)

2-(3H-[1,2,3]triazolo[4,5-b]pyridin-3-yl)-1,1,3,3-tetramethylisouronium hexafluorophosphate(V) (3.42 g, 9.01 mmol) was added to a stirred mixture of (S)-2-chlorophenyl 3-((thiophen-2-ylmethyl)carbamoyl)piperazine-1-carboxylate hydrochloride 1i (2.5 g, 6.00 mmol), (R)-3-cyclohexyl-2-(cyclohexylamino)propanoic acid 1c (2.037 g, 7.51 mmol), 1H-benzo[d][1,2,3]triazol-1-ol hydrate (1.379 g, 9.01 mmol), N-ethyl-N-isopropylpropan-2-amine (3.88 g, 30.0 mmol) in DMF (50 mL). The reaction was allowed to stir at room temperature overnight. Upon completion, the reaction was diluted with water and ethyl acetate. The organic layer was extracted out (2 times) and concentrated in vacuo. The crude was purified via ISCO (330 g column, 0-100% ethyl acetate/hexane to 100% ethyl acetate).

Example 2
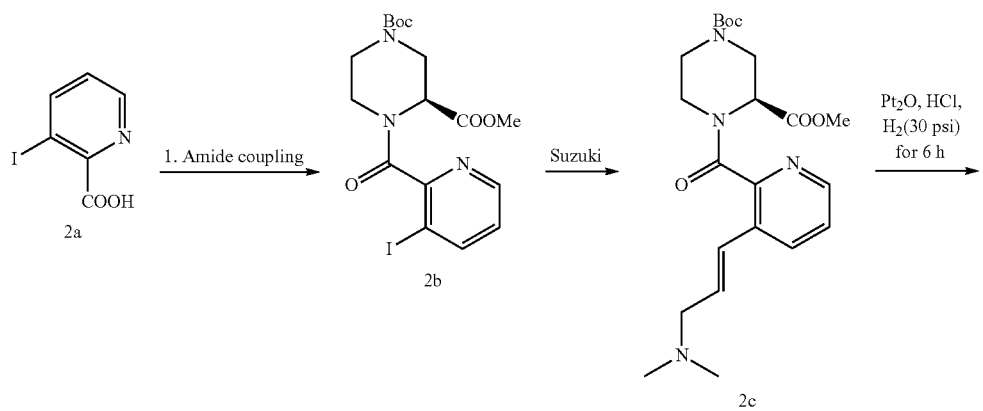
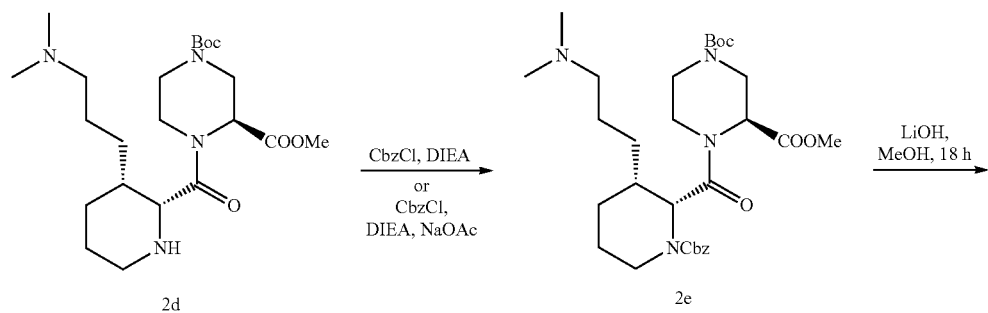
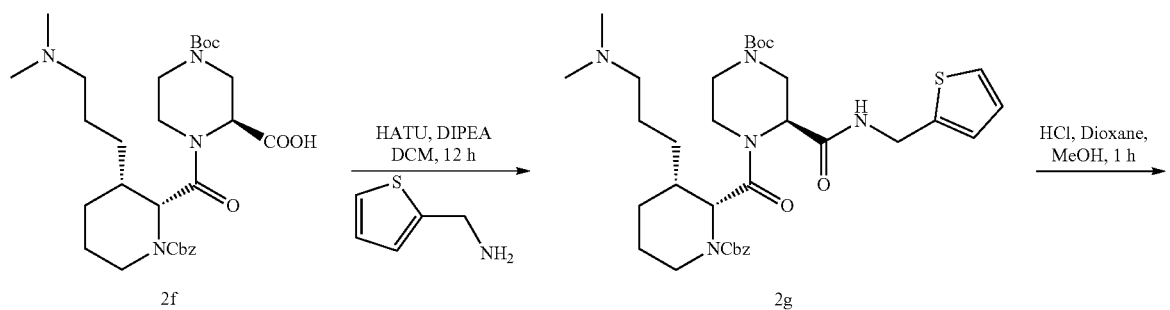
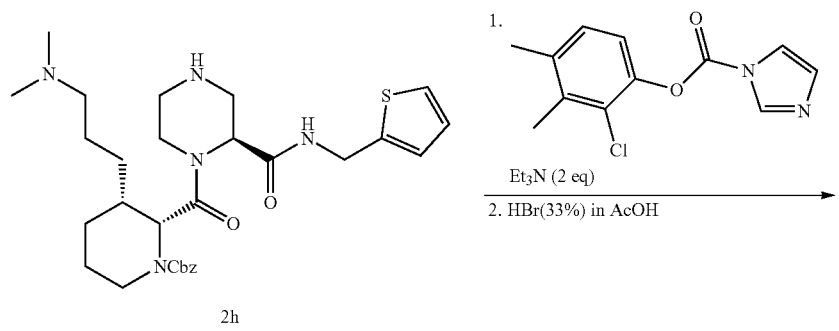

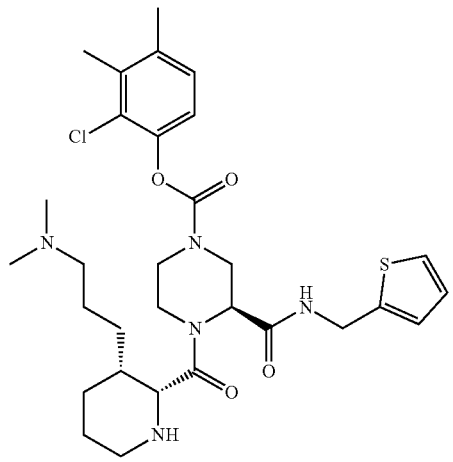

1-(tert-butyl) 3-methyl (S)-4-(3-iodonicolinoyl)piperazine-1,3-dicarboxylate (2b)

A solution of 3-iodopicolinic acid 2a (1.8 g, 7.23 mmol), (S)-1-tert-butyl 3-methyl piperazine-1,3-dicarboxylate (1.766 g, 7.23 mmol), HATU (3.02 g, 7.95 mmol), DIEA (5.05 mL, 28.9 mmol) in DCM (100 mL)/Acetonitrile (20 mL) was stirred at r.t. for 12 h. DCM (50 mL) and satd. NH$_4$Cl (100 mL) were added. The DCM layer was washed with brine, dried over Na$_2$SO$_4$, filtered and concentrated. The reaction was purified by column chromatography and the product was eluted by EtOAc to yield (S)-1-tert-butyl 3-methyl 4-(3-iodopicolinoyl)piperazine-1,3-dicarboxylate 2b.

1-(tert-butyl) 3-methyl (S,E)-4-(3-(3-(dimethylamino)prop-1-en-1-yl)picolinoyl)piperazine-1,3-dicarboxylate (2c)

A microwave vial under nitrogen atmosphere was charged with (S)-1-tert-butyl 3-methyl 4-(3-iodopicolinoyl)piperazine-1,3-dicarboxylate 2b (1 g, 2.104 mmol), (E)-N,N-dimethyl-3-(4,4,5,5-tetramethyl-1,3,2-dioxaborolan-2-yl)prop-2-en-1-amine (0.666 g, 3.16 mmol) and 2nd generation XPHOS precatalyst (0.083 g, 0.105 mmol). Anhydrous ethanol (8 mL) was added followed by potassium phosphate tribasic (1.403 mL, 4.21 mmol). The mixture was degassed with N$_2$ and heated to 60° C. in a microwave reactor for 4 h. Ethanol was removed. DCM (150 mL) was added, washed with brine, dried over Na$_2$SO$_4$, filtered and concentrated. 40% EtOAc in hexane was added, and the mixture was stirred for 20 minutes. The solids were filtered and separated, and the filtrate was concentrated. The crude material was used as such for the next reaction. (S,E)-1-tert-butyl 3-methyl 4-(3-(3-(dimethylamino)prop-1-en-1-yl)picolinoyl)piperazine-1,3-dicarboxylate 2c was obtained.

1-(tert-butyl) 3-methyl (S)-4-((2R,3S)-1-((benzyloxy)carbonyl)-3-(3-(dimethylamino)propyl)piperidine-2-carbonyl)piperazine-1,3-dicarboxylate (2e)

Method I: A solution of (S,E)-1-tert-butyl 3-methyl 4-(3-(3-(dimethylamino)prop-1-en-1-yl)picolinoyl)piperazine-1,3-dicarboxylate 2c (600 mg, 1.387 mmol) in MeOH (50 mL) was degassed thoroughly with N$_2$, and platinum(IV) oxide (126 mg, 0.555 mmol) was added. The reaction was degassed with N$_2$ again. The reaction was shaken under H$_2$ atm at 30 psi over the weekend. LCMS showed a major peak at 434 (M+1) and a minor peak at 440 (M+1). The reaction was filtered, and the filtrate was placed in a Parr shaker flask, and the procedure was repeated. Platinum(IV) oxide (0.268 g, 0.786 mmol) was added, and it was degassed with N$_2$. The reaction was hydrogenated using a Parr shaker under H$_2$ atm at 40 psi for 4 hours. LCMS showed complete conversion to the desired product. The reaction was filtered, concentrated to the half volume, keeping the water bath at ambient temperature. The reaction was cooled to 0° C., and Cbz-Cl (1.980 mL, 13.87 mmol) was added followed by DIEA (2.423 mL, 13.87 mmol) dropwise while maintaining the pH <6.0. The reaction was monitored by LCMS to find the complete conversion to product. The reaction was worked up with DCM (150 mL) and water (30 mL), and then transferred into a seperatory funnel. After the compound was extracted into the DCM layer, the aqueous layer was washed with DCM (2×). The combined organics were washed with brine, dried over Na$_2$SO$_4$, filtered and concentrated.

1-(tert-butyl) 3-methyl (S)-4-((2R,3S)-1-((benzyloxy)carbonyl)-3-(3-(dimethylamino)propyl)piperidine-2-carbonyl)piperazine-1,3-dicarboxylate (2e)

Method II: A solution of (3S)-1-tert-butyl 3-methyl 4-(3-(3-(dimethylamino)propyl)piperidine-2-carbonyl)piperazine-1,3-dicarboxylate 2d (540 mg, 1.226 mmol) in MeOH (0.75 mL)/Water (0.225 mL) was cooled to 0° C. Cbz-Cl (3.50 mL, 24.51 mmol) was added dropwise. After 10 min. LCMS showed no desired product formation and shown only a starting material peak. DIEA (3.85 mL, 22.06 mmol) was added dropwise and the reaction was stirred for 30 min. LCMS showed both the product and staring material peaks. Sodium acetate (503 mg, 6.13 mmol) dissolved in (0.2 mL) water was added dropwise while maintaining the pH <6.0. The reaction was monitored by LCMS to find out the complete conversion to product. The reaction was worked up with DCM (150 mL) and water (30 mL), and then transferred into a seperatory funnel. After the compound was extracted into the DCM layer, the aqueous layer was washed with DCM (2×). The combined organics were washed with brine, dried over Na$_2$SO$_4$, filtered and concentrated. The reaction was purified by reverse phase HPLC system using 0.05% TFA in ACN/H$_2$O.

(S)-1-((2R,3S)-1-((benzyloxy)carbonyl)-3-(3-(dimethylamino)propyl)piperidine-2-carbonyl)-4-(tert-butoxycarbonyl)piperazine-2-carboxylic acid (2f)

LiOH (0.600 mL, 1.201 mmol) was added to a solution of (3S)-1-tert-butyl 3-methyl 4-(1-((benzyloxy)carbonyl)-3-(3-(dimethylamino)propyl)piperidine-2-carbonyl)piperazine-1,3-dicarboxylate 2e (230 mg, 0.400 mmol) in MeOH (3 mL)/Water (1 mL). The reaction was stirred at r.t. for 90 min. LCMS showed a product peak (major) and a starting material peak (minor). The reaction continued, stirring overnight. LCMS showed complete conversion to the product. The pH was adjusted to 6.0 with 1M HCl. The reagents were removed under vacuum at ambient temp. and dried under high vacuum. After work up, LCMS showed a clean M+1 peak at 561. The crude mixture was used as such for the next reaction. (2S)-1-(1-((benzyloxy)carbonyl)-3-(3-(dimethylamino)propyl)piperidine-2-carbonyl)-4-(tert-butoxycarbonyl)piperazine-2-carboxylic acid was obtained.

2-chloro-3,4-dimethylphenyl 1H-imidazole-1-carboxylate (2i)

A solution of 2-chloro-3,4-dimethylphenol (0.750 g, 4.79 mmol) and CDI (1.009 g, 6.23 mmol) in DCM (5 mL) was stirred at r.t. for 15 min. and then refluxed for 4 h. LCMS showed the product peak. The reaction was added to DCM (50 mL), washed with water and brine, and the DCM layer was dried over Na$_2$SO$_4$, filtered and concentrated. The reaction was purified by normal phase (REDISEP column, 40 g), and the compound was eluted by 50% to 60% EtOAc in hexane. 2-chloro-3,4-dimethylphenyl 1H-imidazole-1-carboxylate was obtained.

tert-butyl (S)-4-((2R,3S)-1-((benzyloxy)carbonyl)-3-(3-(dimethylamino)propyl)piperidine-2-carbonyl)-3-((thiophen-2-ylmethyl)carbamoyl)piperazine-1-carboxylate (2g)

A solution of (2S)-1-(1-((benzyloxy)carbonyl)-3-(3-(dimethylamino)propyl)piperidine-2-carbonyl)-4-(tert-butoxycarbonyl)piperazine-2-carboxylic acid (45 mg, 0.080 mmol), HOBT (12.29 mg, 0.080 mmol), EDC (46.2 mg, 0.241 mmol) and 2-thiophenemethylamine (0.013 mL, 0.161 mmol) in DCM (1 mL) and DMA (0.2 mL) was stirred at r.t. for 30 min. LCMS showed the desired product peak and a starting material peak. The reaction continued stirring overnight at r.t. The reaction was added to DCM (10 mL), and washed with water (1 mL). The DCM layer was dried over Na$_2$SO$_4$, filtered and concentrated. The crude product was used as such.

benzyl (2R,3S)-3-(3-(dimethylamino)propyl)-2-((S)-2-((thiophen-2-ylmethyl)carbamoyl)iperazine-1-carbonyl)piperidine-1-carboxylate (2h)

HCl (0.019 mL, 0.076 mmol) was added to a solution of (3S)-tert-butyl 4-(1-((benzyloxy)carbonyl)-3-(3-(dimethylamino)propyl)piperidine-2-carbonyl)-3-((thiophen-2-ylmethyl)carbamoyl)piperazine-1-carboxylate (20 mg, 0.030 mmol) in HCl (0.019 mL, 0.076 mmol). The resulting mixture was stirred for 1 h. at r.t. LCMS showed a product peak. The reagents were removed, and the residue was dried under a high vacuum. The residue was washed with hexane (2 mL), and dried under a high vacuum to obtain 2h.

2-chloro-3,4-dimethylphenyl (S)-4-((2R,3S)-1-((benzyloxy)carbonyl)-3-(3-(dimethylamino)propyl)piperidine-2-carbonyl-3-((thiophen-2-ylmethyl)carbamoyl)piperazine-1-carboxylate A solution of benzyl 3-(3-(dimethylamino)propyl)-2-((S)-2-((thiophen-2-ylmethyl)carbamoyl)piperazine-1-carbonyl)piperidine-1-carboxylate (10 mg, 0.018 mmol) and 2-chloro-3,4-dimethylphenyl 1H-imidazole-1-carboxylate (5.86 mg, 0.023 mmol) in THF (0.6 mL) was stirred at r.t. overnight. LCMS showed product formation. THF was removed, and the residue was added to MeOH (0.5 mL), loaded on column (C18, 12 g), and purified by reverse phase HPLC (CombiFlash).

2-chloro-3,4-dimethylphenyl (S)-4-((2R,3R)-3-(3-(dimethylamino)propyl)piperidine-2-carbonyl)-3-((thiophen-2-ylmethyl)carbamoyl)piperazine-1-carboxylate (2)

HBr (0.011 mL, 0.068 mmol) was added to a solution of (S)-2-chloro-3,4-dimethylphenyl 4-((2R,3S)-1-((benzyloxy)carbonyl)-3-(3-(dimethylamino)propyl)piperidine-2-carbonyl)-3-((thiophen-2-ylmethyl)carbamoyl)piperazine-1-carboxylate (5 mg, 6.77 μmol) in acetic acid (0.03 mL). The resulting mixture was stirred for 20 minutes. LCMS showed Cbz-deprotected compound. HBr was removed by N$_2$, concentrated and dried under a high vacuum. The crude mixture was purified by reverse phase HPLC system using 0.05% TFA in ACN/H$_2$O.

Example 3

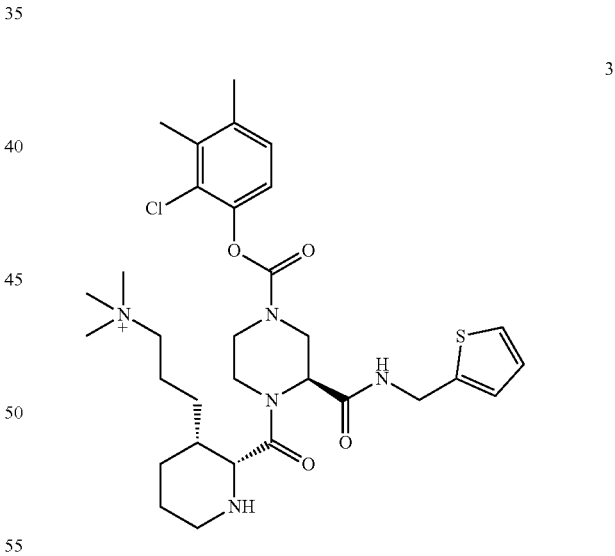

3-((2R,3R)-2-((S)-4-((2-chloro-3,4-dimethylphenoxy)carbonyl)-2-((thiophen-2-ylmethyl)carbamoyl)piperazine-1-carbonyl)piperidin-3-yl)-N,N,N-trimethylpropan-1-aminium chloride (3)

The product 3 was obtained as a side product during the conversion of 2g to 2.
Using the appropriate starting materials and following synthetic sequences similar to those described above, the following compounds of Table 1 were prepared and characterized.

TABLE 1

| Example number | Structure | Name | Exact Mass [M + H]+ | FXIIa IC50 (nM) |
|---|---|---|---|---|
| 1 | 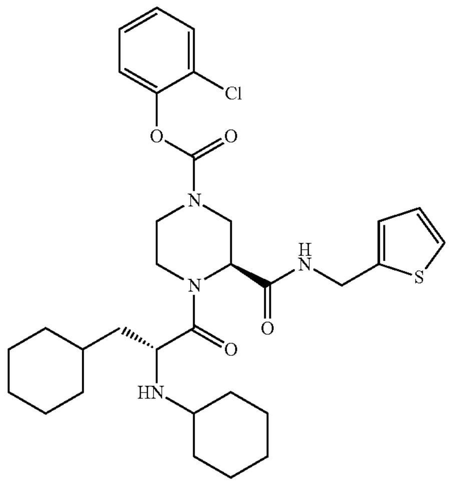 [SMILES: O=C(NCc1cccs1)[C@@H]1CN(C(=O)Oc2ccccc2Cl)CCN1C(=O)[C@@H](CC1CCCCC1)NC1CCCCC1] | 2-chlorophenyl (3S)-4-(N,3-dicyclohexyl-D-alanyl)-3-[(thiophen-2-ylmethyl)carbamoyl]piperazine-1-carboxylate | 615.3 | 27.7 |
| 2 | 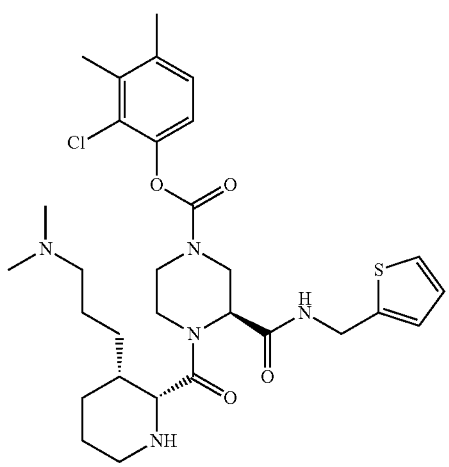 [SMILES: Cc1ccc(OC(=O)N2CCN(C(=O)[C@@H]3NCCC[C@@H]3CCCN(C)C)[C@H](C(=O)NCc3cccs3)C2)c(Cl)c1C] | 2-chloro-3,4-dimethylphenyl (3S)-4-({(2R,3R)-3-[3-(dimethylamino)propyl]piperidin-2-yl}carbonyl)-3-[(thiophen-2-ylmethyl)carbamoyl]piperazine-1-carboxylate | 604.3 | 28.5 |
| 3 | 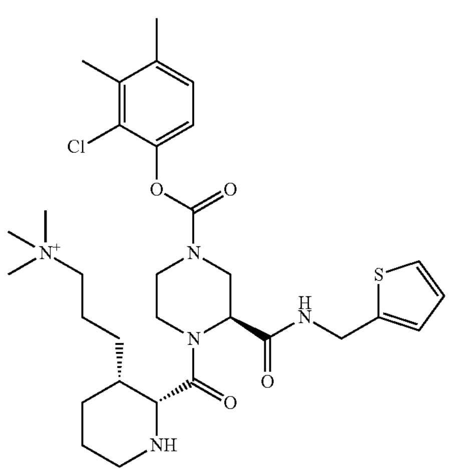 [SMILES: Cc1ccc(OC(=O)N2CCN(C(=O)[C@@H]3NCCC[C@@H]3CCC[N+](C)(C)C)[C@H](C(=O)NCc3cccs3)C2)c(Cl)c1C] | 3-[(2R,3R)-2-({(2S)-4-[(2-chloro-3,4-dimethylphenoxy)carbonyl]-2-[(thiophen-2-ylmethyl)carbamoyl]piperazin-1-yl}carbonyl)piperidin-3-yl]-N,N,N-trimethylpropan-1-aminium | 619.3 | 14.3 |

TABLE 1-continued

| Example number | Structure | Name | Exact Mass [M + H]+ | FXIIa IC50 (nM) |
|---|---|---|---|---|
| 4 | 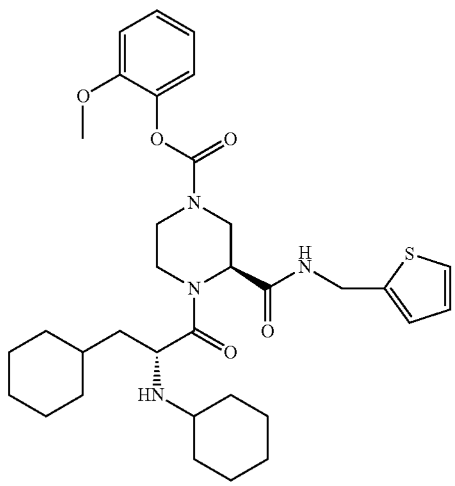 [SMILES: COc1ccccc1OC(=O)N1CCN(C(=O)[C@@H](CC2CCCCC2)NC2CCCCC2)[C@H](C(=O)NCc2cccs2)C1] | 2-methoxyphenyl (3S)-4-(N,3-dicyclohexyl-D-alanyl)-3-[(thiophen-2-ylmethyl)carbamoyl]piperazine-1-carboxylate | 611.3 | 26.4 |
| 5 | 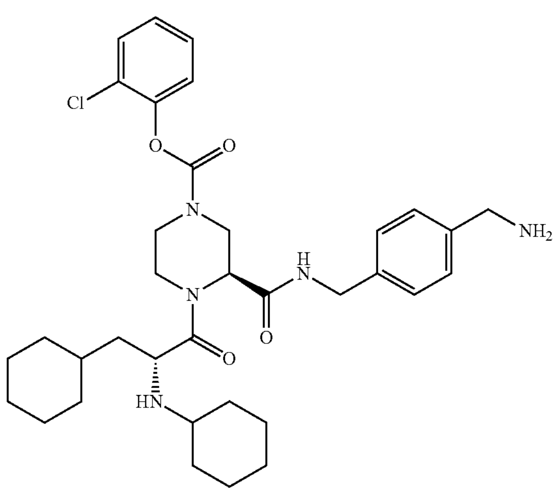 [SMILES: NCc1ccc(CNC(=O)[C@@H]2CN(C(=O)Oc3ccccc3Cl)CCN2C(=O)[C@@H](CC2CCCCC2)NC2CCCCC2)cc1] | 2-chlorophenyl (3S)-3-{[4-(aminomethyl)benzyl]carbamoyl}-4-(N,3-dicyclohexyl-D-alanyl)piperazine-1-carboxylate | 638.5 | 5.9 |

TABLE 1-continued

| Example number | Structure | Name | Exact Mass [M + H]+ | FXIIa IC50 (nM) |
|---|---|---|---|---|
| 6 | 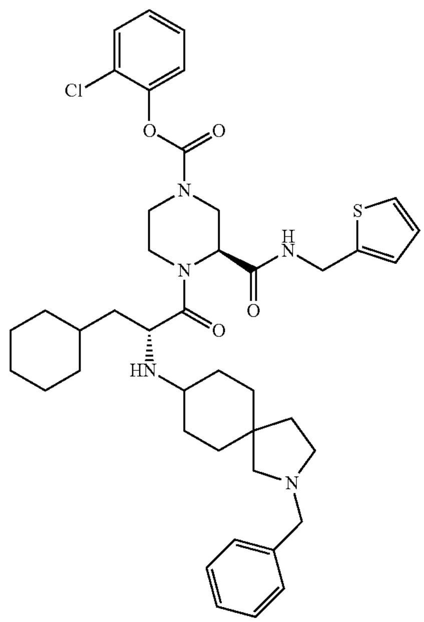 [SMILES: O=C(NCc1cccs1)[C@@H]1CN(C(=O)Oc2ccccc2Cl)CCN1C(=O)[C@@H](CC1CCCCC1)NC1CCC2(CC1)CCN(Cc1ccccc1)C2] | 2-chlorophenyl (3S)-4-[N-(2-benzyl-2-azaspiro[4.5]dec-8-yl)-3-cyclohexyl-D-alanyl]-3-[(thiophen-2-ylmethyl)carbamoyl]piperazine-1-carboxylate | 760.5 | 11.7 |
| 7 | 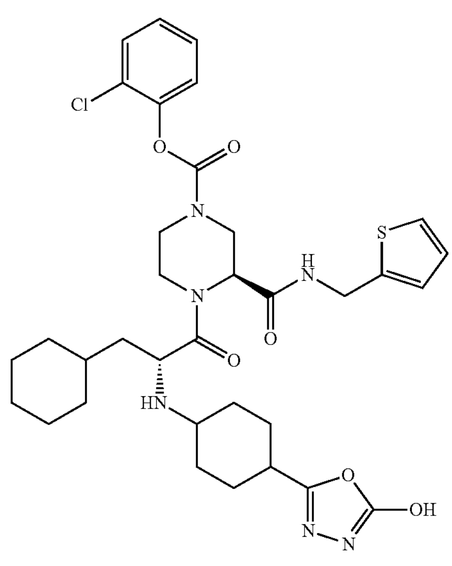 [SMILES: O=C(NCc1cccs1)[C@@H]1CN(C(=O)Oc2ccccc2Cl)CCN1C(=O)[C@@H](CC1CCCCC1)NC1CCC(c2nnc(O)o2)CC1] | 2-chlorophenyl (3S)-4-{3-cyclohexyl-N-[4-(5-hydroxy-1,3,4-oxadiazol-2-yl)cyclohexyl]-D-alanyl}-3-[(thiophen-2-ylmethyl)carbamoyl]piperazine-1-carboxylate | 699.4 | 24.4 |

TABLE 1-continued

| Example number | Structure | Name | Exact Mass [M + H]+ | FXIIa IC50 (nM) |
|---|---|---|---|---|
| 8 | 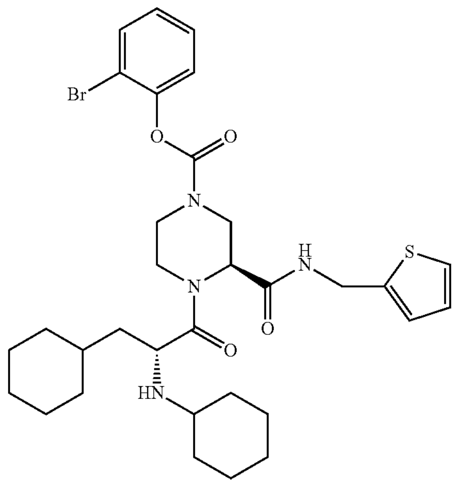 [SMILES: O=C(NCc1cccs1)[C@@H]1CN(C(=O)Oc2ccccc2Br)CCN1C(=O)[C@@H](CC1CCCCC1)NC1CCCCC1] | 2-bromophenyl (3S)-4-(N,3-dicyclohexyl-D-alanyl)-3-[(thiophen-2-ylmethyl)carbamoyl]piperazine-1-carboxylate | 659.2 | 28.7 |
| 9 | 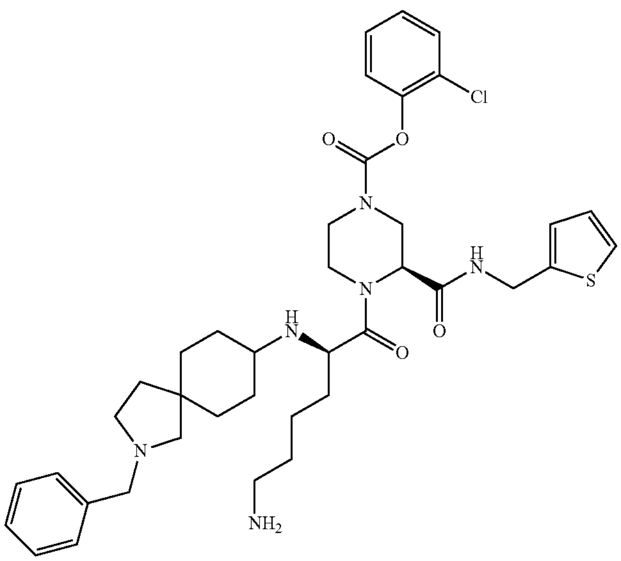 [SMILES: NCCCC[C@@H](NC1CCC2(CC1)CCN(Cc1ccccc1)C2)C(=O)N1CCN(C(=O)Oc2ccccc2Cl)C[C@H]1C(=O)NCc1cccs1] | 2-chlorophenyl (3S)-4-[$N^2$-(2-benzyl-2-azaspiro[4.5]dec-8-yl)-D-lysyl]-3-[(thiophen-2-ylmethyl)carbamoyl]piperazine-1-carboxylate | 753.3 | 24.4 |
| 10 | 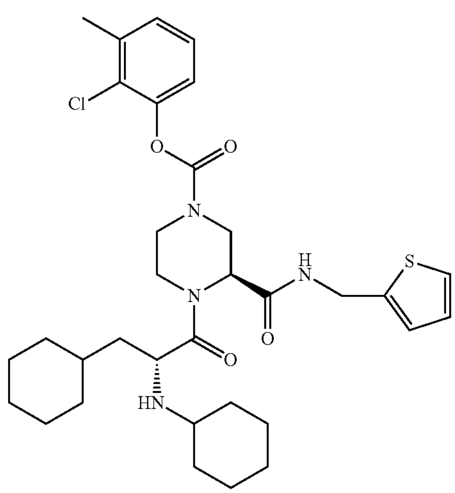 [SMILES: Cc1cccc(OC(=O)N2CCN(C(=O)[C@@H](CC3CCCCC3)NC3CCCCC3)[C@H](C(=O)NCc3cccs3)C2)c1Cl] | 2-chloro-3-methylphenyl (3S)-4-(N,3-dicyclohexyl-D-alanyl)-3-[(thiophen-2-ylmethyl)carbamoyl]piperazine-1-carboxylate | 629.4 | 14.8 |

TABLE 1-continued

| Example number | Structure | Name | Exact Mass [M + H]+ | FXIIa IC50 (nM) |
|---|---|---|---|---|
| 11 | 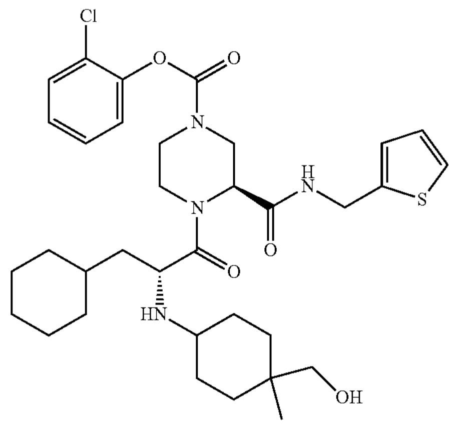 [SMILES: CC1(CO)CCC(N[C@H](CC2CCCCC2)C(=O)N2CCN(C(=O)Oc3ccccc3Cl)C[C@H]2C(=O)NCc2cccs2)CC1] | 2-chlorophenyl (3S)-4-{3-cyclohexyl-N-[4-(hydorxymethyl)-4-methylcyclohexyl]-D-alanyl}-3-[(thiophen-2-ylmethyl)carbamoyl]piperazine-1-carboxylate | 659.3 | 23.3 |
| 12 | 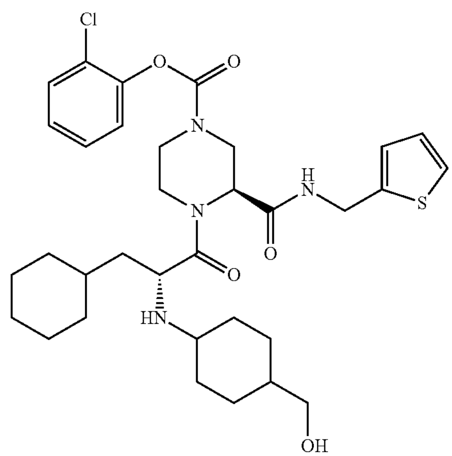 [SMILES: O=C(NCc1cccs1)[C@@H]1CN(C(=O)Oc2ccccc2Cl)CCN1C(=O)[C@@H](CC1CCCCC1)NC1CCC(CO)CC1] | 2-chlorophenyl (3S)-4-{3-cyclohexyl-N-[4-(hydroxymethyl)cyclohexyl]-D-alanyl}-3-[(thiophen-2-ylmethyl)carbamoyl]piperazine-1-carboxylate | 645.3 | 26.6 |
| 13 | 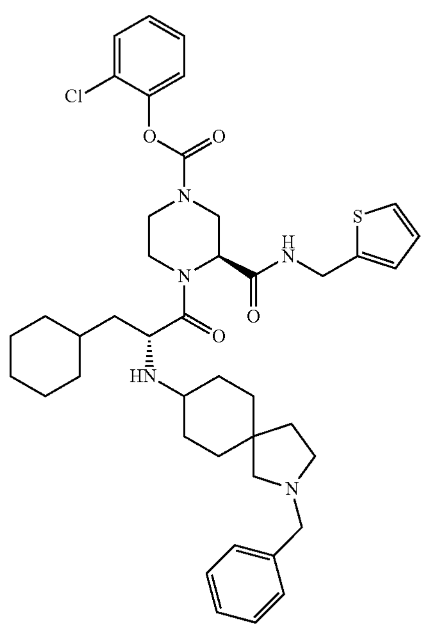 [SMILES: O=C(NCc1cccs1)[C@@H]1CN(C(=O)Oc2ccccc2Cl)CCN1C(=O)[C@@H](CC1CCCCC1)NC1CCC2(CC1)CCN(Cc1ccccc1)C2] | 2-chlorophenyl (3S)-4-[N-(2-benzyl-2-azaspiro[4.5]dec-8-yl)-3-cyclohexyl-D-alanyl]-3-[(thiophen-2-ylmethyl)carbamoyl]piperazine-1-carboxylate | 760.5 | 6.6 |

TABLE 1-continued

| Example number | Structure | Name | Exact Mass [M + H]+ | FXIIa IC50 (nM) |
|---|---|---|---|---|
| 14 | 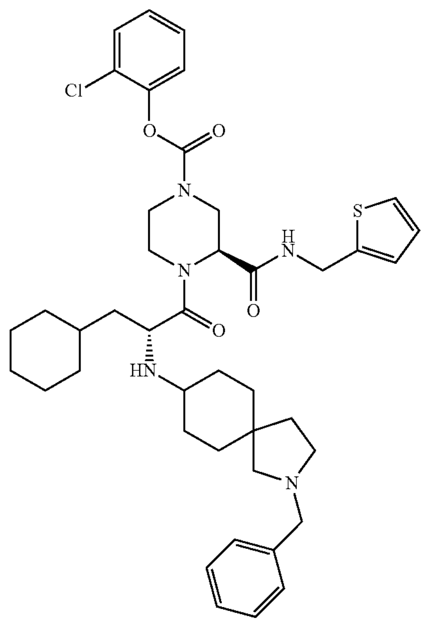 [SMILES: O=C(NCc1cccs1)[C@@H]1CN(C(=O)Oc2ccccc2Cl)CCN1C(=O)[C@@H](CC1CCCCC1)NC1CCC2(CC1)CCN(Cc1ccccc1)C2] | 2-chlorophenyl (3S)-4-[N-(2-benzyl-2-azaspiro[4.5]dec-8-yl)-3-cyclohexyl-D-alanyl]-3-[(thiophen-2-ylmethyl)carbamoyl]piperazine-1-carboxylate | 760.5 | 5.8 |
| 15 | 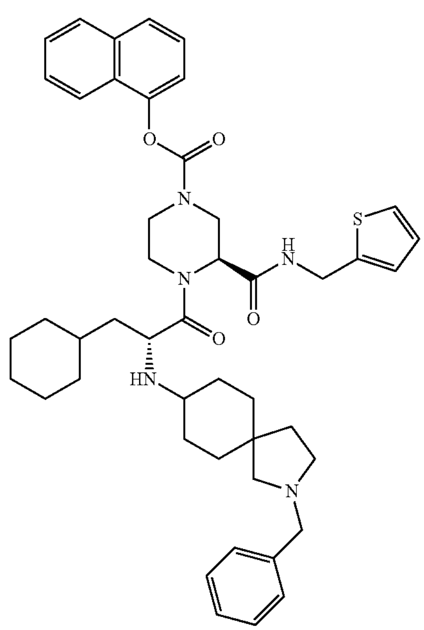 [SMILES: O=C(NCc1cccs1)[C@@H]1CN(C(=O)Oc2cccc3ccccc23)CCN1C(=O)[C@@H](CC1CCCCC1)NC1CCC2(CC1)CCN(Cc1ccccc1)C2] | naphthalen-1-yl (3S)-4-[N-(2-benzyl-2-azaspiro[4.5]dec-8-yl)-3-cyclohexyl-D-alanyl]-3-[(thiophen-2-ylmethyl)carbamoyl]piperazine-1-carboxylate | 776.5 | 16.6 |

TABLE 1-continued

| Example number | Structure | Name | Exact Mass [M + H]+ | FXIIa IC50 (nM) |
|---|---|---|---|---|
| 16 | 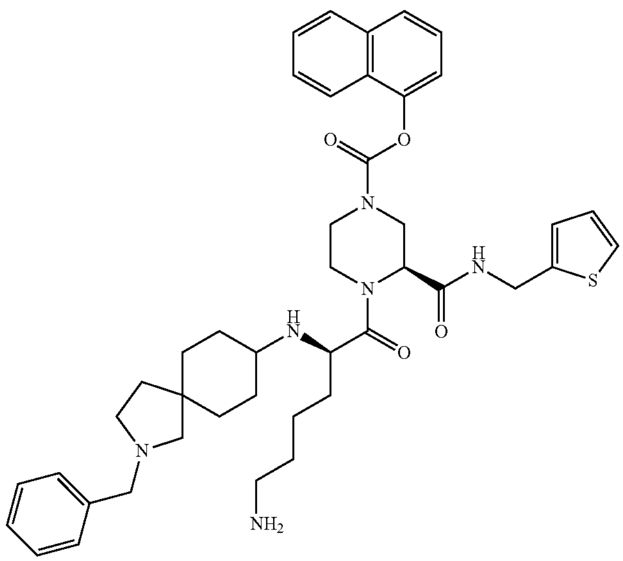 [SMILES: NCCCC[C@@H](NC1CCC2(CC1)CCN(Cc1ccccc1)C2)C(=O)N1CCN(C(=O)Oc2cccc3ccccc23)C[C@H]1C(=O)NCc1cccs1] | naphthalen-1-yl (3S)-4-[N$^2$-(2-benzyl-2-azaspiro[4.5]dec-8-yl)-D-lysyl]-3-[(thiophen-2-ylmethyl)carbamoyl]pipreazine-1-carboxylate | 751.4 | 11.8 |
| 17 | 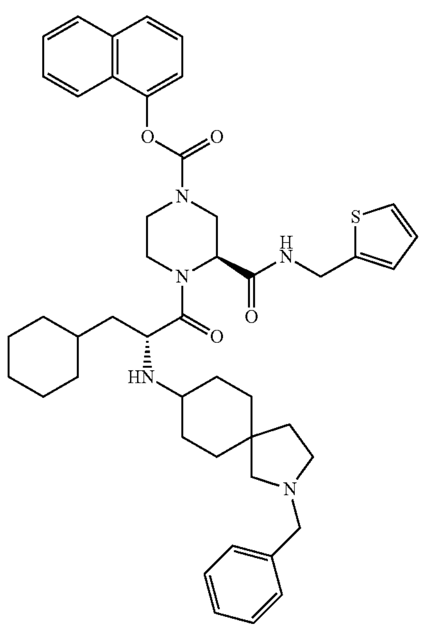 [SMILES: O=C(NCc1cccs1)[C@@H]1CN(C(=O)Oc2cccc3ccccc23)CCN1C(=O)[C@@H](CC1CCCCC1)NC1CCC2(CC1)CCN(Cc1ccccc1)C2] | naphthalen-1-yl (3S)-4-[N-(2-benzyl-2-azaspiro[4.5]dec-8-yl)-3-cyclohexyl-D-alanyl]-3-[(thiophen-2-ylmethyl)carbamoyl]piperazine-1-carboxylate | 776.5 | 8.4 |

TABLE 1-continued

| Example number | Structure | Name | Exact Mass [M + H]+ | FXIIa IC50 (nM) |
|---|---|---|---|---|
| 18 | 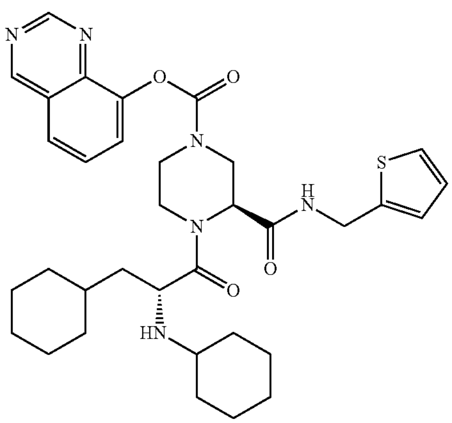 [SMILES: O=C(NCc1cccs1)[C@@H]1CN(C(=O)Oc2cccc3cncnc23)CCN1C(=O)[C@@H](CC1CCCCC1)NC1CCCCC1] | quinazolin-8-yl (3S)-4-(N,3-dicyclohexyl-D-alanyl)-3-[(thiophen-2-ylmethyl)carbamoyl]piperazine-1-carboxylate | 633.3 | 4.5 |
| 19 | 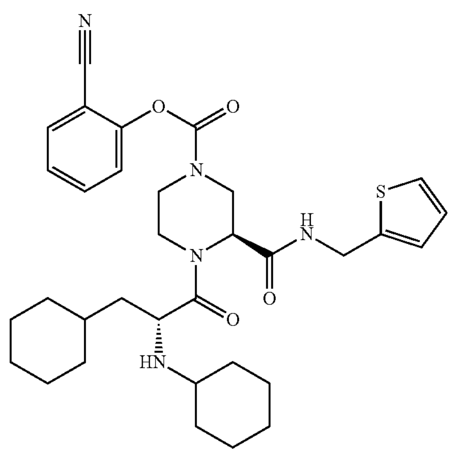 [SMILES: N#Cc1ccccc1OC(=O)N1CCN(C(=O)[C@@H](CC2CCCCC2)NC2CCCCC2)[C@H](C(=O)NCc2cccs2)C1] | 2-cyanophenyl (3S)-4-(N,3-dicyclohexyl-D-alanyl)-3-[(thiophen-2-ylmethyl)carbamoyl]piperazine-1-carboxylate | 606.3 | 15.2 |
| 20 | 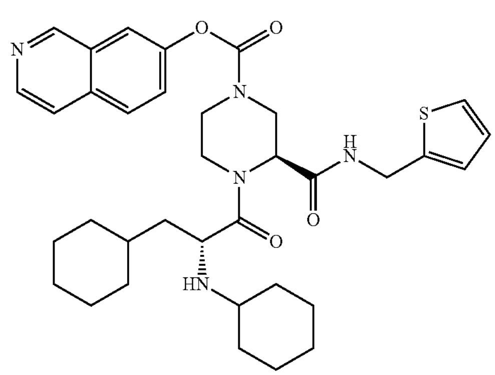 [SMILES: O=C(NCc1cccs1)[C@@H]1CN(C(=O)Oc2ccc3ccncc3c2)CCN1C(=O)[C@@H](CC1CCCCC1)NC1CCCCC1] | isoquinolin-7-yl (3S)-4-(N,3-dicyclohexyl-D-alanyl)-3-[(thiophen-2-ylmethyl)carbamoyl]piperazine-1-carboxylate | 632.3 | 29.1 |

TABLE 1-continued

| Example number | Structure | Name | Exact Mass [M + H]+ | FXIIa IC50 (nM) |
|---|---|---|---|---|
| 21 | 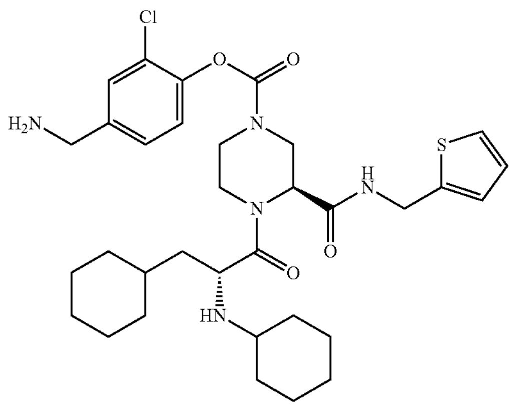 [SMILES: NCc1ccc(OC(=O)N2CCN(C(=O)[C@@H](CC3CCCCC3)NC3CCCCC3)[C@H](C(=O)NCc3cccs3)C2)c(Cl)c1] | 4-(aminomethyl)-2-chlorophenyl (3S)-4-(N,3-dicyclohexyl-D-alanyl)-3-[(thiophen-2-ylmethyl)carbamoyl]piperazine-1-carboxylate | 644.3 | 6.7 |
| 22 | 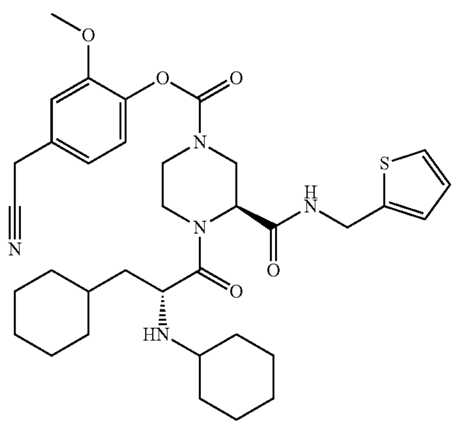 [SMILES: COc1cc(CC#N)ccc1OC(=O)N1CCN(C(=O)[C@@H](CC2CCCCC2)NC2CCCCC2)[C@H](C(=O)NCc2cccs2)C1] | 4-(cyanomethyl)-2-methoxyphenyl (3S)-4-(N,3-dicyclohexyl-D-alanyl)-3-[(thiophen-2-ylmethyl)carbamoyl]piperazine-1-carboxylate | 650.3 | 12.9 |
| 23 | 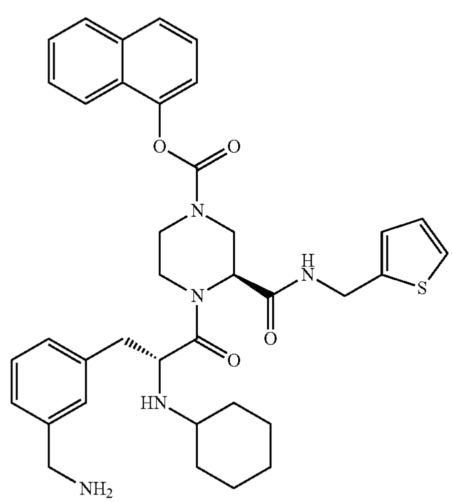 [SMILES: NCc1cccc(C[C@@H](NC2CCCCC2)C(=O)N2CCN(C(=O)Oc3cccc4ccccc34)C[C@H]2C(=O)NCc2cccs2)c1] | naphthalen-1-yl (3S)-4-[3-(aminomethyl)-N-cyclohexyl-D-phenylalanyl]-3-[(thiophen-2-ylmethyl)carbamoyl]piperazine-1-carboxylate | 654.3 | 18.8 |

TABLE 1-continued

| Example number | Structure | Name | Exact Mass [M + H]+ | FXIIa IC50 (nM) |
|---|---|---|---|---|
| 24 | 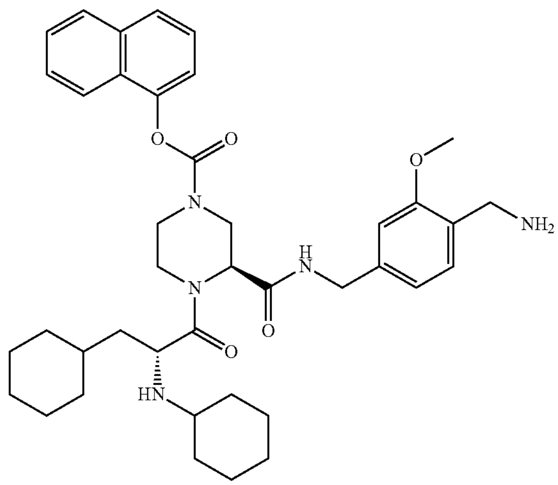 [SMILES: COc1cc(CNC(=O)[C@@H]2CN(C(=O)Oc3cccc4ccccc34)CCN2C(=O)[C@@H](CC2CCCCC2)NC2CCCCC2)ccc1CN] | naphthalen-1-yl (3S)-3-{[4-(aminomethyl)-3-methoxybenzyl]carbamoyl}-4-(N,3-dicyclohexyl-D-alanyl)piperazine-1-carboxylate | 684.4 | 1.6 |
| 25 | 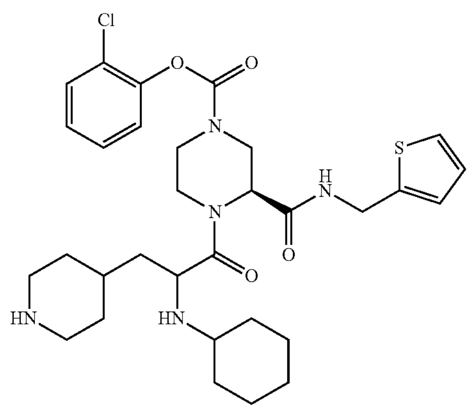 [SMILES: O=C(NCc1cccs1)[C@@H]1CN(C(=O)Oc2ccccc2Cl)CCN1C(=O)C(CC1CCNCC1)NC1CCCCC1] | 2-chlorophenyl (3S)-4-(N-4-cyclohexyl-3-piperidin-4-ylalanyl)-3-[(thiophen-2-ylmethyl)carbamoyl]piperazine-1-carboxylate | 616.3 | 15.7 |
| 26 | 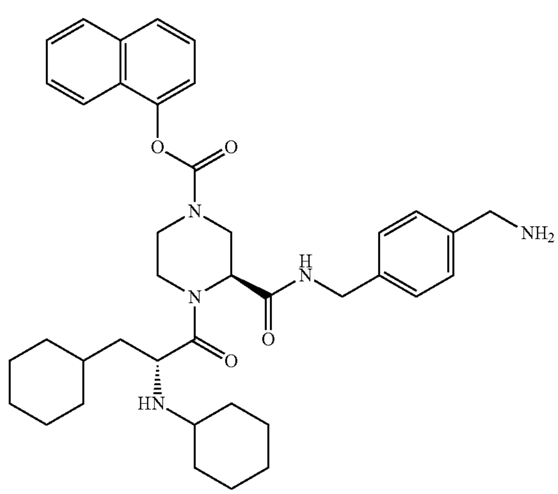 [SMILES: NCc1ccc(CNC(=O)[C@@H]2CN(C(=O)Oc3cccc4ccccc34)CCN2C(=O)[C@@H](CC2CCCCC2)NC2CCCCC2)cc1] | naphthalen-1-yl (3S)-3-{[4-(aminomethyl)benzyl]carbamoyl}-4-(N,3-dicyclohexyl-D-alanyl)piperazine-1-carboxylate | 654.6 | 8.4 |

TABLE 1-continued

| Example number | Structure | Name | Exact Mass [M + H]+ | FXIIa IC50 (nM) |
|---|---|---|---|---|
| 27 | 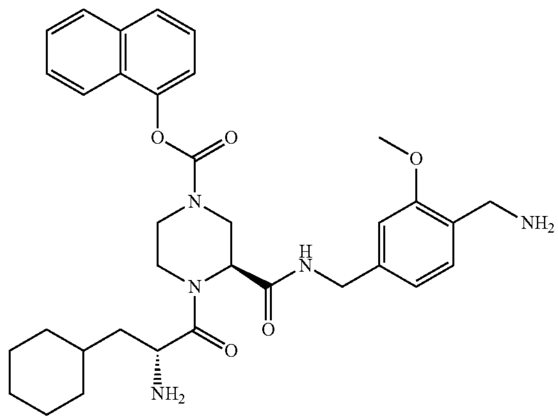 [SMILES: COc1cc(CNC(=O)[C@@H]2CN(C(=O)Oc3cccc4ccccc34)CCN2C(=O)[C@H](N)CC2CCCCC2)ccc1CN] | naphthalen-1-yl (3S)-3-{[4-(aminomethyl)-3-methoxybenzyl]carbamoyl}-4-(3-cyclohexyl-D-alanyl)piperazine-1-carboxylate | 602.5 | 15.6 |
| 28 | 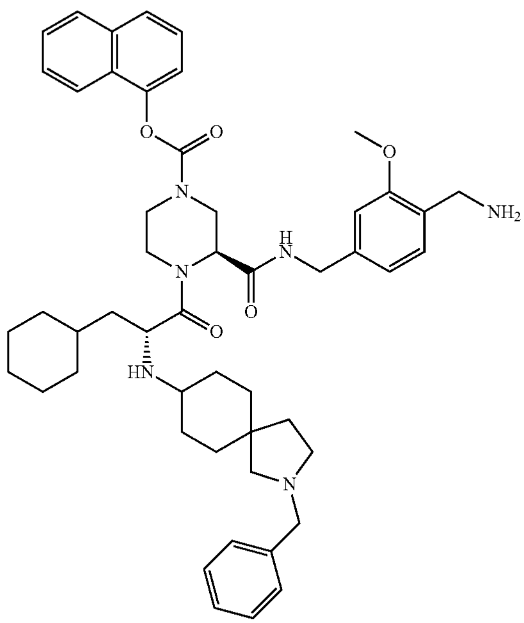 [SMILES: COc1cc(CNC(=O)[C@@H]2CN(C(=O)Oc3cccc4ccccc34)CCN2C(=O)[C@@H](CC2CCCCC2)NC2CCC3(CC2)CCN(Cc2ccccc2)C3)ccc1CN] | naphthalen-1-yl (3S)-3-{[4-(aminomethyl)-3-methoxybenzyl]carbamoyl}-4-[N-(2-benzyl-2-azaspiro[4.5]dec-8-yl)-3-cyclohexyl-D-alanyl]piperazine-1-carboxylate | 829.8 | 3.9 |
| 29 | 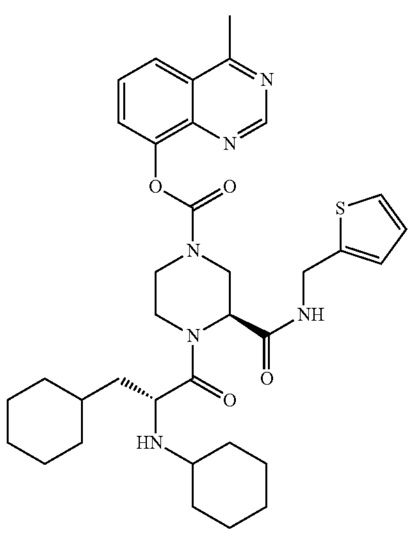 [SMILES: Cc1ncnc2c(OC(=O)N3CCN(C(=O)[C@@H](CC4CCCCC4)NC4CCCCC4)[C@H](C(=O)NCc4cccs4)C3)cccc12] | 4-methylquinazolin-8-yl (3S)-4-(N,3-dicyclohexyl-D-alanyl)-3-[(thiophen-2-ylmethyl)carbamoyl]piperazine-1-carboxylate | 647.3 | 3.3 |

TABLE 1-continued

| Example number | Structure | Name | Exact Mass [M + H]+ | FXIIa IC50 (nM) |
|---|---|---|---|---|
| 30 | 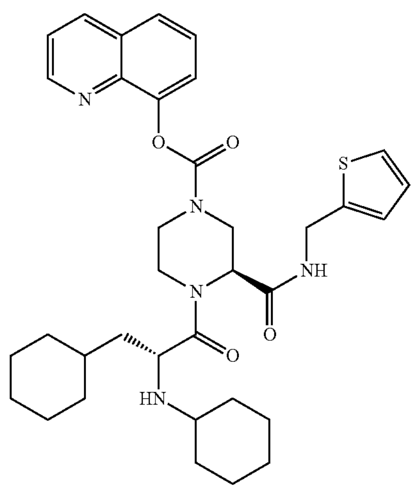 [SMILES: O=C(NCc1cccs1)[C@@H]1CN(C(=O)Oc2cccc3cccnc23)CCN1C(=O)[C@@H](CC1CCCCC1)NC1CCCCC1] | quinolin-8-yl (3S)-4-(N,3-dicyclohexyl-D-alanyl)-3-[(thiophen-2-ylmethyl)carbamoyl]piperazine-1-carboxylate | 632.3 | 5.8 |
| 31 | 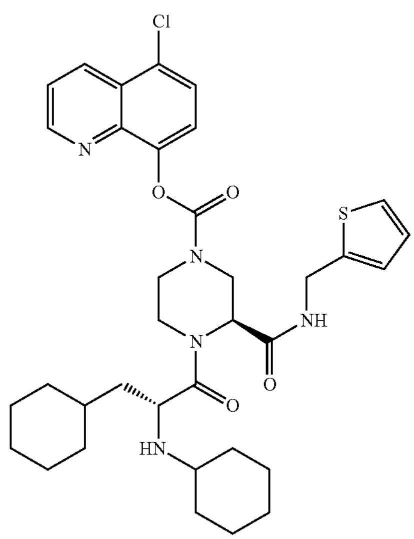 [SMILES: O=C(NCc1cccs1)[C@@H]1CN(C(=O)Oc2ccc(Cl)c3cccnc23)CCN1C(=O)[C@@H](CC1CCCCC1)NC1CCCCC1] | 5-chloroquinolin-8-yl (3S)-4-(N,3-dicyclohexyl-D-alanyl)-3-[(thiophen-2-ylmethyl)carbamoyl]piperazine-1-carboxylate | 666.3 | 16.4 |
| 32 | 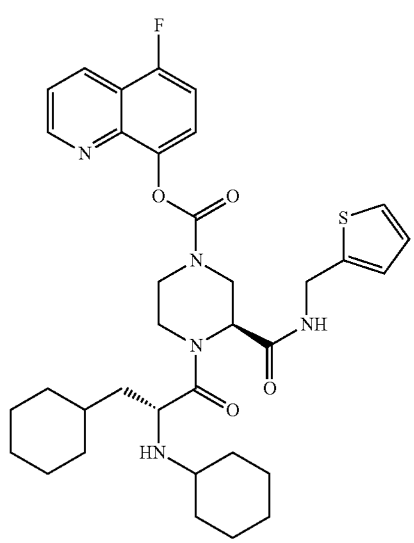 [SMILES: O=C(NCc1cccs1)[C@@H]1CN(C(=O)Oc2ccc(F)c3cccnc23)CCN1C(=O)[C@@H](CC1CCCCC1)NC1CCCCC1] | 5-fluoroquinolin-8-yl (3S)-4-(N,3-dicyclohexyl-D-alanyl)-3-[(thiophen-2-ylmethyl)carbamoyl]piperazine-1-carboxylate | 650.3 | 5.2 |

TABLE 1-continued

| Example number | Name | Exact Mass [M + H]+ | FXIIa IC50 (nM) |
|---|---|---|---|
| 33 | 2-hydroxyquinolin-8-yl (3S)-4-(N,3-dicyclohexyl-D-alanyl)-3-[(thiophen-2-ylmethyl)carbamoyl]piperazine-1-carboxylate | 648.3 | 20.0 |
| 34 | quinolin-5-yl (3S)-4-(N,3-dicyclohexyl-D-alanyl)-3-[(thiophen-2-ylmethyl)carbamoyl]piperazine-1-carboxylate | 632.3 | 17.3 |
| 35 | 4-(aminomethyl)-2-methoxyphenyl (3S)-4-(N,3-dicyclohexyl-D-alanyl)-3-[(thiophen-2-ylmethyl)carbamoyl]piperazine-1-carboxylate | 640.4 | 24.4 |

TABLE 1-continued

| Example number | Structure | Name | Exact Mass [M + H]+ | FXIIa IC50 (nM) |
|---|---|---|---|---|
| 36 | 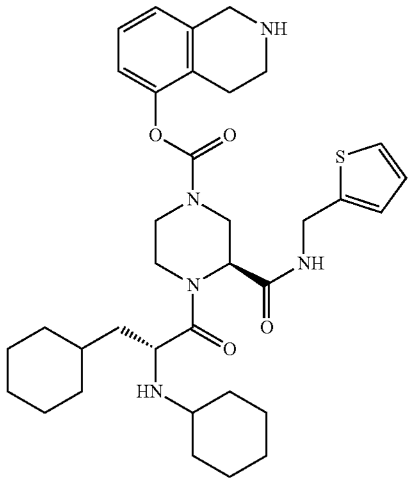 [SMILES: O=C(NCc1cccs1)[C@@H]1CN(C(=O)Oc2cccc3c2CCNC3)CCN1C(=O)[C@@H](CC1CCCCC1)NC1CCCCC1] | 1,2,3,4-tetrahydroisoquinolin-5-yl (3S)-4-(N,3-dicyclohexyl-D-alanyl)-3-[(thiophen-2-ylmethyl)carbamoyl]piperazine-1-carboxylate | 636.4 | 4.1 |
| 37 | 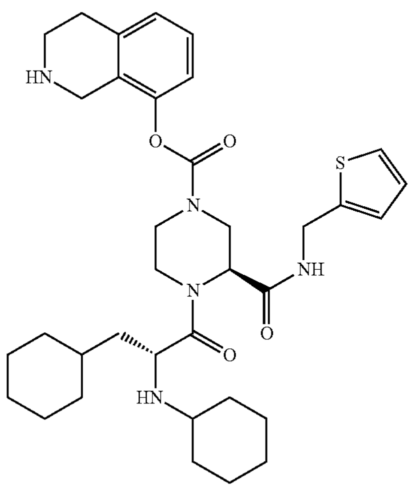 [SMILES: O=C(NCc1cccs1)[C@@H]1CN(C(=O)Oc2cccc3c2CNCC3)CCN1C(=O)[C@@H](CC1CCCCC1)NC1CCCCC1] | 1,2,3,4-tetrahydroisoquinolin-8-yl (3S)-4-(N,3-dicyclohexyl-D-alanyl)-3-[(thiophen-2-ylmethyl)carbamoyl]piperazine-1-carboxylate | 636.4 | 5.3 |
| 38 | 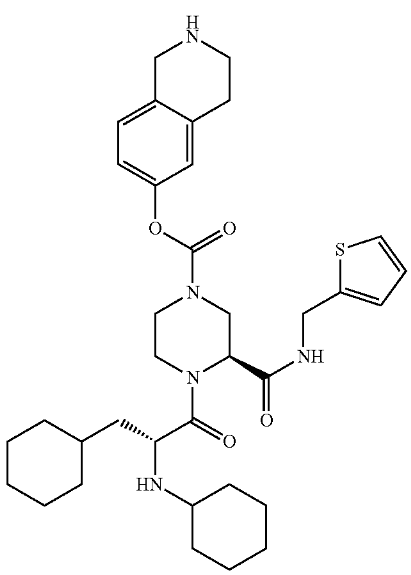 [SMILES: O=C(NCc1cccs1)[C@@H]1CN(C(=O)Oc2ccc3c(c2)CCNC3)CCN1C(=O)[C@@H](CC1CCCCC1)NC1CCCCC1] | 1,2,3,4-tetrahydroisoquinolin-6-yl (3S)-4-(N,3-dicyclohexyl-D-alanyl)-3-[(thiophen-2-ylmethyl)carbamoyl]piperazine-1-carboxylate | 636.4 | 18.7 |

TABLE 1-continued

| Example number | Structure | Name | Exact Mass [M + H]+ | FXIIa IC50 (nM) |
|---|---|---|---|---|
| 39 | 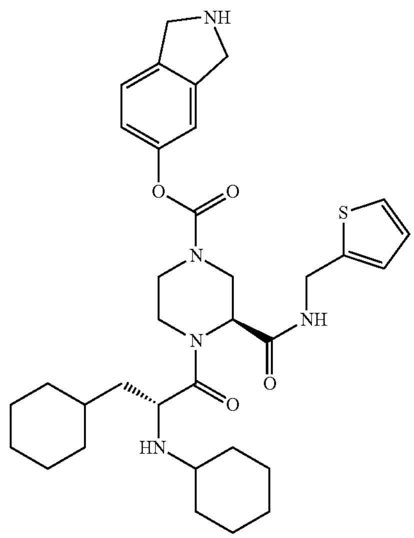 [SMILES: O=C(NCc1cccs1)[C@@H]1CN(C(=O)Oc2ccc3c(c2)CNC3)CCN1C(=O)[C@@H](CC1CCCCC1)NC1CCCCC1] | 2,3-dihydro-1H-isoindol-5-yl (3S)-4-(N,3-dicyclohexyl-D-alanyl)-3-[(thiophen-2-ylmethyl)carbamoyl]piperazine-1-carboxylate | 622.3 | 23.3 |
| 40 | 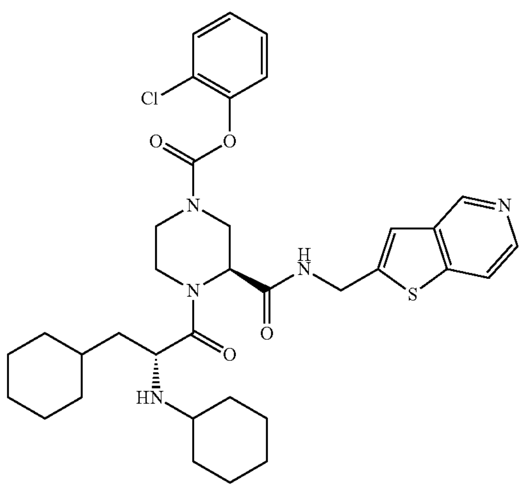 [SMILES: O=C(NCc1cc2cnccc2s1)[C@@H]1CN(C(=O)Oc2ccccc2Cl)CCN1C(=O)[C@@H](CC1CCCCC1)NC1CCCCC1] | 2-chlorophenyl (3S)-4-(N,3-dicyclohexyl-D-alanyl)-3-[(thieno[3,2-c]pyridin-2-ylmethyl)carbamoyl]piperazine-1-carboxylate | 666.3 | 27.3 |
| 41 | 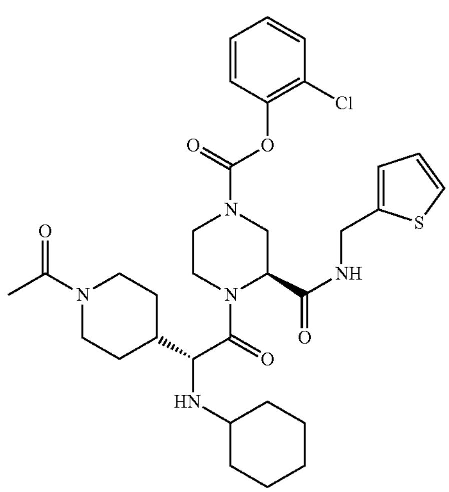 [SMILES: CC(=O)N1CCC([C@@H](NC2CCCCC2)C(=O)N2CCN(C(=O)Oc3ccccc3Cl)C[C@H]2C(=O)NCc2cccs2)CC1] | 2-chlorophenyl (3S)-4-[(2R)-2-(1-acetylpiperidin-4-yl)-2-(cyclohexylamino)acetyl]-3-[(thiophen-2-ylmethyl)carbamoyl]piperazine-1-carboxylate | 644.3 | 19.5 |

TABLE 1-continued

| Example number | Structure | Name | Exact Mass [M + H]+ | FXIIa IC50 (nM) |
|---|---|---|---|---|
| 42 | 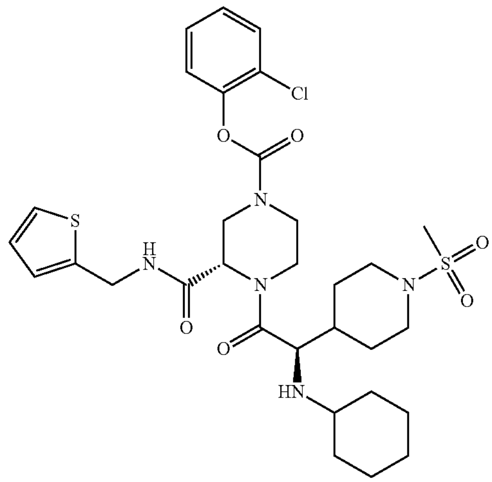 [SMILES: CS(=O)(=O)N1CCC([C@@H](NC2CCCCC2)C(=O)N2CCN(C(=O)Oc3ccccc3Cl)C[C@H]2C(=O)NCc2cccs2)CC1] | 2-chlorophenyl (3S)-4-{(2R)-2-(cyclohexylamino)-2-[1-(methylsulfonyl)piperidin-4-yl]acetyl}-3-[(thiophen-2-ylmethyl)carbamoyl]piperazine-1-carboxylate | 680.2 | 6.0 |
| 43 | 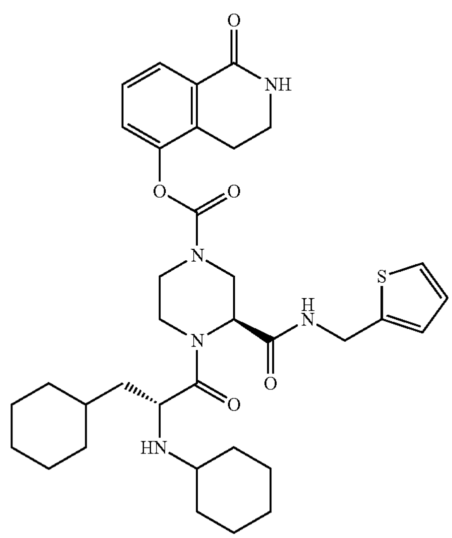 [SMILES: O=C1NCCc2c(OC(=O)N3CCN(C(=O)[C@@H](CC4CCCCC4)NC4CCCCC4)[C@H](C(=O)NCc4cccs4)C3)cccc21] | 1-oxo-1,2,3,4-tetrahydroisoquinolin-5-yl (3S)-4-(N,3-dicyclohexyl-D-alanyl)-3-[(thiophpen-2-ylmethyl)carbamoyl]piperazine-1-carboxylate | 650.3 | 20.2 |
| 44 | 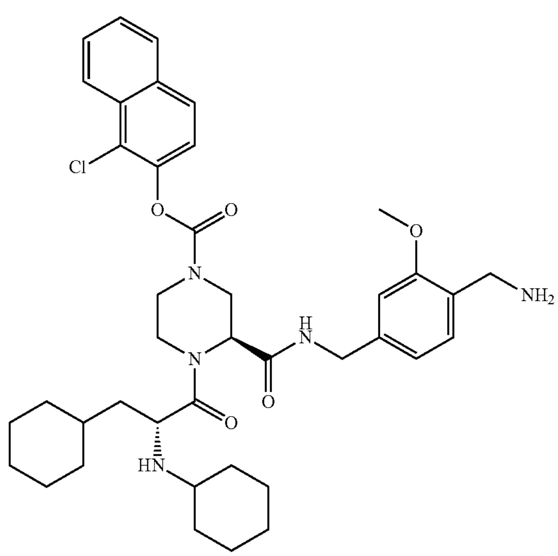 [SMILES: COc1cc(CNC(=O)[C@@H]2CN(C(=O)Oc3ccc4ccccc4c3Cl)CCN2C(=O)[C@@H](CC2CCCCC2)NC2CCCCC2)ccc1CN] | 1-chloronaphthalen-2-yl (3S)-3-{[4-(aminomethyl)-3-methoxybenzyl]carbamoyl}-4-(N,3-dicyclohexyl-D-alanyl)piperazine-1-carboxylate | 718.7 | 2.7 |

TABLE 1-continued

| Example number | Structure | Name | Exact Mass [M + H]+ | FXIIa IC50 (nM) |
|---|---|---|---|---|
| 45 | 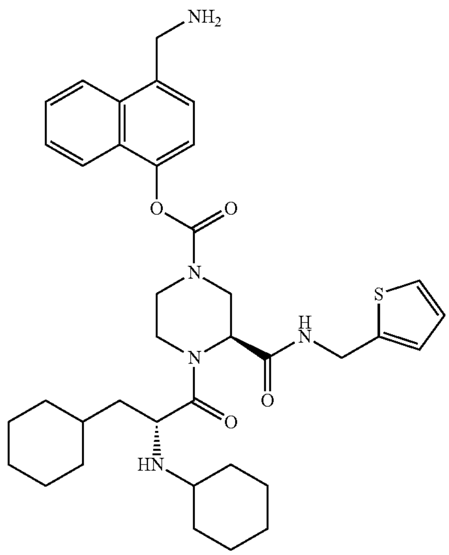 [SMILES: NCc1ccc(OC(=O)N2CCN(C(=O)[C@@H](CC3CCCCC3)NC3CCCCC3)[C@H](C(=O)NCc3cccs3)C2)c2ccccc12] | 4-(aminomethyl)naphthalen-1-yl (3S)-4-(N,3-dicyclohexyl-D-alanyl)-3-[(thiophen-2-ylmethyl)carbamoyl]piperazine-1-carboxylate | 660.6 | 12.8 |
| 46 | 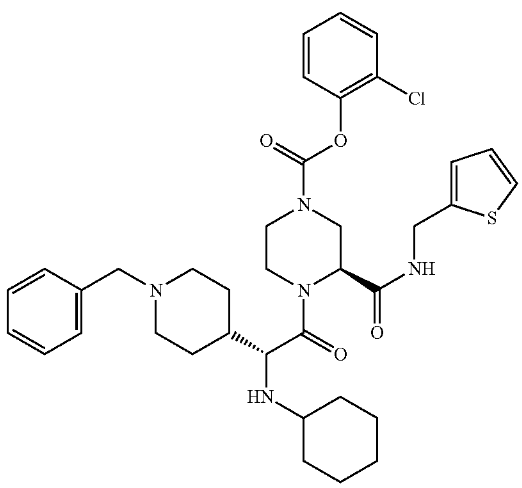 [SMILES: O=C(NCc1cccs1)[C@@H]1CN(C(=O)Oc2ccccc2Cl)CCN1C(=O)[C@H](NC1CCCCC1)C1CCN(Cc2ccccc2)CC1] | 2-chlorophenyl (3S)-4-[(2R)-2-(1-benzylpiperidin-4-yl)-2-(cyclohexylamino)acetyl]-3-[(thiophen-2-ylmethyl)carbamoyl]piperazine-1-carboxylate | 692.3 | 26.2 |
| 47 | 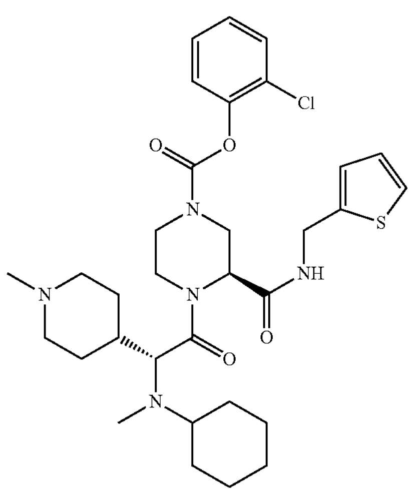 [SMILES: CN1CCC([C@H](C(=O)N2CCN(C(=O)Oc3ccccc3Cl)C[C@H]2C(=O)NCc2cccs2)N(C)C2CCCCC2)CC1] | 2-chlorophenyl (3S)-4-[(2R)-2-[cyclohexyl(methyl)amino]-2-(1-methylpiperidin-4-yl)acetyl]-3-[(thiophen-2-ylmethyl)carbamoyl]piperazine-1-carboxylate | 630.3 | 29.8 |

TABLE 1-continued

| Example number | Structure | Name | Exact Mass [M + H]+ | FXIIa IC50 (nM) |
|---|---|---|---|---|
| 48 | 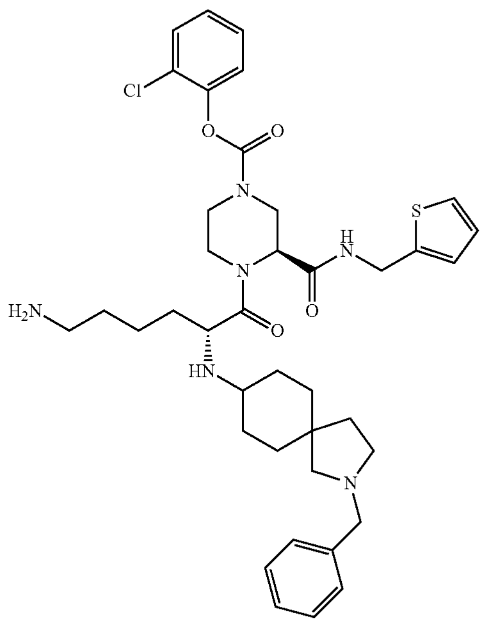 [SMILES: NCCCC[C@@H](NC1CCC2(CC1)CCN(Cc1ccccc1)C2)C(=O)N1CCN(C(=O)Oc2ccccc2Cl)C[C@H]1C(=O)NCc1cccs1] | 2-chlorophenyl (3S)-4-[N$^2$-(2-benzyl-2-azaspiro[4.5]dec-8-yl)-D-lysyl]-3-[(thiophen-2-ylmethyl)carbamoyl]piperazine-1-carboxylate | 735.6 | 20.3 |
| 49 | 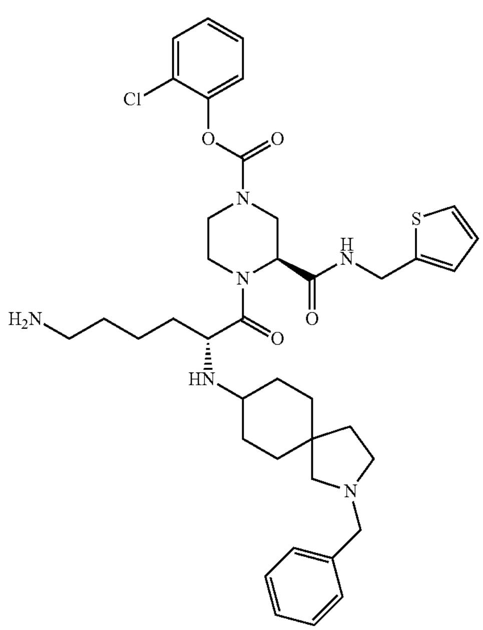 [SMILES: NCCCC[C@@H](NC1CCC2(CC1)CCN(Cc1ccccc1)C2)C(=O)N1CCN(C(=O)Oc2ccccc2Cl)C[C@H]1C(=O)NCc1cccs1] | 2-chlorophenyl (3S)-4-[N$^2$-(2-benzyl-2-azaspiro[4.5]dec-8-yl)-D-lysyl]-3-[(thiophen-2-ylmethyl)carbamoyl]piperazine-1-carboxylate | 735.6 | 18.3 |

TABLE 1-continued

| Example number | Structure | Name | Exact Mass [M + H]+ | FXIIa IC50 (nM) |
|---|---|---|---|---|
| 50 | 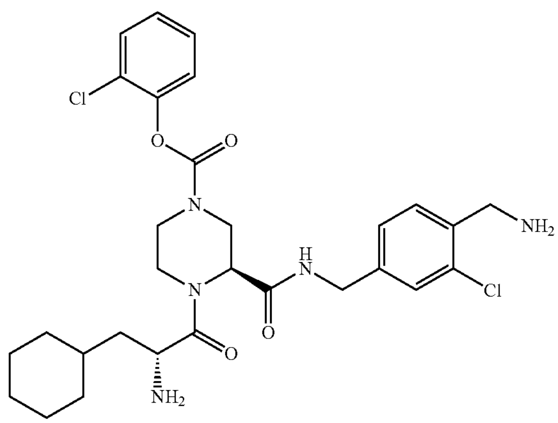 [SMILES: NCc1ccc(CNC(=O)[C@@H]2CN(C(=O)Oc3ccccc3Cl)CCN2C(=O)[C@H](N)CC2CCCCC2)cc1Cl] | 2-chlorophenyl (3S)-3-{[4-(aminomethyl)-3-chlorobenzyl]carbamoyl}-4-(3-cyclohexyl-D-alanyl)piperazine-1-carboxylate | 590.2 | 29.2 |
| 51 | 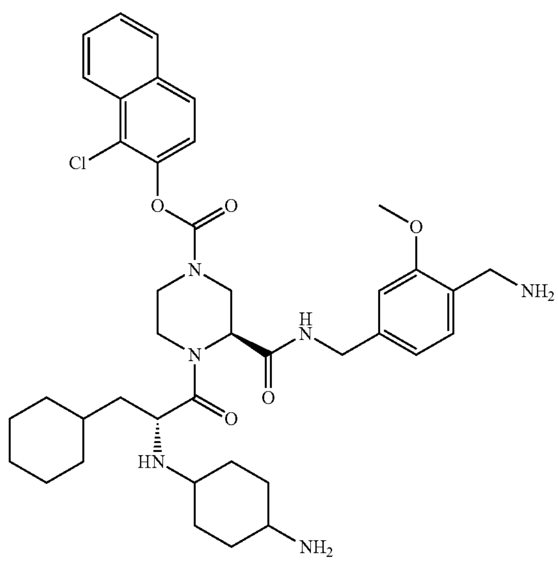 [SMILES: COc1cc(CNC(=O)[C@@H]2CN(C(=O)Oc3ccc4ccccc4c3Cl)CCN2C(=O)[C@@H](CC2CCCCC2)NC2CCC(N)CC2)ccc1CN] | 1-chloronaphthalen-2-yl (3S)-4-[N-(4-aminocyclohexyl)-3-cyclohexyl-D-alanyl]-3-{[4-(aminomethyl)-3-methoxybenzyl]carbamoyl}piperazine-1-carboxylate | 733.8 | 16.7 |
| 52 | 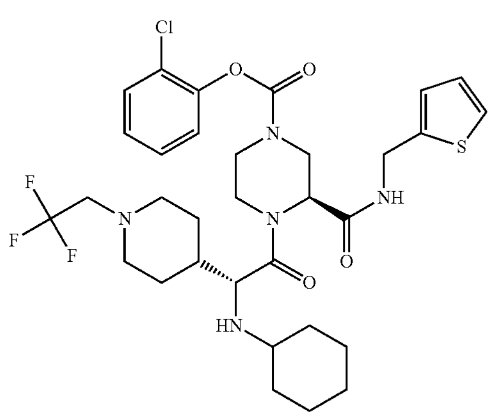 [SMILES: O=C(NCc1cccs1)[C@@H]1CN(C(=O)Oc2ccccc2Cl)CCN1C(=O)[C@H](NC1CCCCC1)C1CCN(CC(F)(F)F)CC1] | 2-chlorophenyl (3S)-4-{(2R)-2-(cyclohexylamino)-2-[1-(2,2,2-trifluoroethyl)piperidin-4-yl]acetyl}-3-[(thiophen-2-ylmethyl)carbamoyl]piperazine-1-carboxylate | 684.3 | 23.4 |

TABLE 1-continued

| Example number | Structure | Name | Exact Mass [M + H]+ | FXIIa IC50 (nM) |
|---|---|---|---|---|
| 53 | 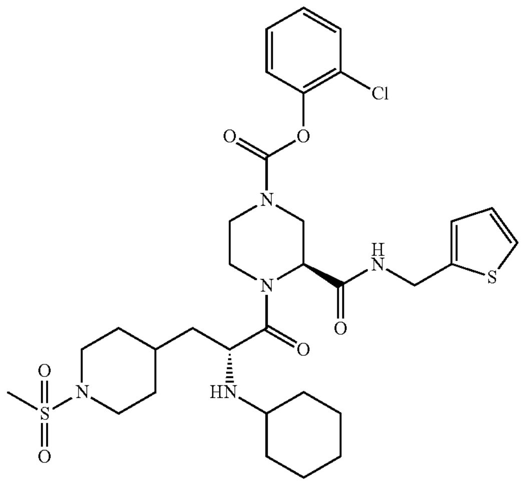 [SMILES: CS(=O)(=O)N1CCC(C[C@@H](NC2CCCCC2)C(=O)N2CCN(C(=O)Oc3ccccc3Cl)C[C@H]2C(=O)NCc2cccs2)CC1] | 2-chlorophenyl (3S)-4-{N-cyclohexyl-3-[1-(methylsulfonyl)piperidin-4-yl]-D-alanyl}-3-[(thiophen-2-ylmethyl)carbamoyl]piperazine-1-carboxylate | 694.2 | 19.7 |
| 54 | 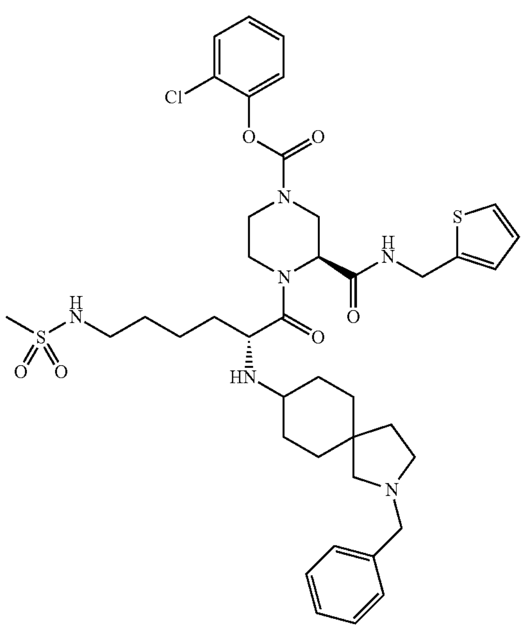 [SMILES: CS(=O)(=O)NCCCC[C@@H](NC1CCC2(CC1)CCN(Cc1ccccc1)C2)C(=O)N1CCN(C(=O)Oc2ccccc2Cl)C[C@H]1C(=O)NCc1cccs1] | 2-chlorophenyl (3S)-4-[$N^2$-(2-benzyl-2-azaspiro[4.5]dec-8-yl)-N~6~-(methylsulfonyl)-D-lysyl]-3-[(thiophen-2-ylmethyl)carbamoyl]piperazine-1-carboxylate | 813.6 | 8.1 |

TABLE 1-continued

| Example number | Structure | Name | Exact Mass [M + H]+ | FXIIa IC50 (nM) |
|---|---|---|---|---|
| 55 | 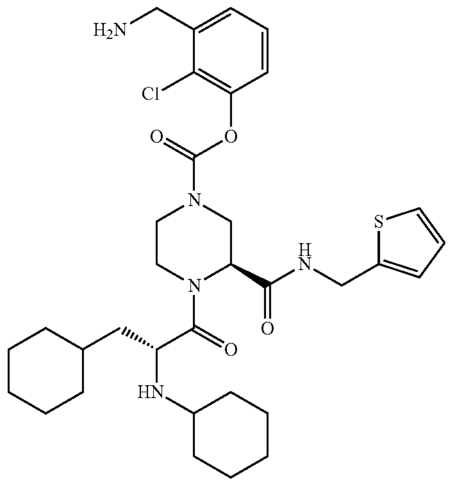 [SMILES: NCc1cccc(OC(=O)N2CCN(C(=O)[C@@H](CC3CCCCC3)NC3CCCCC3)[C@H](C(=O)NCc3cccs3)C2)c1Cl] | 3-(aminomethyl)-2-chlorophenyl (3S)-4-(N,3-dicyclohexyl-D-alanyl)-3-[(thiophen-2-ylmethyl)carbamoyl]piperazine-1-carboxylate | 644.3 | 1.1 |
| 56 | 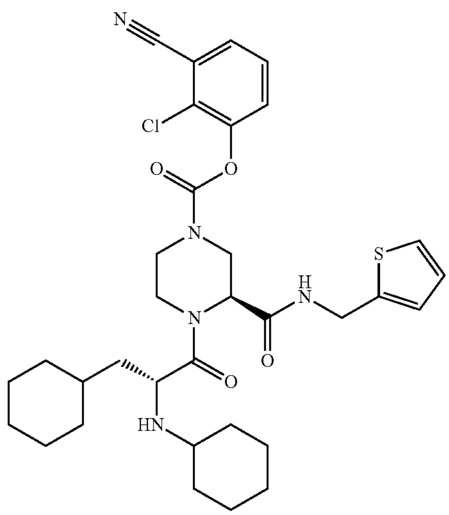 [SMILES: N#Cc1cccc(OC(=O)N2CCN(C(=O)[C@@H](CC3CCCCC3)NC3CCCCC3)[C@H](C(=O)NCc3cccs3)C2)c1Cl] | 2-chloro-3-cyanophenyl (3S)-4-(N,3-dicyclohexyl-D-alanyl)-3-[(thiophen-2-ylmethyl)carbamoyl]piperazine-1-carboxylate | 640.3 | 10.4 |
| 57 | 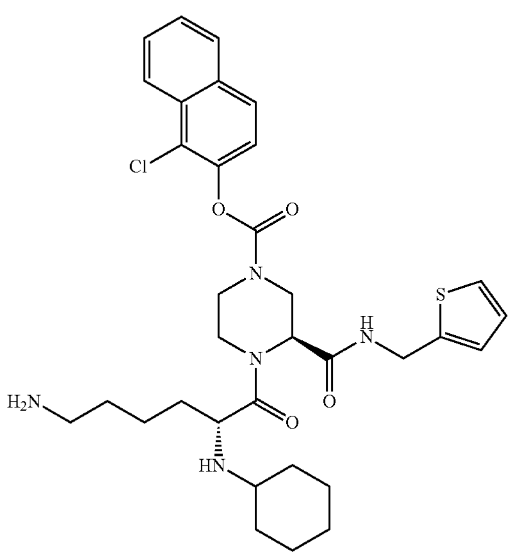 [SMILES: NCCCC[C@@H](NC1CCCCC1)C(=O)N1CCN(C(=O)Oc2ccc3ccccc3c2Cl)C[C@H]1C(=O)NCc1cccs1] | 1-chloronaphthalen-2-yl (3S)-4-($N^2$-cyclohexyl-D-lysyl)-3-[(thiophen-2-ylmethyl)carbamoyl]piperazine-1-carboxylate | 640.6 | 29.8 |

TABLE 1-continued

| Example number | Structure | Name | Exact Mass [M + H]+ | FXIIa IC50 (nM) |
|---|---|---|---|---|
| 58 | 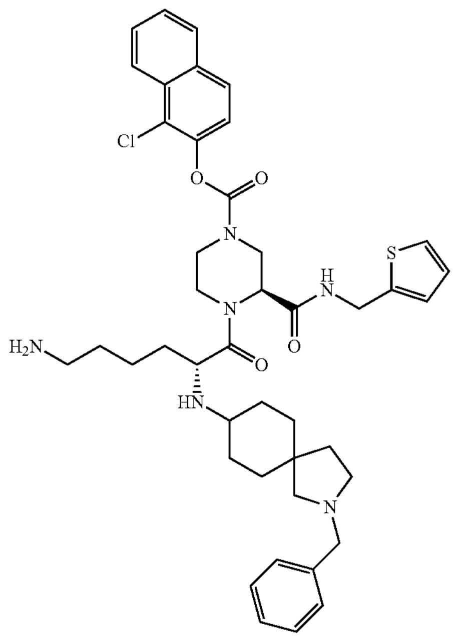 [SMILES: NCCCC[C@@H](NC1CCC2(CC1)CCN(Cc1ccccc1)C2)C(=O)N1CCN(C(=O)Oc2ccc3ccccc3c2Cl)C[C@H]1C(=O)NCc1cccs1] | 1-chloronaphthalen-2-yl (3S)-4-[N²-(2-benzyl-2-azaspiro[4.5]dec-8-yl)-D-lysyl]-3-[(thiophen-2-ylmethyl)carbamoyl]piperazine-1-carboxylate | 785.5 | 22.7 |
| 59 | 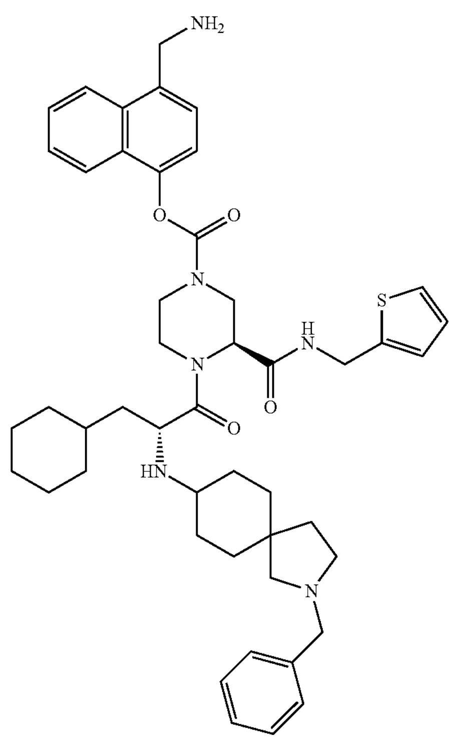 [SMILES: NCc1ccc(OC(=O)N2CCN(C(=O)[C@@H](CC3CCCCC3)NC3CCC4(CC3)CCN(Cc3ccccc3)C4)[C@H](C(=O)NCc3cccs3)C2)c2ccccc12] | 4-(aminomethyl)naphthalen-1-yl (3S)-4-[N-(2-benzyl-2-azaspiro[4.5]dec-8-yl)-3-cyclohexyl-D-alanyl]-3-[(thiophen-2-ylmethyl)carbamoyl]piperazine-1-carboxylate | 805.8 | 4.6 |

TABLE 1-continued

| Example number | Structure | Name | Exact Mass [M + H]+ | FXIIa IC50 (nM) |
|---|---|---|---|---|
| 60 | 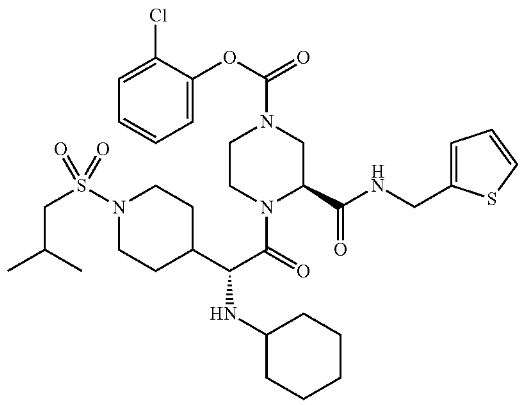 [SMILES: CC(C)CS(=O)(=O)N1CCC([C@@H](NC2CCCCC2)C(=O)N2CCN(C(=O)Oc3ccccc3Cl)C[C@H]2C(=O)NCc2cccs2)CC1] | 2-chlorophenyl (3S)-4-[(2R)-2-(cyclohexylamino)-2-{1-[(2-methylpropyl)sulfonyl]piperidin-4-yl}acetyl]-3-[(thiophen-2-ylmethyl)carbamoyl]piperazine-1-carboxylate | 722.3 | 22.6 |
| 61 | 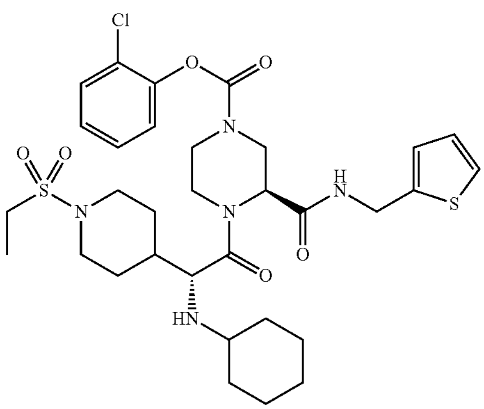 [SMILES: CCS(=O)(=O)N1CCC([C@@H](NC2CCCCC2)C(=O)N2CCN(C(=O)Oc3ccccc3Cl)C[C@H]2C(=O)NCc2cccs2)CC1] | 2-chlorophenyl (3S)-4-{(2R)-2-(cyclohexylamino)-2-[1-(ethylsulfonyl)piperidin-4-yl]acetyl}-3-[(thiophen-2-ylmethyl)carbamoyl]piperazine-1-carboxylate | 694.2 | 4.2 |
| 62 | 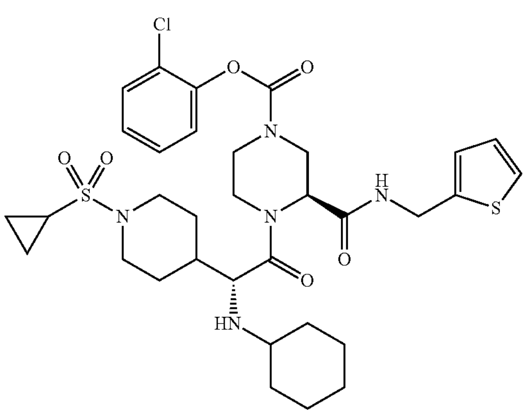 [SMILES: O=C(NCc1cccs1)[C@@H]1CN(C(=O)Oc2ccccc2Cl)CCN1C(=O)[C@H](NC1CCCCC1)C1CCN(S(=O)(=O)C2CC2)CC1] | 2-chlorophenyl (3S)-4-{(2R)-2-(cyclohexylamino)-2-[1-(cyclopropylsulfonyl)piperidin-4-yl]acetyl}-3-[(thiophen-2-ylmethyl)carbamoyl]piperazine-1-carboxylate | 706.2 | 1.7 |

TABLE 1-continued

| Example number | Structure | Name | Exact Mass [M + H]+ | FXIIa IC50 (nM) |
|---|---|---|---|---|
| 63 | 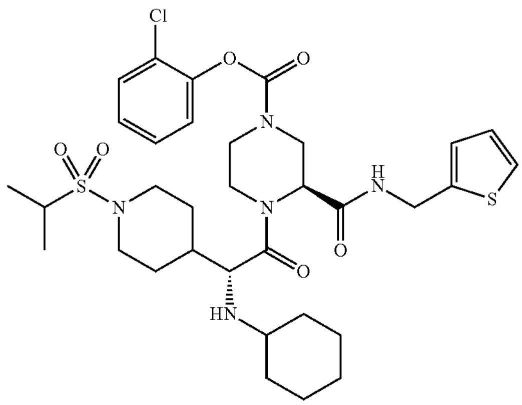 [SMILES: CC(C)S(=O)(=O)N1CCC([C@@H](NC2CCCCC2)C(=O)N2CCN(C(=O)Oc3ccccc3Cl)C[C@H]2C(=O)NCc2cccs2)CC1] | 2-chlorophenyl (3S)-4-[(2R)-2-(cyclohexylamino)-2-{1-[(1-methylethyl)sulfonyl]piperidin-4-yl}acetyl]-3-[(thiophen-2-ylmethyl)carbamoyl]piperazine-1-carboxylate | 708.3 | 2.6 |
| 64 | 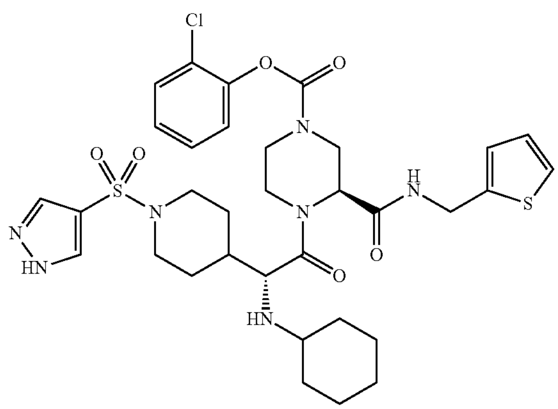 [SMILES: O=C(NCc1cccs1)[C@@H]1CN(C(=O)Oc2ccccc2Cl)CCN1C(=O)[C@H](NC1CCCCC1)C1CCN(S(=O)(=O)c2cn[nH]c2)CC1] | 2-chlorophenyl (3S)-4-{2(R)-2-(cyclohexylamino)-2-[1-(1H-pyrazol-4-ylsulfonyl)piperidin-4-yl]acetyl}-3-[(thiophen-2-ylmethyl)carbamoyl]piperzine-1-carboxylate | 732.2 | 21.1 |
| 65 | 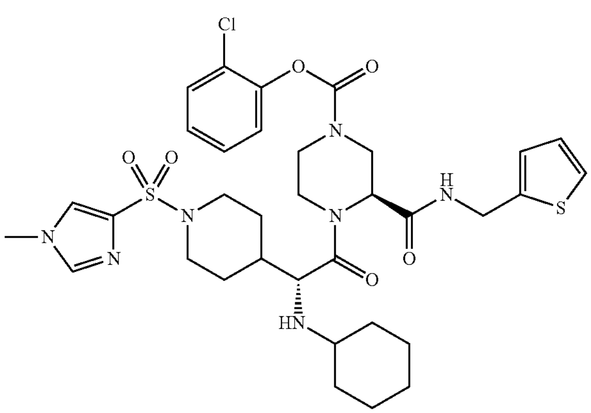 [SMILES: Cn1cnc(S(=O)(=O)N2CCC([C@@H](NC3CCCCC3)C(=O)N3CCN(C(=O)Oc4ccccc4Cl)C[C@H]3C(=O)NCc3cccs3)CC2)c1] | 2-chlorophenyl (3S)-4-[(2R)-2-(cyclohexylamino)-2-{1-[(1-methyl-1H-imidazol-4-yl)sulfonyl]piperidin-4-yl}acetyl]-3-[(thiophen-2-ylmethyl)carbamoyl]piperazine-1-carboxylate | 746.3 | 29.5 |

TABLE 1-continued

| Example number | Structure | Name | Exact Mass [M + H]+ | FXIIa IC50 (nM) |
|---|---|---|---|---|
| 66 | 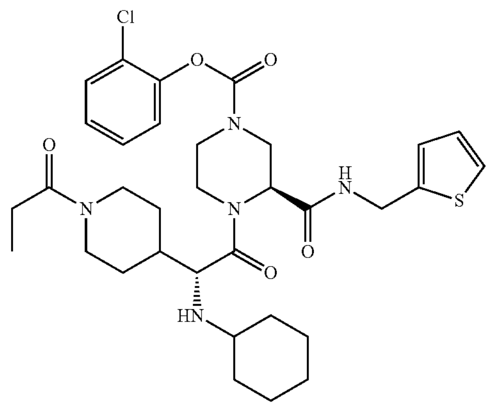 [SMILES: CCC(=O)N1CCC([C@@H](NC2CCCCC2)C(=O)N2CCN(C(=O)Oc3ccccc3Cl)C[C@H]2C(=O)NCc2cccs2)CC1] | 2-chlorophenyl (3S)-4-[(2R)-2-(cyclohexylamino)-2-(1-propanoylpiperidin-4-yl)acetyl]-3-[(thiophen-2-ylmethyl)carbamoyl]piperazine-1-carboxylate | 658.3 | 10.9 |
| 67 | 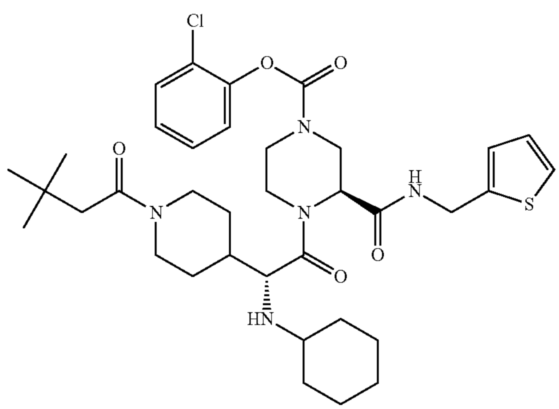 [SMILES: CC(C)(C)CC(=O)N1CCC([C@@H](NC2CCCCC2)C(=O)N2CCN(C(=O)Oc3ccccc3Cl)C[C@H]2C(=O)NCc2cccs2)CC1] | 2-chlorophenyl (3S)-4-{(2R)-2-(cyclohexylamino)-2-[1-(3,3-dimethylbutanoyl)piperidin-4-yl]acetyl}-3-[(thiophen-2-ylmethyl)carbamoyl]piperazine-1-carboxylate | 700.3 | 22.5 |
| 68 | 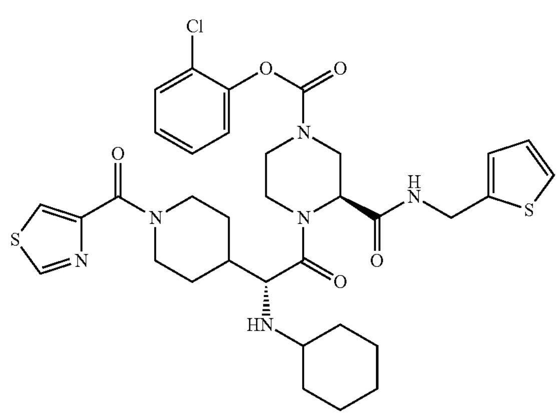 [SMILES: O=C(NCc1cccs1)[C@@H]1CN(C(=O)Oc2ccccc2Cl)CCN1C(=O)[C@H](NC1CCCCC1)C1CCN(C(=O)c2cscn2)CC1] | 2-chlorophenyl (3S)-4-{(2R)-2-(cyclohexylamino)-2-[1-(1,3-thiazol-4-ylcarbonyl)piperidin-4-yl]acetyl}-3-[(thiophen-2-ylmethyl)carbamoyl]piperazine-1-carboxylate | 713.2 | 15.7 |

TABLE 1-continued
| Example number | Structure | Name | Exact Mass [M + H]+ | FXIIa IC50 (nM) |
|---|---|---|---|---|
| 69 | 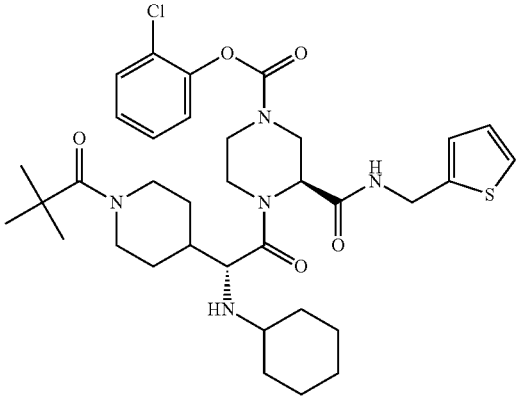 [SMILES: CC(C)(C)C(=O)N1CCC([C@@H](NC2CCCCC2)C(=O)N2CCN(C(=O)Oc3ccccc3Cl)C[C@H]2C(=O)NCc2cccs2)CC1] | 2-chlorophenyl (3S)-4-{(2R)-2-(cyclohexylamino)-2-[1-(2,2-dimethylpropanoyl)piperidin-4-yl]acetyl}-3-[(thiophen-2-ylmethyl)carbamoyl]piperazine-1-carboxylate | 686.3 | 8.4 |
| 70 | 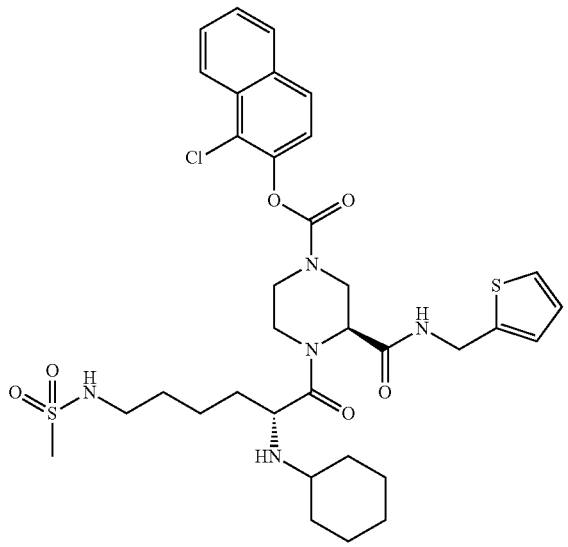 [SMILES: CS(=O)(=O)NCCCC[C@@H](NC1CCCCC1)C(=O)N1CCN(C(=O)Oc2ccc3ccccc3c2Cl)C[C@H]1C(=O)NCc1cccs1] | 1-chloronaphthalen-2-yl (3S)-4-[$N^2$-cyclohexyl-$N^6$-(methylsulfonyl)-D-lysyl]-3-[(thiophen-2-ylmethyl)carbamoyl]piperazine-1-carboxylate | 718.5 | 20.0 |

TABLE 1-continued

| Example number | Structure | Name | Exact Mass [M + H]+ | FXIIa IC50 (nM) |
|---|---|---|---|---|
| 71 | 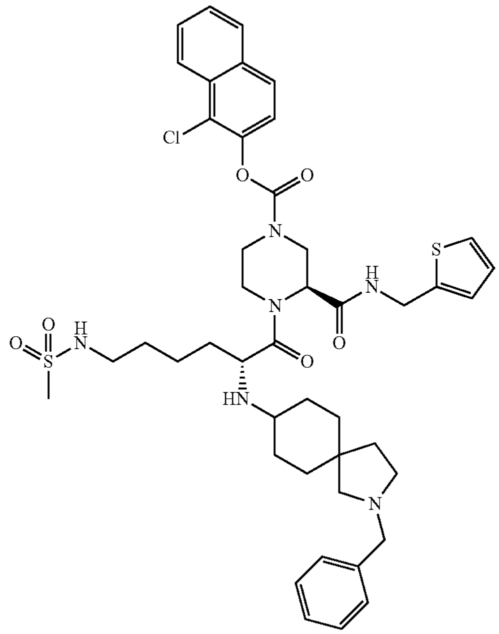 [SMILES: CS(=O)(=O)NCCCC[C@@H](NC1CCC2(CC1)CCN(Cc1ccccc1)C2)C(=O)N1CCN(C(=O)Oc2ccc3ccccc3c2Cl)C[C@H]1C(=O)NCc1cccs1] | 1-chloronaphthalen-2-yl (3S)-4-[$N^2$-(2-benzyl-2-azaspiro[4.5]dec-8-yl)-$N^6$-(methylsulfonyl)-D-lysyl]-3-[(thiophen-2-ylmethyl)carbamoyl]piperazine-1-carboxylate | 863.4 | 10.6 |
| 72 | 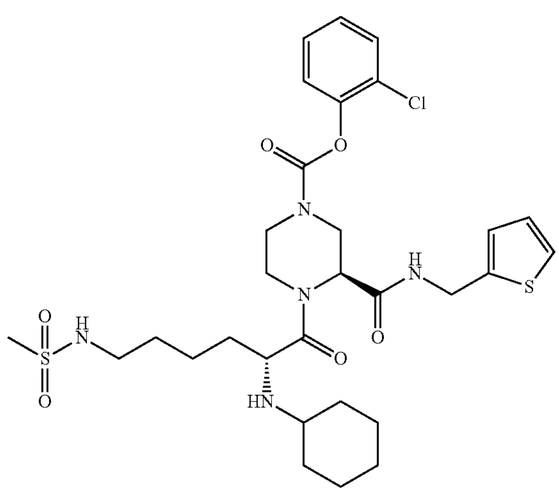 [SMILES: CS(=O)(=O)NCCCC[C@@H](NC1CCCCC1)C(=O)N1CCN(C(=O)Oc2ccccc2Cl)C[C@H]1C(=O)NCc1cccs1] | 2-chlorophenyl (3S)-4-[$N^2$-cyclohexyl-$N^6$-(methylsulfonyl)-D-lysyl]-3-[(thiophen-2-ylmethyl)carbamoyl]piperazine-1-carboxylate | 668.2 | 14.2 |

TABLE 1-continued

| Example number | Structure | Name | Exact Mass [M + H]+ | FXIIa IC50 (nM) |
|---|---|---|---|---|
| 73 | 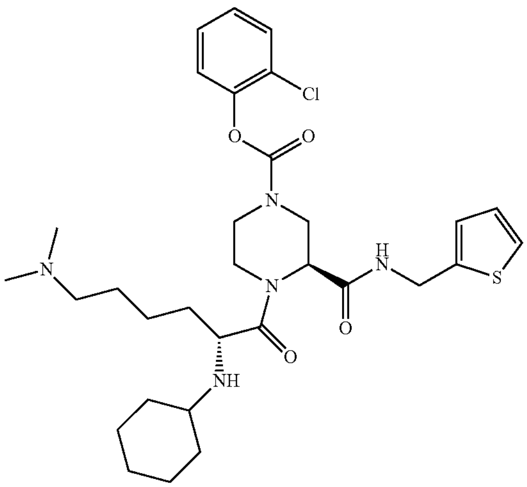 [SMILES: CN(C)CCCC[C@@H](NC1CCCCC1)C(=O)N1CCN(C(=O)Oc2ccccc2Cl)C[C@H]1C(=O)NCc1cccs1] | 2-chlorophenyl (3S)-4-(N$^2$-cyclohexyl-N$^6$,N$^6$-dimethyl-D-lysyl)-3-[(thiophen-2-ylmethyl)carbamoyl]piperazine-1-carboxylate | 618.3 | 1.1 |
| 74 | 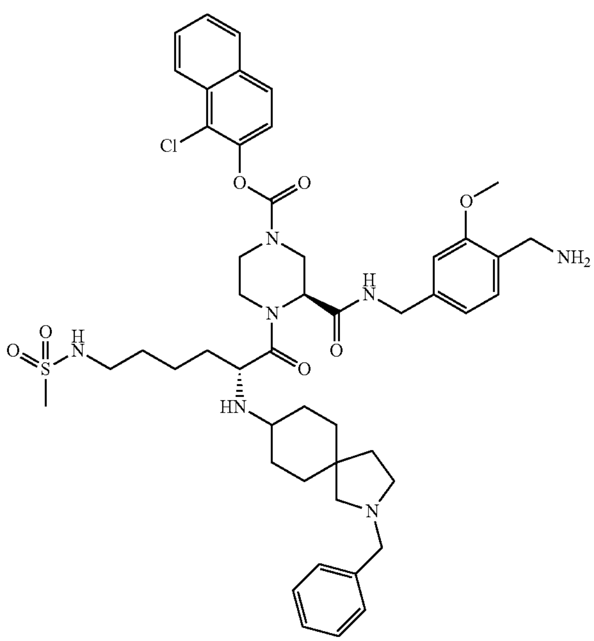 [SMILES: COc1cc(CNC(=O)[C@@H]2CN(C(=O)Oc3ccc4ccccc4c3Cl)CCN2C(=O)[C@@H](CCCCNS(C)(=O)=O)NC2CCC3(CC2)CCN(Cc2ccccc2)C3)ccc1CN] | 1-chloronaphthalen-2-yl (3S)-3-{[4-(aminomethyl)-3-methoxybenzyl]carbamoyl}-4-[N$^2$-(2-benzyl-2-azaspiro[4.5]dec-8-yl)-N$^6$-(methylsulfonyl)-D-lysyl]piperazine-1-carboxylate | 916.9 | 3.7 |

TABLE 1-continued

| Example number | Structure | Name | Exact Mass [M + H]+ | FXIIa IC50 (nM) |
|---|---|---|---|---|
| 75 | 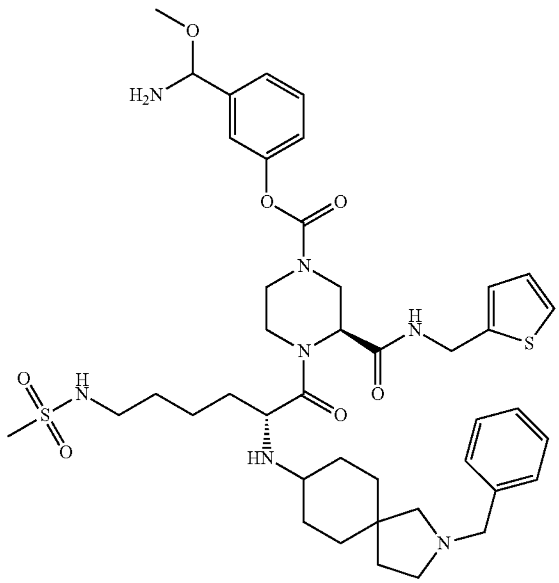 [SMILES: COC(N)c1cccc(OC(=O)N2CCN(C(=O)[C@@H](CCCCNS(C)(=O)=O)NC3CCC4(CC3)CCN(Cc3ccccc3)C4)[C@H](C(=O)NCc3cccs3)C2)c1] | 3-[amino(methoxy)methyl]phenyl (3S)-4-[N²-(2-benzyl-2-azaspiro[4.5]dec-8-yl)-N⁶-(methylsulfonyl)-D-lysyl]-3-[(thiophen-2-ylmethyl)carbamoyl]piperazine-1-carboxylate | 838.4 | 5.7 |
| 76 | 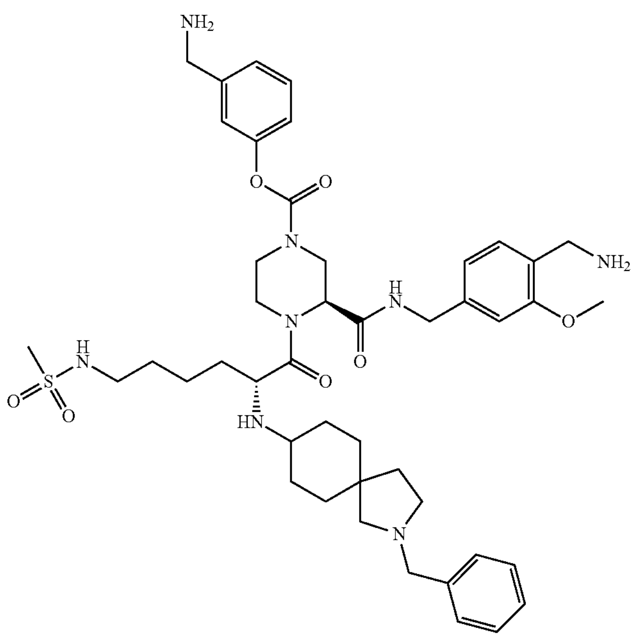 [SMILES: COc1cc(CNC(=O)[C@@H]2CN(C(=O)Oc3cccc(CN)c3)CCN2C(=O)[C@@H](CCCCNS(C)(=O)=O)NC2CCC3(CC2)CCN(Cc2ccccc2)C3)ccc1CN] | 3-(aminomethyl)phenyl (3S)-3-{[4-(aminomethyl)-3-methoxybenzyl]carbamoyl}-4-[N²-(2-benzyl-2-azaspiro[4.5]dec-8-yl)-N⁶=(methylsulfonyl)-D-lysyl]piperazine-1-carboxylate | 861.5 | 4.1 |

TABLE 1-continued

| Example number | Structure | Name | Exact Mass [M + H]+ | FXIIa IC50 (nM) |
|---|---|---|---|---|
| 77 | 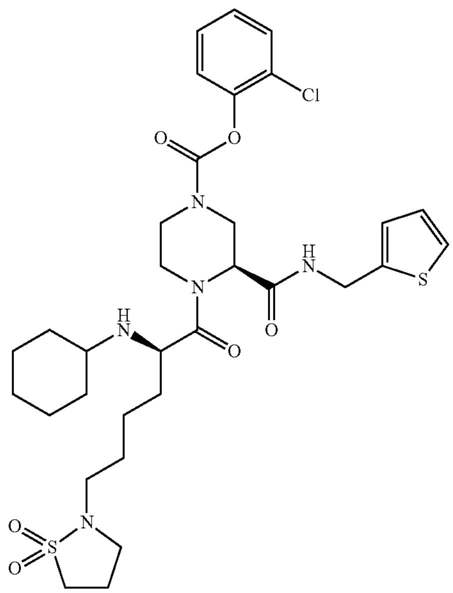 [SMILES: O=C(NCc1cccs1)[C@@H]1CN(C(=O)Oc2ccccc2Cl)CCN1C(=O)[C@@H](CCCCN1CCCS1(=O)=O)NC1CCCCC1] | 2-chlorophenyl (3S)-4-[N-cyclohexyl-6-(1,1-dioxidoisothiazolidin-2-yl)-D-norleucyl]-3-[(thiophen-2-ylmethyl)carbamoyl]piperazine-1-carboxylate | 694.2 | 4.6 |
| 78 | 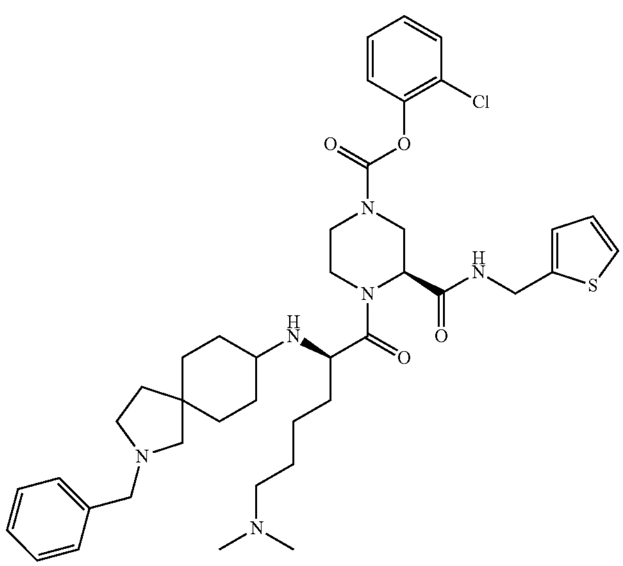 [SMILES: CN(C)CCCC[C@@H](NC1CCC2(CC1)CCN(Cc1ccccc1)C2)C(=O)N1CCN(C(=O)Oc2ccccc2Cl)C[C@H]1C(=O)NCc1cccs1] | 2-chlorophenyl (3S)-4-[$N^2$-(2-benzyl-2-azaspiro[4.5]dec-8-yl)-$N^6$,$N^6$-dimethyl-D-lysyl]-3-[(thiophen-2-ylmethyl)carbamoyl]piperazine-1-carboxylate | 763.4 | 0.9 |

TABLE 1-continued

| Example number | Structure | Name | Exact Mass [M + H]+ | FXIIa IC50 (nM) |
|---|---|---|---|---|
| 79 | 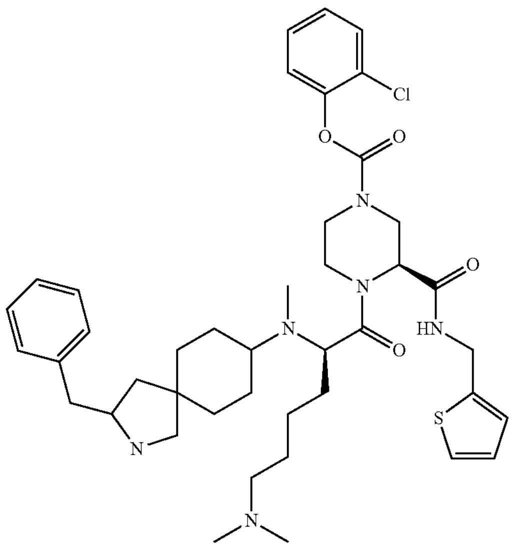 [SMILES: CN(C)CCCC[C@H](C(=O)N1CCN(C(=O)Oc2ccccc2Cl)C[C@H]1C(=O)NCc1cccs1)N(C)C1CCC2(CC1)CNC(Cc1ccccc1)C2] | 2-chlorophenyl (3S)-4-[N²-(2-benzyl-2-azaspiro[4.5]dec-8-yl)-N⁶,N⁶,N⁶-trimethyl-D-lysyl]-3-[(thiophen-2-ylmethyl)carbamoyl]piperazine-1-carboxylate | 777.4 | 1.1 |
| 80 | 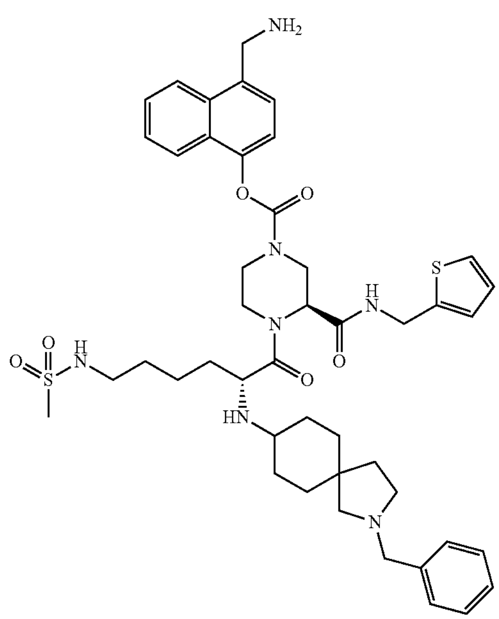 [SMILES: CS(=O)(=O)NCCCC[C@@H](NC1CCC2(CC1)CCN(Cc1ccccc1)C2)C(=O)N1CCN(C(=O)Oc2ccc(CN)c3ccccc23)C[C@H]1C(=O)NCc1cccs1] | 4-(aminomethyl)naphthalen-1-yl (3S)-4-[N²-(2-benzyl-2-azaspiro[4.5]dec-8-yl)-N⁶-(methylsulfonyl)-D-lysyl]-3-[(thiophen-2-ylmethyl)carbamoyl]piperazine-1-carboxylate | 858.6 | 15.5 |

TABLE 1-continued

| Example number | Structure | Name | Exact Mass [M + H]+ | FXIIa IC50 (nM) |
|---|---|---|---|---|
| 81 | 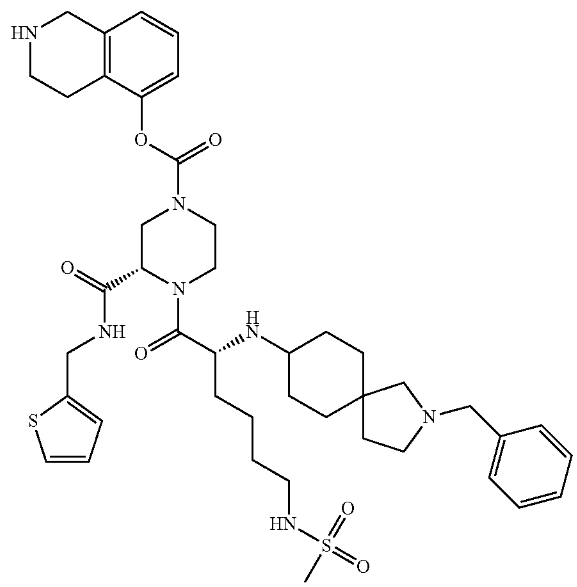 [SMILES: CS(=O)(=O)NCCCC[C@@H](NC1CCC2(CC1)CCN(Cc1ccccc1)C2)C(=O)N1CCN(C(=O)Oc2cccc3c2CCNC3)C[C@H]1C(=O)NCc1cccs1] | 1,2,3,4-tetrahydroisoquinolin-5-yl (3S)-4-[N²-(2-benzyl-2-azaspiro[4.5]dec-8-yl)-N⁶-(methylsulfonyl)-D-lysyl]-3-[(thiophen-2-ylmethyl)carbamoyl]piperazine-1-carboxylate | 834.4 | 3.4 |
| 82 | 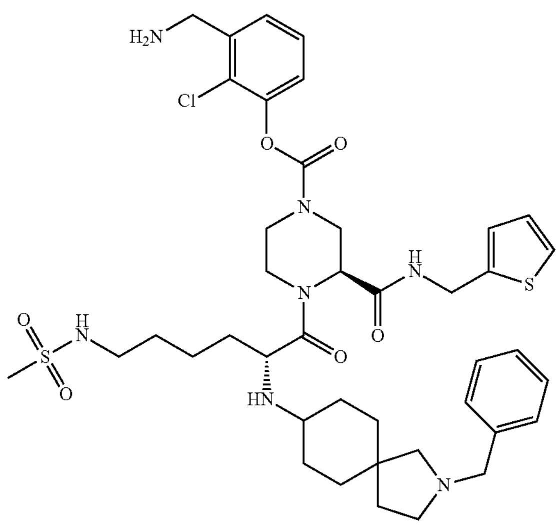 [SMILES: CS(=O)(=O)NCCCC[C@@H](NC1CCC2(CC1)CCN(Cc1ccccc1)C2)C(=O)N1CCN(C(=O)Oc2cccc(CN)c2Cl)C[C@H]1C(=O)NCc1cccs1] | 3-(aminomethyl)-2-chlorophenyl (3S)-4-[N²-(2-benzyl-2-azaspiro[4.5]dec-8-yl)-N⁶-(methylsulfonyl)-D-lysyl]-3-[(thiophen-2-ylmethyl)carbamoyl]piperazine-1-carboxylate | 842.3 | 2.1 |
| 83 | 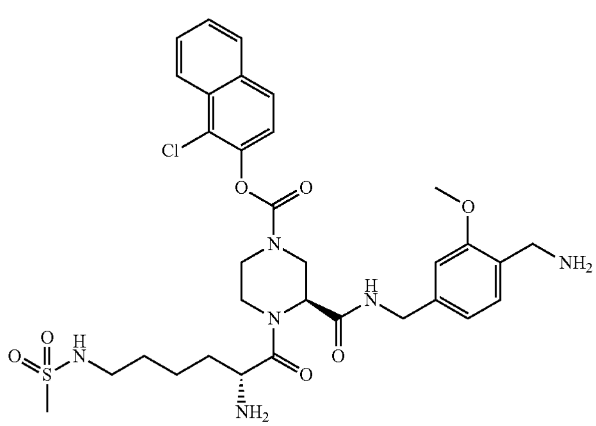 [SMILES: COc1cc(CNC(=O)[C@@H]2CN(C(=O)Oc3ccc4ccccc4c3Cl)CCN2C(=O)[C@H](N)CCCCNS(C)(=O)=O)ccc1CN] | 1-chloronaphthalen-2-yl (3S)-3-{[4-(aminomethyl)-3-methoxybenzyl]carbamoyl}-4-[N⁶-(methylsulfonyl)-D-lysyl]piperazine-1-carboxylate | 689.4 | 28.4 |

TABLE 1-continued

| Example number | Structure | Name | Exact Mass [M + H]+ | FXIIa IC50 (nM) |
|---|---|---|---|---|
| 84 | 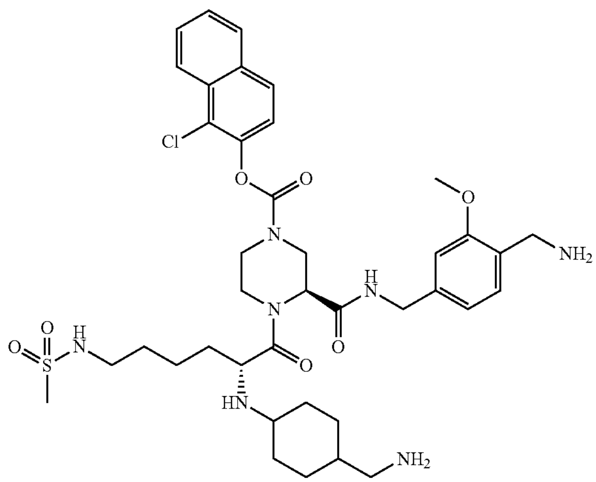 [SMILES: COc1cc(CNC(=O)[C@@H]2CN(C(=O)Oc3ccc4ccccc4c3Cl)CCN2C(=O)[C@@H](CCCCNS(C)(=O)=O)NC2CCC(CN)CC2)ccc1CN] | 1-chloronaphthalen-2-yl (3S)-4-{$N^2$-[4-(aminomethyl)cyclohexyl]-$N^6$-(methylsulfonyl)-D-lysyl}-3-{[4-(aminomethyl)-3-methoxybenzyl]carbamoyl}piperazine-1-carboxylate | 800.5 | 28.9 |
| 85 | 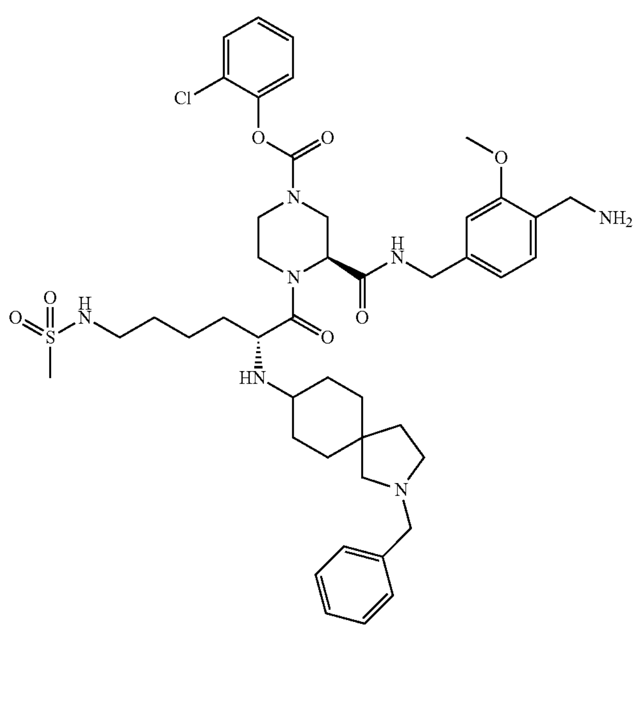 [SMILES: COc1cc(CNC(=O)[C@@H]2CN(C(=O)Oc3ccccc3Cl)CCN2C(=O)[C@@H](CCCCNS(C)(=O)=O)NC2CCC3(CC2)CCN(Cc2ccccc2)C3)ccc1CN] | 2-chlorophenyl (3S)-3-{[4-(aminomethyl)-3-methoxybenzyl]carbamoyl}-4-[$N^2$-(2-benzyl-2-azaspiro[4.5]dec-8-yl)-$N^6$-(methylsulfonyl)-D-lysyl]piperazine-1-carboxylate | 866.5 | 8.3 |

TABLE 1-continued

| Example number | Structure | Name | Exact Mass [M + H]+ | FXIIa IC50 (nM) |
|---|---|---|---|---|
| 86 | 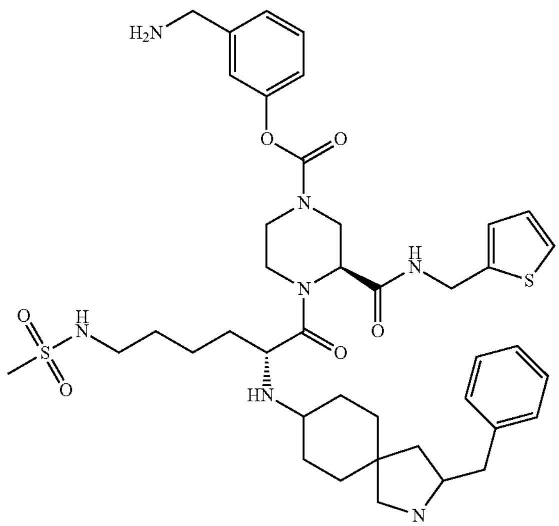 [SMILES: CS(=O)(=O)NCCCC[C@@H](NC1CCC2(CC1)CNC(Cc1ccccc1)C2)C(=O)N1CCN(C(=O)Oc2cccc(CN)c2)C[C@H]1C(=O)NCc1cccs1] | 3-(aminomethyl)phenyl (3S)-4-[$N^2$-(2-benzyl-2-azaspiro[4.5]dec-8-yl)-$N^6$-(methylsulfonyl)-D-lysyl]-3-[(thiophen-2-ylmethyl)carbamoyl]piperazine-1-carboxylate | 808.4 | 16.0 |
| 87 | 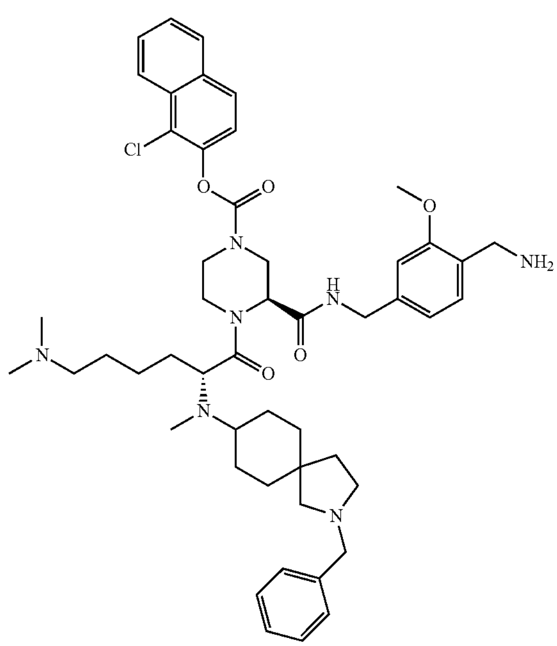 [SMILES: COc1cc(CNC(=O)[C@@H]2CN(C(=O)Oc3ccc4ccccc4c3Cl)CCN2C(=O)[C@@H](CCCCN(C)C)N(C)C2CCC3(CC2)CCN(Cc2ccccc2)C3)ccc1CN] | 1-chloronaphthalen-2-yl (3S)-3-{[4-(aminomethyl)-3-methoxybenzyl]carbamoyl}-4-[$N^2$-(2-benzyl-2-azaspiro[4.5]dec-8-yl)-$N^2$,$N^6$,$N^6$-trimethyl-D-lysyl]piperazine-1-carboxylate | 880.5 | 1.0 |

TABLE 1-continued

| Example number | Structure | Name | Exact Mass [M + H]+ | FXIIa IC50 (nM) |
|---|---|---|---|---|
| 88 | 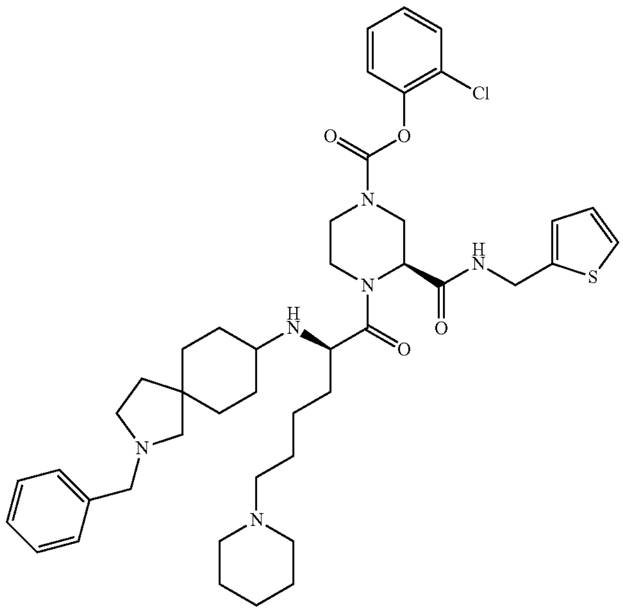 [SMILES: O=C(NCc1cccs1)[C@@H]1CN(C(=O)Oc2ccccc2Cl)CCN1C(=O)[C@@H](CCCCN1CCCCC1)NC1CCC2(CC1)CCN(Cc1ccccc1)C2] | 2-chlorophenyl (3S)-4-[N-(2-benzyl-2-azaspiro[4.5]dec-8-yl)-6-piperidin-1-yl-D-norleucyl]-3-[(thiophen-2-ylmethyl)carbamoyl]piperazine-1-carboxylate | 803.4 | 0.9 |
| 89 | 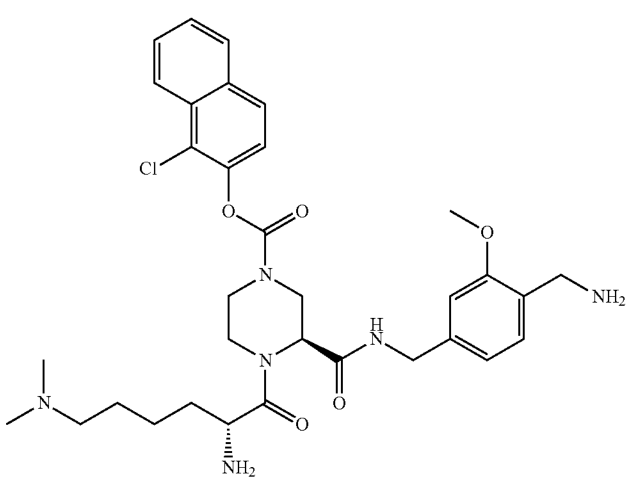 [SMILES: COc1cc(CNC(=O)[C@@H]2CN(C(=O)Oc3ccc4ccccc4c3Cl)CCN2C(=O)[C@H](N)CCCCN(C)C)ccc1CN] | 1-chloronaphthalen-2-yl (3S)-3-{[4-(aminomethyl)-3-methoxybenzyl]carbamoyl}-4-($N^6,N^6$-dimethyl-D-lysyl)piperazine-1-carboxylate | 639.5 | 1.7 |

TABLE 1-continued

| Example number | Structure | Name | Exact Mass [M + H]+ | FXIIa IC50 (nM) |
|---|---|---|---|---|
| 90 | 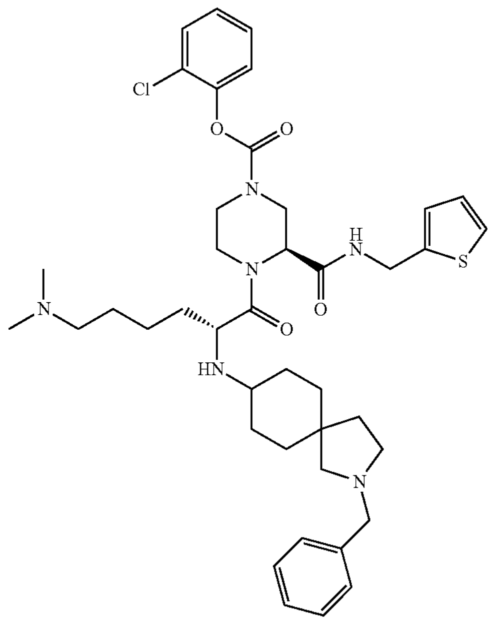 [SMILES: CN(C)CCCC[C@@H](NC1CCC2(CC1)CCN(Cc1ccccc1)C2)C(=O)N1CCN(C(=O)Oc2ccccc2Cl)C[C@H]1C(=O)NCc1cccs1] | 2-chlorophenyl (3S)-4-[N²-(2-benzyl-2-azaspiro[4.5]dec-8-yl)-N⁶,N⁶-dimethyl-D-lysyl]-3-[(thiophen-2-ylmethyl)carbamoyl]piperazine-1-carboxylate | 763.4 | 0.7 |
| 91 | 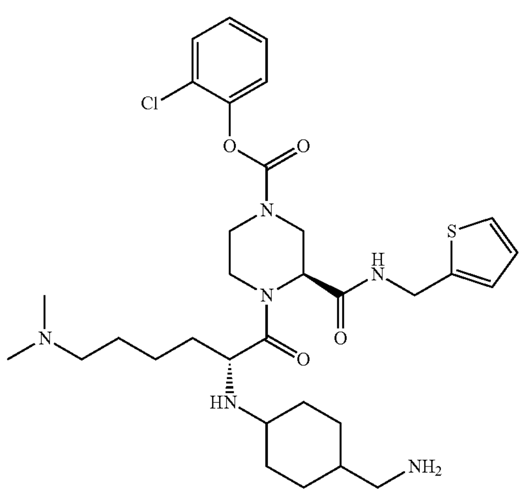 [SMILES: CN(C)CCCC[C@@H](NC1CCC(CN)CC1)C(=O)N1CCN(C(=O)Oc2ccccc2Cl)C[C@H]1C(=O)NCc1cccs1] | 2-chlorophenyl (3S)-4-{N²-[4-(aminomethyl)cyclohexyl]-N⁶,N⁶-dimethyl-D-lysyl}-3-[(thiophen-2-ylmethyl)carbamoyl]piperazine-1-carboxylate | 647.5 | 12.3 |

TABLE 1-continued

| Example number | Structure | Name | Exact Mass [M + H]+ | FXIIa IC50 (nM) |
|---|---|---|---|---|
| 92 | 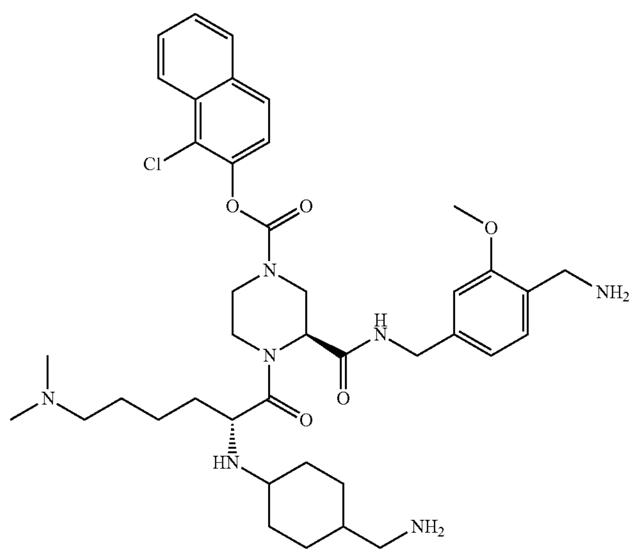 [SMILES: COc1cc(CNC(=O)[C@@H]2CN(C(=O)Oc3ccc4ccccc4c3Cl)CCN2C(=O)[C@@H](CCCCN(C)C)NC2CCC(CN)CC2)ccc1CN] | 1-chloronaphthalen-2-yl (3S)-4-{N$^2$-[4-(aminomethyl)cyclohexyl]-N$^6$,N$^6$-dimethyl-D-lysyl}-3-{[4-(aminomethyl)-3-methoxybenzyl]carbamoyl}piperazine-1-carboxylate | 750.7 | 2.9 |
| 93 | 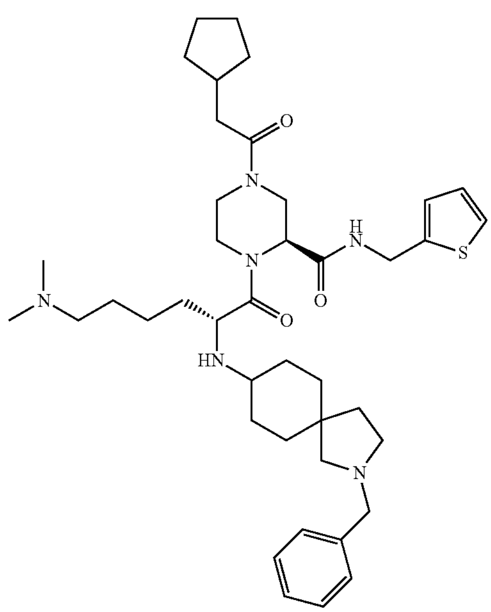 [SMILES: CN(C)CCCC[C@@H](NC1CCC2(CC1)CCN(Cc1ccccc1)C2)C(=O)N1CCN(C(=O)CC2CCCC2)C[C@H]1C(=O)NCc1cccs1] | (2S)-1-[N$^2$-(2-benzyl-2-azaspiro[4.5]dec-8-yl)-N$^6$,N$^6$-dimethyl-D-lysyl]-4-(cyclopentylacetyl)-N-(thiophen-2-ylmethyl)piperazine-2-carboxamide | 719.5 | 23.5 |

TABLE 1-continued

| Example number | Structure | Name | Exact Mass [M + H]+ | FXIIa IC50 (nM) |
|---|---|---|---|---|
| 94 | 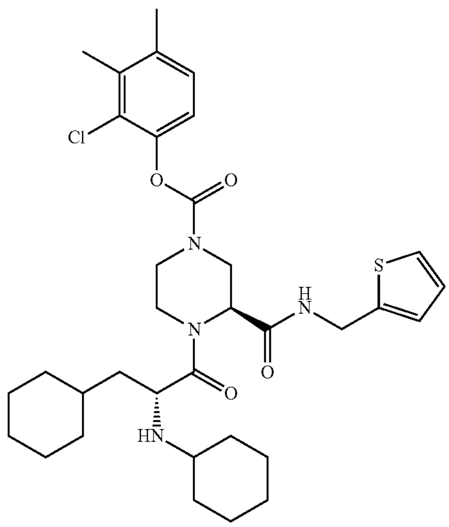 [SMILES: Cc1ccc(OC(=O)N2CCN(C(=O)[C@@H](CC3CCCCC3)NC3CCCCC3)[C@H](C(=O)NCc3cccs3)C2)c(Cl)c1C] | 2-chloro-3,4-dimethylphenyl (3S)-4-(N,3-dicyclohexyl-D-alanyl)-3-[(thiophen-2-ylmethyl)carbamoyl]piperazine-1-carboxylate | 643.5 | 7.5 |
| 95 | 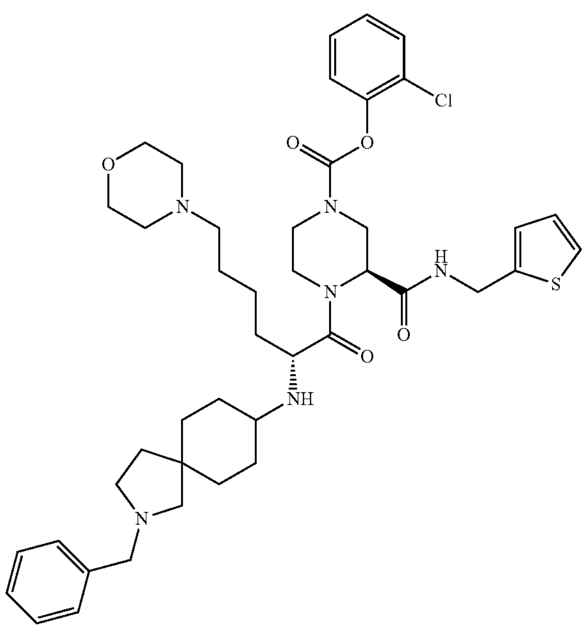 [SMILES: O=C(NCc1cccs1)[C@@H]1CN(C(=O)Oc2ccccc2Cl)CCN1C(=O)[C@@H](CCCCN1CCOCC1)NC1CCC2(CC1)CCN(Cc1ccccc1)C2] | 2-chlorophenyl (3S)-4-[N-(2-benzyl-2-azaspiro[4.5]dec-8-yl)-6-morpholin-4-yl-D-norleucyl]-3-[(thiophen-2-ylmethyl)carbamoyl]piperazine-1-carboxylate | 805.4 | 1.8 |

TABLE 1-continued

| Example number | Structure | Name | Exact Mass [M + H]+ | FXIIa IC50 (nM) |
|---|---|---|---|---|
| 96 | 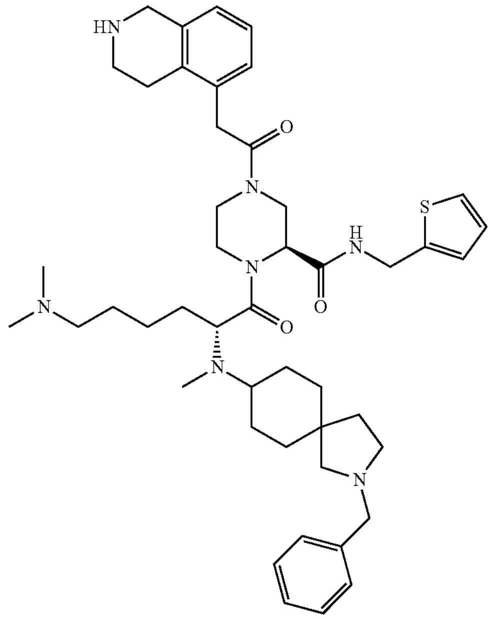 [SMILES: CN(C)CCCC[C@H](C(=O)N1CCN(C(=O)Cc2cccc3c2CCNC3)C[C@H]1C(=O)NCc1cccs1)N(C)C1CCC2(CC1)CCN(Cc1ccccc1)C2] | (2S)-1-[N²-(2-benzyl-2-azaspiro[4.5]dec-8-yl)-N²,N⁶,N⁶-trimethyl-D-lysyl]-4-(1,2,3,4-tetrahydroisoquinolin-5-ylacetyl)-N-(thiophen-2-ylmethyl)piperazine-2-carboxamide | 796.7 | 11.9 |
| 97 | 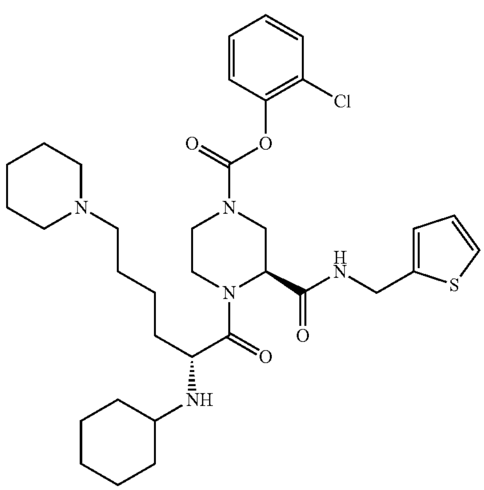 [SMILES: O=C(NCc1cccs1)[C@@H]1CN(C(=O)Oc2ccccc2Cl)CCN1C(=O)[C@@H](CCCCN1CCCCC1)NC1CCCCC1] | 2-chlorophenyl (3S)-4-(N-cyclohexyl-6-piperidin-1-yl-D-norleucyl)-3-[(thiophen-2-ylmethyl)carbamoyl]piperazine-1-carboxylate | 658.3 | 0.7 |
| 98 | 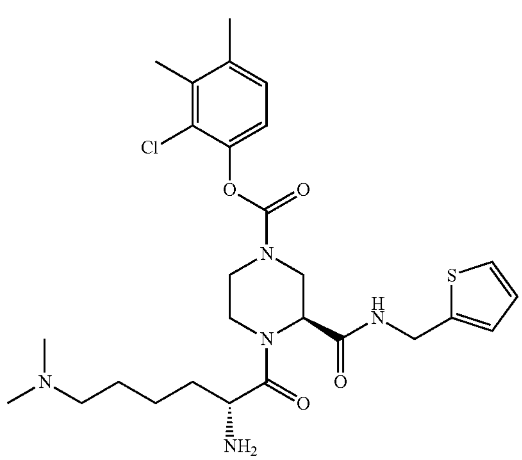 [SMILES: Cc1ccc(OC(=O)N2CCN(C(=O)[C@H](N)CCCCN(C)C)[C@H](C(=O)NCc3cccs3)C2)c(Cl)c1C] | 2-chloro-3,4-dimethylphenyl (3S)-4-(N⁶,N⁶-dimethyl-D-lysyl)-3-[(thiophen-2-ylmethyl)carbamoyl]piperazine-1-carboxylate | 564.4 | 7.2 |

TABLE 1-continued

| Example number | Structure | Name | Exact Mass [M + H]+ | FXIIa IC50 (nM) |
|---|---|---|---|---|
| 99 | 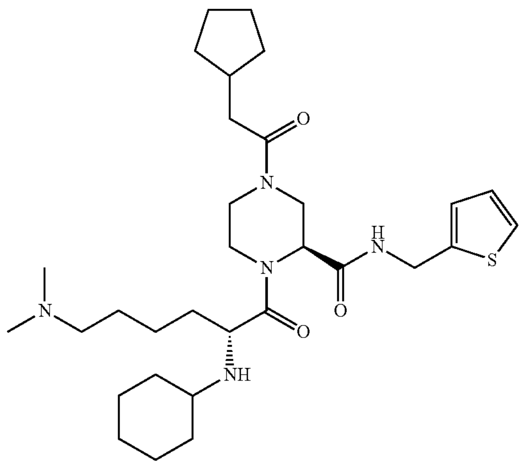 [SMILES: CN(C)CCCC[C@@H](NC1CCCCC1)C(=O)N1CCN(C(=O)CC2CCCC2)C[C@H]1C(=O)NCc1cccs1] | (2S)-1-(N²-cyclohexyl-N⁶,N⁶-dimethyl-D-lysyl)-4-(cyclopentylacetyl)-N-(thiophen-2-ylmethyl)piperazine-2-carboxamide | 574.4 | 29.7 |
| 100 | 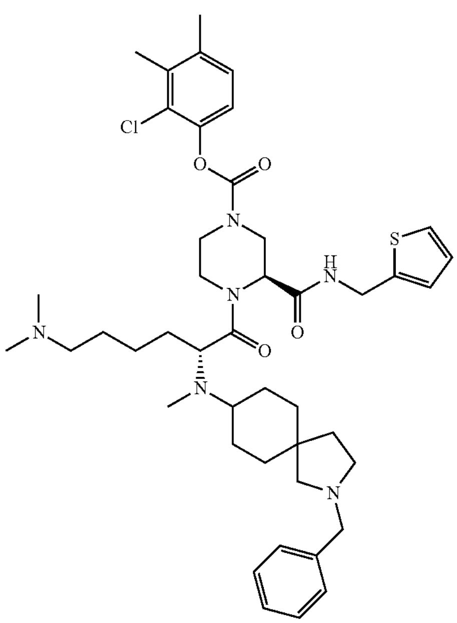 [SMILES: Cc1ccc(OC(=O)N2CCN(C(=O)[C@@H](CCCCN(C)C)N(C)C3CCC4(CC3)CCN(Cc3ccccc3)C4)[C@H](C(=O)NCc3cccs3)C2)c(Cl)c1C] | 2-chloro-3,4-dimethylphenyl (3S)-4-[N²-(2-benzyl-2-azaspiro[4.5]dec-8-yl)-N²,N⁶,N⁶-trimethyl-D-lysyl]-3-[(thiophen-2-ylmethyl)carbamoyl]piperazine-1-carboxylate | 805.4 | 0.5 |

TABLE 1-continued

| Example number | Structure | Name | Exact Mass [M + H]+ | FXIIa IC50 (nM) |
|---|---|---|---|---|
| 101 | 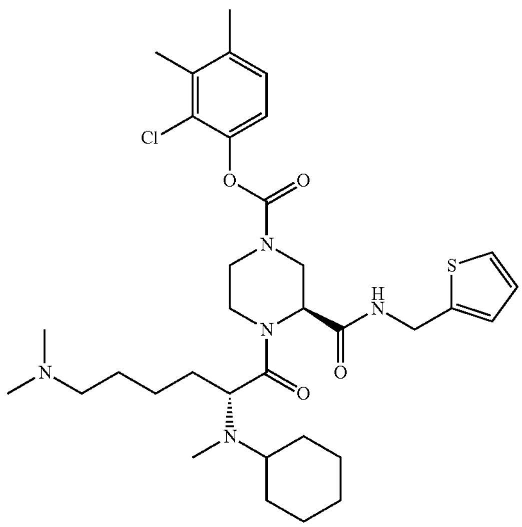 [SMILES: Cc1ccc(OC(=O)N2CCN(C(=O)[C@@H](CCCCN(C)C)N(C)C3CCCCC3)[C@H](C(=O)NCc3cccs3)C2)c(Cl)c1C] | 2-chloro-3,4-dimethylphenyl (3S)-4-($N^2$-cyclohexyl-$N^2$,$N^6$,$N^6$-trimethyl-D-lysyl)-3-[(thiophen-2-ylmethyl)carbamoyl]piperazine-1-carboxylate | 660.4 | 0.1 |
| 102 | 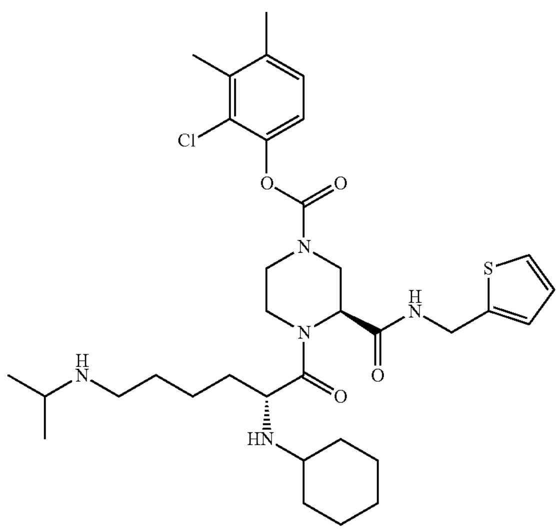 [SMILES: Cc1ccc(OC(=O)N2CCN(C(=O)[C@@H](CCCCNC(C)C)NC3CCCCC3)[C@H](C(=O)NCc3cccs3)C2)c(Cl)c1C] | 2-chloro-3,4-dimethylphenyl (3S)-4-[$N^2$-cyclohexyl-$N^6$-(1-methylethyl)-D-lysyl]-3-[(thiophen-2-ylmethyl)carbamoyl]piperazine-1-carboxylate | 660.3 | 0.7 |
| 103 | 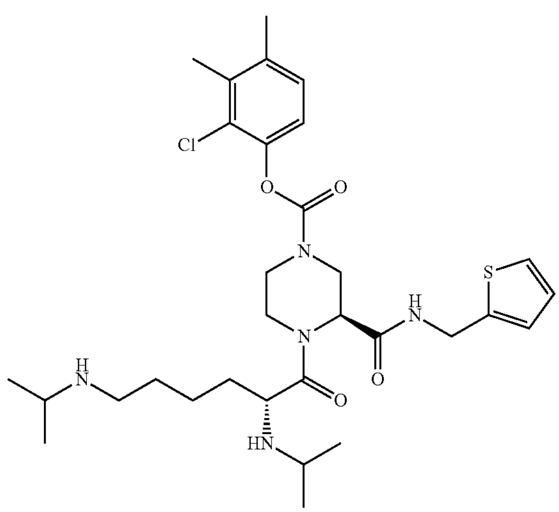 [SMILES: Cc1ccc(OC(=O)N2CCN(C(=O)[C@@H](CCCCNC(C)C)NC(C)C)[C@H](C(=O)NCc3cccs3)C2)c(Cl)c1C] | 2-chloro-3,4-dimethylphenyl (3S)-4-[$N^2$,$N^6$-bis(1-methylethyl)-D-lysyl]-3-[(thiophen-2-ylmethyl)carbamoyl]piperazine-1-carboxylate | 620.4 | 1.4 |

TABLE 1-continued

| Example number | Structure | Name | Exact Mass [M + H]+ | FXIIa IC50 (nM) |
|---|---|---|---|---|
| 104 | 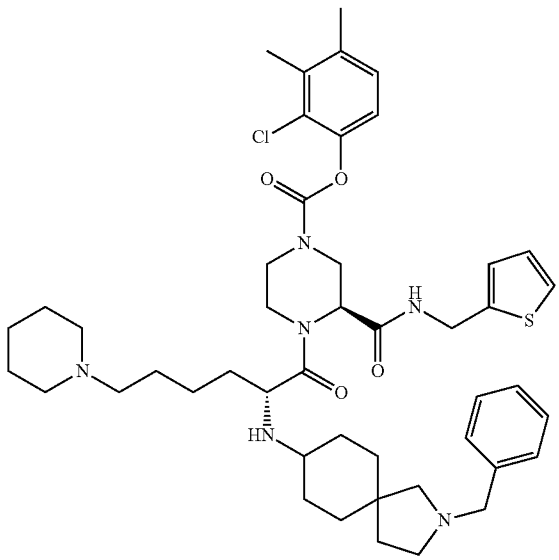 [SMILES: Cc1ccc(OC(=O)N2CCN(C(=O)[C@@H](CCCCN3CCCCC3)NC3CCC4(CC3)CCN(Cc3ccccc3)C4)[C@H](C(=O)NCc3cccs3)C2)c(Cl)c1C] | 2-chloro-3,4-dimethylphenyl (3S)-4-[N-(2-benzyl-2-azaspiro[4.5]dec-8-yl)-6-piperidin-1-yl-D-norleucyl]-3-[(thiophen-2-ylmethyl)carbamoyl]piperazine-1-carboxylate | 831.4 | 0.2 |
| 105 | 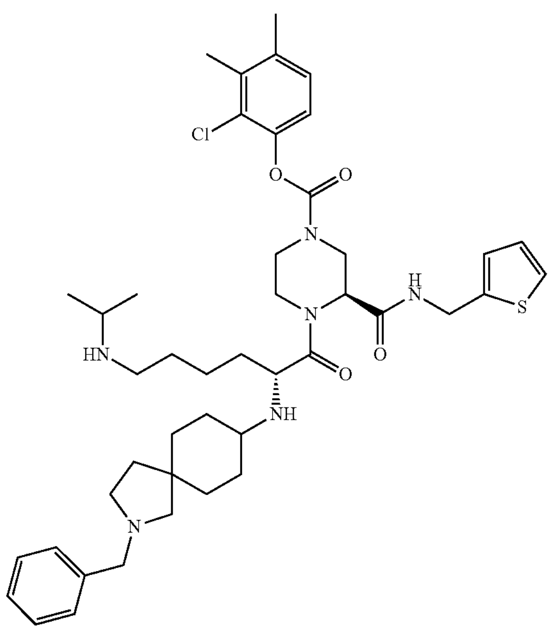 [SMILES: Cc1ccc(OC(=O)N2CCN(C(=O)[C@@H](CCCCNC(C)C)NC3CCC4(CC3)CCN(Cc3ccccc3)C4)[C@H](C(=O)NCc3cccs3)C2)c(Cl)c1C] | 2-chloro-3,4-dimethylphenyl (3S)-4-[N$^2$-(2-benzyl-2-azaspiro[4.5]dec-8-yl)-N$^6$-(1-methylethyl)-D-lysyl]-3-[(thiophen-2-ylmethyl)carbamoyl]piperazine-1-carboxylate | 805.4 | 0.5 |

| Example number | Structure | Name | Exact Mass [M + H]+ | FXIIa IC50 (nM) |
|---|---|---|---|---|
| 106 | 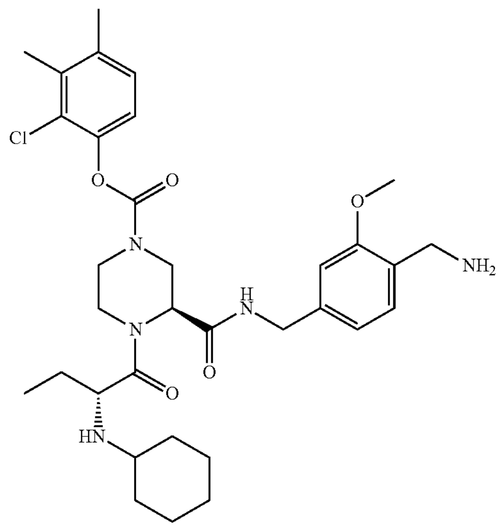 [SMILES: CC[C@@H](NC1CCCCC1)C(=O)N1CCN(C(=O)Oc2ccc(C)c(C)c2Cl)C[C@H]1C(=O)NCc1ccc(CN)c(OC)c1] | 2-chloro-3,4-dimethylphenyl (3S)-3-{[4-(aminomethyl)-3-methoxybenzyl]carbamoyl}-4-[(2R)-2-(cyclohexylamino)butanoyl]piperazine-1-carboxylate | 628.5 | 6.2 |
| 107 | 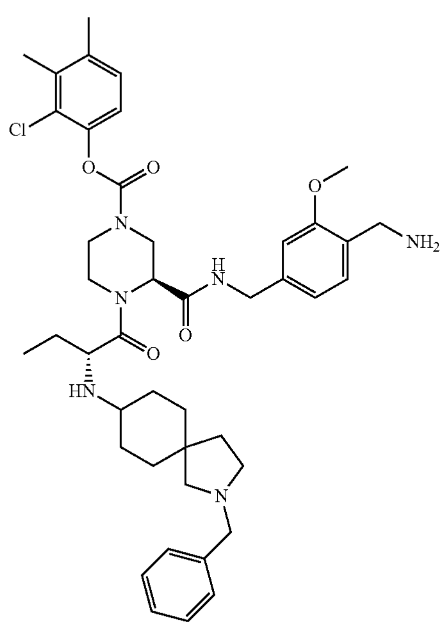 [SMILES: CC[C@@H](NC1CCC2(CC1)CCN(Cc1ccccc1)C2)C(=O)N1CCN(C(=O)Oc2ccc(C)c(C)c2Cl)C[C@H]1C(=O)NCc1ccc(CN)c(OC)c1] | 2-chloro-3,4-dimethylphenyl (3S)-3-{[4-(aminomethyl)-3-methoxybenzyl]carbamoyl}-4-{(2R)-2-[(2-benzyl-2-azaspiro[4.5]dec-8-yl)amino]butanoyl}piperazine-1-carboxylate | 773.7 | 14.0 |

TABLE 1-continued

| Example number | Structure | Name | Exact Mass [M + H]+ | FXIIa IC50 (nM) |
|---|---|---|---|---|
| 108 | 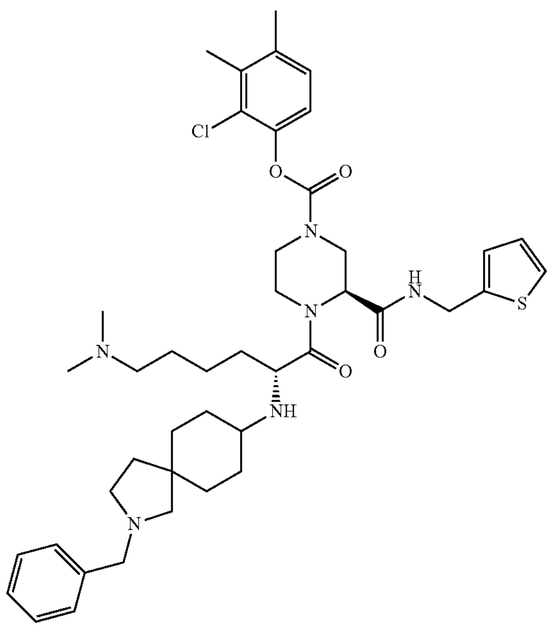 [SMILES: Cc1ccc(OC(=O)N2CCN(C(=O)[C@@H](CCCCN(C)C)NC3CCC4(CC3)CCN(Cc3ccccc3)C4)[C@H](C(=O)NCc3cccs3)C2)c(Cl)c1C] | 2-chloro-3,4-dimethylphenyl (3S)-4-[N²-(2-benzyl-2-azaspiro[4.5]dec-8-yl)-N⁶,N⁶-dimethyl-D-lysyl]-3-[(thiophen-2-ylmethyl)carbamoyl]piperazine-1-carboxylate | 791.4 | 0.3 |
| 109 | 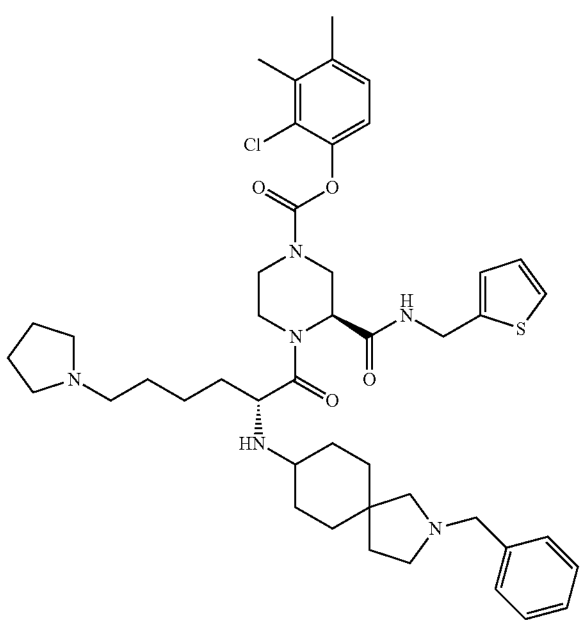 [SMILES: Cc1ccc(OC(=O)N2CCN(C(=O)[C@@H](CCCCN3CCCC3)NC3CCC4(CC3)CCN(Cc3ccccc3)C4)[C@H](C(=O)NCc3cccs3)C2)c(Cl)c1C] | 2-chloro-3,4-dimethylphenyl (3S)-4-[N-(2-benzyl-2-azaspiro[4.5]dec-8-yl)-6-pyrrolidin-1-yl-D-norleucyl]-3-[(thiophen-2-ylmethyl)carbamoyl]piperazine-1-carboxylate | 817.4 | 1.0 |

TABLE 1-continued

| Example number | Structure | Name | Exact Mass [M + H]+ | FXIIa IC50 (nM) |
|---|---|---|---|---|
| 110 | 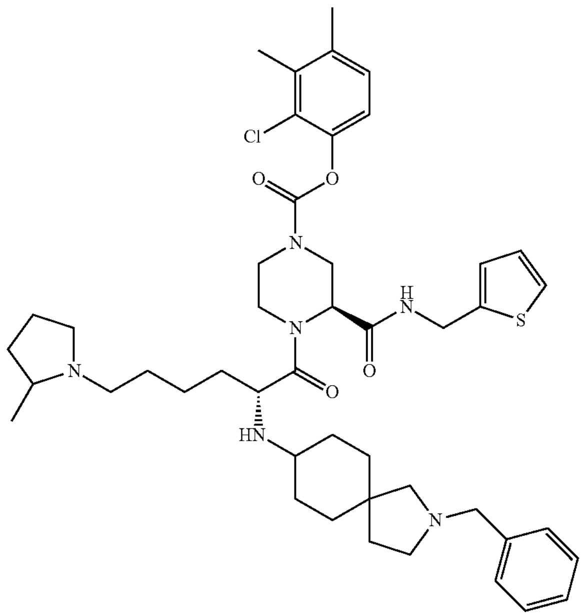 [SMILES: Cc1ccc(OC(=O)N2CCN(C(=O)[C@@H](CCCCN3CCCC3C)NC3CCC4(CC3)CCN(Cc3ccccc3)C4)[C@H](C(=O)NCc3cccs3)C2)c(Cl)c1C] | 2-chloro-3,4-dimethylphenyl (3S)-4-[N-(2-benzyl-2-azaspiro[4.5]dec-8-yl)-6-(2-methylpyrrolidin-1-yl)-D-norleucyl]-3-[(thiophen-2-ylmethyl)carbamoyl]piperazine-1-carboxylate | 831.4 | 0.3 |
| 111 | 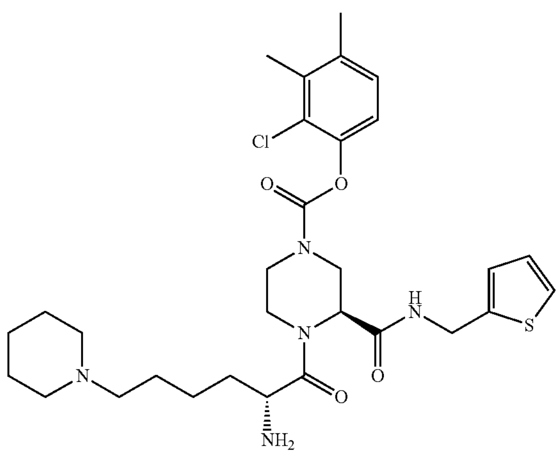 [SMILES: Cc1ccc(OC(=O)N2CCN(C(=O)[C@H](N)CCCCN3CCCCC3)[C@H](C(=O)NCc3cccs3)C2)c(Cl)c1C] | 2-chloro-3,4-dimethylphenyl (3S)-4-(6-piperidin-1-yl-D-norleucyl)-3-[(thiophen-2-ylmethyl)carbamoyl]piperazine-1-carboxylate | 604.3 | 5.0 |
| 112 | 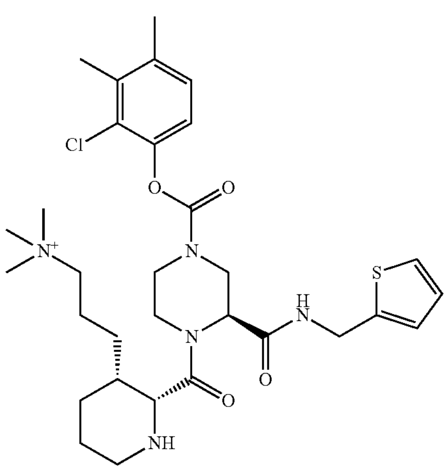 [SMILES: Cc1ccc(OC(=O)N2CCN(C(=O)[C@@H]3NCCC[C@@H]3CCC[N+](C)(C)C)[C@H](C(=O)NCc3cccs3)C2)c(Cl)c1C] | 3-[(2R,3R)-2-({(2S)-4-[(2-chloro-3,4-dimethylphenoxy)carbonyl]-2-[(thiophen-2-ylmethyl)carbamoyl]piperazin-1-yl}carbonyl)piperidin-3-yl]-N,N,N-trimethylpropan-1-aminium | 619.3 | 13.3 |

TABLE 1-continued

| Example number | Structure | Name | Exact Mass [M + H]+ | FXIIa IC50 (nM) |
|---|---|---|---|---|
| 113 | 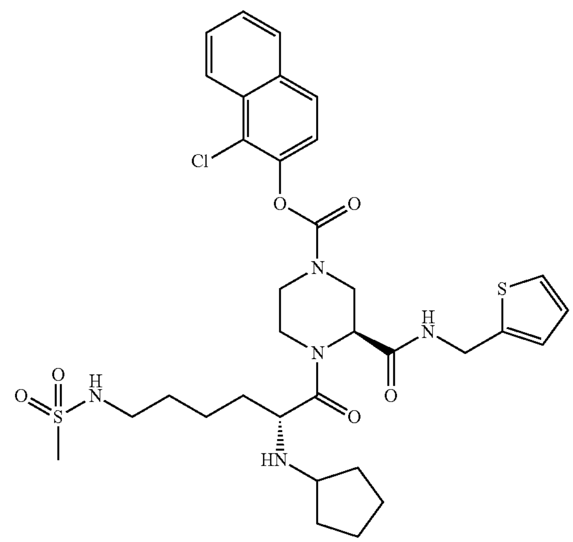 [SMILES: CS(=O)(=O)NCCCC[C@@H](NC1CCCC1)C(=O)N1CCN(C(=O)Oc2ccc3ccccc3c2Cl)C[C@H]1C(=O)NCc1cccs1] | 1-chloronaphthalen-2-yl (3S)-4-[N$^2$-cyclopentyl-N~6~-(methylsulfonyl)-D-lysyl]-3-[(thiophen-2-ylmethyl)carbamoyl]piperazine-1-carboxylate | 704.2 | 8.4 |

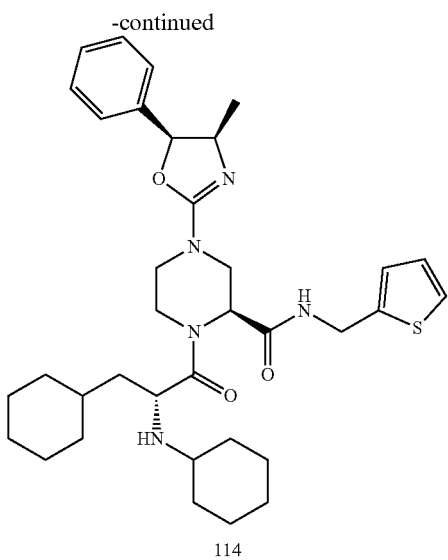

114

(9H-fluoren-9-yl)methyl (S)-3-((thiophen-2-ylmethyl)carbamoyl)piperazine-1-carboxylate hydrochloride (114d)

4.0 M HCl (53.7 mL, 215 mmol) in 1,4-dioxane was added to a stirred mixture of (S)-4-((9H-fluoren-9-yl) methyl) 1-tert-butyl 2-((thiophen-2-ylmethyl)carbamoyl) piperazine-1,4-dicarboxylate 114c (11.76 g, 21.47 mmol) in CH₂Cl₂ (30 mL) and the mixture was stirred at room temperature for 2 h. The reaction was monitored by LCMS. After completion, the excess solvent was concentrated and dried overnight. The product was used as such.

(9H-fluoren-9-yl)methyl (S)-4-((R)-3-cyclohexyl-2-(cyclohexylamino)propanoyl)-3-((thiophen-2-ylmethyl)carbamoyl)piperazine-1-carboxylate (114d)

HATU (7.86 g, 20.66 mmol) was added to a stirred mixture of (S)-(9H-fluoren-9-yl)methyl 3-((thiophen-2-ylmethyl)carbamoyl)piperazine-1-carboxylate hydrochloride 114d (5.00 g, 10.33 mmol), (R)-3-cyclohexyl-2-(cyclohexylamino)propanoic acid Ic (2.62 g, 10.33 mmol) and Hunig's base (7.22 mL, 41.3 mmol) in CH₂Cl₂ (25 mL) and the mixture was stirred at room temperature overnight. Upon completion, the reaction was diluted with water, extracted with CH₂Cl₂, dried over Na₂SO₄, filtered and concentrated in vacuo. The residue was purified by column chromatography on silica gel Teledyne ISCO REDISEP[330 g prepacked] eluting with 0-80% EtOAc/isohexane to give 114d.

(S)-1-((R)-3-cyclohexyl-2-(cyclohexylamino)propanoyl)-N-(thiophen-2-ylmethyl)piperazine-2-carboxamide (114f)

Piperidine (6.09 mL, 61.5 mmol) was added to a stirred mixture of (S)-(9H-fluoren-9-yl)methyl 4-((R)-3-cyclohexyl-2-(cyclohexylamino)propanoyl)-3-((thiophen-2-ylmethyl)carbamoyl)piperazine-1-carboxylate 114d (7.0 g, 10.25 mmol) in DMF (10 mL) and the mixture was stirred at room temperature for 2 h. The mixture was diluted with water, extracted with EtOAc, washed with brine, dried over Na₂SO₄, filtered and concentrated in vacuo. The residue was purified by column chromatography on silica gel Teledyne ISCO REDISEP[220 g prepacked] eluting with 0-20% MeOH/CH₂C2 to give 114f.

(S)-1-((R)-3-cyclohexyl-2-(cyclohexylamino)propanoyl)-4-((4R,5S)-4-methyl-5-phenyl-4,5-dihydrooxazol-2-yl)-N-(thiophen-2-ylmethyl)piperazine-2-carboxamide (114)

(4R,5S)-2-methoxy-4-methyl-5-phenyl-4,5-dihydrooxazole 3b (31.1 mg, 0.163 mmol) was added to a stirred mixture of (S)-1-((R)-3-cyclohexyl-2-(cyclohexylamino) propanoyl)-N-(thiophen-2-ylmethyl)piperazine-2-carboxamide 114f (50 mg, 0.109 mmol) in MeOH (2 mL) and the mixture was stirred at 60° C. overnight. The excess solvent was concentrated in vacuo and purified by reverse phase HPLC system using 0.05% TFA in ACN/H₂O to yield the desired product 114. The crude mixture was purified by reverse phase HPLC system using 0.05% TFA in ACN/H₂O.

Example 115

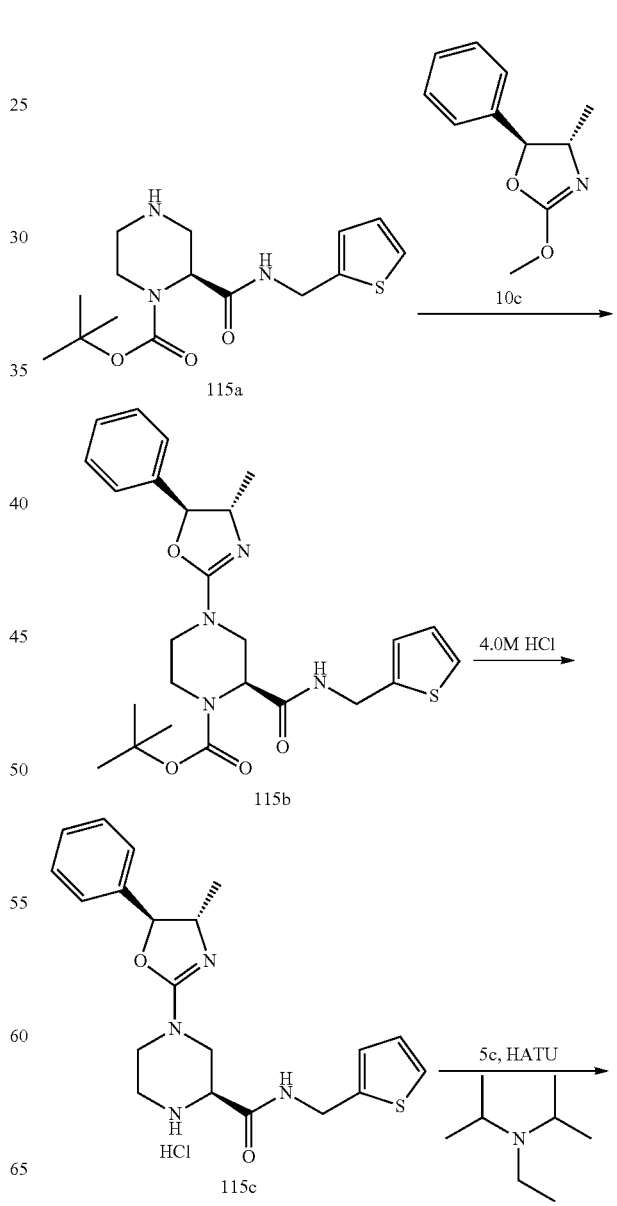

135
-continued

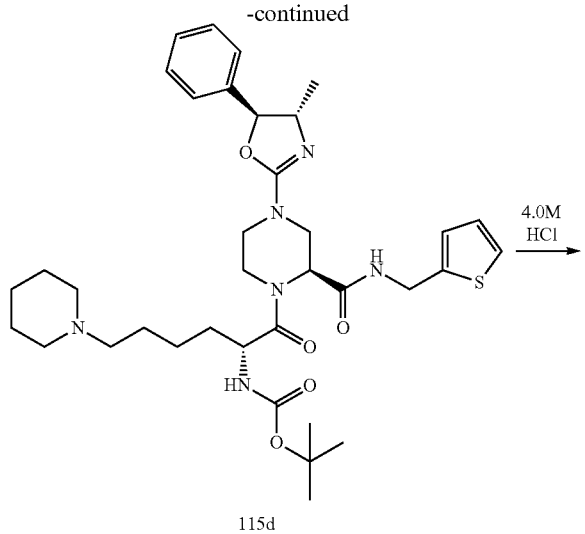

115d

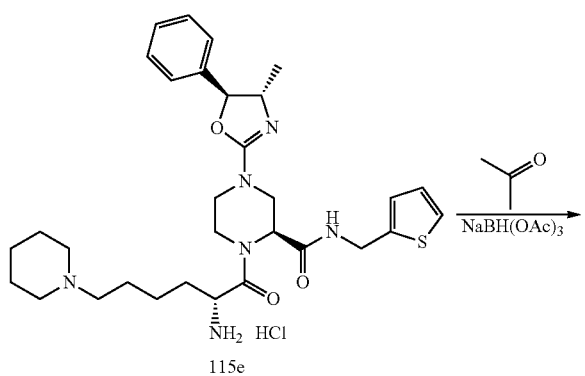

115e

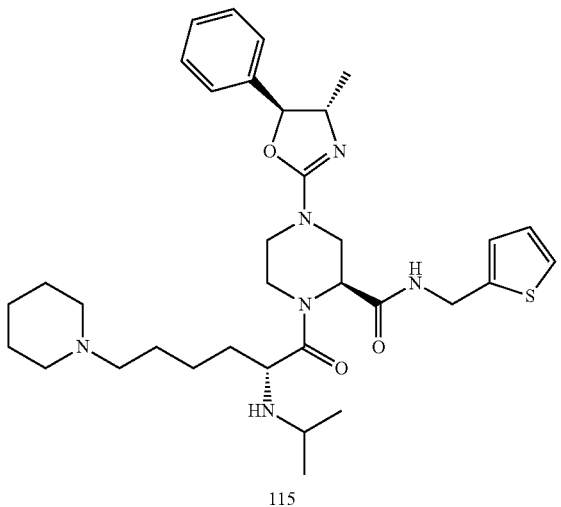

115 tert-butyl (S)-4-((4S,5S)-4-methyl-5-phenyl-4,5-dihydrooxazol-2-yl)-2-((thiophen-2-ylmethyl)carbamoyl)piperazine-1-carboxylate (115b)

(4S,5S)-2-methoxy-4-methyl-5-phenyl-4,5-dihydrooxazole (823 mg, 4.30 mmol) was added to a stirred mixture of (S)-tert-butyl 2-((thiophen-2-ylmethyl)carbamoyl)piperazine-1-carboxylate 115a (700 mg, 2.151 mmol) and Hunig's base (0.751 mL, 4.30 mmol) in toluene (5 mL), and the mixture was stirred at 60° C. overnight. After cooling to room temperature, the reaction mixture was concentrated

136 and the residue was purified by column chromatography on silica gel Teledyne ISCO REDISEP[24 g prepacked] eluting with 0-40-60% EtOAc:EtOH (3:1)/hexanes to give 115b.

(S)-4-((4S,5S)-4-methyl-5-phenyl-4,5-dihydrooxazol-2-yl-N-(thiophen-2-ylmethyl)piperazine-2-carboxamide hydrochloride (115c)

HCl (5.06 mL, 20.22 mmol, 4.0 M) in 1,4-dioxane was added to a stirred mixture of (S)-tert-butyl 4-((4S,5S)-4-methyl-5-phenyl-4,5-dihydrooxazol-2-yl)-2-((thiophen-2-ylmethyl)carbamoyl)piperazine-1-carboxylate 115b (980 mg, 2.022 mmol) in MeOH (4 mL) and the mixture was stirred at room temperature for 3 h. The reaction was monitored by LCMS. Upon completion, the reaction mixture was concentrated and dried overnight to yield 115c. The product was used as such without further purification.

tert-butyl ((R)-1-((S)-4-((4S,5S)-4-methyl-5-phenyl-4,5-dihydrooxazol-2-yl)-2-((thiophen-2-ylmethyl)carbamoyl)piperazin-1-yl)-1-oxo-6-(piperidin-1-yl)hexan-2-yl)carbamate (115d)

A mixture of (S)-4-((4S,5S)-4-methyl-5-phenyl-4,5-dihydrooxazol-2-yl)-N-(thiophen-2-ylmethyl)piperazine-2-carboxamide 115c (850 mg, 2.211 mmol), (R)-2-((tert-butoxycarbonyl)amino)-6-(piperidin-1-yl)hexanoic acid 5c (834 mg, 2.65 mmol), HATU (1681 mg, 4.42 mmol) and Hunig's base (1.158 mL, 6.63 mmol) in CH$_2$Cl$_2$ (5 mL) was stirred at room temperature overnight. The reaction was monitored by LCMS. Upon completion, the residue was purified by column chromatography on silica gel Teledyne ISCO REDISEP[40 g prepacked] eluting with 0-40-60-80-100% EtOAc:EtOH (3:1)/hexanes followed by 0-10-15-25-40% MeOH/DCM to give 115d.

(S)-1-((R)-2-amino-6-(piperidin-1-yl)hexanoyl)-4-((4S,5S)-4-methyl-5-phenyl-4,5-dihydrooxazol-2-yl)-N-(thiophen-2-ylmethyl)piperazine-2-carboxamide hydrochloride (115e)

4.0 M HCl (1.469 mL, 5.87 mmol) in 1,4-dioxane was added to a stirred mixture of tert-butyl ((R)-1-((S)-4-((4S,5S)-4-methyl-5-phenyl-4,5-dihydrooxazol-2-yl)-2-((thiophen-2-ylmethyl)carbamoyl)piperazin-1-yl)-1-oxo-6-(piperidin-1-yl)hexan-2-yl)carbamate 115d (400 mg, 0.587 mmol) in MeOH (1 mL) and the mixture was stirred at room temperature for 3 h. The reaction was monitored by LCMS. LCMS showed a product peak and the mixture was concentrated and dried. The residue was purified by preparative HPLC Reverse phase (C-18) eluting with acetonitrile/water+0.05% TFA to give 115e after lyophilization.

(S)-1-((R)-2-(isopropylamino)-6-(piperidin-1-yl)hexanoyl)-4-((4S,5S)-4-methyl-5-phenyl-4,5-dihydrooxazol-2-yl-N-(thiophen-2-ylmethyl)piperazine-2-carboxamide (115)

Cyanoborohydride, polymer supported (0.689 mmol) (345 mg), was added to a stirred mixture of (S)-1-((R)-2-amino-6-(piperidin-1-yl)hexanoyl)-4-((4S,5S)-4-methyl-5-phenyl-4,5-dihydrooxazol-2-yl)-N-(thiophen-2-ylmethyl)piperazine-2-carboxamide 115e (100 mg, 0.172 mmol), acetone (0.126 mL, 1.722 mmol) and acetic acid (4.93 µl, 0.086 mmol) in MeOH (1 mL) and the mixture was stirred at room temperature for 2 h. The reaction was monitored by LCMS. After LCMS confirmation of product formation, the mixture was concentrated. The residue was purified by preparative HPLC Reverse phase (C-18) eluting with acetonitrile/water+0.05% TFA to give 115 after lyophilization.

Example 116

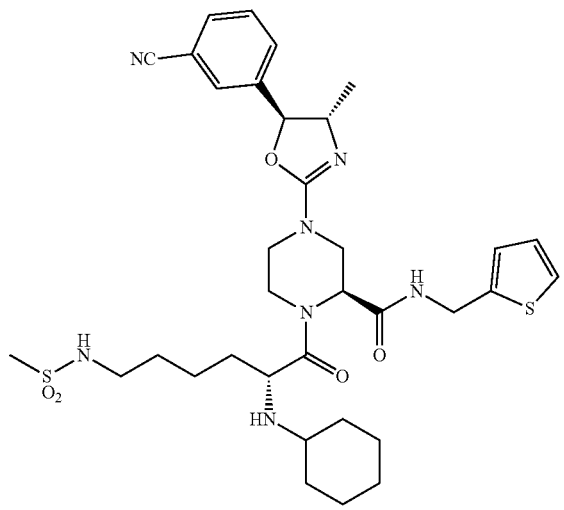

116

(S)-4-((4S,5S)-5-(3-cyanophenyl)-4-methyl-4,5-dihydrooxazol-2-yl)-1-(N²-cyclohexyl-N⁶-(methylsulfonyl)-D-lysyl)-N-(thiophen-2-ylmethyl)piperazine-2-carboxamide (116)

Compound 116 was prepared using appropriate starting materials with procedures analogous to those described in Example 115.

Example 117

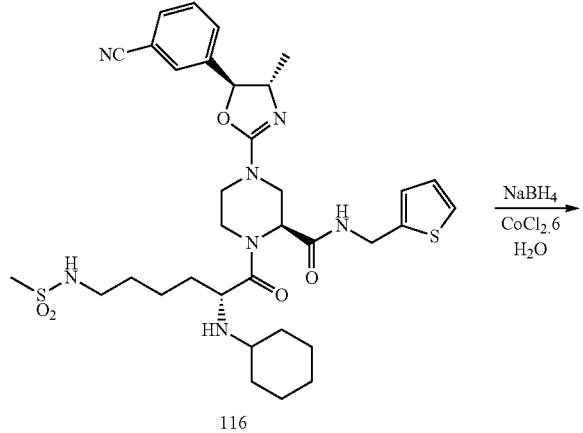

116

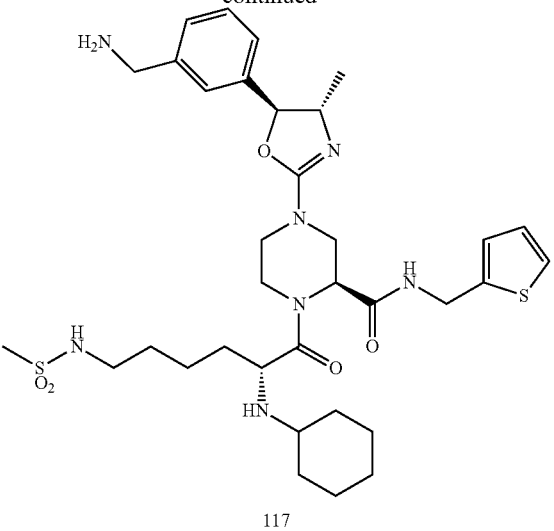

117

(S)-4-((4S,5S)-5-(3-(aminomethyl)phenyl)-4-methyl-4,5-dihydrooxazol-2-yl)-1-(N²-cyclohexyl-N⁶-(methylsulfonyl)-D-lysyl)-N-(thiophen-2-ylmethyl)piperazine-2-carboxamide (117)

NaBH₄ (4.34 mg, 0.115 mmol) was added to a stirred mixture of (S)-4-((4S,5S)-5-(3-cyanophenyl)-4-methyl-4,5-dihydrooxazol-2-yl)-1-((R)-2-(cyclohexylamino)-6-(methylsulfonamido)hexanoyl)-N-(thiophen-2-ylmethyl)piperazine-2-carboxamide 116 (20 mg, 0.029 mmol) and cobalt(II) chloride hexahydrate (3.41 mg, 0.014 mmol) in MeOH (1 mL) and the mixture was stirred at room temperature for 3 h. The reaction was monitored by LCMS. After the disappearance of starting material, the reaction mixture was acidified with 1 N HCl and filtered. The residue was purified by preparative HPLC Reverse phase (C-18) eluting with MeCN/water+0.05% TFA to give 117.

Example 118

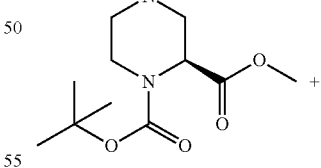

118a

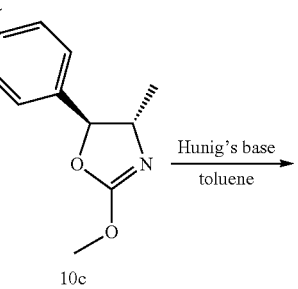

10c

139
-continued
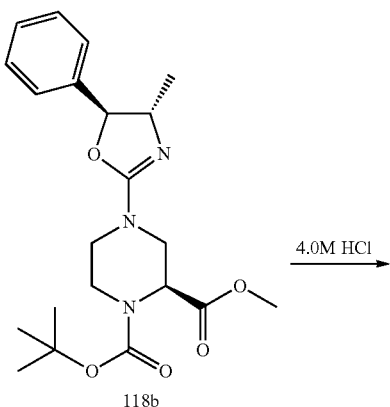
118b
↓ 4.0M HCl
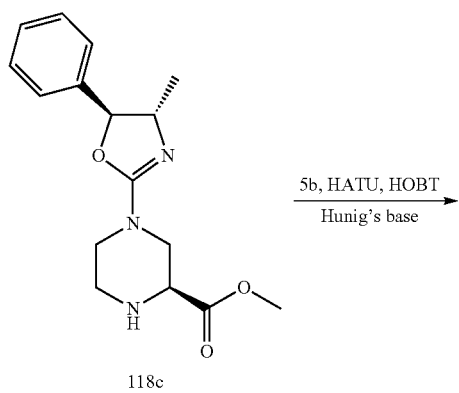
118c
↓ 5b, HATU, HOBT
Hunig's base
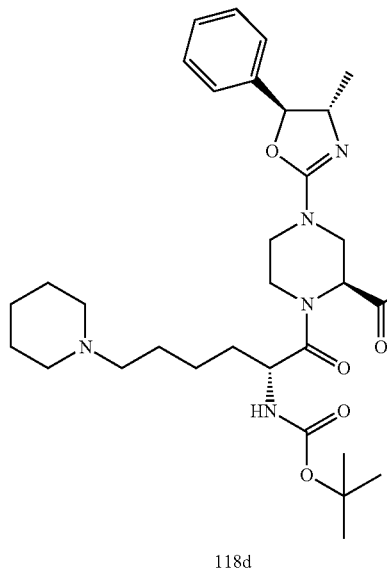
118d
140
-continued
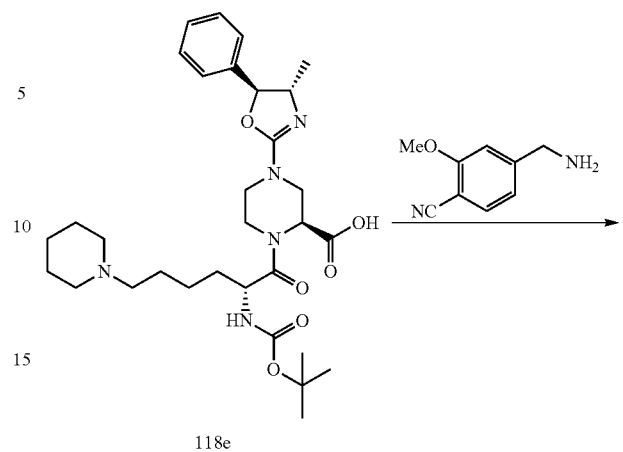
118e
↓ KOSiMe₃
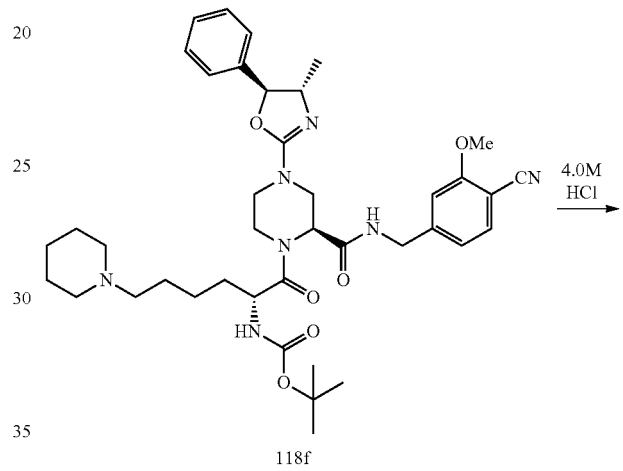
118f
↓ 4.0M HCl
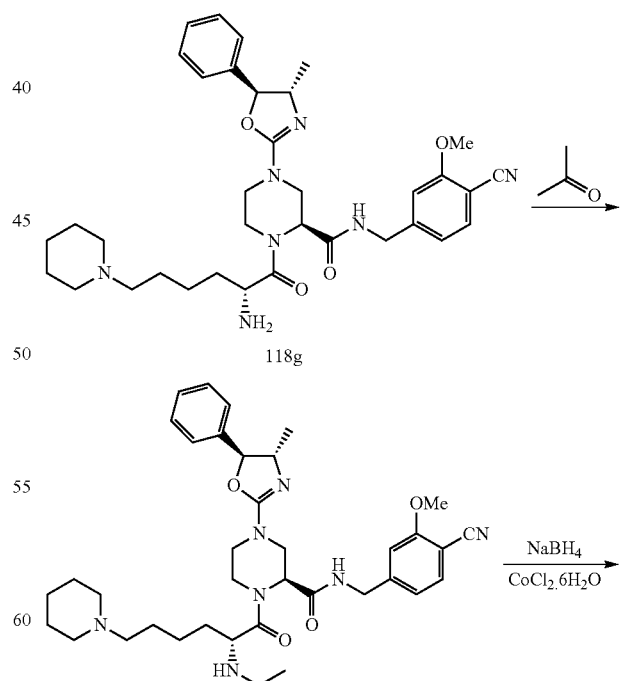
118g
↓ acetone
118h
↓ NaBH₄ / CoCl₂·6H₂O -continued

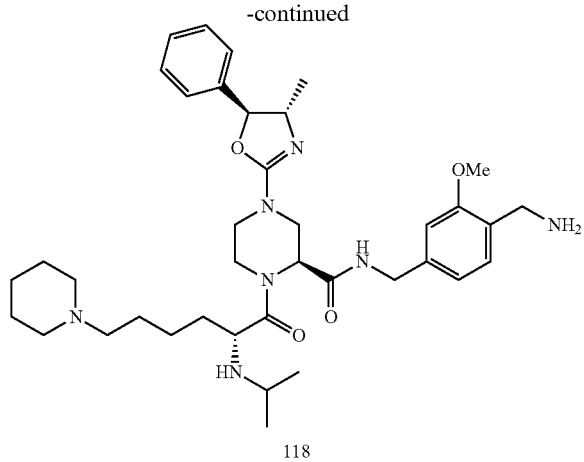

118

1-(tert-butyl) 2-methyl (S)-4-(4S,5S)-4-methyl-5-phenyl-4,5-dihydrooxazol-2-yl)piperazine-1,2-dicarboxylate (118b)

(4S,5 S)-2-methoxy-4-methyl-5-phenyl-4,5-dihydrooxazole 10c (235 mg, 1.228 mmol) was added to a stirred mixture of (S)-1-tert-butyl 2-methyl piperazine-1,2-dicarboxylate 118a (150 mg, 0.614 mmol) and Hunig's base (0.214 mL, 1.228 mmol) in toluene (1 mL) and the mixture was stirred at 60° C. overnight. The reaction was monitored by LCMS. Upon completion, the reaction mixture was concentrated in vacuo. The residue was purified by column chromatography on silica gel Teledyne ISCO REDISEP[12 g prepacked] eluting with 0-20% EtOAc-EtOH (3:1)/hexanes to give 118b.

Methyl (S)-4-((4S,5S)-4-methyl-5-phenyl-4,5-dihydrooxazol-2-yl)iperazine-2-carboxylate (118c)

4.0 M HCl (15 mL, 60.0 mmol) in 1,4-dioxane was added to a stirred mixture of 1-(tert-butyl) 2-methyl (S)-4-((4S,5S)-4-methyl-5-phenyl-4,5-dihydrooxazol-2-yl)piperazine-1,2-dicarboxylate 118b (5.0 g, 12.39 mmol) in MeOH (25 mL) and the mixture was stirred at room temperature for 1 h. The reaction was monitored by LCMS. LCMS showed a product peak and the mixture was concentrated and dried to yield 118c. The product was used as such.

Methyl (S)-1-((R)-2-((tert-butoxycarbonyl)amino)-6-(piperidin-1-yl)hexanoyl)-4-((4S,5S)-4-methyl-5-phenyl-4,5-dihydrooxazol-2-yl)piperazine-2-carboxylate (118d)

A mixture of ethyl (S)-4-((4S,5S)-4-methyl-5-phenyl-4,5-dihydrooxazol-2-yl)piperazine-2-carboxylate 118c (2.5 g, 8.24 mmol), (R)-2-((tert-butoxycarbonyl)amino)-6-(piperidin-1-yl)hexanoic acid 5b (3.88 g, 12.35 mmol), HATU (5.0 g, 13.2 mmol) and Hunig's base (3.6 mL, 20.6 mmol) in $CH_2Cl_2$ (80 mL) was stirred at room temperature overnight. The reaction was monitored by LCMS. Upon completion, the residue was purified by column chromatography on silica gel Teledyne ISCO REDISEP[40 g prepacked] eluting with 0-40-60-80-100% EtOAc:EtOH (3:1)/hexanes followed by $NH_4OH$ to give 118d.

(S)-1-((R)-2-((tert-butoxycarbonyl)amino)-6-(piperidin-1-yl)hexanoyl)-4-((4S,5S)-4-methyl-5-phenyl-4,5-dihydrooxazol-2-yl)piperazine-2-carboxylic acid (118e)

Potassium trimethylsilanolate (2.89 g, 22.51 mmol) was added to a stirred mixture of methyl (S)-1-((R)-2-((tert-butoxycarbonyl)amino)-6-(piperidin-1-yl)hexanoyl)-4-((4S,5 S)-4-methyl-5-phenyl-4,5-dihydrooxazol-2-yl)piperazine-2-carboxylate 118d (2.70 g 4.50 mmol) in a 1:2:3 of $H_2O$/MeOH/THF (60 mL) and the reaction was stirred for 30 min. The reaction was monitored by LCMS. After 30 min, the reaction was quenched by the addition of 1 N HCl and the pH was adjusted to 5.0 by the addition of sat. $NaHCO_3$. The residue was concentrated in vacuo and purified by preparative HPLC Reverse phase (C-18) eluting with MeCN/water+0.05% TFA to give 118e.

tert-Butyl ((R)-1-((S)-2-((4-cyano-3-methoxybenzyl)carbamoyl)-4-((4S,5S)-4-methyl-5-phenyl-4,5-dihydrooxazol-2-yl)piperazin-1-yl)-1-oxo-6-(piperidin-1-yl)hexan-2-yl)carbamate (118f)

A mixture of (S)-1-((R)-2-((tert-butoxycarbonyl)amino)-6-(piperidin-1-yl)hexanoyl)-4-((4S,5 S)-4-methyl-5-phenyl-4,5-dihydrooxazol-2-yl)piperazine-2-carboxylic acid 118e (360 mg, 0.492 mmol), 4-(aminomethyl)-2-methoxy benzonitrile (199 mg, 1.23 mmol), HATU (280 mg, 0.738 mmol) and Hunig's base (0.69 mL, 3.93 mmol) in $CH_2Cl_2$ (2 mL) was stirred at room temperature overnight. The reaction was monitored by LCMS. Upon completion, the residue was concentrated in vacuo and dried to yield 118f. The product was used as such without further purification.

(S)-1-((R)-2-amino-6-(piperidin-1-yl)hexanoyl)-N-(4-cyano-3-methoxybenzyl)-4-((4S,5S)-4-methyl-5-phenyl-4,5-dihydrooxazol-2-yl)piperazine-2-carboxamide (118g)

4.0 M HCl (1.3 mL, 4.92 mmol) in 1,4-dioxane was added to a stirred mixture of tert-Butyl ((R)-1-((S)-2-((4-cyano-3-methoxybenzyl)carbamoyl)-4-((4S,5 S)-4-methyl-5-phenyl-4,5-dihydrooxazol-2-yl)piperazin-1-yl)-1-oxo-6-(piperidin-1-yl)hexan-2-yl)carbamate 118f (350 mg, 0.48 mmol) in MeOH (2 mL) and the mixture was stirred at room temperature for 1 h. The reaction was monitored by LCMS. LCMS showed product peak and the mixture was concentrated and dried to yield 118g. The product was used as such without further purification.

(S)—N-(4-cyano-3-methoxybenzyl)-1-((R)-2-(isopropylamino)-6-(piperidin-1-yl)hexanoyl)-4-((4S,5S)-4-methyl-5-phenyl-4,5-dihydrooxazol-2-yl)piperazine-2-carboxamide (118h)

MP-$CNBH_3$ (193 mg, 1.0 mmol, 2.43 mmol/g) was added to a stirred mixture of (S)-1-((R)-2-amino-6-(piperidin-1-yl)hexanoyl)-N-(4-cyano-3-methoxybenzyl)-4-((4S,5 S)-4-methyl-5-phenyl-4,5-dihydrooxazol-2-yl)piperazine-2-carboxamide 118g (86 mg, 0.1 mmol), propan-2-one (116 mg, 2.0 mmol) and acetic acid (1.3 uL, 0.023 mmol) in MeOH (1 mL) and the reaction was stirred slowly for 50 min. The reaction was monitored by LCMS. Upon completion, the reaction mixture was filtered, washed with MeOH and concentrated in vacuo to yield 118h. The product was used as such without further purification.

(S)—N-(4-(aminomethyl)-3-methoxybenzyl)-1-((R)-2-(isopropylamino)-6-(piperidin-1-yl)hexanoyl)-4-((4S,5S)-4-methyl-5-phenyl-4,5-dihydrooxazol-2-yl)piperazine-2-carboxamide (118)

NaBH$_4$ (8.9 mg, 0.235 mmol) was added to a stirred mixture of (S)—N-(4-cyano-3-methoxybenzyl)-1-((R)-2-(isopropylamino)-6-(piperidin-1-yl)hexanoyl)-4-((4S,5S)-4-methyl-5-phenyl-4,5-dihydrooxazol-2-yl)piperazine-2-carboxamide 118h (30 mg, 0.047 mmol) and cobalt(II) chloride hexahydrate (5.6 mg, 0.024 mmol) in MeOH (1 mL) and the mixture was stirred at room temperature for 2 h. The reaction was monitored by LCMS. After the disappearance of starting material, the reaction mixture was acidified with 1 N HCl and filtered. The residue was purified by preparative HPLC Reverse phase (C-18) eluting with MeCN/water+0.05% TFA to give 118.

Example 119

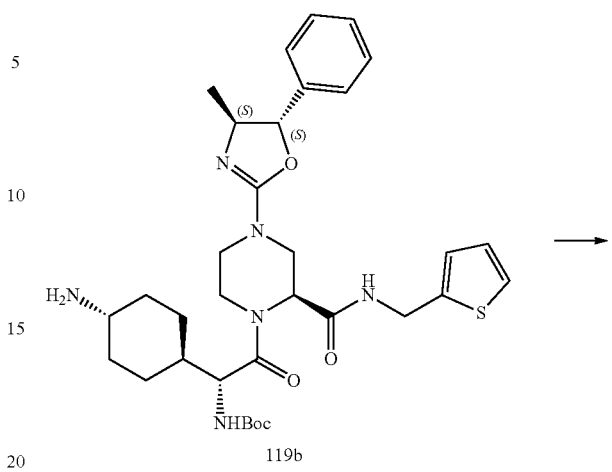

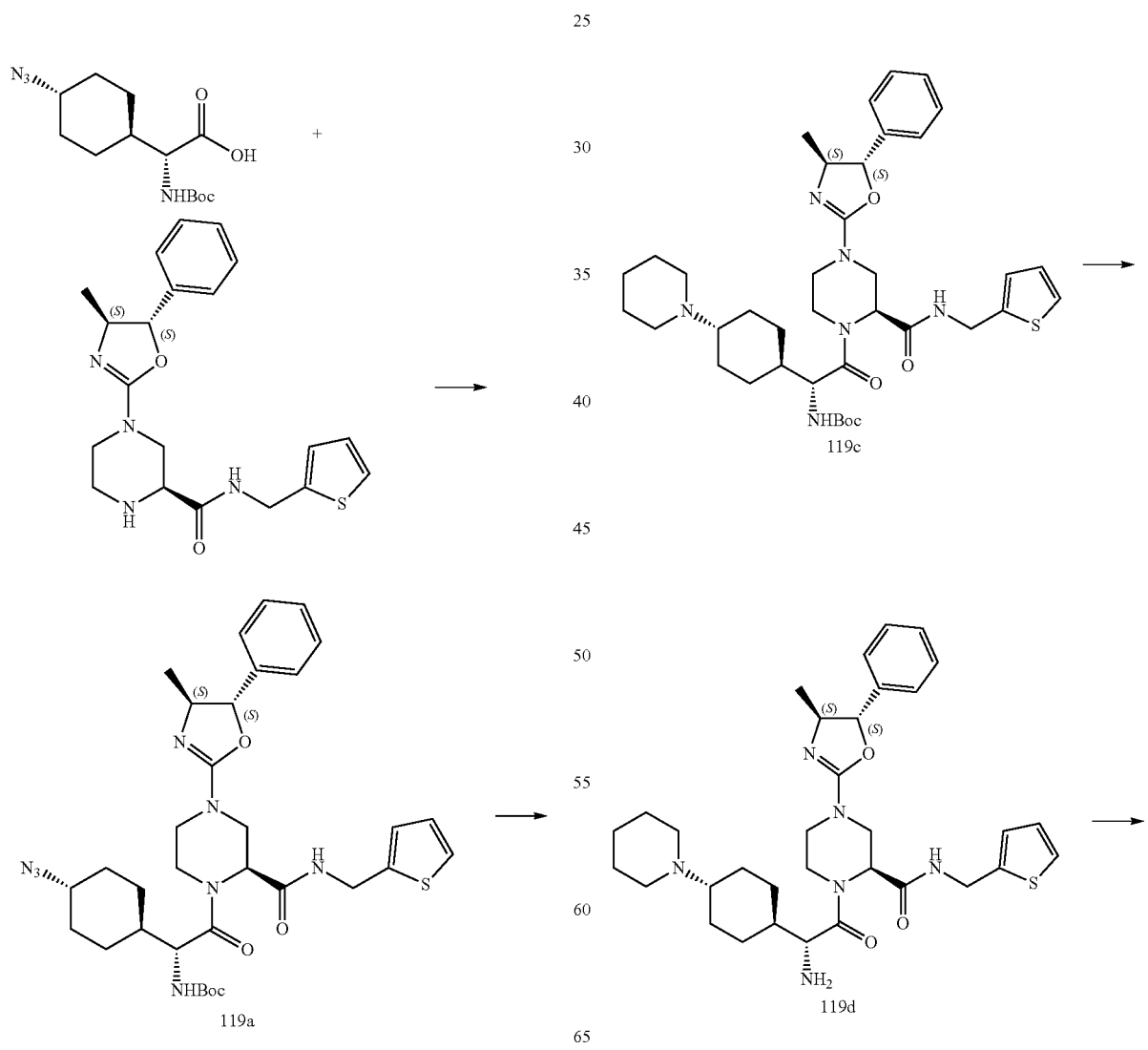

145
-continued

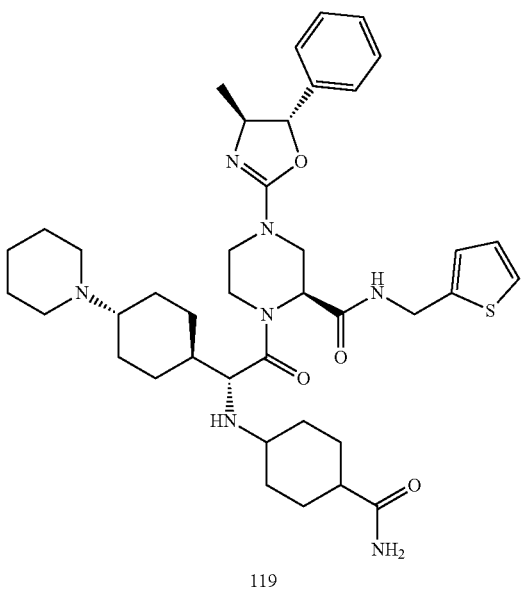

119 tert-butyl ((R)-1-((1r,4R)-4-azidocyclohexyl)-2-((S)-4-((4S,5S)-4-methyl-5-phenyl-4,5-dihydrooxazol-2-yl)-2-((thiophen-2-ylmethyl)carbamoyl)piperazin-1-yl)-2-oxoethyl)carbamate (119a)

A solution of (R)-2-((1r,4R)-4-azidocyclohexyl)-2-((tert-butoxycarbonyl)amino)acetic acid (454 mg, 1.520 mmol), DIEA (1.062 mL, 6.08 mmol), HATU (578 mg, 1.520 mmol) and (S)-4-((4S,5S)-4-methyl-5-phenyl-4,5-dihydrooxazol-2-yl)-N-(thiophen-2-ylmethyl)piperazine-2-carboxamide hydrochloride (640 mg, 1.520 mmol) in N,N-Dimethylformamide (5 ml) was stirred for 30 min. LCMS showed a product peak. The reaction was continued with stirring for 1 h. DCM (50 mL) (2×) was added, and it washed with water (20 mL). The DCM layer was washed with brine (10 mL), dried over Na₂SO₄, filtered and concentrated. The reaction was purified by normal phase chromatography (REDISEP, 40 g) and the product was eluted by 85% to 90% EtOAc in hexane to obtain 119a.

tert-butyl ((R)-1-((1r,4R)-4-aminocyclohexyl)-2-((S)-4-((4S,5S)-4-methyl-5-phenyl-4,5-dihydrooxazol-2-yl)-2-((thiophen-2-ylmethyl)carbamoyl)piperazin-1-yl)-2-oxoethyl)carbamate (119b)

Tin(II) chloride dihydrate (407 mg, 1.805 mmol) was added to a solution of tert-butyl ((R)-1-((1r,4R)-4-azidocyclohexyl)-2-((S)-4-((4S,5 S)-4-methyl-5-phenyl-4,5-dihydrooxazol-2-yl)-2-((thiophen-2-ylmethyl)carbamoyl)piperazin-1-yl)-2-oxoethyl)carbamate 119a (300 mg, 0.451 mmol) in EtOAc (6 mL)/ethanol (3.00 mL) was stirred at r.t. for 2 h. LCMS showed a product peak. Water (2 mL) was added and the solvents were removed in vacuo. EtOAc was added, and it was washed with sat. aq. NaHCO₃ and water. The EtOAc layer was dried over Na₂SO₄, filtered and concentrated. The reaction was purified by reverse phase HPLC system using 0.05% TFA in MeCN/water, loading the compound on (C18 REDISEP column (40 g)) to obtain desired compound 119b.

tert-butyl ((R)-2-((S)-4-((4S,5S)-4-methyl-5-phenyl-4,5-dihydrooxazol-2-yl)-2-((thiophen-2-ylmethyl)carbamoyl)piperazin-1-yl-2-oxo-1-((1r,4R)-4-(piperidin-1-yl)cyclohexyl)ethyl)carbamate (119c)

1,5-Dibromopentane (5.12 µL, 0.038 mmol) was added to a solution of tert-butyl ((R)-1-((1r,4R)-4-aminocyclohexyl)-2-((S)-4-((4S,5 S)-4-methyl-5-phenyl-4,5-dihydrooxazol-2-yl)-2-((thiophen-2-ylmethyl)carbamoyl)piperazin-1-yl)-2-oxoethyl)carbamate 119b (25 mg, 0.031 mmol) and K₂CO₃ (15.14 mg, 0.110 mmol) in DMF (1 mL). The reaction was stirred at 60° C. for 2 h. LCMS showed product formation. DCM (10 mL)/water (2 mL) was added. The DCM layer was dried over Na₂SO₄, filtered and concentrated. The reaction was purified by reverse phase HPLC by using 0.05% TFA in MeCN/water and the desired product was eluted with the 0%-70% gradient on a reverse phase to obtain 119c.

(S)-1-((R)-2-amino-2-((1r,4R)-4-(piperidin-1-yl)cyclohexyl)acetyl)-4-((4S,5S)-4-methyl-5-phenyl-4,5-dihydrooxazol-2-yl-N-(thiophen-2-ylmethyl)iperazine-2-carboxamide (119d)

4.0 M HCl in dioxane (0.021 mL, 0.085 mmol) was added to a solution of tert-butyl ((R)-2-((S)-4-((4S,5 S)-4-methyl-5-phenyl-4,5-dihydrooxazol-2-yl)-2-((thiophen-2-ylmethyl)carbamoyl)piperazin-1-yl)-2-oxo-1-((1r,4R)-4-(piperidin-1-yl)cyclohexyl)ethyl)carbamate 119c (6 mg, 8.49 µmol) in 1,4-Dioxane (0.1 mL). The resulting mixture was stirred at ambient temperature for 2 h. The excess reagents were removed, and it was dried under high vacuum. 119d was used as such for the next reaction.

(S)-1-((R)-2-((4-carbamoylcyclohexyl)amino)-2-((1r,4R)-4-(piperidin-1-yl)cyclohexyl)acetyl)-4-((4S,5S)-4-methyl-5-phenyl-4,5dihydrooxazol-2-yl)-N-(thiophen-2-ylmethyl)piperazine-2-carboxamide (119)

A solution of 4-oxocyclohexanecarboxamide (3.49 mg, 0.025 mmol), acetic acid (1.415 µL, 0.025 mmol) in THF (0.3 mL) was added to (S)-1-((R)-2-amino-2-((1r,4R)-4-(piperidin-1-yl)cyclohexyl)acetyl)-4-((4S,5 S)-4-methyl-5-phenyl-4,5-dihydrooxazol-2-yl)-N-(thiophen-2-ylmethyl)piperazine-2-carboxamide 119d (5 mg, 8.24 µmol), DIEA (5.76 µL, 0.033 mmol) in THF (0.300 mL). The resulting mixture was stirred for 2 h. LCMS showed complete conversion to product. The reagents were removed under a high vacuum. The reaction was purified by reverse phase HPLC by using 0.05% TFA in MeCN/water to obtain 119.

Example 120

(S)-1-((R)-2-amino-2-((1r,4R)-4-aminocyclohexyl)acetyl)-4-((4S,5S)-4-methyl-5-phenyl-4,5-dihydrooxazol-2-yl)-N-(thiophen-2-ylmethyl)piperazine-2-carboxamide (120a)

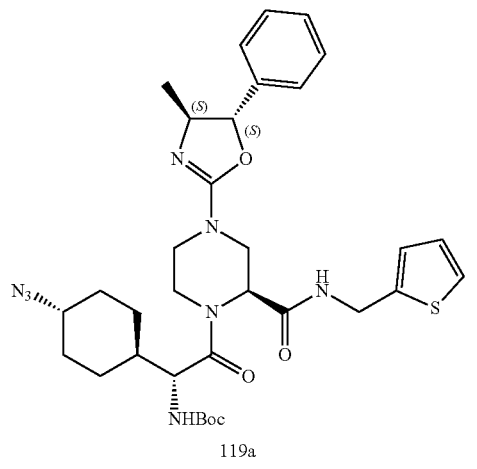

119a

Tin(II) chloride dihydrate (407 mg, 1.805 mmol) was added to a solution of tert-butyl ((R)-1-((1r,4R)-4-azidocyclohexyl)-2-((S)-4-((4S,5 S)-4-methyl-5-phenyl-4,5-dihydrooxazol-2-yl)-2-((thiophen-2-ylmethyl)carbamoyl)piperazin-1-yl)-2-oxoethyl)carbamate 119a (300 mg, 0.451 mmol) in EtOAc (6 mL)/ethanol (3.00 mL) that was stirred at r.t. for 2 h. LCMS showed a product peak. Water (2 mL) was added and the solvents were removed. EtOAc was added and it was washed with NaHCO₃ and water. The EtOAc layer was dried over Na₂SO₄, filtered and concentrated. The reaction was purified by reverse phase HPLC system using 0.05% TFA in MeCN/water. the compound was loaded on (C18 REDISEP column (40 g)) by 18 min. run.

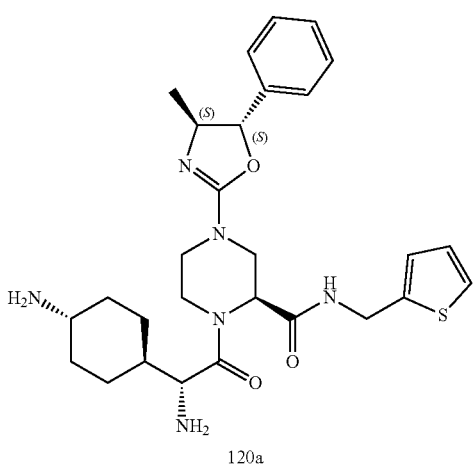

120a

(S)-1-((R)-2-(isopropylamino)-2-((1r,4R)-4-(isopropylamino)cyclohexyl)acetyl)-4-((4S,5S)-4-methyl-5-phenyl-4,5-dihydrooxazol-2-yl)-N-(thiophen-2-ylmethyl)piperazine-2-carboxamide (120)

A solution of (S)-1-((R)-2-amino-2-((1r,4R)-4-aminocyclohexyl)acetyl)-4-((4S,5 S)-4-methyl-5-phenyl-4,5-dihydrooxazol-2-yl)-N-(thiophen-2-ylmethyl)piperazine-2-carboxamide 19a (45 mg, 0.084 mmol), acetone (0.061 mL, 0.835 mmol) and AcOH (0.012 mL, 0.209 mmol) in THF (2 ml) was stirred for 10 min. MP-Cyanoborohydride (306 mg, 0.668 mmol) was added and the reaction was stirred overnight. The reaction was filtered and concentrated. The reaction was purified by reverse phase HPLC system using 0.05% TFA in MeCN/water to obtain 120.

Example 121

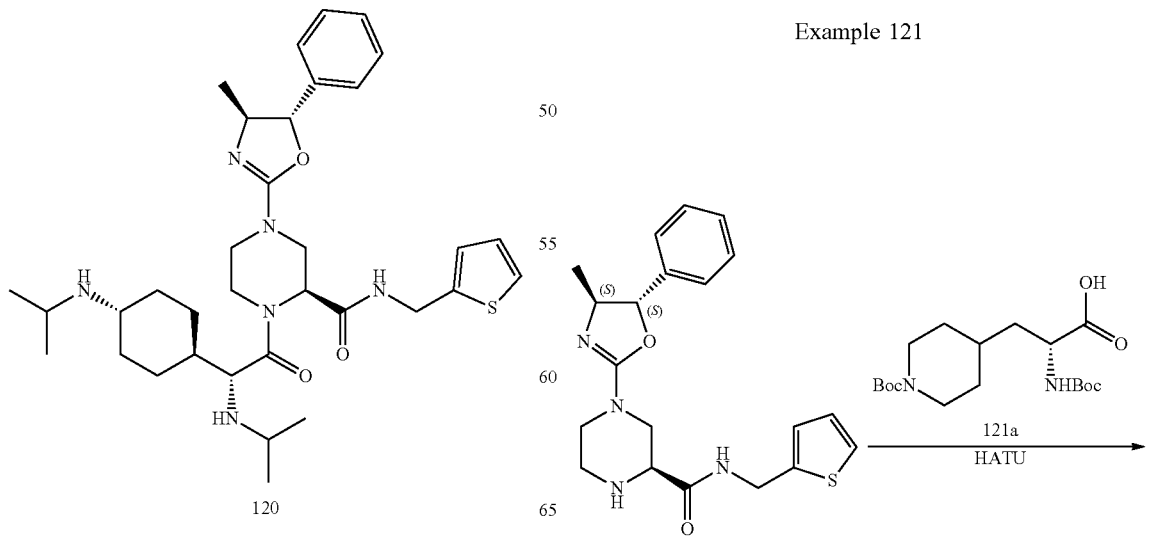

-continued

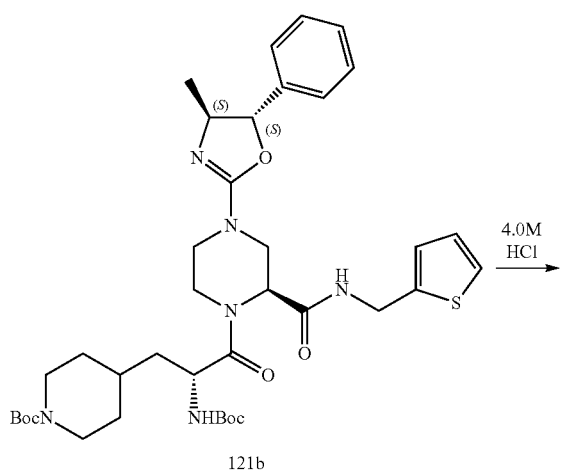

121b

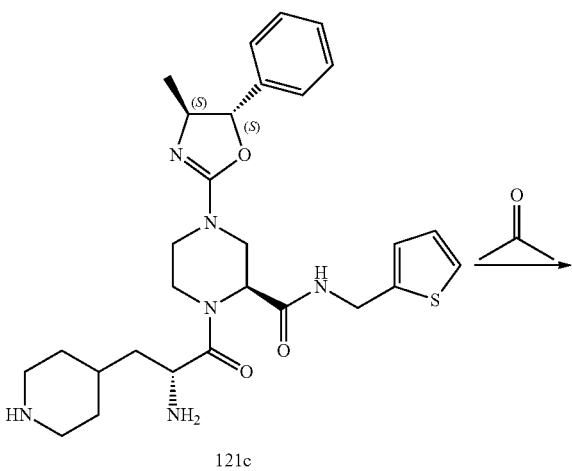

121c

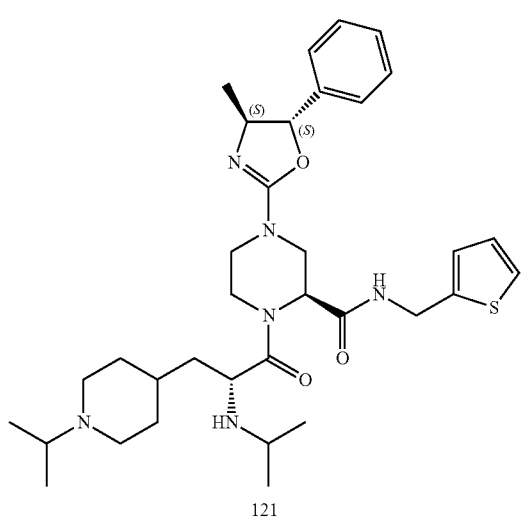

121 tert-butyl 4-((R)-2-((tert-butoxycarbonyl)amino)-3-((S)-4-((4S,5S)-4-methyl-5-phenyl-4,5-dihydrooxazol-2-yl-2-((thiophen-2-ylmethyl)carbamoyl)piperazin-1-yl-3-oxopropyl)piperidine-1-carboxylate (121b)

HATU (0.903 g, 2.376 mmol) was added to a solution of (R)-2-((tert-butoxycarbonyl)amino)-3-(1-(tert-butoxycarbonyl)piperidin-4-yl)propanoic acid 121a (1.678 g, 2.376 mmol) and DIPEA (1.245 mL, 7.13 mmol) in DMF (10 mL) followed by (S)-4-((4S,5S)-4-methyl-5-phenyl-4,5-dihydrooxazol-2-yl)-N-(thiophen-2-ylmethyl)piperazine-2-carboxamide hydrochloride (1 g, 2.376 mmol). The reaction was stirred for 1 h. LCMS showed a product peak along with SM peak. The reaction stirred overnight. LCMS showed a product peak. DCM (100 mL)/water (30 mL) was added, and the water layer was washed with DCM. The combined DCM layers were washed with brine (20 mL), dried over $Na_2SO_4$, filtered and concentrated. The reaction was purified by reverse phase column chromatography to obtain tert-butyl 4-((R)-2-((tert-butoxycarbonyl)amino)-3-((S)-4-((4S,5S)-4-methyl-5-phenyl-4,5-dihydrooxazol-2-yl)-2-((thiophen-2-ylmethyl)carbamoyl)piperazin-1-yl)-3-oxopropyl)piperidine-1-carboxylate 121b.

(S)-1-((R)-2-amino-3-(piperidin-4-yl)propanoyl)-4-((4S,5S)-4-methyl-5-phenyl-4,5-dihydrooxazol-2-yl)-N-(thiophen-2-ylmethyl)piperazine-2-carboxamide (121c)

4.0 M HCl in Dioxane (1.015 mL, 4.06 mmol) was added to a solution of tert-butyl 4-((R)-2-((tert-butoxycarbonyl)amino)-3-((4S,5 S)-4-methyl-5-phenyl-4,5-dihydrooxazol-2-yl)-2-((thiophen-2-ylmethyl)carbamoyl)piperazin-1-yl)-3-oxopropyl)piperidine-1-carboxylate 121b (200 mg, 0.271 mmol) in Dioxane (0.5 mL). The resulting mixture was stirred for 1 h. LCMS showed complete conversion to product. The reagents were removed and it was dried under a high vacuum. (S)-1-((R)-2-amino-3-(piperidin-4-yl)propanoyl)-4-((4S,5S)-4-methyl-5-phenyl-4,5-dihydrooxazol-2-yl)-N-(thiophen-2-ylmethyl)piperazine-2-carboxamide hydrochloride 121c was obtained. The crude was used as such for the next reaction.

(S)-1-((R)-2-(isopropylamino)-3-(1-isopropylpiperidin-4-yl)propanoyl)-4-((4S,5S)-4-methyl-5-phenyl-4,5-dihydrooxazol-2-yl)-N-(thiophen-2-ylmethyl)piperazine-2-carboxamide (121)

A solution of (S)-1-((R)-2-amino-3-(piperidin-4-yl)propanoyl)-4-((4S,5S)-4-methyl-5-phenyl-4,5-dihydrooxazol-2-yl)-N-(thiophen-2-ylmethyl)piperazine-2-carboxamide hydrochloride 19c (25 mg, 0.043 mmol) and DIEA (0.046 mL, 0.261 mmol) in tetrahydrofuran (1 mL) was stirred for a minute. Acetone (0.064 mL, 0.869 mmol) was added, and the resulting mixture was stirred for 20 min. $NaCNBH_4$ in THF (0.130 mL, 0.130 mmol) was added and stirring was continued overnight. The reagents were removed. MeOH/DMSO (0.5 mL/0.5 mL) were added and the mixture was purified by reverse phase HPLC system using 0.05% TFA in MeCN/water. (S)-1-((R)-2-(isopropylamino)-3-(1-isopropylpiperidin-4-yl)propanoyl)-4-((4S,5S)-4-methyl-5-phenyl-4,5-dihydrooxazol-2-yl)-N-(thiophen-2-ylmethyl)piperazine-2-carboxamide 121 was obtained. Using the appropriate starting materials and following similar synthetic sequences to those described above, the following compounds of Table 2 were prepared.

TABLE 2

| Example number | Structure | Name | Exact Mass [M + H]+ | FXIIa IC50 (nM) |
|---|---|---|---|---|
| 114 | 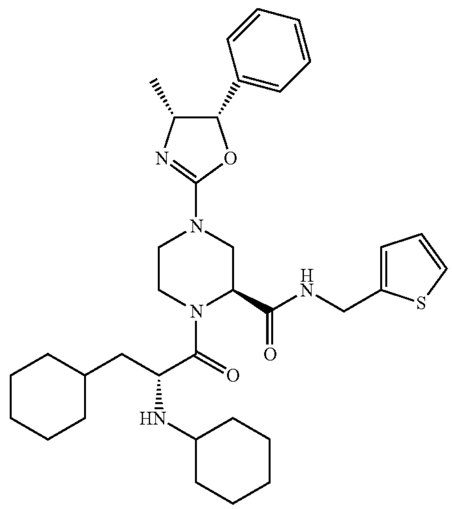 [SMILES: C[C@H]1N=C(N2CCN(C(=O)[C@@H](CC3CCCCC3)NC3CCCCC3)[C@H](C(=O)NCc3cccs3)C2)O[C@H]1c1ccccc1] | (2S)-1-(N,3-dicyclohexyl-D-alanyl)-4-[(4R,5S)-4-methyl-5-phenyl-4,5-dihydro-1,3-oxazol-2-yl]-N-(thiophen-2-ylmethyl)piperazine-2-carboxamide | 620.4 | 17.1 |
| 115 | 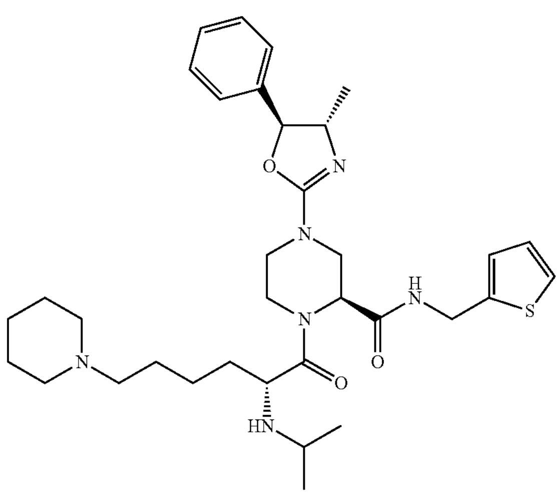 [SMILES: CC(C)N[C@H](CCCCN1CCCCC1)C(=O)N1CCN(C2=N[C@@H](C)[C@H](c3ccccc3)O2)C[C@H]1C(=O)NCc1cccs1] | (2S)-1-[N-(1-methylethyl)-6-piperidin-1-yl-D-norleucyl]-4-[(4S,5S)-4-methyl-5-phenyl-4,5-dihydro-1,3-oxazol-2-yl]-N-(thiophen-2-ylmethyl)piperazine-2-carboxamide | 623.4 | 3.8 |

TABLE 2-continued

| Example number | Structure | Name | Exact Mass [M + H]+ | FXIIa IC50 (nM) |
|---|---|---|---|---|
| 116 | 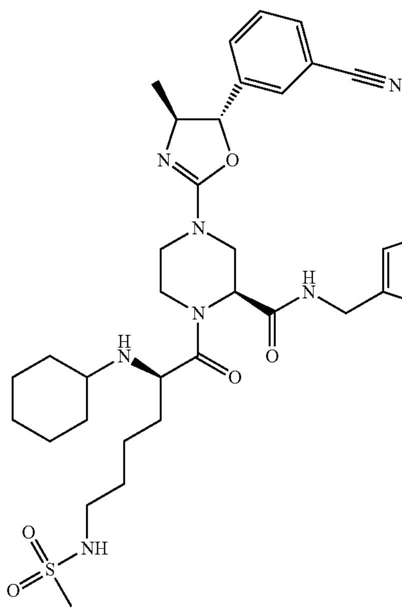 | (2S)-4-[(4S,5S)-5-(3-cyanophenyl)-4-methyl-4,5-dihydro-1,3-oxazol-2-yl]-1-[N$^2$-cyclohexyl-N$^6$-(methylsulfonyl)-D-lysyl]-N-(thiophen-2-ylmethyl)piperazine-2-carboxamide | 698.3 | 17.8 |
| 117 | 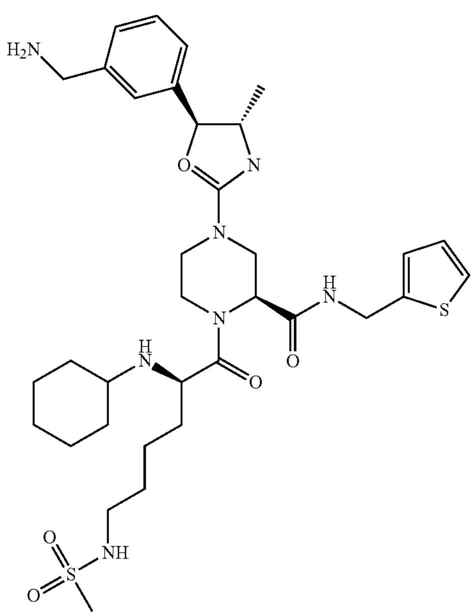 | (2S)-4-{(4S,5S)-5-[3-(aminomethyl)phenyl]-4-methyl-4,5-dihydro-1,3-oxazol-2-yl}-1-[N$^2$-cyclohexyl-N$^6$-(methylsulfonyl)-D-lysyl]-N-(thiophen-2-ylmethyl)piperazine-2-carboxamide | 702.3 | 5.2 |

TABLE 2-continued

| Example number | Structure | Name | Exact Mass [M + H]+ | FXIIa IC50 (nM) |
|---|---|---|---|---|
| 118 | 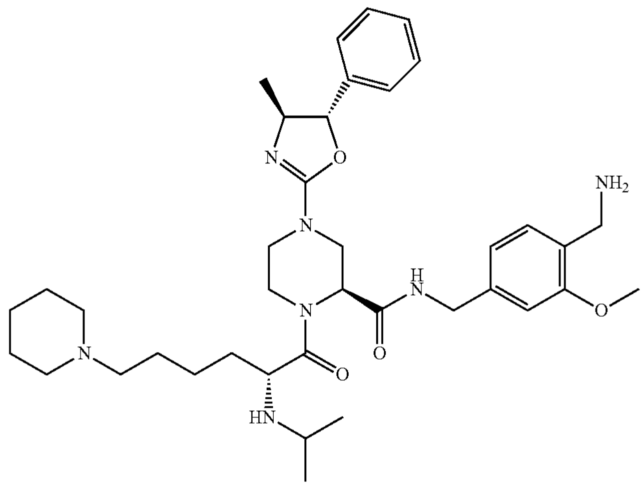 [SMILES: COc1cc(CNC(=O)[C@@H]2CN(C3=N[C@@H](C)[C@H](c4ccccc4)O3)CCN2C(=O)[C@@H](CCCCN2CCCCC2)NC(C)C)ccc1CN] | (2S)-N-[4-(aminomethyl)-3-methoxybenzyl]-1-[N-(1-methylethyl)-6-piperidin-1-yl-D-norleucyl]-4-[(4S,5S)-4-methyl-5-phenyl-4,5-dihydro-1,3-oxazol-2-yl]piperazine-2-carboxamide | 676.5 | 8.1 |
| 119 | 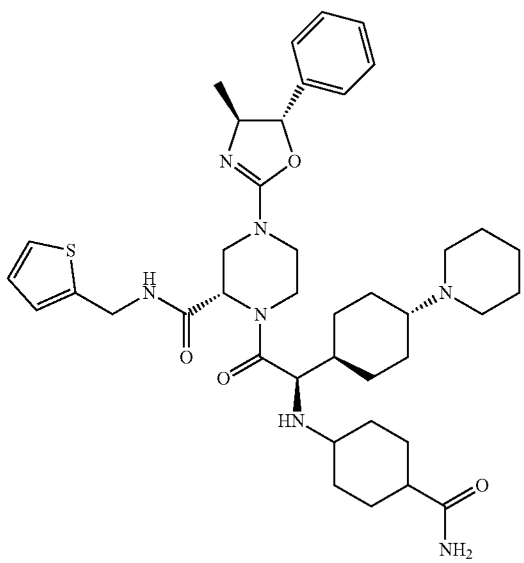 [SMILES: C[C@@H]1N=C(N2CCN(C(=O)[C@H](NC3CCC(C(N)=O)CC3)[C@H]3CC[C@H](N4CCCCC4)CC3)[C@H](C(=O)NCc3cccs3)C2)O[C@H]1c1ccccc1] | (2S)-1-[(2R)-2-[(4-carbamoylcyclohexyl)amino]-2-(trans-4-piperidin-1-ylcyclohexyl)acetyl]-4-[(4S,5S)-4-methyl-5-phenyl-4,5-dihydro-1,3-oxazol-2-yl]-N-(thiophen-2-ylmethyl)piperazine-2-carboxamide | 732.4 | 1.5 |
| 120 | 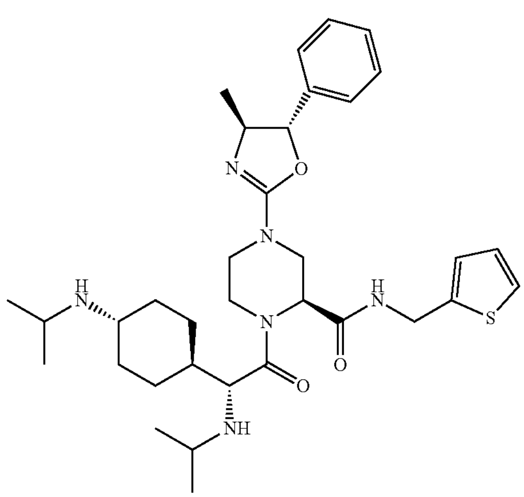 [SMILES: CC(C)N[C@@H](C(=O)N1CCN(C2=N[C@@H](C)[C@H](c3ccccc3)O2)C[C@H]1C(=O)NCc1cccs1)[C@H]1CC[C@H](NC(C)C)CC1] | (2S)-1-[(2R)-2-[(1-methylethyl)amino]-2-{trans-4-[(1-methylethyl)amino]cyclohexyl}acetyl]-4-[(4S,5S)-4-methyl-5-phenyl-4,5-dihydro-1,3-oxazol-2-yl]-N-(thiophen-2-ylmethyl)piperazine-2-carboxamide | 623.4 | 5.6 |

TABLE 2-continued

| Example number | Structure | Name | Exact Mass [M + H]+ | FXIIa IC50 (nM) |
|---|---|---|---|---|
| 121 | 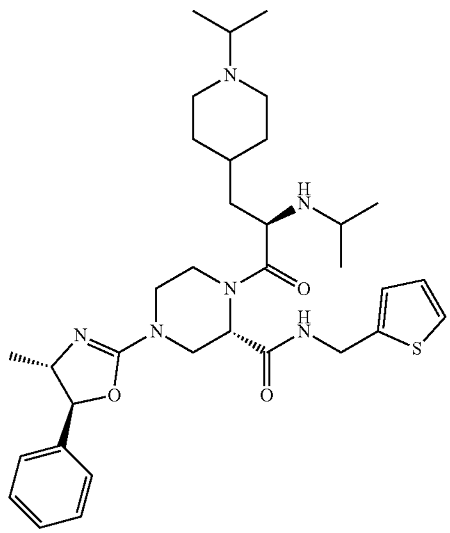 [SMILES: CC(C)N[C@H](CC1CCN(C(C)C)CC1)C(=O)N1CCN(C2=N[C@@H](C)[C@H](c3ccccc3)O2)C[C@H]1C(=O)NCc1cccs1] | (2S)-1-{N-(1-methylethyl)-3-[1-(1-methylethyl)piperidin-4-yl]-D-alanyl}-4-[(4S,5S)-4-methyl-5-phenyl-4,5-dihydro-1,3-oxazol-2-yl]-N-(thiophen-2-ylmethyl)piperazine-2-carboxamide | 623.4 | 10.0 |
| 122 | 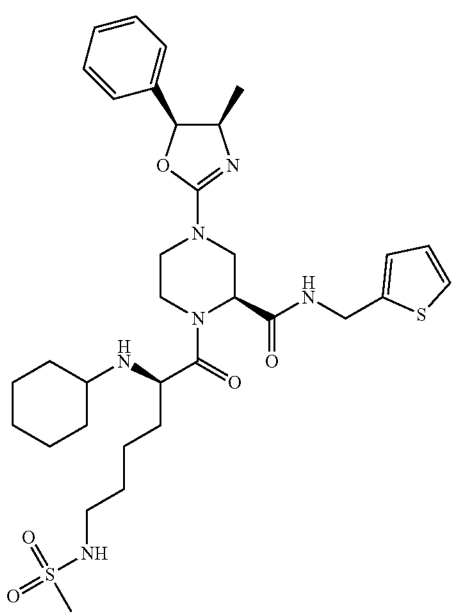 [SMILES: C[C@H]1N=C(N2CCN(C(=O)[C@@H](CCCCNS(C)(=O)=O)NC3CCCCC3)[C@H](C(=O)NCc3cccs3)C2)O[C@H]1c1ccccc1] | (2S)-1-[N$^2$-cyclohexyl-N$^6$-(methylsulfonyl)-D-lysyl]-4-[(4R,5S)-4-methyl-5-phenyl-4,5-dihydro-1,3-oxazol-2-yl]-N-(thiophen-2-ylmethyl)piperazine-2-carboxamide | 673.3 | 13.5 |

TABLE 2-continued

| Example number | Structure | Name | Exact Mass [M + H]+ | FXIIa IC50 (nM) |
|---|---|---|---|---|
| 123 | 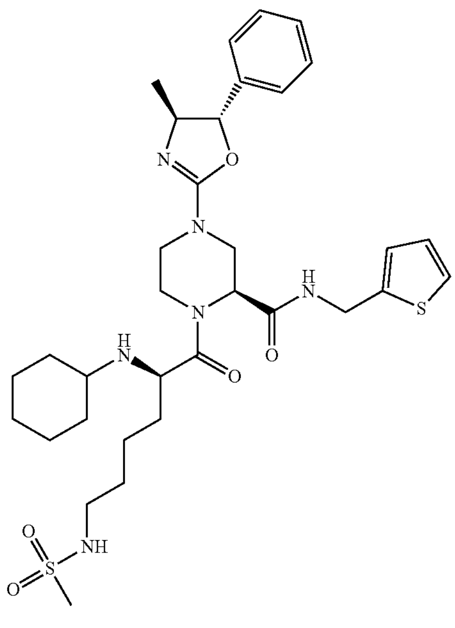 [SMILES: C[C@@H]1N=C(N2CCN(C(=O)[C@@H](CCCCNS(C)(=O)=O)NC3CCCCC3)[C@H](C(=O)NCc3cccs3)C2)O[C@H]1c1ccccc1] | (2S)-1-[N$^2$-cyclohexyl-N$^6$-(methylsulfonyl)-D-lysyl]-4-[(4S,5S)-4-methyl-5-phenyl-4,5-dihydro-1,3-oxazol-2-yl]-N-(thiophen-2-ylmethyl)piperazine-2-carboxamide | 673.3 | 7.0 |
| 124 | 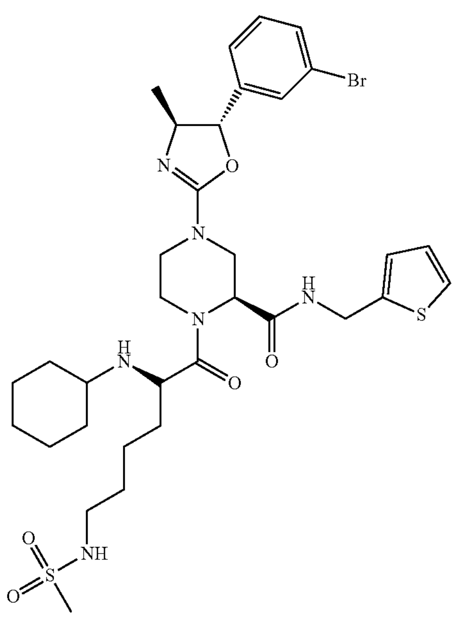 | (2S)-4-[(4S,5S)-5-(3-bromophenyl)-4-methyl-4,5-dihydro-1,3-oxazol-2-yl]-1-[N$^2$-cyclohexyl-N$^6$-(methylsulfonyl)-D-lysyl]-N-(thiophen-2-ylmethyl)piperazine-2-carboxamide | 751.2 | 24.6 |

TABLE 2-continued

| Example number | Structure | Name | Exact Mass [M + H]+ | FXIIa IC50 (nM) |
|---|---|---|---|---|
| 125 | 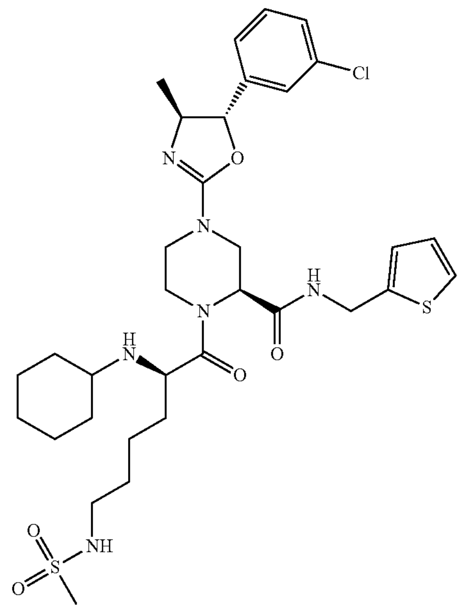 [SMILES: C[C@@H]1N=C(N2CCN(C(=O)[C@@H](CCCCNS(C)(=O)=O)NC3CCCCC3)[C@H](C(=O)NCc3cccs3)C2)O[C@H]1c1cccc(Cl)c1] | (2S)-4-[(4S,5S)-5-(3-chlorophenyl)-4-methyl-4,5-dihydro-1,3-oxazol-2-yl]-1-[$N^2$-cyclohexyl-$N^6$-(methylsulfonyl)-D-lysyl]-N-(thiophen-2-ylmethyl)piperazine-2-carboxamide | 707.3 | 23.0 |
| 126 | 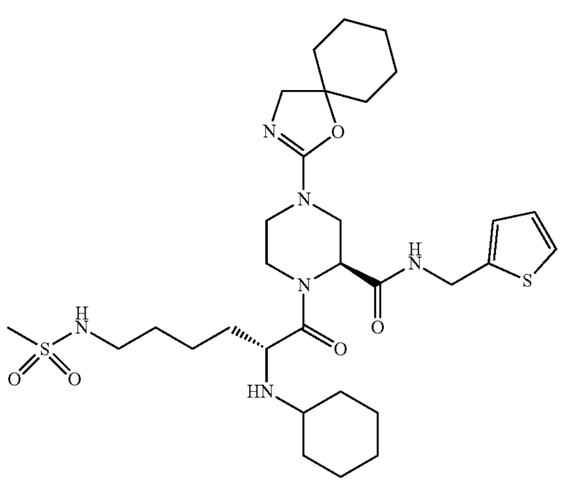 [SMILES: CS(=O)(=O)NCCCC[C@@H](NC1CCCCC1)C(=O)N1CCN(C2=NCC3(CCCCC3)O2)C[C@H]1C(=O)NCc1cccs1] | (2S)-1-[$N^2$-cyclohexyl-$N^6$-(methylsulfonyl)-D-lysyl]-4-(1-oxa-3-azaspiro[4.5]dec-2-en-2-yl)-N-(thiophen-2-ylmethyl)piperazine-2-carboxamide | 651.3 | 21.1 |

TABLE 2-continued

| Example number | Structure | Name | Exact Mass [M + H]+ | FXIIa IC50 (nM) |
|---|---|---|---|---|
| 127 | 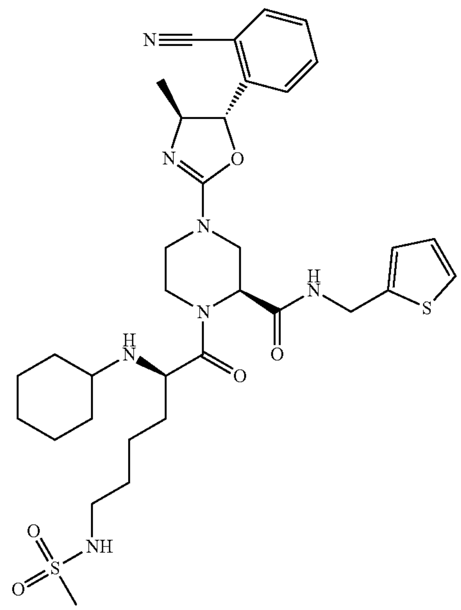 [SMILES: C[C@@H]1N=C(N2CCN(C(=O)[C@@H](CCCCNS(C)(=O)=O)NC3CCCCC3)[C@H](C(=O)NCc3cccs3)C2)O[C@H]1c1ccccc1C#N] | (2S)-4-[(4S,5S)-5-(2-cyanophenyl)-4-methyl-4,5-dihydro-1,3-oxazol-2-yl]-1-[N²-cyclohexyl-N⁶-(methylsulfonyl)-D-lysyl]-N-(thiophen-2-ylmethyl)piperazine-2-carboxamide | 698.3 | 18.7 |
| 128 | 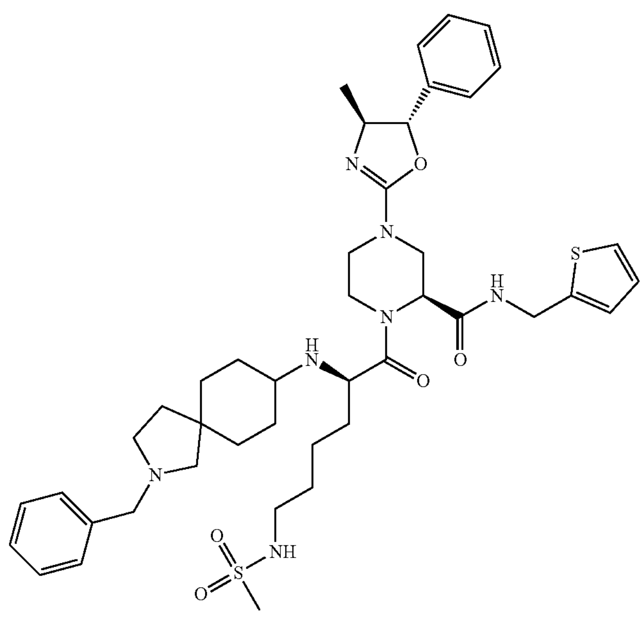 [SMILES: C[C@@H]1N=C(N2CCN(C(=O)[C@@H](CCCCNS(C)(=O)=O)NC3CCC4(CC3)CCN(Cc3ccccc3)C4)[C@H](C(=O)NCc3cccs3)C2)O[C@H]1c1ccccc1] | (2S)-1-[N²-(2-benzyl-2-azaspiro[4.5]dec-8-yl)-N⁶-(methylsulfonyl)-D-lysyl]-4-[(4S,5S)-4-methyl-5-phenyl-4,5-dihydro-1,3-oxazol-2-yl]-N-(thiophen-2-ylmethyl)piperazine-2-carboxamide | 818.4 | 10.2 |

TABLE 2-continued

| Example number | Structure | Name | Exact Mass [M + H]+ | FXIIa IC50 (nM) |
|---|---|---|---|---|
| 129 | 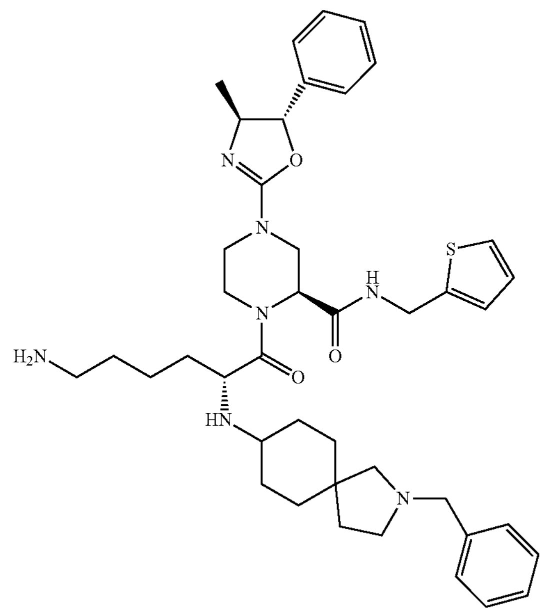 [SMILES: C[C@@H]1N=C(N2CCN(C(=O)[C@@H](CCCCN)NC3CCC4(CC3)CCN(Cc3ccccc3)C4)[C@H](C(=O)NCc3cccs3)C2)O[C@H]1c1ccccc1] | (2S)-1-[N²-(2-benzyl-2-azaspiro[4.5]dec-8-yl)-D-lysyl]-4-[(4S,5S)-4-methyl-5-phenyl-4,5-dihydro-1,3-oxazol-2-yl]-N-(thiophen-2-ylmethyl)piperazine-2-carboxamide | 740.4 | 13.0 |
| 130 | 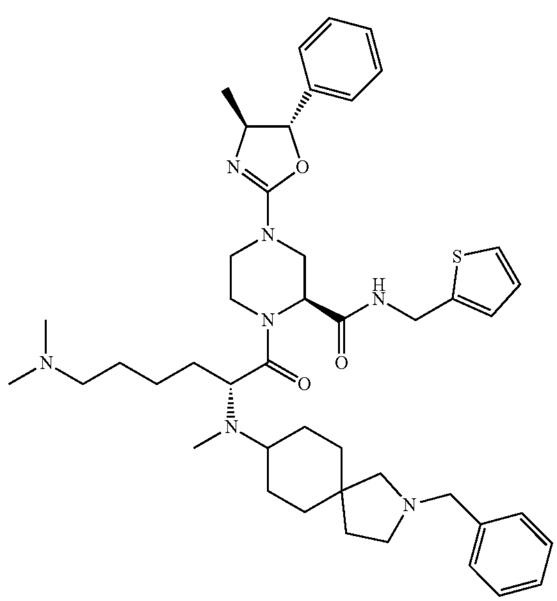 [SMILES: C[C@@H]1N=C(N2CCN(C(=O)[C@@H](CCCCN(C)C)N(C)C3CCC4(CC3)CCN(Cc3ccccc3)C4)[C@H](C(=O)NCc3cccs3)C2)O[C@H]1c1ccccc1] | (2S)-1-[N²-(2-benzyl-2-azaspiro[4.5]dec-8-yl)-N⁶,N⁶-dimethyl-D-lysyl]-4-[(4S,5S)-4-methyl-5-phenyl-4,5-dihydro-1,3-oxazol-2-yl]-N-(thiophen-2-ylmethyl)piperazine-2-carboxamide | 768.5 | 1.2 |

TABLE 2-continued

| Example number | Structure | Name | Exact Mass [M + H]+ | FXIIa IC50 (nM) |
|---|---|---|---|---|
| 131 | 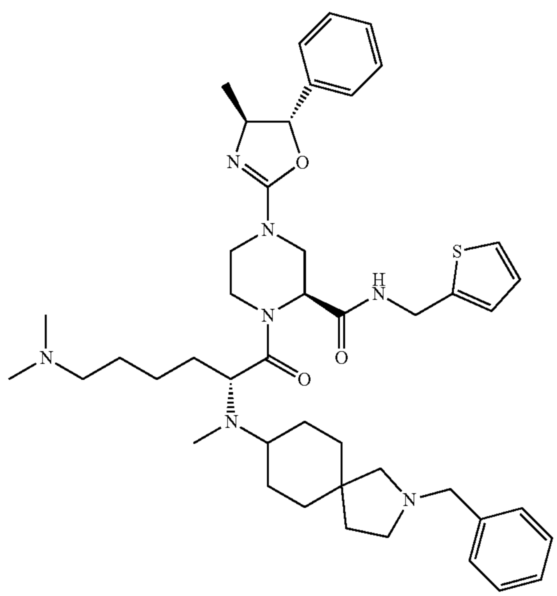 [SMILES: C[C@@H]1N=C(N2CCN(C(=O)[C@@H](CCCCN(C)C)N(C)C3CCC4(CC3)CCN(Cc3ccccc3)C4)[C@H](C(=O)NCc3cccs3)C2)O[C@H]1c1ccccc1] | (2S)-1-[$N^2$-(2-benzyl-2-azaspiro[4.5]dec-8-yl)-$N^2$,$N^6$,$N^6$-trimethyl-D-lysl]-4-[(4S,5S)-4-methyl-5-phenyl-4,5-dihydro-1,3-oxazol-2-yl]-N-(thiophen-2-ylmethyl)piperazine-2-carboxamide | 782.5 | 1.8 |
| 132 | 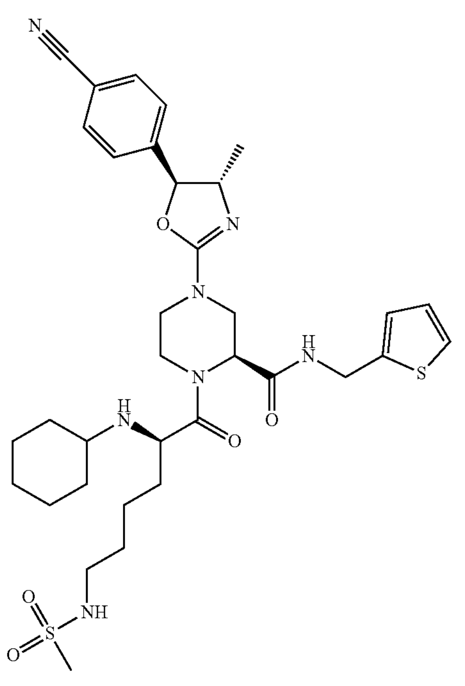 [SMILES: C[C@@H]1N=C(N2CCN(C(=O)[C@@H](CCCCNS(C)(=O)=O)NC3CCCCC3)[C@H](C(=O)NCc3cccs3)C2)O[C@H]1c1ccc(C#N)cc1] | (2S)-[(4S,5S)-5-(4-cyanophenyl)-4-methyl-4,5-dihydro-1,3-oxazol-2-yl]-1-[$N^2$-cyclohexyl-$N^6$-(methylsulfonyl)-D-lysyl]-N-(thiophen-2-ylmethyl)piperazine-2-carboxamide | 698.3 | 52.6 |

TABLE 2-continued

| Example number | Structure | Name | Exact Mass [M + H]+ | FXIIa IC50 (nM) |
|---|---|---|---|---|
| 133 | 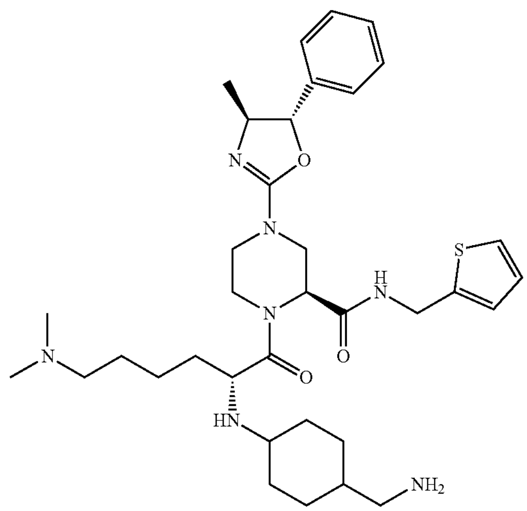 [SMILES: C[C@@H]1N=C(N2CCN(C(=O)[C@@H](CCCCN(C)C)NC3CCC(CN)CC3)[C@H](C(=O)NCc3cccs3)C2)O[C@H]1c1ccccc1] | (2S)-1-{N²-[4-(aminomethyl)cyclohexyl]-N⁶,N⁶-dimethyl-D-lysyl}-4-[(4S,5S)-4-methyl-5-phenyl-4,5-dihydro-1,3-oxazol-2-yl]-N-(thiophen-2-ylmethyl)piperazine-2-carboxamide | 652.6 | 6.6 |
| 134 | 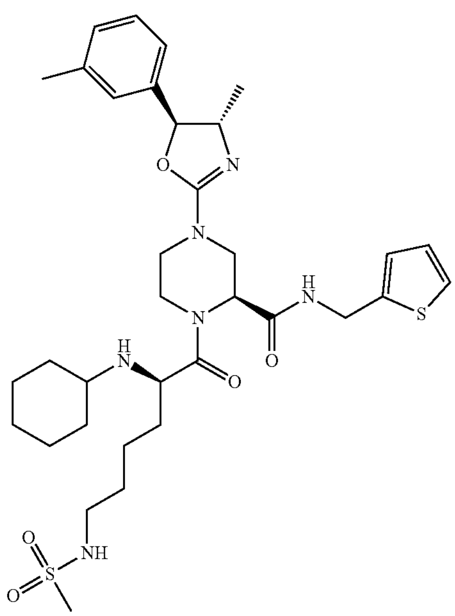 [SMILES: Cc1cccc([C@@H]2OC(N3CCN(C(=O)[C@@H](CCCCNS(C)(=O)=O)NC4CCCCC4)[C@H](C(=O)NCc4cccs4)C3)=N[C@H]2C)c1] | (2S)-1-[N²-cyclohexyl-N⁶-(methylsulfonyl)-D-lysyl]-4-[(4S,5S)-4-methyl-5-(3-methylphenyl)-4,5-dihydro-1,3-oxazol-2-yl]-N-(thiophen-2-ylmethyl)piperazine-2-carboxamide | 687.3 | 10.3 |

TABLE 2-continued

| Example number | Structure | Name | Exact Mass [M + H]+ | FXIIa IC50 (nM) |
|---|---|---|---|---|
| 135 | 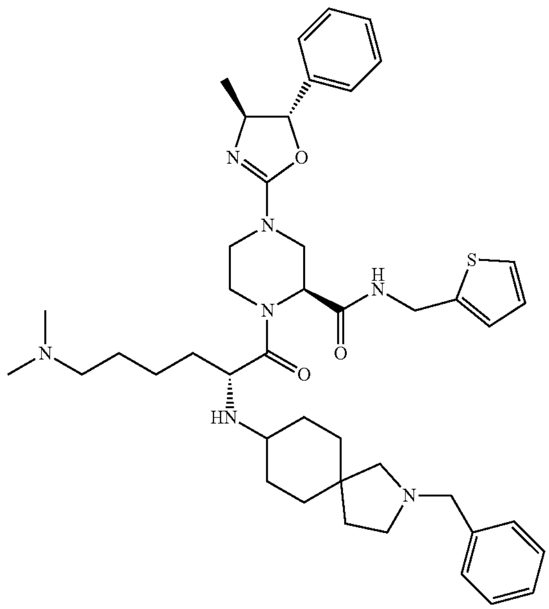 [SMILES: C[C@@H]1N=C(N2CCN(C(=O)[C@@H](CCCCN(C)C)NC3CCC4(CC3)CCN(Cc3ccccc3)C4)[C@H](C(=O)NCc3cccs3)C2)O[C@H]1c1ccccc1] | (2S)-1-[N²-(2-benzyl-2-azaspiro[4.5]dec-8-yl)-N⁶,N⁶-dimethyl-D-lysyl]-4-[(4S,5S)-4-methyl-5-phenyl-4,5-dihydro-1,3-oxazol-2-yl]-N-(thiophen-2-ylmethyl)piperazine-2-carboxamide | 768.5 | 0.8 |
| 136 | 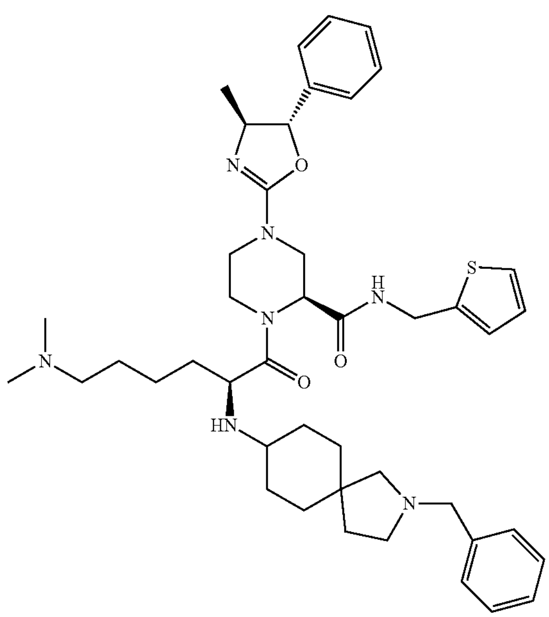 [SMILES: C[C@@H]1N=C(N2CCN(C(=O)[C@H](CCCCN(C)C)NC3CCC4(CC3)CCN(Cc3ccccc3)C4)[C@H](C(=O)NCc3cccs3)C2)O[C@H]1c1ccccc1] | (2S)-1-N²-(2-benzyl-2-azaspiro[4.5]dec-8-yl)-N⁶,N⁶-dimethyl-L-lysyl]-4-[(4S,5S)-4-methyl-5-phenyl-4,5-dihydro-1,3-oxazol-2-yl]-N-(thiophen-2-ylmethyl)piperazine-2-carboxamide | 768.5 | 23.2 |

TABLE 2-continued

| Example number | Structure | Name | Exact Mass [M + H]+ | FXIIa IC50 (nM) |
|---|---|---|---|---|
| 137 | 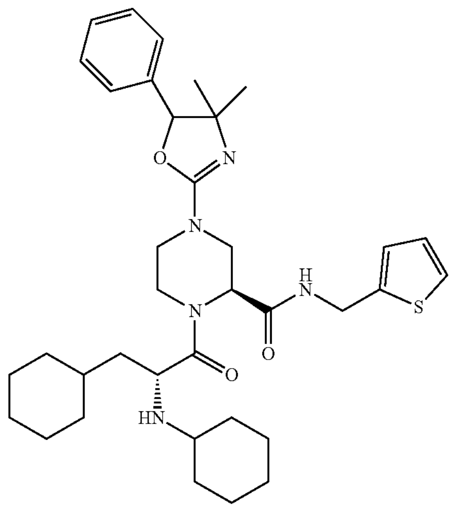 [SMILES: CC1(C)N=C(N2CCN(C(=O)[C@@H](CC3CCCCC3)NC3CCCCC3)[C@H](C(=O)NCc3cccs3)C2)OC1c1ccccc1] | (2S)-1-(N,3-dicyclohexyl-D-alanyl)-4-(4,4-dimethyl-5-phenyl-4,5-dihydro-1,3-oxazol-2-yl)-N-(thiophen-2-ylmethyl)piperazine-2-carboxamide | 634.5 | 23.2 |
| 138 | 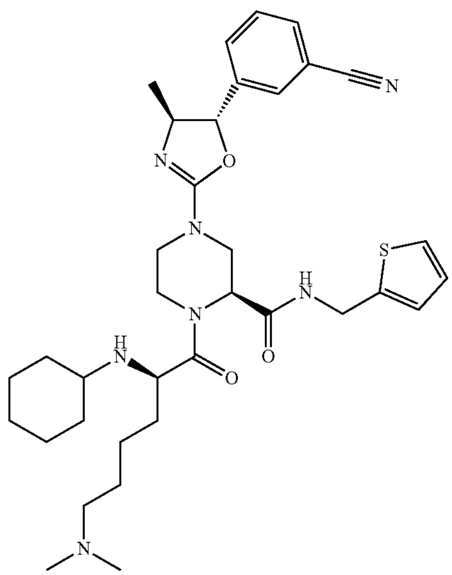 [SMILES: C[C@@H]1N=C(N2CCN(C(=O)[C@@H](CCCCN(C)C)NC3CCCCC3)[C@H](C(=O)NCc3cccs3)C2)O[C@H]1c1cccc(C#N)c1] | (2S)-4-[(4S,5S)-5-(3-cyanophenyl)-4-methyl-4,5-dihydro-1,3-oxazol-2-yl]-1-($N^2$-cyclohexyl-$N^6$,$N^6$-dimethyl-D-lysyl)-N-(thiophen-2-ylmethyl)piperazine-2-carboxamide | 648.4 | 1.4 |
| 139 | 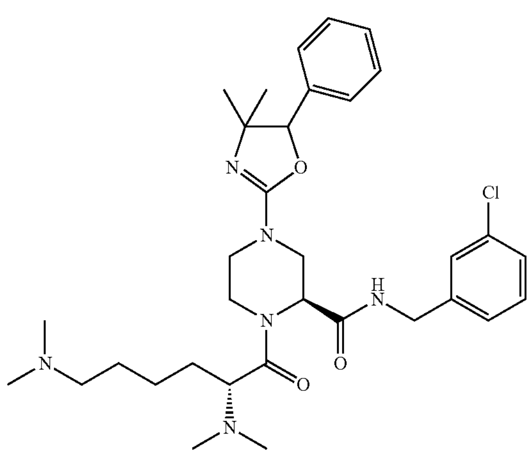 [SMILES: CN(C)CCCC[C@H](C(=O)N1CCN(C2=NC(C)(C)C(c3ccccc3)O2)C[C@H]1C(=O)NCc1cccc(Cl)c1)N(C)C] | (2S)-N-(3-chlorobenzyl)-4-(4,4-dimethyl-5-phenyl-4,5-dihydro-1,3-oxazol-2-yl)-1-($N^2$,$N^2$,$N^6$,$N^6$-tetramethyl-D-lysyl)piperazine-2-carboxamide | 611.3 | 52.4 |

| Example number | Structure | Name | Exact Mass [M + H]+ | FXIIa IC50 (nM) |
|---|---|---|---|---|
| 140 | 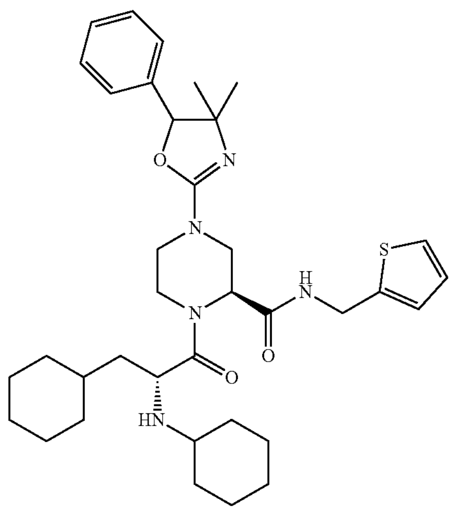 [SMILES: CC1(C)N=C(N2CCN(C(=O)[C@@H](CC3CCCCC3)NC3CCCCC3)[C@H](C(=O)NCc3cccs3)C2)OC1c1ccccc1] | (2S)-1-(N,3-dicyclohexyl-D-alanyl)-4-(4,4-dimethyl-5-phenyl-4,5-dihydro-1,3-oxazol-2-yl)-N-(thiophen-2-ylmethyl)piperazine-2-carboxamide | 634.4 | 19.0 |
| 141 | 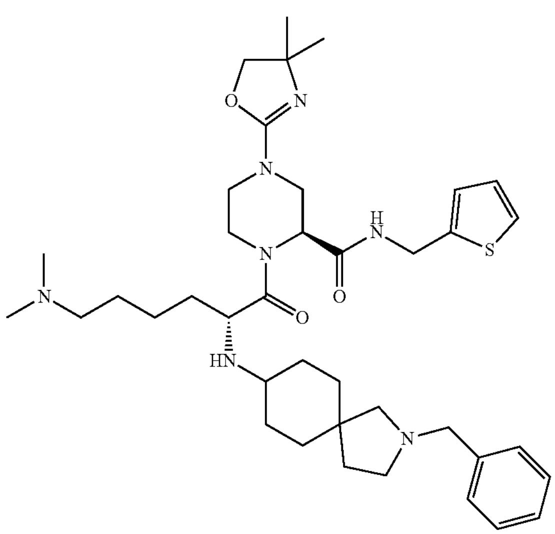 [SMILES: CN(C)CCCC[C@@H](NC1CCC2(CC1)CCN(Cc1ccccc1)C2)C(=O)N1CCN(C2=NC(C)(C)CO2)C[C@H]1C(=O)NCc1cccs1] | (2S)-1-[$N^2$-(2-benzyl-2-azaspiro[4.5]dec-8-yl)-$N^6$,$N^6$-dimethyl-D-lysyl]-4-(4,4-dimethyl-4,5-dihydro-1,3-oxazol-2-yl)-N-(thiophen-2-ylmethyl)piperazine-2-carboxamide | 706.4 | 9.2 |

TABLE 2-continued
| Example number | Structure | Name | Exact Mass [M + H]+ | FXIIa IC50 (nM) |
|---|---|---|---|---|
| 142 | 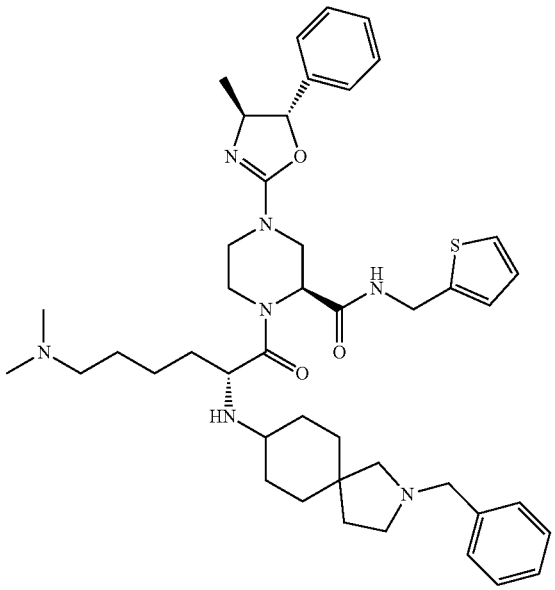 [SMILES: C[C@@H]1N=C(N2CCN(C(=O)[C@@H](CCCCN(C)C)NC3CCC4(CC3)CCN(Cc3ccccc3)C4)[C@H](C(=O)NCc3cccs3)C2)O[C@H]1c1ccccc1] | (2S)-1-[N²-(2-benzyl-2-azaspiro[4.5]dec-8-yl)-N⁶,N⁶-dimethyl-D-lysyl]-4-[(4S,5S)-4-methyl-5-phenyl-4,5-dihydro-1,3-oxazol-2-yl]-N-(thiophen-2-ylmethyl)piperazine-2-carboxamide | 768.5 | 0.4 |
| 143 | 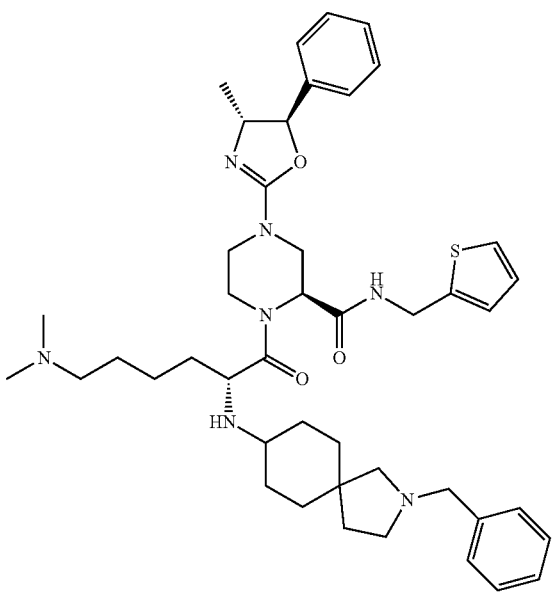 [SMILES: C[C@H]1N=C(N2CCN(C(=O)[C@@H](CCCCN(C)C)NC3CCC4(CC3)CCN(Cc3ccccc3)C4)[C@H](C(=O)NCc3cccs3)C2)O[C@@H]1c1ccccc1] | (2S)-1[N²-(2-benzyl-2-azaspiro[4.5]dec-8-yl)-N⁶,N⁶-dimethyl-D-lysyl]-4-[(4R,5R)-4-methyl-5-phenyl-4,5-dihydro-1,3-oxazol-2-yl]-N-(thiophen-2-ylmethyl)piperazine-2-carboxamide | 768.5 | 9.4 |

TABLE 2-continued

| Example number | Structure | Name | Exact Mass [M + H]+ | FXIIa IC50 (nM) |
|---|---|---|---|---|
| 144 | 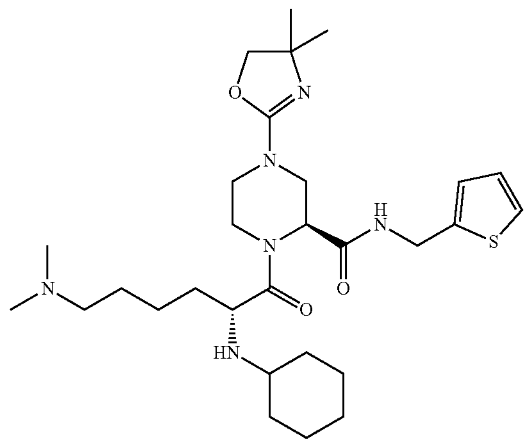 [SMILES: CN(C)CCCC[C@@H](NC1CCCCC1)C(=O)N1CCN(C2=NC(C)(C)CO2)C[C@H]1C(=O)NCc1cccs1] | (2S)-1-(N²-cyclohexyl-N⁶,N⁶-dimethyl-D-lysyl)-4-(4,4-dimethyl-4,5-dihydro-1,3-oxazol-2-yl)-N-(thiophen-2-ylmethyl)piperazine-2-carboxamide | 561.4 | 29.7 |
| 145 | 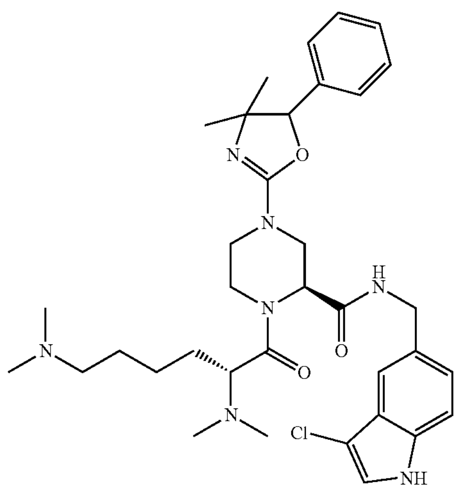 [SMILES: CN(C)CCCC[C@H](C(=O)N1CCN(C2=NC(C)(C)C(c3ccccc3)O2)C[C@H]1C(=O)NCc1ccc2[nH]cc(Cl)c2c1)N(C)C] | (2S)-N-[(3-chloro-1H-indol-5-yl)methyl]-4-(4,4-dimethyl-5-phenyl-4,5-dihydro-1,3-oxazol-2-yl)-1-(N²,N²,N⁶,N⁶-tetramethyl-D-lysyl)piperazine-2-carboxamide | 650.4 | 6.7 |
| 146 | 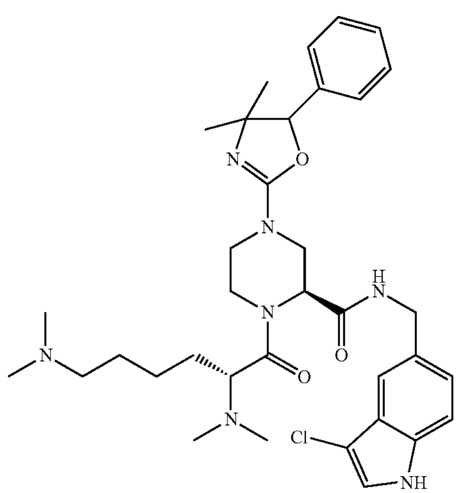 [SMILES: CN(C)CCCC[C@H](C(=O)N1CCN(C2=NC(C)(C)C(c3ccccc3)O2)C[C@H]1C(=O)NCc1ccc2[nH]cc(Cl)c2c1)N(C)C] | (2S)-N-[(3-chloro-1H-indol-5-yl)methyl]-4-(4,4-dimethyl-5-phenyl-4,5-dihydro-1,3-oxazol-2-yl)-1-(N²,N²,N⁶,N⁶-tetramethyl-D-lysyl)piperazine-2-carboxamide | 650.4 | 5.7 |

TABLE 2-continued

| Example number | Structure | Name | Exact Mass [M + H]+ | FXIIa IC50 (nM) |
|---|---|---|---|---|
| 147 | 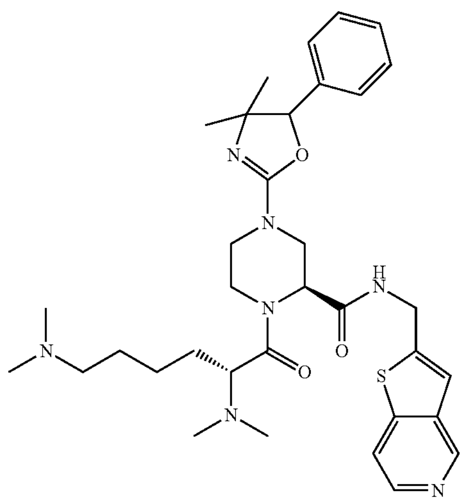 [SMILES: CN(C)CCCC[C@H](C(=O)N1CCN(C2=NC(C)(C)C(c3ccccc3)O2)C[C@H]1C(=O)NCc1cc2cnccc2s1)N(C)C] | (2S)-4-(4,4-dimethyl-5-phenyl-4,5-dihydro-1,3-oxazol-2-yl)-1-($N^2,N^2,N^6,N^6$-tetramethyl-D-lysyl)-N-(thieno[3,2-c]pyridin-2-ylmethyl)piperazine-2-carboxamide | 634.4 | 44.1 |
| 148 | 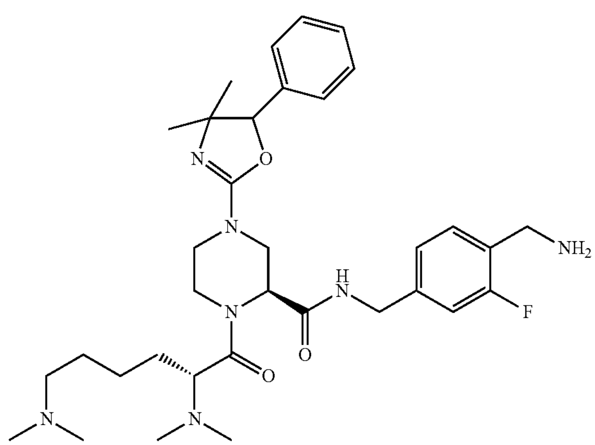 [SMILES: CN(C)CCCC[C@H](C(=O)N1CCN(C2=NC(C)(C)C(c3ccccc3)O2)C[C@H]1C(=O)NCc1ccc(CN)c(Cl)c1)N(C)C] | (2S)-N-[4-(aminomethyl)-3-fluorobenzyl]-4-(4,4-dimethyl-5-phenyl-4,5-dihydro-1,3-oxazol-2-yl)-1-($N^2,N^2,N^6,N^6$-tetramethyl-D-lysyl)piperazine-2-carboxamide | 624.4 | 12.7 |
| 149 | 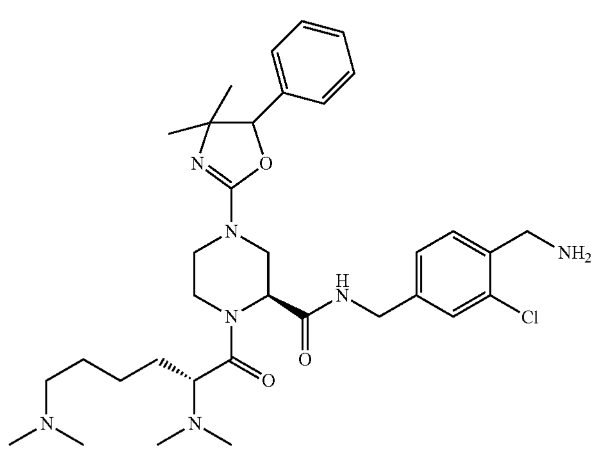 | (2S)-N-[4-(aminomethyl)-3-chlorobenzyl]-4-(4,4-dimethyl-5-phenyl-4,5-dihydro-1,3-oxazol-2-yl)-1-($N^2,N^2,N^6,N^6$-tetramethyl-D-lysyl)piperazine-2-carboxamide | 640.4 | 34.9 |

TABLE 2-continued

| Example number | Structure | Name | Exact Mass [M + H]+ | FXIIa IC50 (nM) |
|---|---|---|---|---|
| 150 | 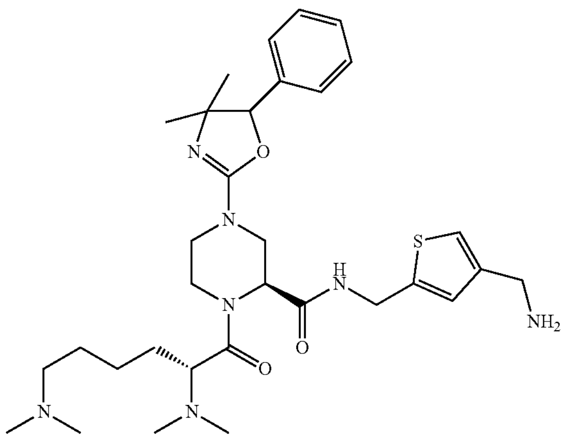 [SMILES: CN(C)CCCC[C@H](C(=O)N1CCN(C2=NC(C)(C)C(c3ccccc3)O2)C[C@H]1C(=O)NCc1cc(CN)cs1)N(C)C] | (2S)-N-{[4-(aminomethyl)thiophen-2-yl]methyl}-4-(4,4-dimethyl-5-phenyl-4,5-dihydro-1,3-oxazol-2-yl)-1-($N^2,N^2,N^6,N^6$-tetramethyl-D-lysyl)piperazine-2-carboxamide | 612.4 | 48.5 |
| 151 | 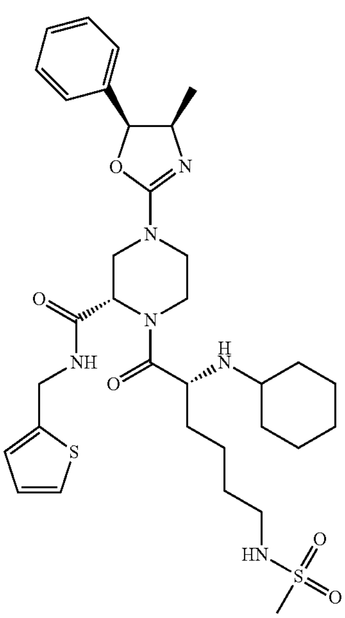 [SMILES: C[C@H]1N=C(N2CCN(C(=O)[C@@H](CCCCNS(C)(=O)=O)NC3CCCCC3)[C@H](C(=O)NCc3cccs3)C2)O[C@H]1c1ccccc1] | (2S)-1-[$N^2$-cyclohexyl-$N^6$-(methylsulfonyl)-D-lysyl]-4-[(4R,5S)-4-methyl-5-phenyl-4,5-dihydro-1,3-oxazol-2-yl]-N-(thiophen-2-ylmethyl)piperazine-2-carboxamide | 673.3 | 14.2 |

TABLE 2-continued

| Example number | Structure | Name | Exact Mass [M + H]+ | FXIIa IC50 (nM) |
|---|---|---|---|---|
| 152 | 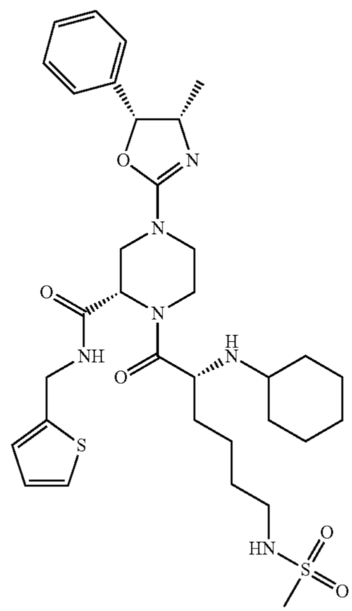 [SMILES: C[C@@H]1N=C(N2CCN(C(=O)[C@@H](CCCCNS(C)(=O)=O)NC3CCCCC3)[C@H](C(=O)NCc3cccs3)C2)O[C@@H]1c1ccccc1] | (2S)-1-[N²-cyclohexyl-N⁶-(methylsulfonyl)-D-lysyl]-4-[(4S,5R)-4-methyl-5-phenyl-4,5-dihydro-1,3-oxazol-2-yl]-N-(thiophen-2-ylmethyl)piperazine-2-carboxamide | 673.3 | 34.2 |
| 153 | 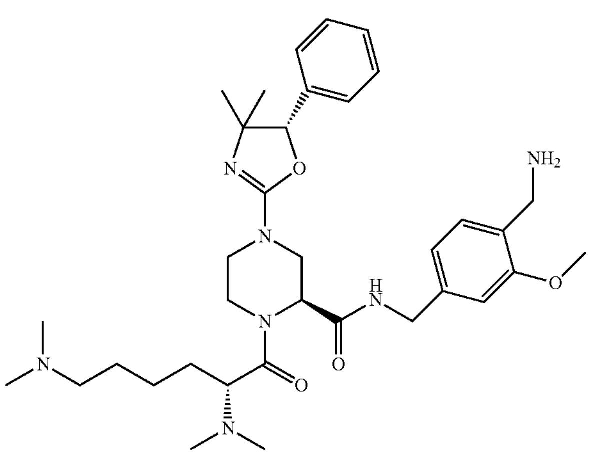 | (2S)-N-[4-(aminomethyl)-3-methoxybenzyl]-4-[(5S)-4,4-dimethyl-5-phenyl-4,5-dihydro-1,3-oxazol-2-yl]-1-(N²,N²,N⁶,N⁶-tetramethyl-D-lysyl)piperazine-2-carboxamide | 636.4 | 7.4 |

TABLE 2-continued

| Example number | Structure | Name | Exact Mass [M + H]+ | FXIIa IC50 (nM) |
|---|---|---|---|---|
| 154 | 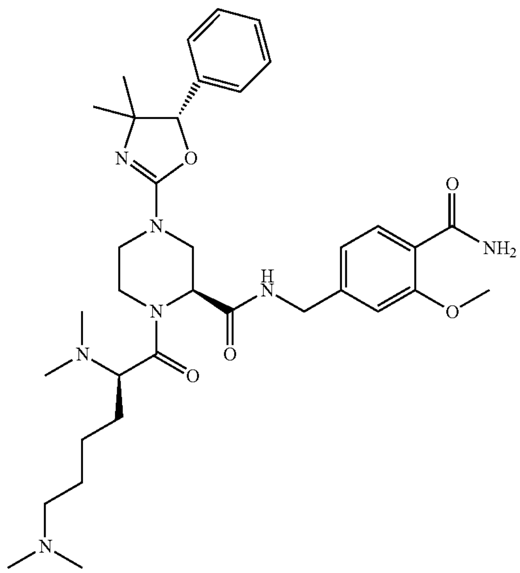 | (2S)-N-(4-carbamoyl-3-methoxybenzyl)-4-[(5S)-4,4-dimethyl-5-phenyl-4,5-dihydro-1,3-oxazol-2-yl]-1-(N$^2$,N$^2$,N$^6$,N$^6$-tetramethyl-D-lysyl)piperazine-2-carboxamide | 650.4 | 12.4 |
| 155 | 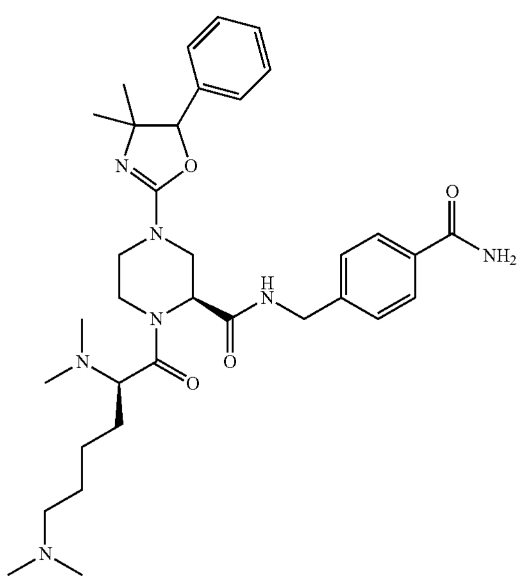 [SMILES: CN(C)CCCC[C@H](C(=O)N1CCN(C2=NC(C)(C)C(c3ccccc3)O2)C[C@H]1C(=O)NCc1ccc(C(N)=O)cc1)N(C)C] | (2S)-N-(4-carbamoylbenzyl)-4-(4,4-dimethyl-5-phenyl-4,5-dihydro-1,3-oxazol-2-yl)-1-(N$^2$,N$^2$,N$^6$,N$^6$-tetramethyl-D-lysyl)piperazine-2-carboxamide | 620.4 | 53.6 |

TABLE 2-continued

| Example number | Structure | Name | Exact Mass [M + H]+ | FXIIa IC50 (nM) |
|---|---|---|---|---|
| 156 | 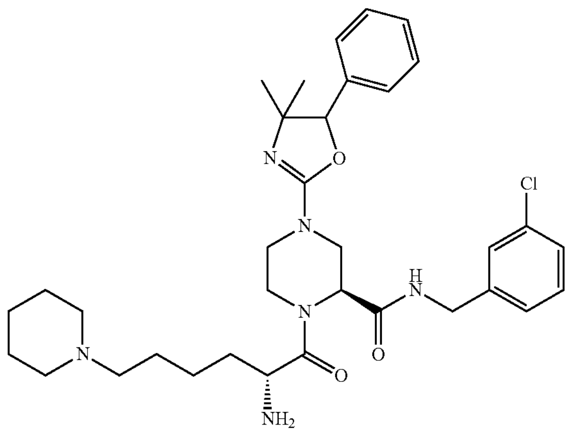 [SMILES: CC1(C)N=C(N2CCN(C(=O)[C@H](N)CCCCN3CCCCC3)[C@H](C(=O)NCc3cccc(Cl)c3)C2)OC1c1ccccc1] | (2S)-N-(3-chlorobenzyl)-4-(4,4-dimethyl-5-phenyl-4,5-dihydro-1,3-oxazol-2-yl)-1-(6-piperidin-1-yl-D-norleucyl)piperazine-2-carboxamide | 623.3 | 52.3 |
| 157 | 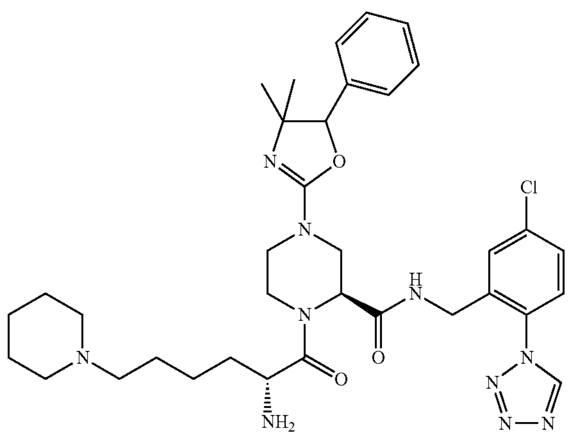 [SMILES: CC1(C)N=C(N2CCN(C(=O)[C@H](N)CCCCN3CCCCC3)[C@H](C(=O)NCc3cc(Cl)ccc3-n3cnnn3)C2)OC1c1ccccc1] | (2S)-N-[5-chloro-2-(1H-tetrazol-1-yl)benzyl]-4-(4,4-dimethyl-5-phenyl-4,5-dihydro-1,3-oxazol-2-yl)-1-(6-piperidin-1-yl-D-norleucyl)piperazine-2-carboxamide | 691.4 | 54.8 |
| 158 | 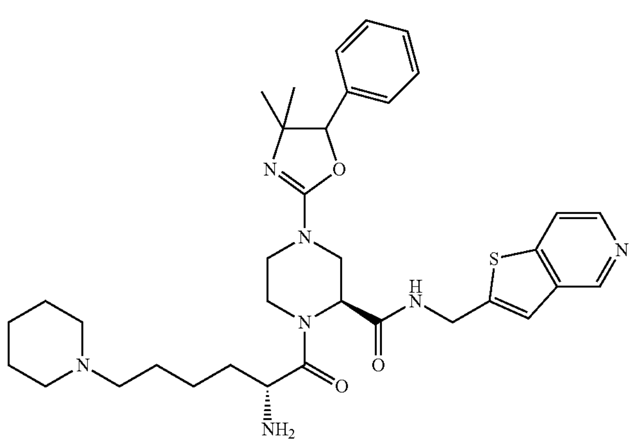 [SMILES: CC1(C)N=C(N2CCN(C(=O)[C@H](N)CCCCN3CCCCC3)[C@H](C(=O)NCc3cc4cnccc4s3)C2)OC1c1ccccc1] | (2S)-4-(4,4-dimethyl-5-phenyl-4,5-dihydro-1,3-oxazol-2-yl)-1-(6-piperidin-1-yl-D-norleucyl)-N-(thieno[3,2-c]pyridin-2-ylmethyl)piperazine-2-carboxamide | 646.4 | 54.4 |

TABLE 2-continued

| Example number | Structure | Name | Exact Mass [M + H]+ | FXIIa IC50 (nM) |
|---|---|---|---|---|
| 159 | 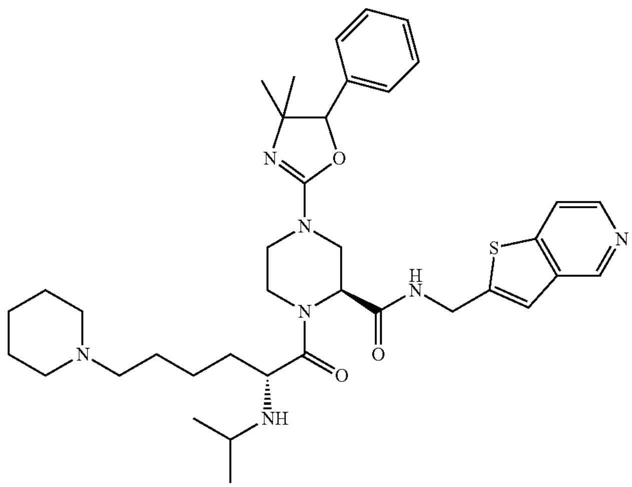 [SMILES: CC(C)N[C@H](CCCCN1CCCCC1)C(=O)N1CCN(C2=NC(C)(C)C(c3ccccc3)O2)C[C@H]1C(=O)NCc1cc2cnccc2s1] | (2S)-4-(4,4-dimethyl-5-phenyl-4,5-dihydro-1,3-oxazol-2-yl)-1-[N-(1-methylethyl)-6-piperidin-1-yl-D-norleucyl]-N-(thieno[3,2-c]pyridin-2-ylmethyl)piperazine-2-carboxamide | 688.4 | 27.4 |
| 160 | 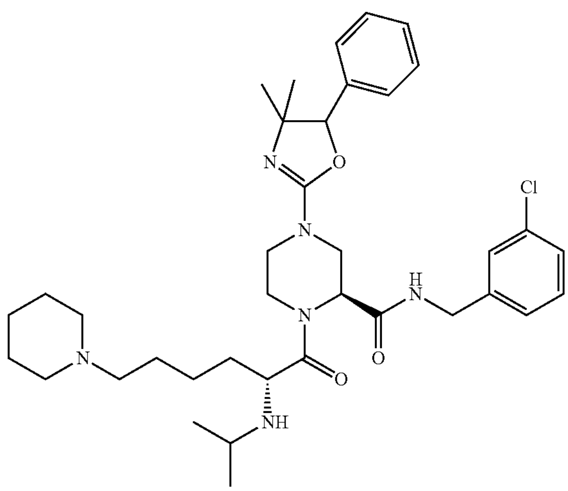 [SMILES: CC(C)N[C@H](CCCCN1CCCCC1)C(=O)N1CCN(C2=NC(C)(C)C(c3ccccc3)O2)C[C@H]1C(=O)NCc1cccc(Cl)c1] | (2S)-N-(3-chlorobenzyl)-4-(4,4-dimethyl-5-phenyl-4,5-dihydro-1,3-oxazol-2-yl)-1-[N-(1-methylethyl)-6-piperidin-1-yl-D-norleucyl]piperazine-2-carboxamide | 665.4 | 13.8 |
| 161 | 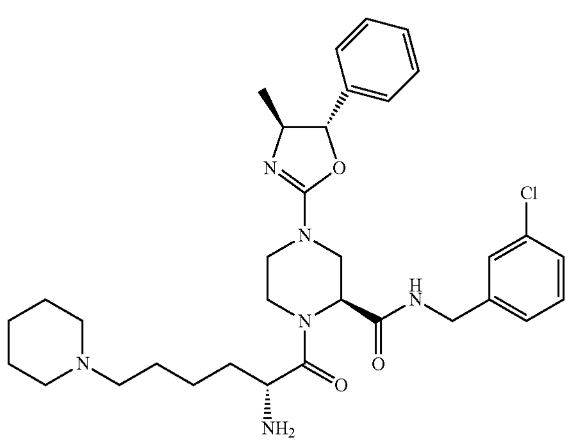 [SMILES: C[C@@H]1N=C(N2CCN(C(=O)[C@H](N)CCCCN3CCCCC3)[C@H](C(=O)NCc3cccc(Cl)c3)C2)O[C@H]1c1ccccc1] | (2S)-N-(3-chlorobenzyl)-4-[(4S,5S)-4-methyl-5-phenyl-4,5-dihydro-1,3-oxazol-2-yl]-1-(6-piperidin-1-yl-D-norleucyl)piperazine-2-carboxamide | 609.3 | 22.0 |

TABLE 2-continued

| Example number | Structure | Name | Exact Mass [M + H]+ | FXIIa IC50 (nM) |
|---|---|---|---|---|
| 162 | 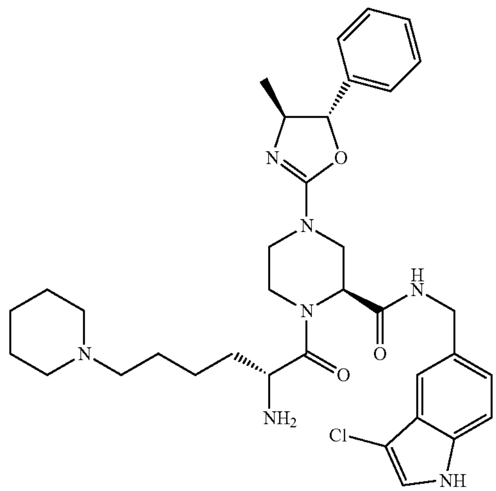 [SMILES: C[C@@H]1N=C(N2CCN(C(=O)[C@H](N)CCCCN3CCCCC3)[C@H](C(=O)NCc3ccc4[nH]cc(Cl)c4c3)C2)O[C@H]1c1ccccc1] | (2S)-N-[(3-chloro-1H-indol-5-yl)methyl]-4-[(4S,5S)-4-methyl-5-phenyl-4,5-dihydro-1,3-oxazol-2-yl]-1-(6-piperidin-1-yl-D-norleucyl)piperazine-2-carboxamide | 648.3 | 8.4 |
| 163 | 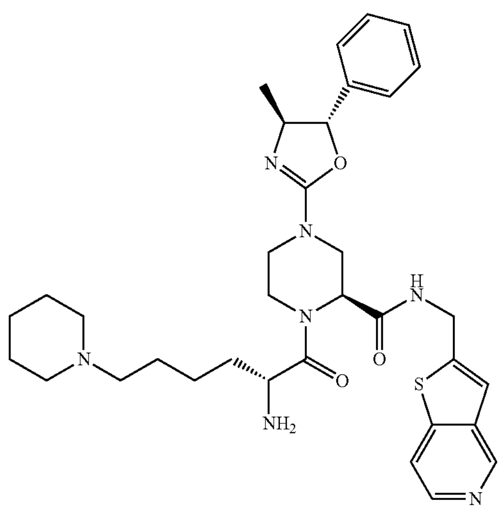 [SMILES: C[C@@H]1N=C(N2CCN(C(=O)[C@H](N)CCCCN3CCCCC3)[C@H](C(=O)NCc3cc4cnccc4s3)C2)O[C@H]1c1ccccc1] | (2S)-4-[(4S,5S)-4-methyl-5-phenyl-4,5-dihydro-1,3-oxazol-2-yl]-1-(6-piperidin-1-yl-D-norleucyl)-N-(thieno[3,2-c]pyridin-2-ylmethyl)piperazine-2-carboxamide | 632.3 | 15.0 |
| 164 | 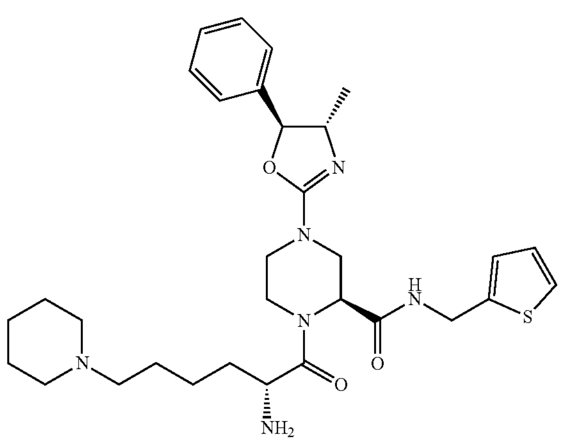 [SMILES: C[C@@H]1N=C(N2CCN(C(=O)[C@H](N)CCCCN3CCCCC3)[C@H](C(=O)NCc3cccs3)C2)O[C@H]1c1ccccc1] | (2S)-4-[(4S,5S)-4-methyl-5-phenyl-4,5-dihydro-1,3-oxazol-2-yl]-1-(6-piperidin-1-yl-D-norleucyl)-N-(thiophen-2-ylmethyl)piperazine-2-carboxamide | 581.3 | 22.8 |

TABLE 2-continued

| Example number | Structure | Name | Exact Mass [M + H]+ | FXIIa IC50 (nM) |
|---|---|---|---|---|
| 165 | 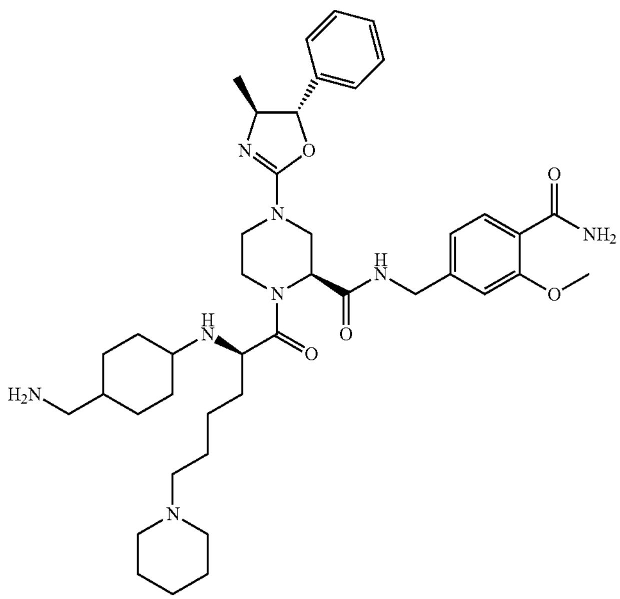 [SMILES: COc1cc(CNC(=O)[C@@H]2CN(C3=N[C@@H](C)[C@H](c4ccccc4)O3)CCN2C(=O)[C@@H](CCCCN2CCCCC2)NC2CCC(CN)CC2)ccc1C(N)=O] | (2S)-1-{N-[4-(aminomethyl)cyclohexyl]-6-piperidin-1-yl-D-norleucyl}-N-(4-carbamoyl-3-methoxybenzyl)-4-[(4S,5S)-4-methyl-5-phenyl-4,5-dihydro-1,3-oxazol-2-yl]piperazine-2-carboxamide | 759.5 | 41.1 |
| 166 | 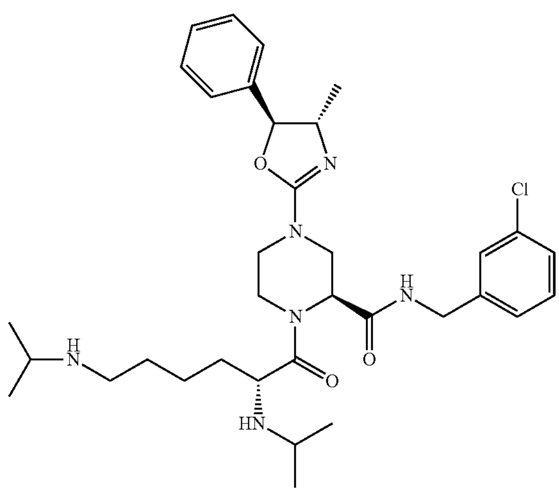 [SMILES: CC(C)NCCCC[C@@H](NC(C)C)C(=O)N1CCN(C2=N[C@@H](C)[C@H](c3ccccc3)O2)C[C@H]1C(=O)NCc1cccc(Cl)c1] | (2S)-1-[$N^2$,$N^6$-bis(1-methylethyl)-D-lysyl]-N-(3-chlorobenzyl)-4-[(4S,5S)-4-methyl-5-phenyl-4,5-dihydro-1,3-oxazol-2-yl]piperazine-2-carboxamide | 625.4 | 6.8 |
| 167 | 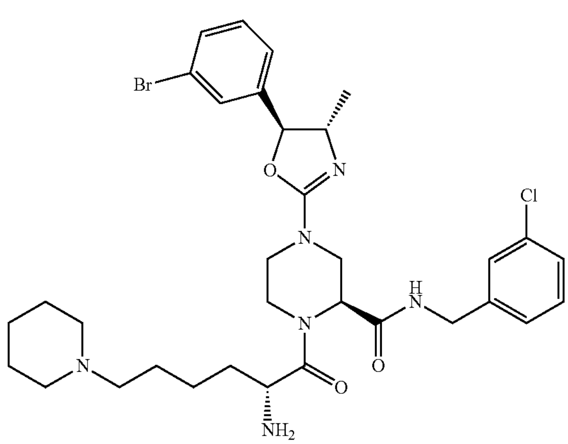 [SMILES: C[C@@H]1N=C(N2CCN(C(=O)[C@H](N)CCCCN3CCCCC3)[C@H](C(=O)NCc3cccc(Cl)c3)C2)O[C@H]1c1cccc(Br)c1] | (2S)-4-[(4S,5S)-5-(3-bromophenyl)-4-methyl-4,5-dihydro-1,3-oxazol-2-yl]-N-(3-chlorobenzyl)-1-(6-piperidin-1-yl-D-norleucyl)piperazine-2-carboxamide | 687.2 | 36.1 |

TABLE 2-continued

| Example number | Structure | Name | Exact Mass [M + H]+ | FXIIa IC50 (nM) |
|---|---|---|---|---|
| 168 | 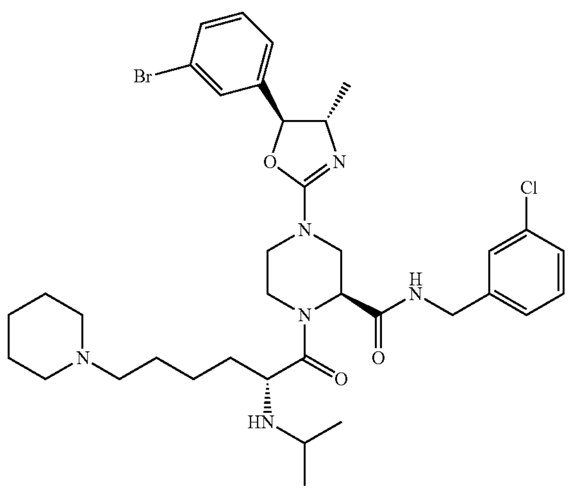 [SMILES: CC(C)N[C@H](CCCCN1CCCCC1)C(=O)N1CCN(C2=N[C@@H](C)[C@H](c3cccc(Br)c3)O2)C[C@H]1C(=O)NCc1cccc(Cl)c1] | (2S)-4-[(4S,5S)-5-(3-bromophenyl)-4-methyl-4,5-dihydro-1,3-oxazol-2-yl]-N-(3-chlorobenzyl)-1-[N-(1-methylethyl)-6-piperidin-1-yl-D-norleucyl]piperazine-2-carboxamide | 729.3 | 8.2 |
| 169 | 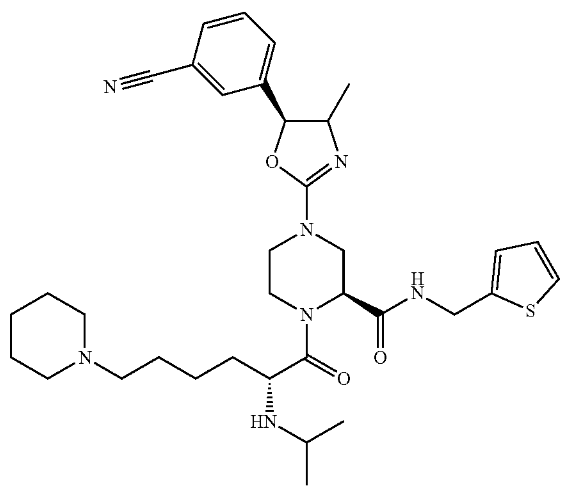 [SMILES: CC(C)N[C@H](CCCCN1CCCCC1)C(=O)N1CCN(C2=NC(C)[C@H](c3cccc(C#N)c3)O2)C[C@H]1C(=O)NCc1cccs1] | (2S)-4[5-(3-cyanophenyl)-4-methyl-4,5-dihydro-1,3-oxazol-2-yl]-1-[N-(1-methylethyl)-6-piperidin-1-yl-D-norleucyl]-N-(thiophen-2-ylmethyl)piperazine-2-carboxamide | 648.4 | 12.5 |
| 170 | 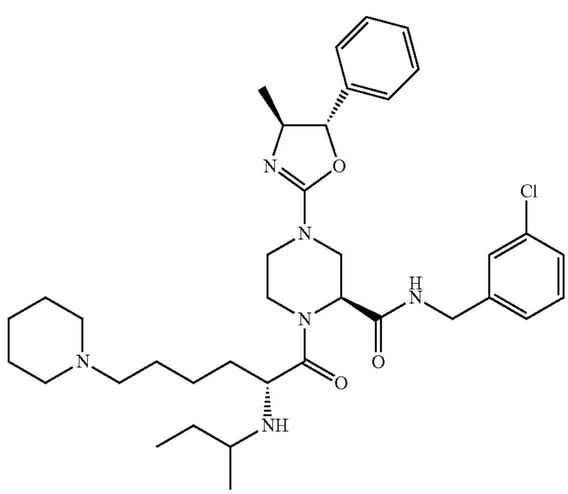 [SMILES: CCC(C)N[C@H](CCCCN1CCCCC1)C(=O)N1CCN(C2=N[C@@H](C)[C@H](c3ccccc3)O2)C[C@H]1C(=O)NCc1cccc(Cl)c1] | (2S)-N-(3-chlorobenzyl)-4-[(4S,5S)-4-methyl-5-phenyl-4,5-dihydro-1,3-oxazol-2-yl]-1-{N-[(1R)-1-methylpropyl]-6-piperidin-1-yl-D-norleucyl}piperazine-2-carboxamide | 665.4 | 2.5 |

TABLE 2-continued

| Example number | Structure | Name | Exact Mass [M + H]+ | FXIIa IC50 (nM) |
|---|---|---|---|---|
| 171 | 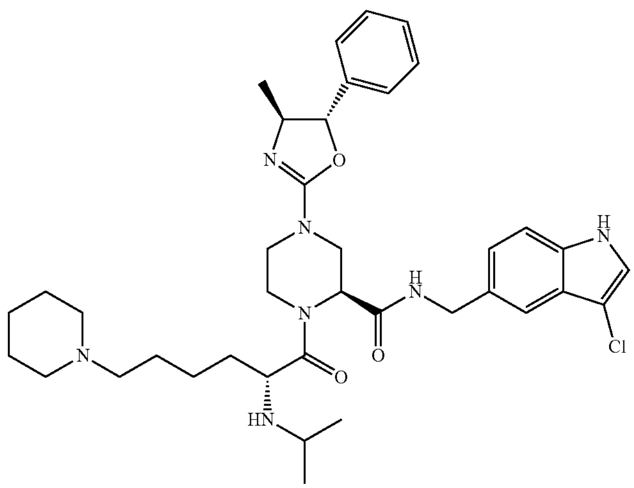 [SMILES: CC(C)N[C@H](CCCCN1CCCCC1)C(=O)N1CCN(C2=N[C@@H](C)[C@H](c3ccccc3)O2)C[C@H]1C(=O)NCc1ccc2[nH]cc(Cl)c2c1] | (2S)-N-[(3-chloro-1H-indol-5-yl)methyl]-1-[N-(1-methylethyl)-6-piperidin-1-yl-D-norleucyl]-4-[(4S,5S)-4-methyl-5-phenyl-4,5-dihydro-1,3-oxazol-2-yl]piperazine-2-carboxamide | 690.4 | 0.5 |
| 172 | 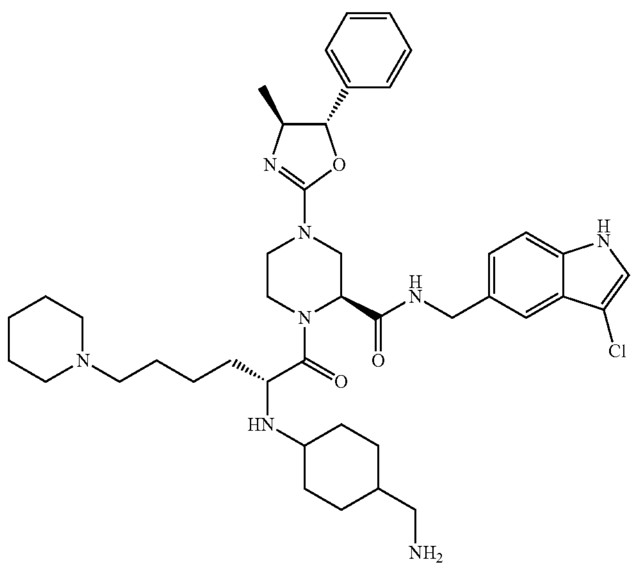 [SMILES: C[C@@H]1N=C(N2CCN(C(=O)[C@@H](CCCCN3CCCCC3)NC3CCC(CN)CC3)[C@H](C(=O)NCc3ccc4[nH]cc(Cl)c4c3)C2)O[C@H]1c1ccccc1] | (2S)-1-{N-[4-(aminomethyl)cyclohexyl]-6-piperidin-1-yl-D-norleucyl}-N-[(3-chloro-1H-indol-5-yl)methyl]-4-[(4S,5S)-4-methyl-5-phenyl-4,5-dihydro-1,3-oxazol-2-yl]piperazine-2-carboxamide | 759.4 | 0.6 |
| 173 | 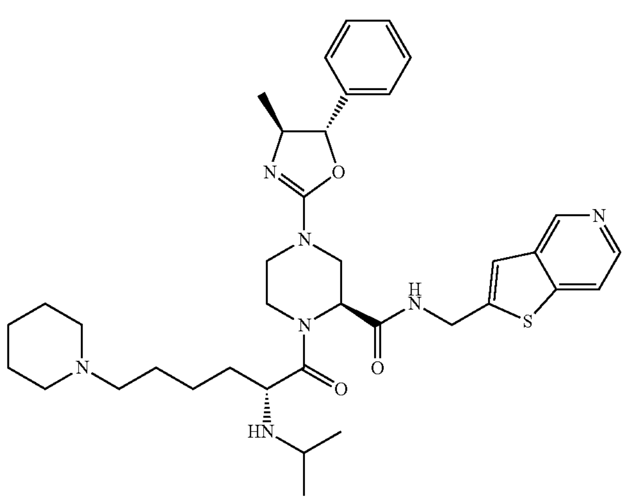 [SMILES: CC(C)N[C@H](CCCCN1CCCCC1)C(=O)N1CCN(C2=N[C@@H](C)[C@H](c3ccccc3)O2)C[C@H]1C(=O)NCc1cc2cnccc2s1] | (2S)-1-[N-(1-methylethyl)-6-piperidin-1-yl-D-norleucyl]-4-[(4S,5S)-4-methyl-5-phenyl-4,5-dihydro-1,3-oxazol-2-yl]-N-(thieno[3,2-c]pyridin-2-ylmethyl)piperazine-2-carboxamide | 674.4 | 3.9 |

TABLE 2-continued

| Example number | Structure | Name | Exact Mass [M + H]+ | FXIIa IC50 (nM) |
| --- | --- | --- | --- | --- |
| 174 | 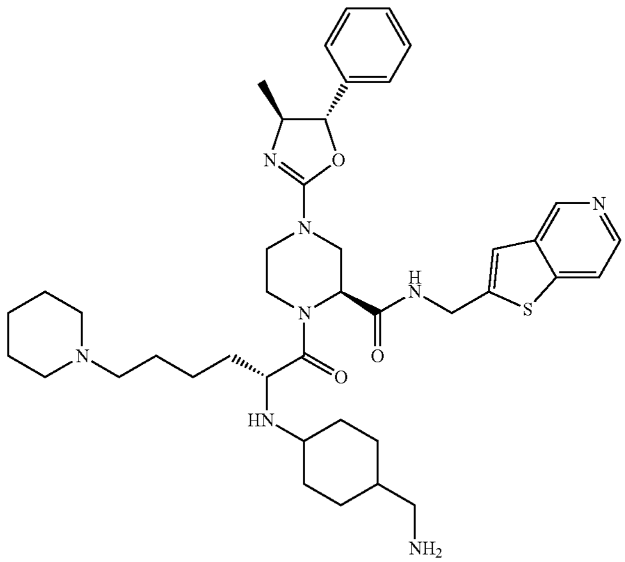 [SMILES: C[C@@H]1N=C(N2CCN(C(=O)[C@@H](CCCCN3CCCCC3)NC3CCC(CN)CC3)[C@H](C(=O)NCc3cc4cnccc4s3)C2)O[C@H]1c1ccccc1] | (2S)-1-{N-[4-(aminomethyl)cyclohexyl]-6-piperidin-1-yl-D-norleucyl}-4-[(4S,5S)-4-methyl-5-phenyl-4,5-dihydro-1,3-oxazol-2-yl]-N-(thieno[3,2-c]pyridin-2-ylmethyl)piperazine-2-carboxamide | 743.4 | 3.0 |
| 175 | 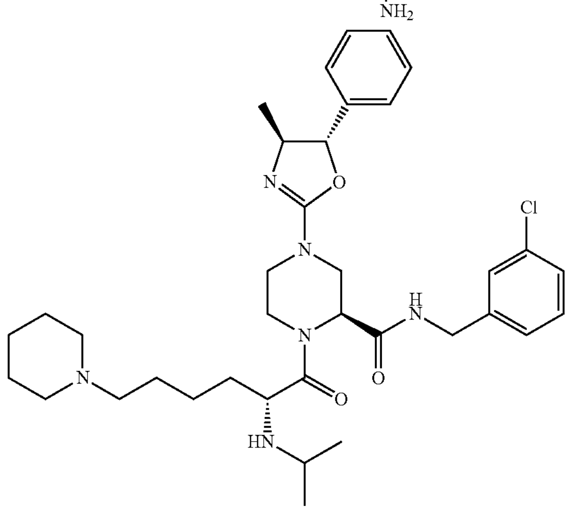 | (2S)-N-(3-chlorobenzyl)-1-[N-(1-methylethyl)-6-piperidin-1-yl-D-norleucyl]-4-[(4S,5S)-4-methyl-5-phenyl-4,5-dihydro-1,3-oxazol-2-yl]piperazine-2-carboxamide | 651.4 | 6.6 |
| 176 | 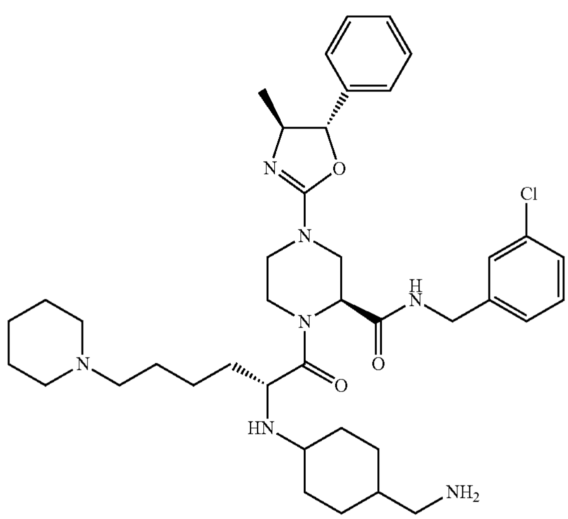 [SMILES: C[C@@H]1N=C(N2CCN(C(=O)[C@@H](CCCCN3CCCCC3)NC3CCC(CN)CC3)[C@H](C(=O)NCc3cccc(Cl)c3)C2)O[C@H]1c1ccccc1] | (2S)-1-{N-[4-(aminomethyl)cyclohexyl]-6-piperidin-1-yl-D-norleucyl}-N-(3-chlorobenzyl)-4-[(4S,5S)-4-methyl-5-phenyl-4,5-dihydro-1,3-oxazol-2-yl]piperazine-2-carboxamide | 720.4 | 29.0 |

TABLE 2-continued

| Example number | Structure | Name | Exact Mass [M + H]+ | FXIIa IC50 (nM) |
|---|---|---|---|---|
| 177 | 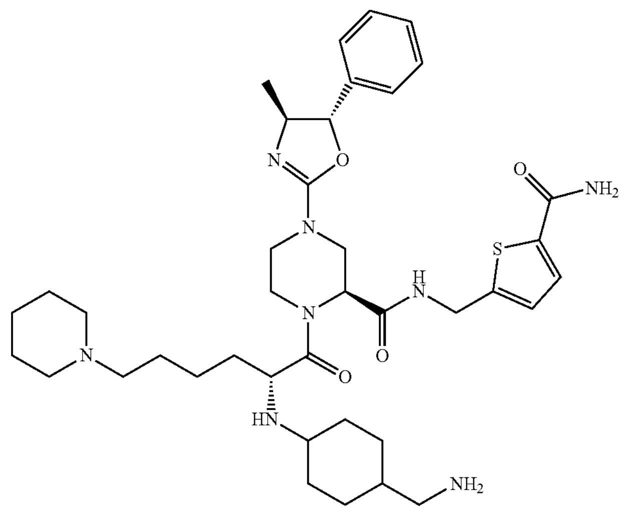 [SMILES: C[C@@H]1N=C(N2CCN(C(=O)[C@@H](CCCCN3CCCCC3)NC3CCC(CN)CC3)[C@H](C(=O)NCc3ccc(C(N)=O)s3)C2)O[C@H]1c1ccccc1] | (2S)-1-{N-[4-(aminomethyl)cyclohexyl]-6-piperidin-1-yl-D-norleucyl}-N-[(5-carbamoylthiophen-2-yl)methyl]-4-[(4S,5S)-4-methyl-5-phenyl-4,5-dihydro-1,3-oxazol-2-yl]piperazine-2-carboxamide | 735.4 | 27.9 |
| 178 | 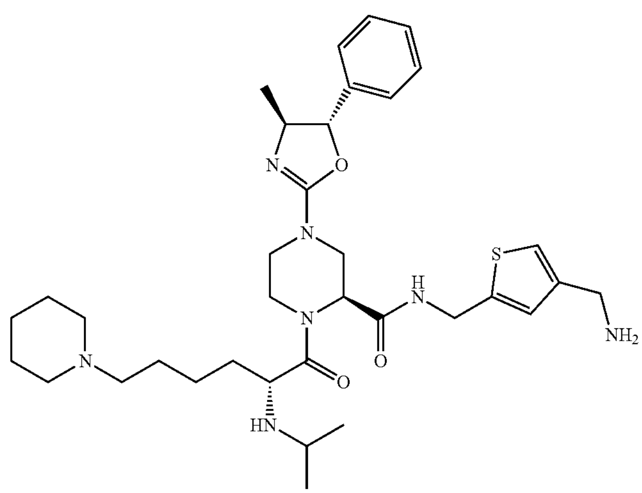 [SMILES: CC(C)N[C@H](CCCCN1CCCCC1)C(=O)N1CCN(C2=N[C@@H](C)[C@H](c3ccccc3)O2)C[C@H]1C(=O)NCc1cc(CN)cs1] | (2S)-N-{[4-(aminomethyl)thiophen-2-yl]methyl}-1-[N-(1-methylethyl)-6-piperidin-1-yl-D-norleucyl]-4-[(4S,5S)-4-methyl-5-phenyl-4,5-dihydro-1,3-oxazol-2-yl]piperazine-2-carboxamide | 652.4 | 4.6 |
| 179 | 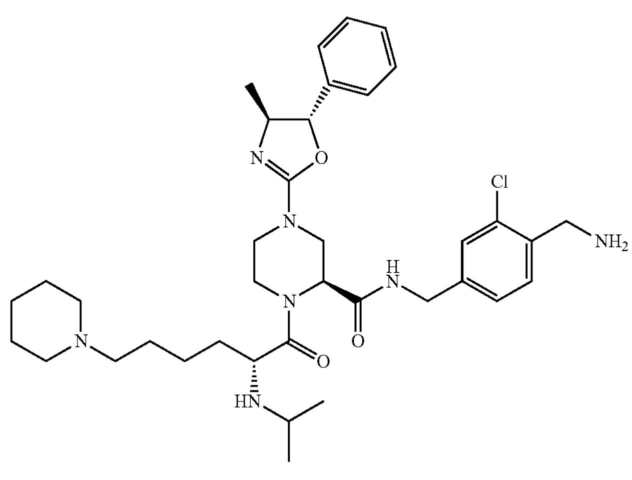 [SMILES: CC(C)N[C@H](CCCCN1CCCCC1)C(=O)N1CCN(C2=N[C@@H](C)[C@H](c3ccccc3)O2)C[C@H]1C(=O)NCc1ccc(CN)c(Cl)c1] | (2S)-N-[4-(aminomethyl)-3-chlorobenzyl]-1-[N-(1-methylethyl)-6-piperidin-1-yl-D-norleucyl]-4-[(4S,5S)-4-methyl-5-phenyl-4,5-dihydro-1,3-oxazol-2-yl]piperazine-2-carboxamide | 680.4 | 1.7 |

| Example number | Structure | Name | Exact Mass [M + H]+ | FXIIa IC50 (nM) |
|---|---|---|---|---|
| 180 | 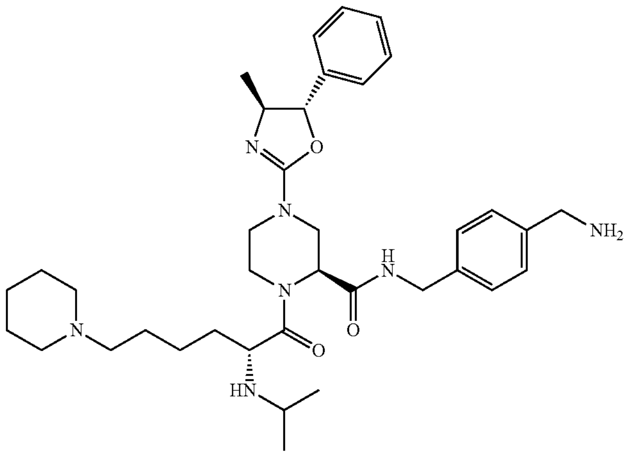 [SMILES: CC(C)N[C@H](CCCCN1CCCCC1)C(=O)N1CCN(C2=N[C@@H](C)[C@H](c3ccccc3)O2)C[C@H]1C(=O)NCc1ccc(CN)cc1] | (2S)-N-[4-(aminomethyl)benzyl]-1-[N-(1-methylethyl)-6-piperidin-1-yl-D-norleucyl]-4-[(4S,5S)-4-methyl-5-phenyl-4,5-dihydro-1,3-oxazol-2-yl]piperazine-2-carboxamide | 646.4 | 47.1 |
| 181 | 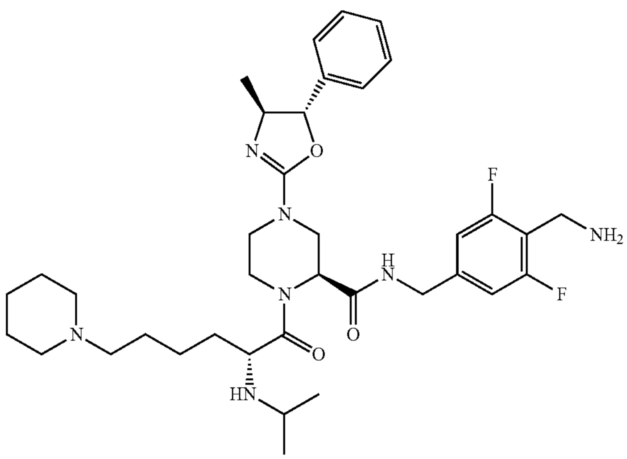 [SMILES: CC(C)N[C@H](CCCCN1CCCCC1)C(=O)N1CCN(C2=N[C@@H](C)[C@H](c3ccccc3)O2)C[C@H]1C(=O)NCc1cc(F)c(CN)c(F)c1] | (2S)-N-[4-(aminomethyl)-3,5-difluorobenzyl]-1-[N-(1-methylethyl)-6-piperidin-1-yl-D-norleucyl]-4-[(4S,5S)-4-methyl-5-phenyl-4,5-dihydro-1,3-oxazol-2-yl]piperazine-2-carboxamide | 682.4 | 44.4 |
| 182 | 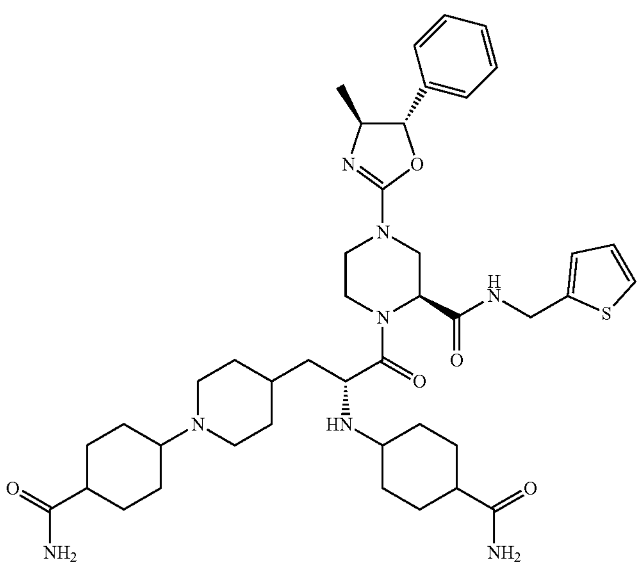 [SMILES: C[C@@H]1N=C(N2CCN(C(=O)[C@@H](CC3CCN(C4CCC(C(N)=O)CC4)CC3)NC3CCC(C(N)=O)CC3)[C@H](C(=O)NCc3cccs3)C2)O[C@H]1c1ccccc1] | (2S)-1-{N-(4-carbamoylcyclohexyl)-3-[1-(4-carbamoylcyclohexyl)piperidin-4-yl]-D-alanyl}-4-[(4S,5S)-4-methyl-5-phenyl-4,5-dihydro-1,3-oxazol-2-yl]-N-(thiophen-2-ylmethyl)piperazine-2-carboxamide | 789.4 | 34.2 |

TABLE 2-continued

| Example number | Structure | Name | Exact Mass [M + H]+ | FXIIa IC50 (nM) |
|---|---|---|---|---|
| 183 | 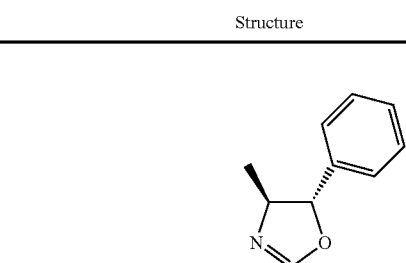 | (2S)-[N-cyclohexyl-3-(1-cyclohexylpiperidin-4-yl)-D-alanyl]-4-[(4S,5S)-4-methyl-5-phenyl-4,5-dihydro-1,3-oxazol-2-yl]-N-(thiophen-2-ylmethyl)piperazine-2-carboxamide | 703.4 | 2.4 |

Factor XIIa Assay

The effectiveness of a compound of the present invention as an inhibitor of Coagulation Factor XIIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the IC50, the inhibitor concentration causing a 50% decrease in Factor XIIa protease activity.

Factor XIIa activity determinations were made in 50 mM HEPES buffer containing 150 mM NaCl, 5 mM $CaCl_2$, and 0.1% PEG 8000 (polyethylene glycol; JT Baker or Fisher Scientific) at pH 7.4. Determinations were made using purified human Factor XIIa at a final concentration of 500 pM (Sekisui Diagnostics) and the synthetic substrate, n-Acetyl-Lys-Pro-Arg-AFC, TFA salt (Sigma #C6608) at a concentration of 100 µM.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. IC50 was determined as the concentration of I yielding $V_i=V_o/2$.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

What is claimed is:
1. A compound of the formula: wherein X is

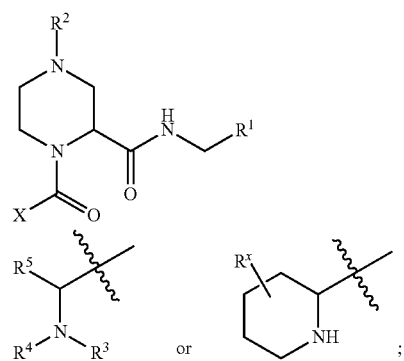

$R^1$ is aryl or heteroaryl, wherein said aryl and heteroaryl groups are optionally substituted with one to three substituents independently selected from the group consisting of hydroxyl, cyano, halo, $C_{1-3}$ alkyl, O(C$_{1-3}$ alkyl), NR$^{10}$R$^{11}$, CH$_2$NR$^{10}$R$^{11}$, (C=O)NR$^{10}$R$^{11}$ or heteroaryl;

R$^2$ is (C=O)OR$^6$, (C=O)CH$_2$R$^6$,

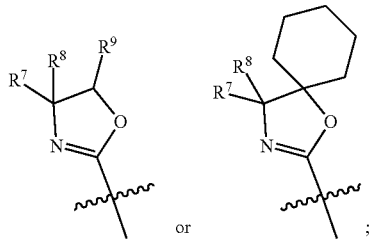

or

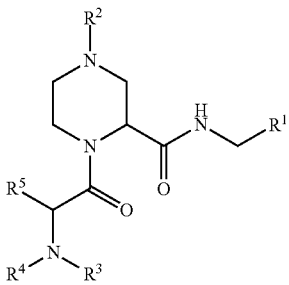

;

R$^3$ is C$_{1-3}$ alkyl,

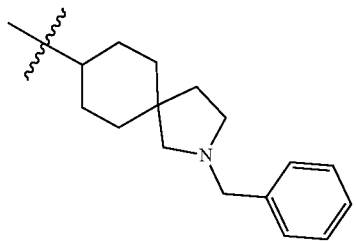

or C$_{3-7}$ cycloalkyl, which is optionally substituted with one or two substituents independently selected from the group consisting of R$^6$, R$^{11}$, NR$^{10}$R$^{11}$, (C=O)NR$^{10}$R$^{11}$ and CH$_2$NR$^{10}$R$^{11}$;

R$^4$ is hydrogen or C$_{1-4}$ alkyl;

R$^5$ is
(a) hydrogen,
(b) (CH$_2$)$_m$-cyclohexyl, which is optionally substituted with NR$^{10}$R$^{11}$ or heterocyclyl,
(c) (CH$_2$)$_n$-piperidinyl, which is optionally substituted with benzyl, R$^{11}$, SO$_2$R$^{10}$, SO$_2$R$^6$, (C=O)R$^6$, R$^6$ or (C=O)R$^{10}$,
(d) C$_{1-4}$ alkyl which is optionally substituted with R$^6$, NR$^{10}$R$^{11}$ or NHSO$_2$CH$_3$;

each R$^6$ is independently aryl, heteroaryl, heterocyclyl or C$_{3-6}$ cycloalkyl, wherein said aryl and heteroaryl groups are optionally substituted with one to three substituents independently selected from the group consisting of hydroxyl, oxo, cyano, halo, C$_{1-3}$ alkyl, C$_{1-3}$ haloalkyl, O(C$_{1-3}$ alkyl), NR$^{10}$R$^{11}$, CH$_2$NR$^{10}$R$^{11}$, CH$_2$CN, (C=O)NR$^{10}$R$^{11}$ and CH(NH$_2$)(OCH$_3$);

R$^7$ is hydrogen or C$_{1-3}$ alkyl;

R$^8$ is hydrogen or C$_{1-3}$ alkyl;

R$^9$ is hydrogen, C$_{1-3}$ alkyl, C$_{1-3}$ haloalkyl or phenyl, wherein said phenyl group is optionally substituted with halo, cyano, methyl or CH$_2$NR$^{10}$R$^{11}$;

each R$^{10}$ is independently hydrogen or C$_{1-5}$ alkyl;

each R$^{11}$ is independently hydrogen or C$_{1-3}$ alkyl, which is optionally substituted with one to three substituents independently selected from the group consisting of halo and hydroxyl;

R$^x$ is hydrogen or C$_{1-4}$ alkyl, which is optionally substituted with one to three substituents independently selected from the group consisting of halo, hydroxyl, N$^+$CH$_{-3}$R$^{10}$R$^{11}$ and NR$^{10}$R$^1$;

m is zero or one;
n is zero or one;
or a pharmaceutically acceptable salt thereof.

2. The compound of claim 1 of the formula

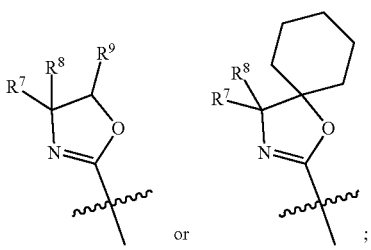

wherein R$^1$ is aryl or heteroaryl, wherein said aryl and heteroaryl groups are optionally substituted with one to three substituents independently selected from the group consisting of hydroxyl, cyano, halo, C$_{1-3}$ alkyl, O(C$_{1-3}$ alkyl), NR$^{10}$R$^{11}$, CH$_2$NR$^{10}$R$^{11}$, (C=O)NR$^{10}$R$^{11}$ or heteroaryl;

R$^2$ is (C=O)OR$^6$, (C=O)CH$_2$R$^6$,

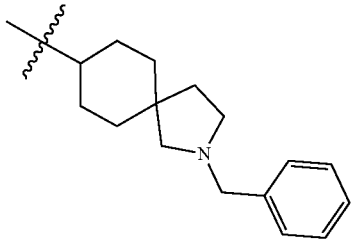 [SMILES: *C1CCC2(CC1)CCN(Cc1ccccc1)C2]

or ;

R$^3$ is C$_{1-3}$ alkyl,

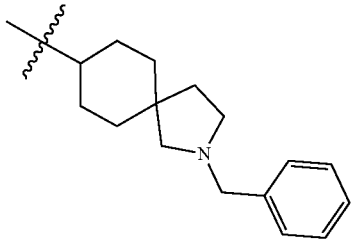 [SMILES: *C1CCC2(CC1)CCN(Cc1ccccc1)C2]

or C$_{3-7}$ cycloalkyl, which is optionally substituted with one or two substituents independently selected from the group consisting of R$^6$, R$^{11}$, NR$^{10}$R$^{11}$, (C=O)NR$^{10}$R$^{11}$ and CH$_2$NR$^{10}$R$^{11}$;

R$^4$ is hydrogen or C$_{1-4}$ alkyl;

R$^5$ is
(a) hydrogen,
(b) (CH$_2$)$_m$-cyclohexyl, which is optionally substituted with NR$^{10}$R$^{11}$ or heterocyclyl,
(c) (CH$_2$)$_n$-piperidinyl, which is optionally substituted with benzyl, R$^{11}$, SO$_2$R$^{10}$, SO$_2$R$^6$, (C=O)R$^6$, R$^6$ or (C=O)R$^{10}$,
(d) C$_{1-4}$ alkyl which is optionally substituted with R$^6$, NR$^{10}$R$^{11}$ or NHSO$_2$CH$_3$;

each R$^6$ is independently aryl, heteroaryl, heterocyclyl or C$_{3-6}$ cycloalkyl, wherein said aryl and heteroaryl groups are optionally substituted with one to three substituents independently selected from the group consisting of hydroxyl, oxo, cyano, halo, C$_{1-3}$ alkyl, $C_{1-3}$ haloalkyl, $O(C_{1-3}$ alkyl), $NR^{10}R^{11}$, $CH_2NR^{10}R^{11}$, $CH_2CN$, $(C=O)NR^{10}R^{11}$ and $CH(NH_2)(OCH_3)$;

$R^7$ is hydrogen or $C_{1-3}$ alkyl;

$R^8$ is hydrogen or $C_{1-3}$ alkyl;

$R^9$ is hydrogen or phenyl, which is optionally substituted with halo, cyano, methyl or $CH_2NR^{10}R^{11}$;

each $R^{10}$ is independently hydrogen or $C_{1-5}$ alkyl;

each $R^{11}$ is independently hydrogen or $C_{1-3}$ alkyl, which is optionally substituted with one to three substituents independently selected from the group consisting of halo and hydroxyl;

m is zero or one;

n is zero or one;

or a pharmaceutically acceptable salt thereof.

3. The compound of claim 1 wherein $R^1$ is phenyl, thiophenyl, indolyl or thienopyridinyl, wherein said phenyl, thiophenyl, indolyl or thienopyridinyl groups are optionally substituted with one to three substituents independently selected from the group consisting of halo, $O(C_{1-3}$ alkyl), $CH_2NR^{10}R^{11}$, $(C=O)NR^{10}R^{11}$ or tetrazolyl; or a pharmaceutically acceptable salt thereof.

4. The compound of claim 1 wherein $R^3$ is $C_{1-3}$ alkyl,

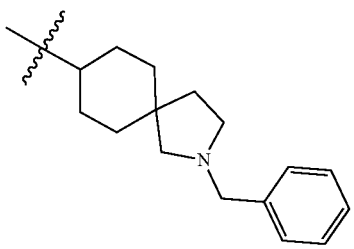 [SMILES: *C1CCC2(CC1)CCN(Cc1ccccc1)C2]

or $C_{5-6}$ cycloalkyl, which is optionally substituted with one or two substituents independently selected from the group consisting of $R^6$, $NR^{10}R^{11}$, $(C=O)NR^{10}R^{11}$ and $CH_2NR^{10}R^{11}$, or a pharmaceutically acceptable salt thereof.

5. The compound of claim 1 wherein $R^4$ is hydrogen or methyl, or a pharmaceutically acceptable salt thereof.

6. The compound of claim 1 wherein $R^5$ is (a) $CH_2$-cyclohexyl, or (b) $C_{1-4}$ alkyl which is optionally substituted with $R^6$, $R^{11}$, $NR^{10}R^{11}$ or $NHSO_2CH_3$, or a pharmaceutically acceptable salt thereof.

7. The compound selected from

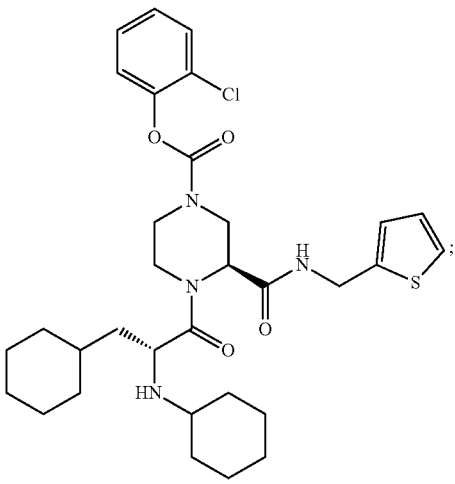

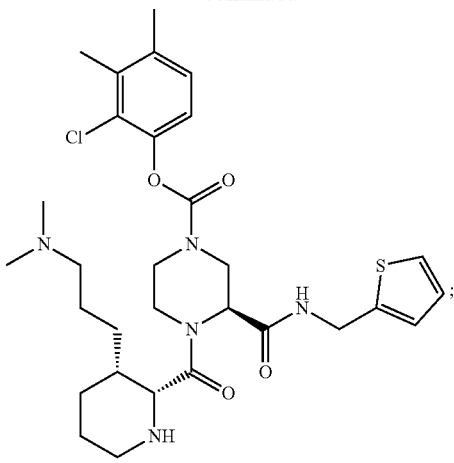

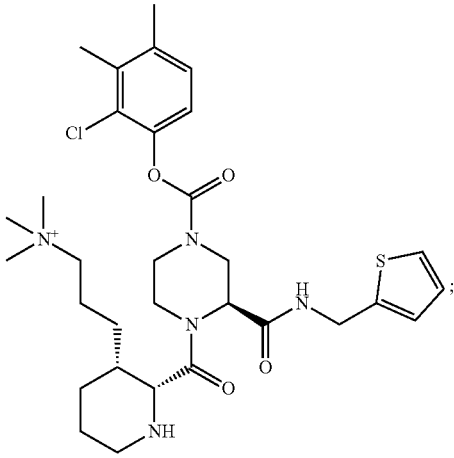

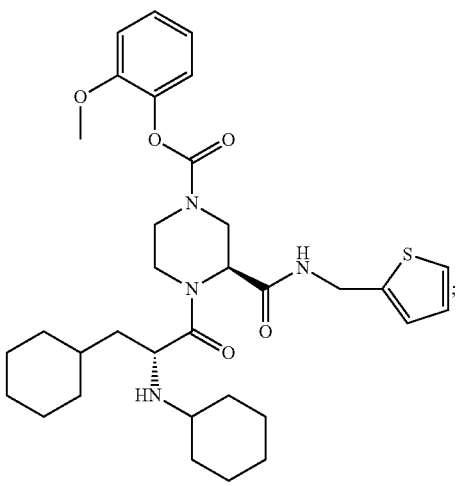

213
-continued
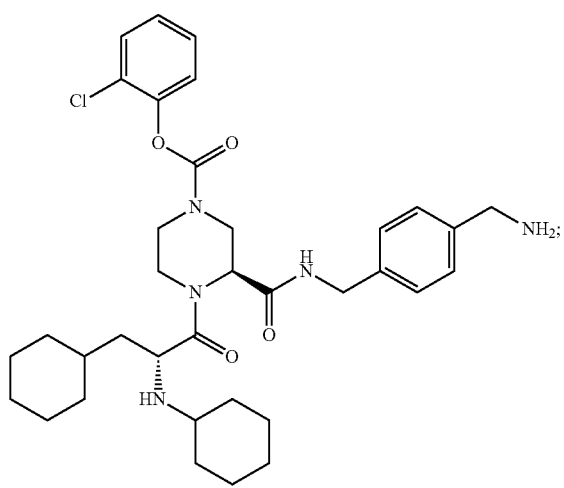
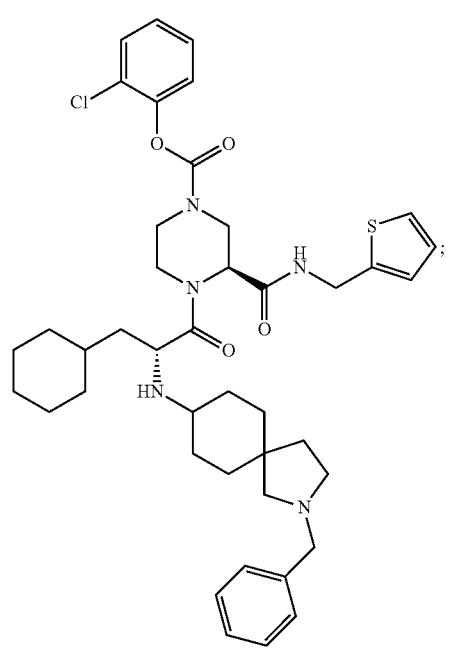
214
-continued
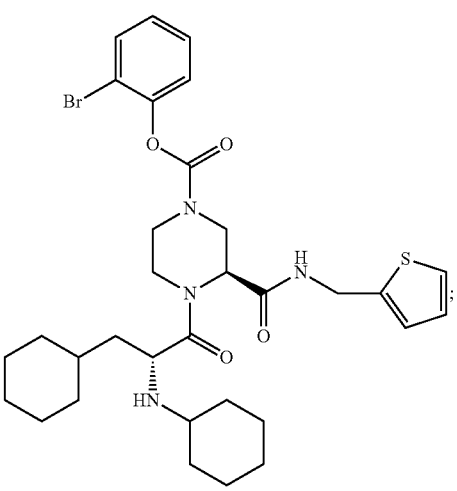
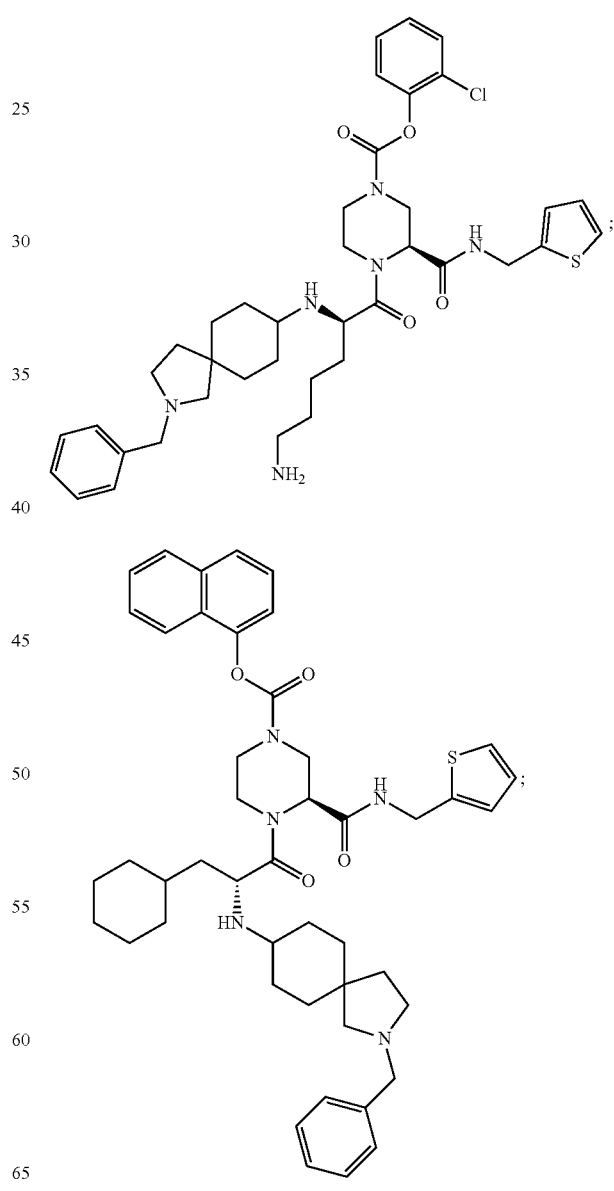

215
-continued
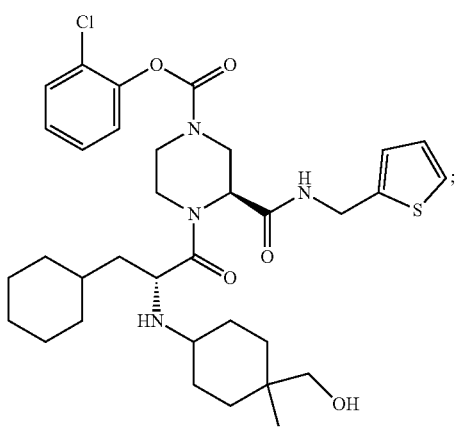
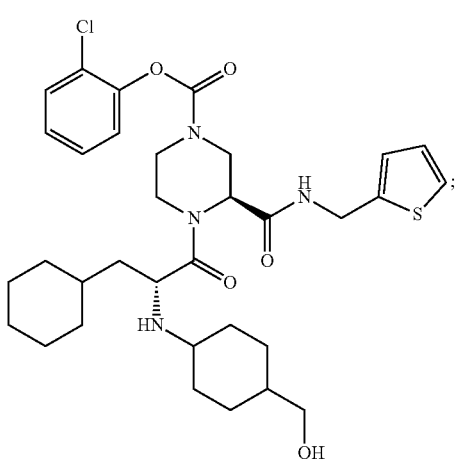
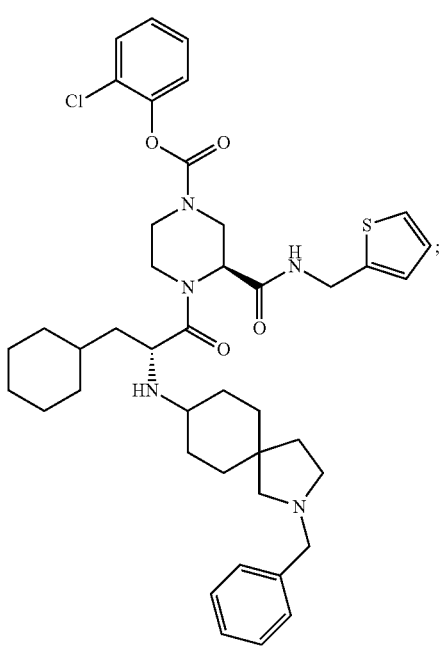
216
-continued
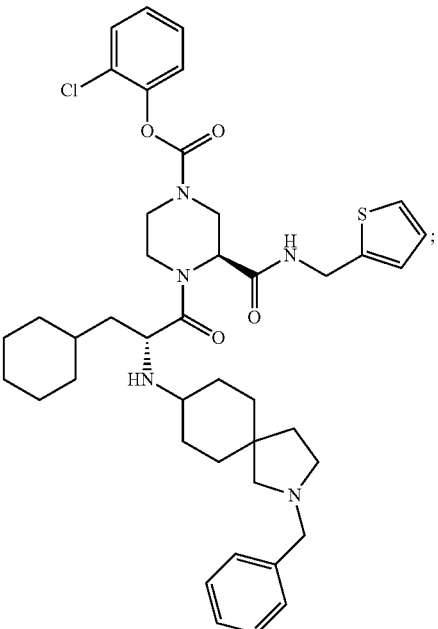
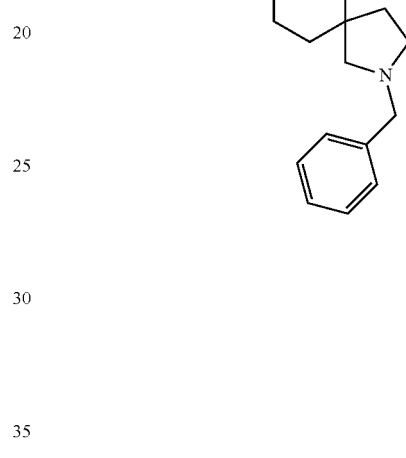
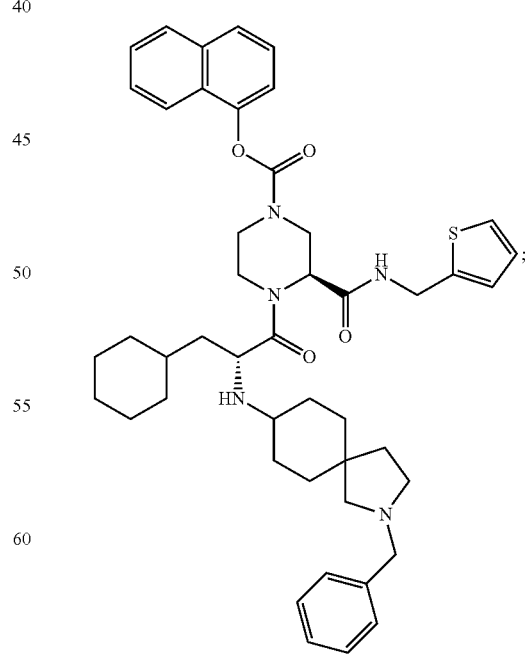

217
-continued
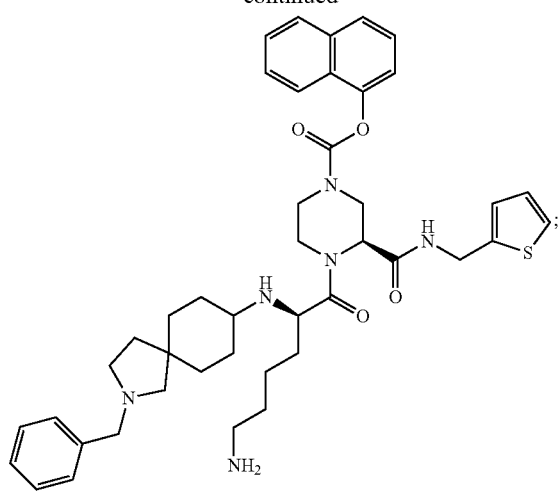
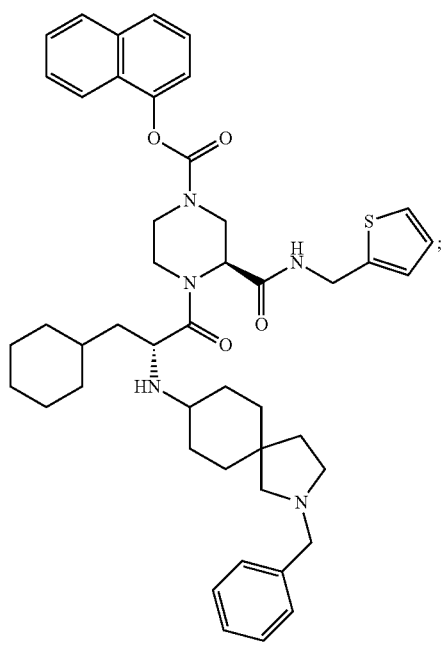 [SMILES: O=C(NCc1cccs1)[C@@H]1CN(C(=O)Oc2cccc3ccccc23)CCN1C(=O)[C@@H](CC1CCCCC1)NC1CCC2(CC1)CCN(Cc1ccccc1)C2]
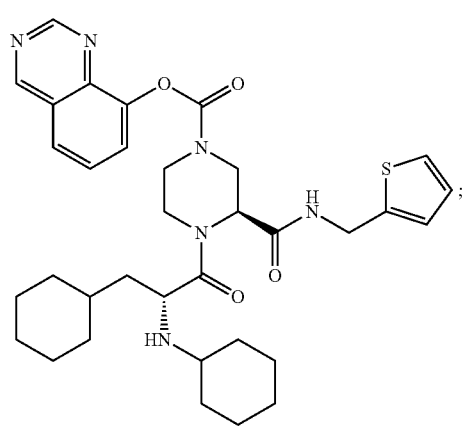
218
-continued
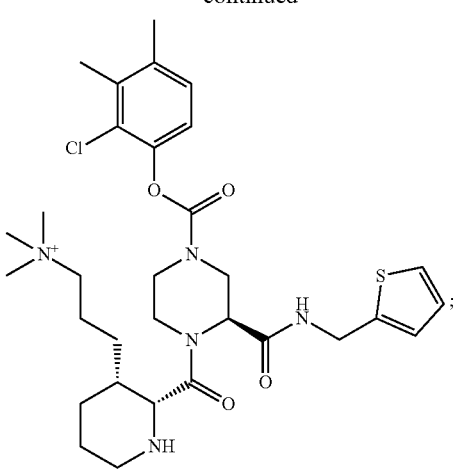
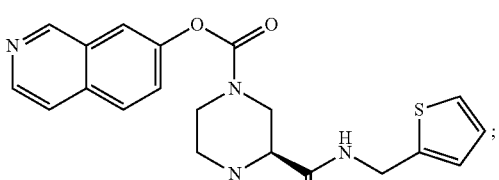
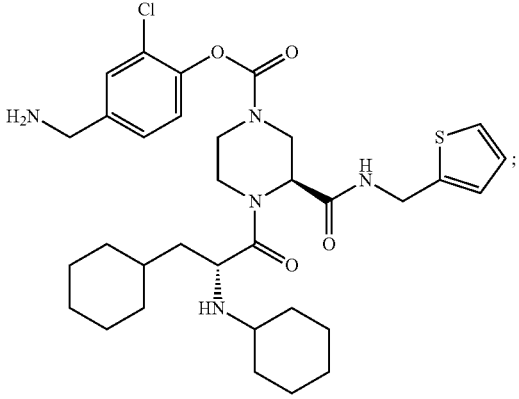
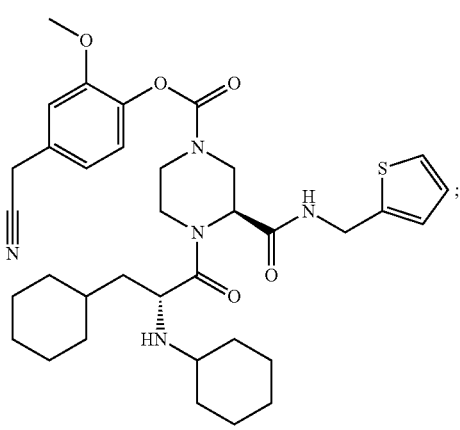

219
-continued
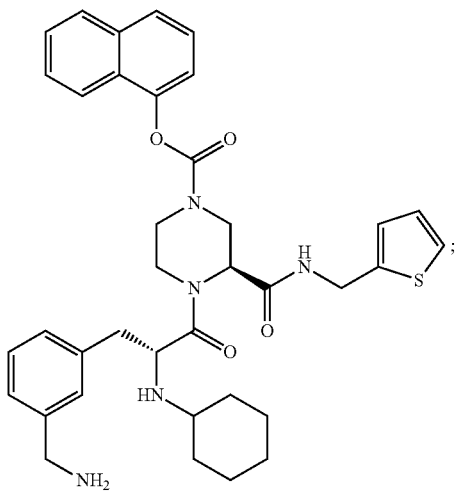
220
-continued
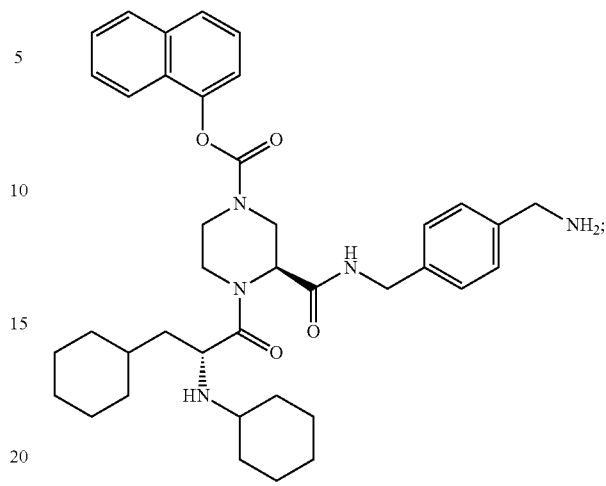
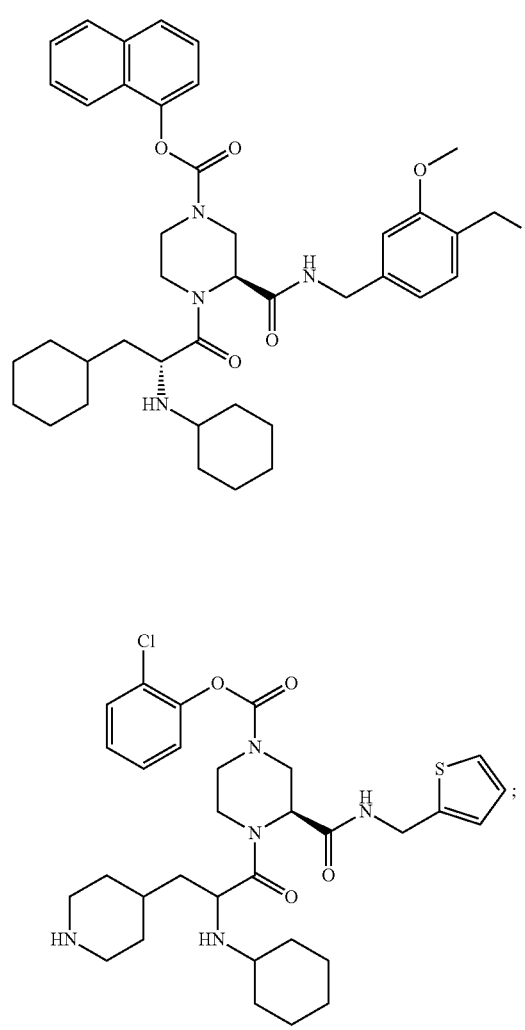
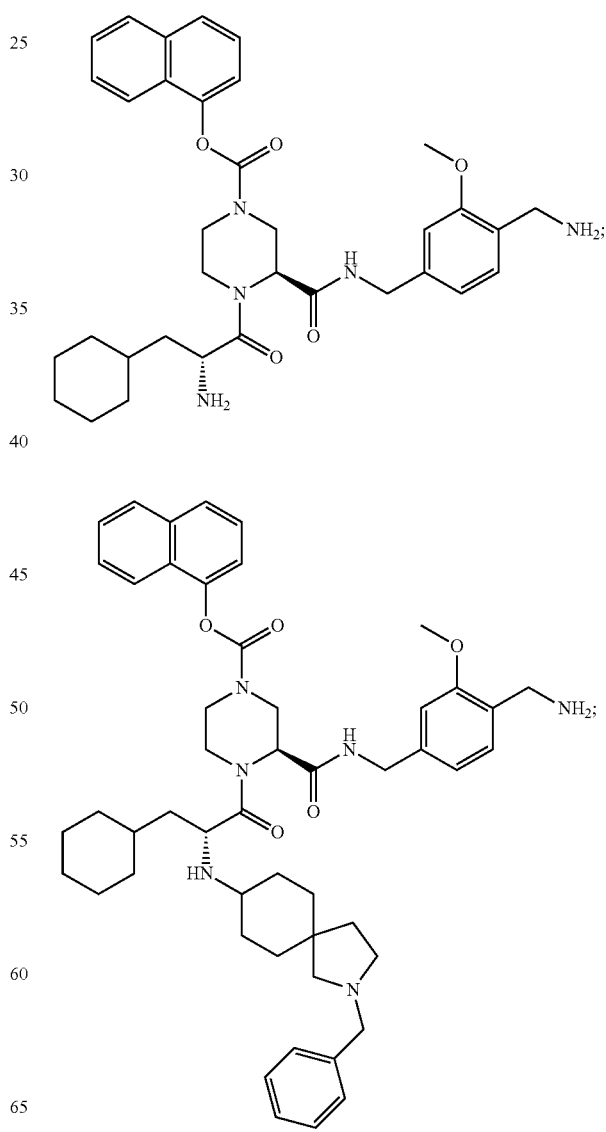

221
-continued
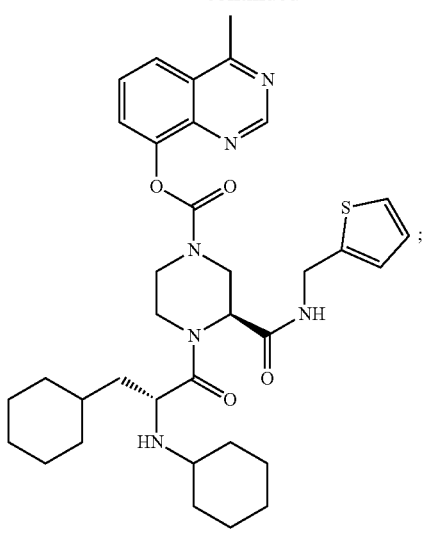
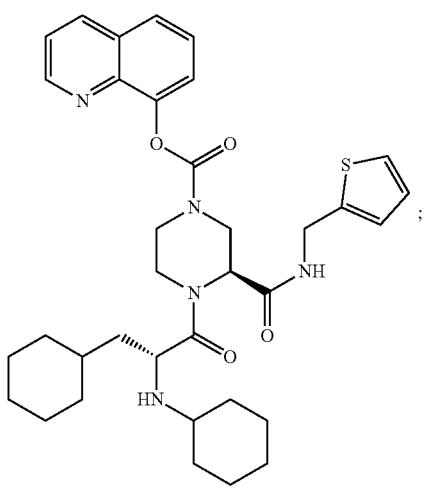
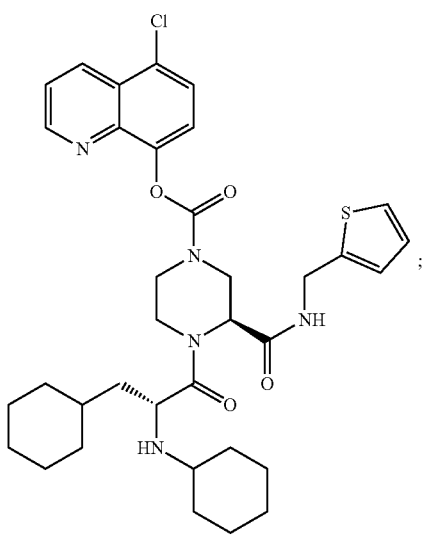
222
-continued
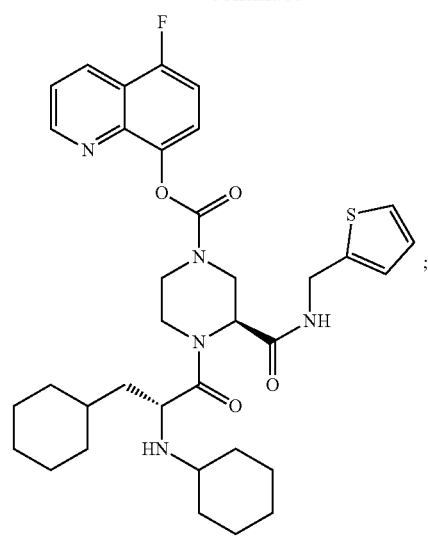
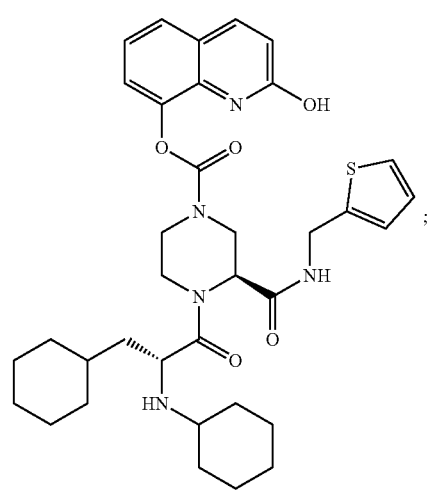
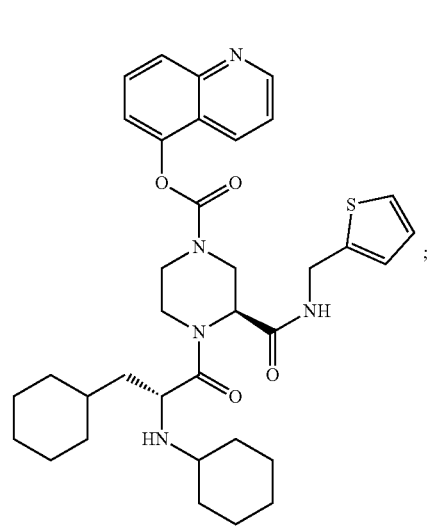

223
-continued
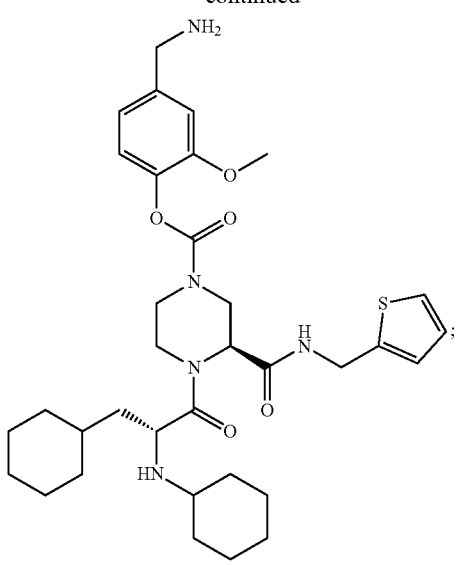
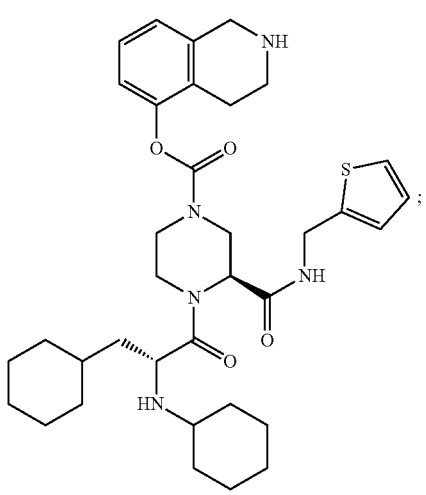
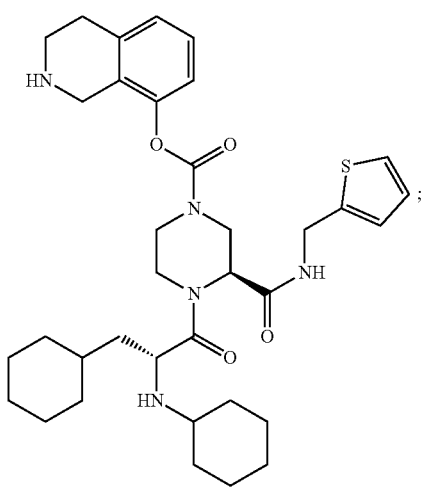
224
-continued
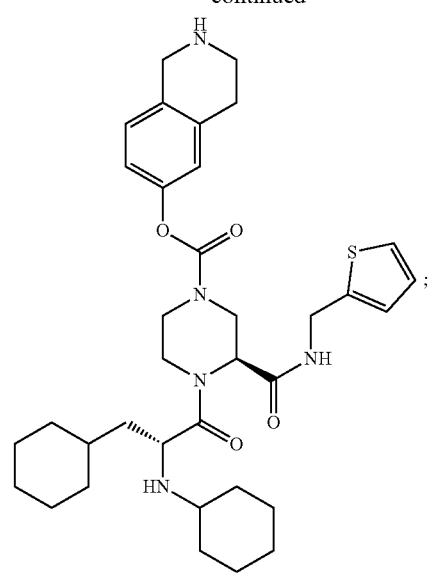
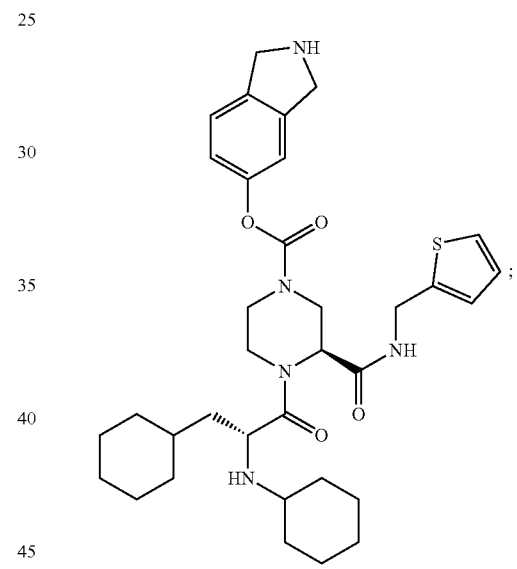
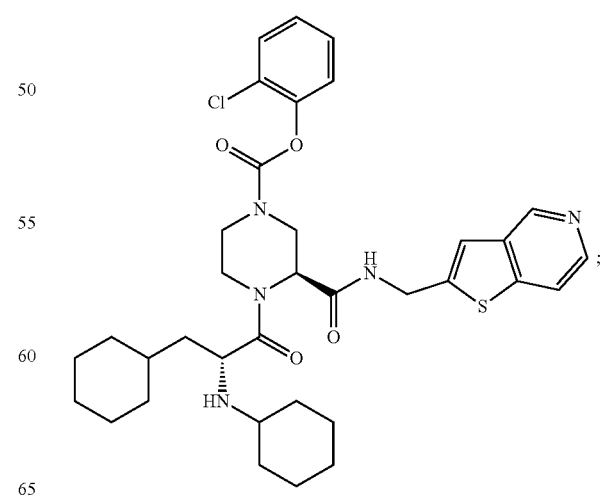

225
-continued
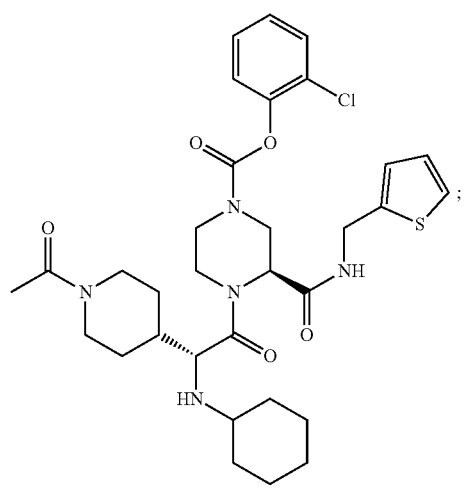
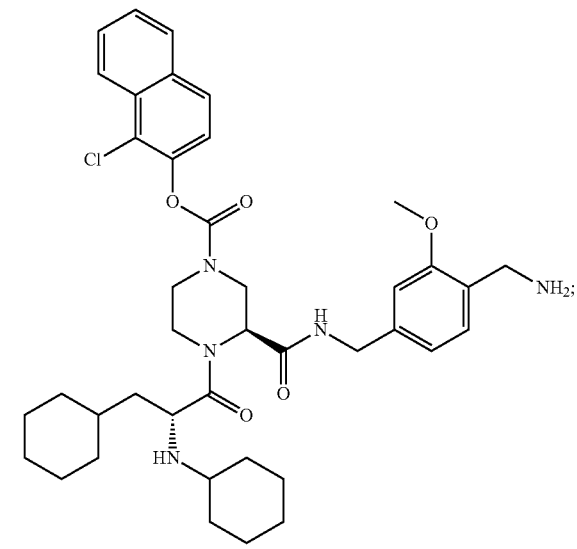
226
-continued
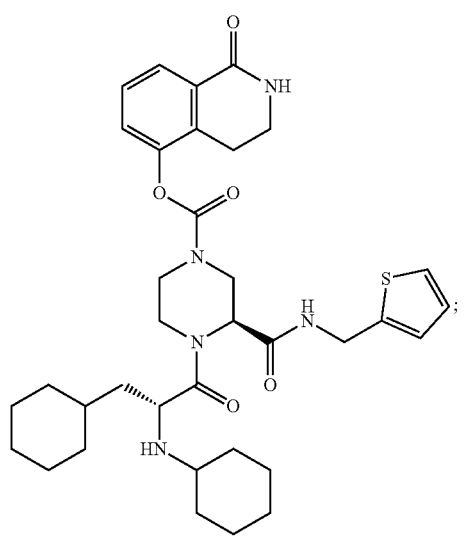
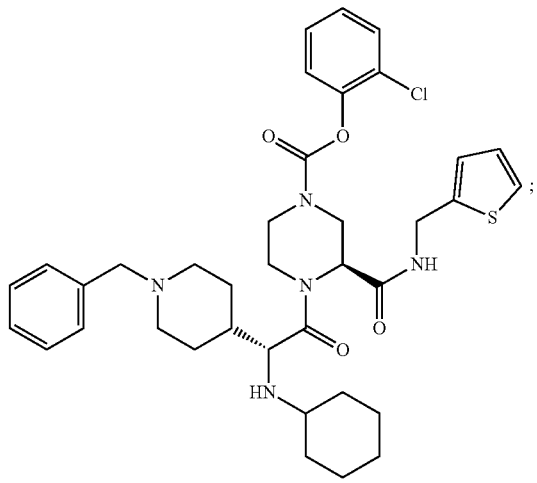

227
-continued
228
-continued
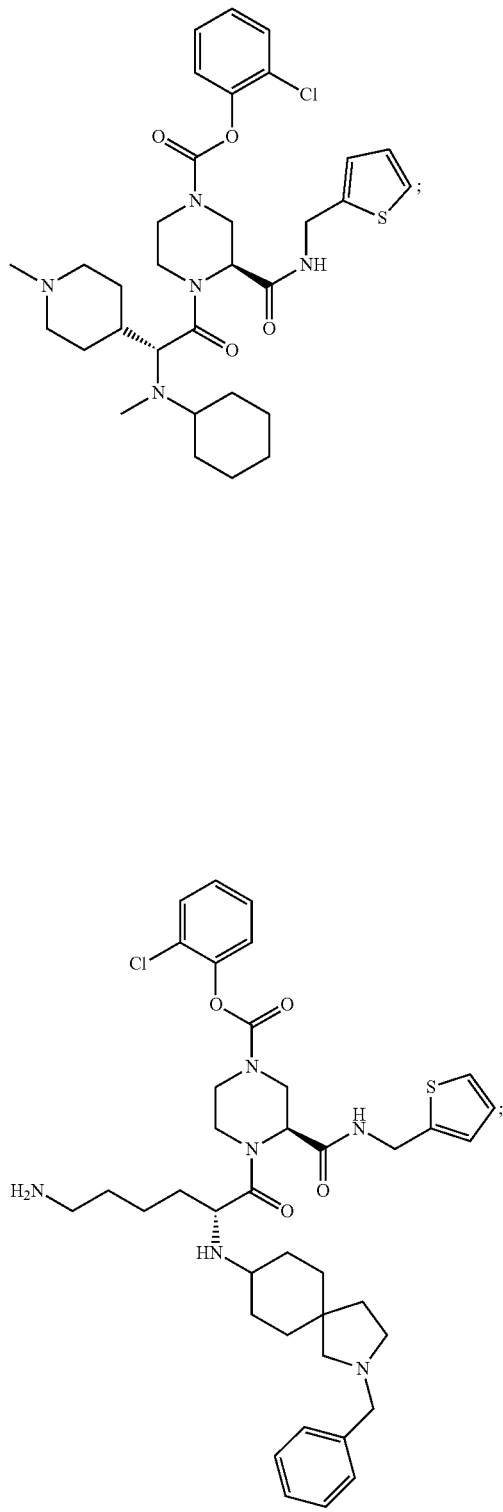
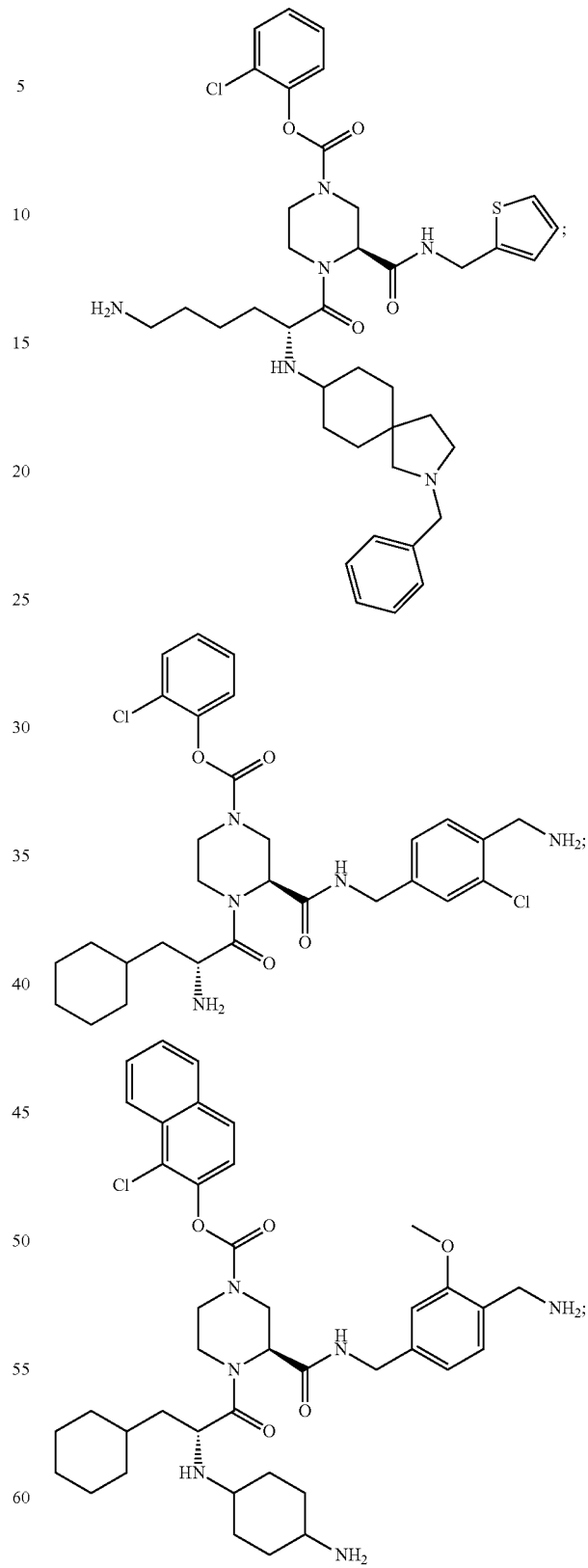

229
-continued
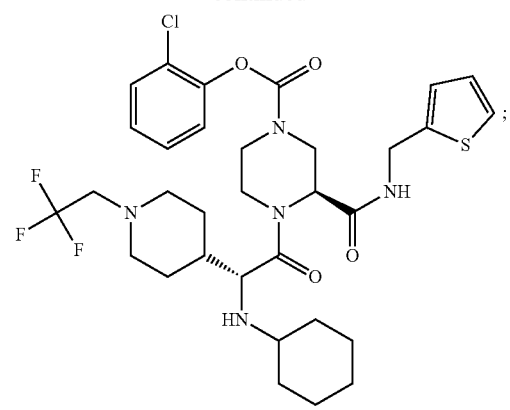
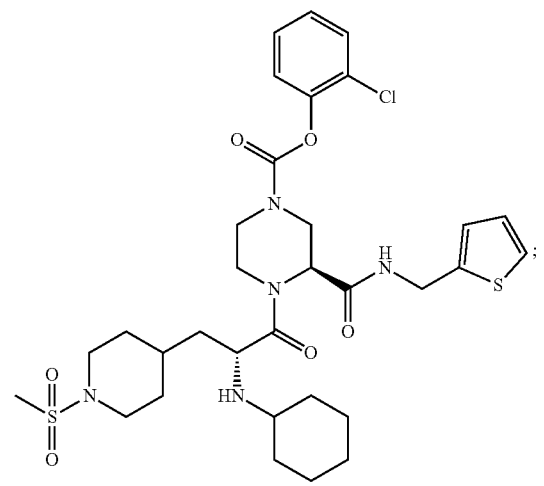
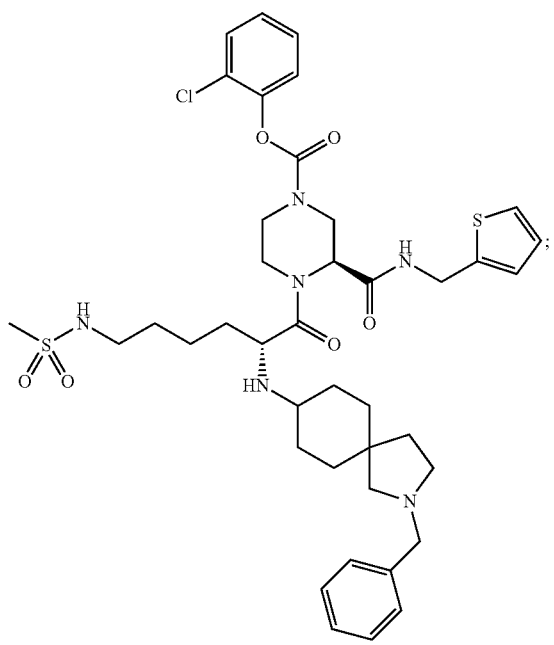
230
-continued
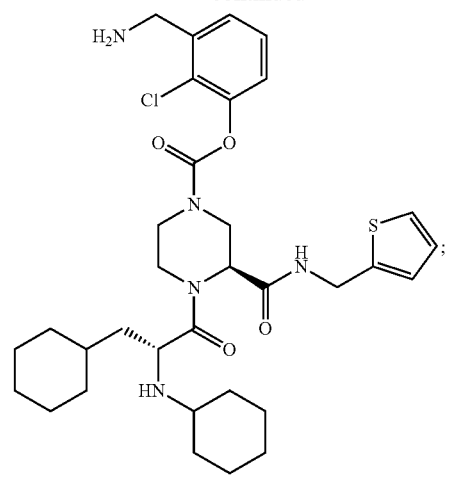
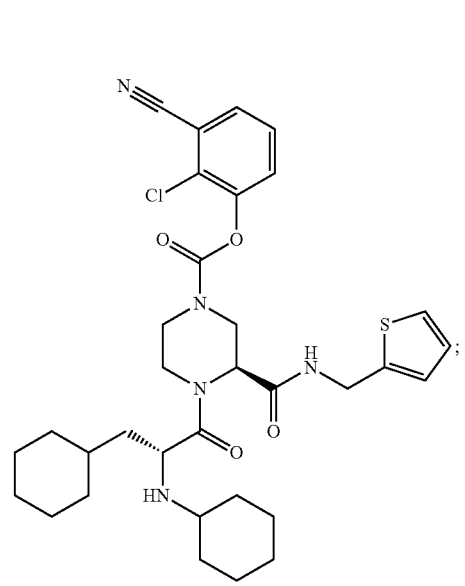
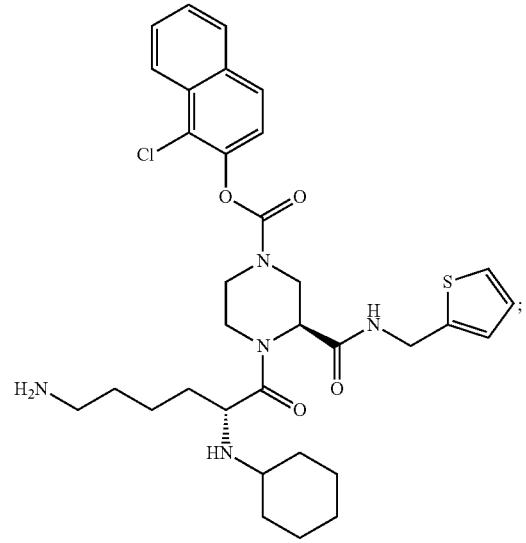

231
-continued
232
-continued
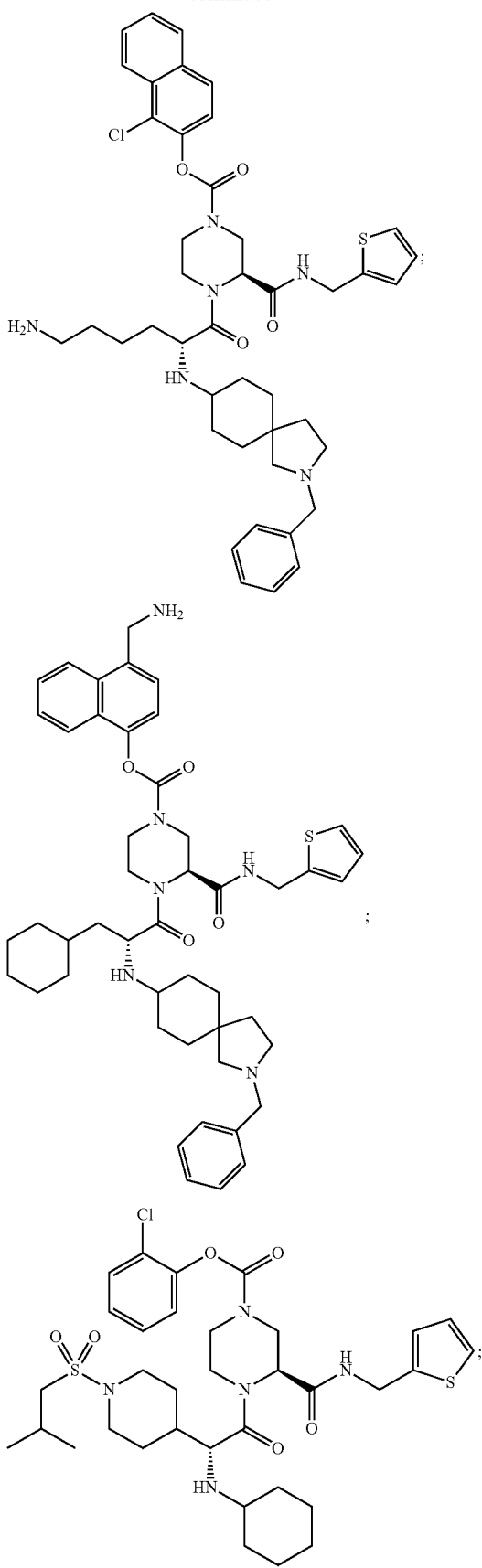
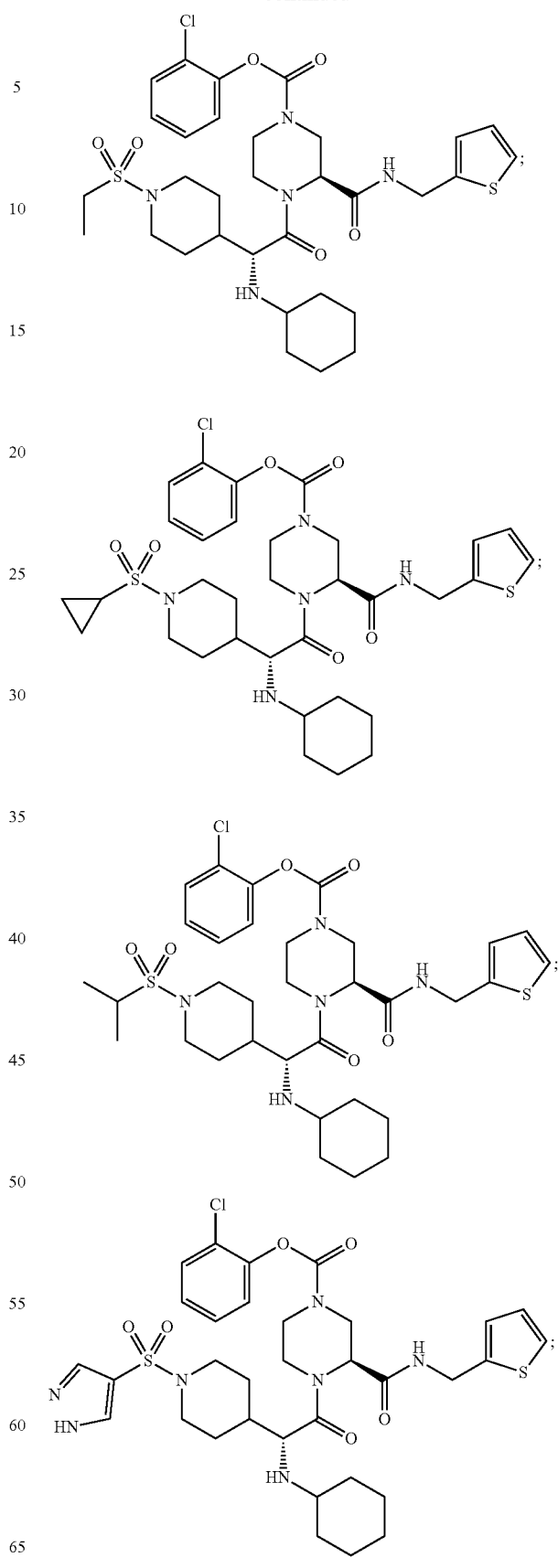

233
-continued
234
-continued
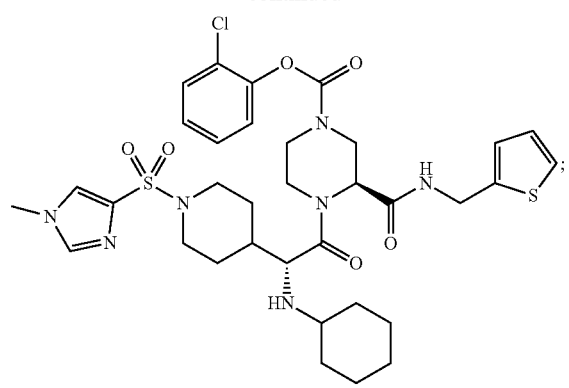
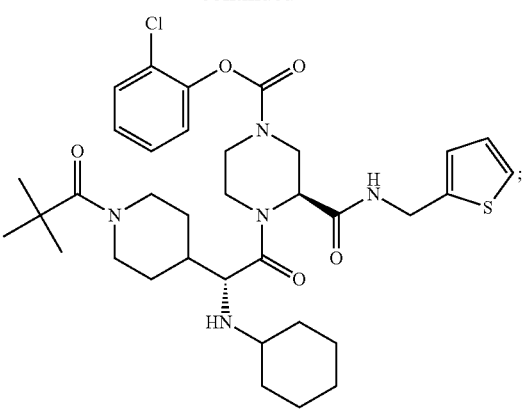
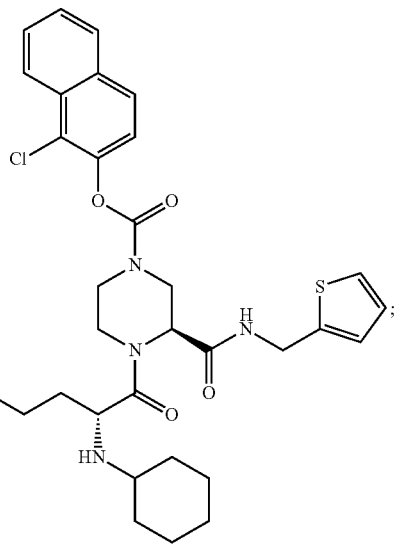
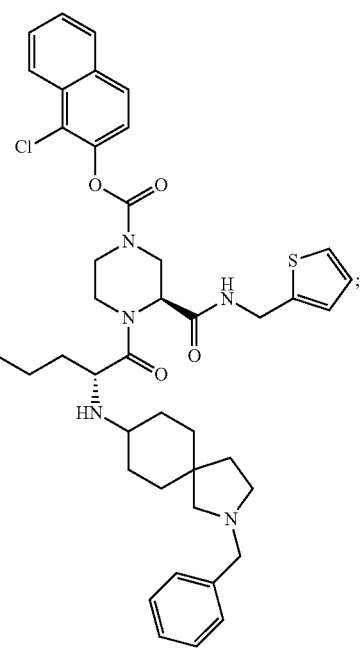

235
-continued
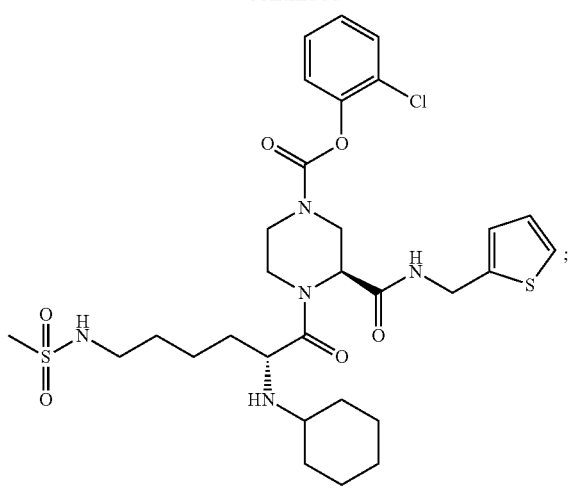
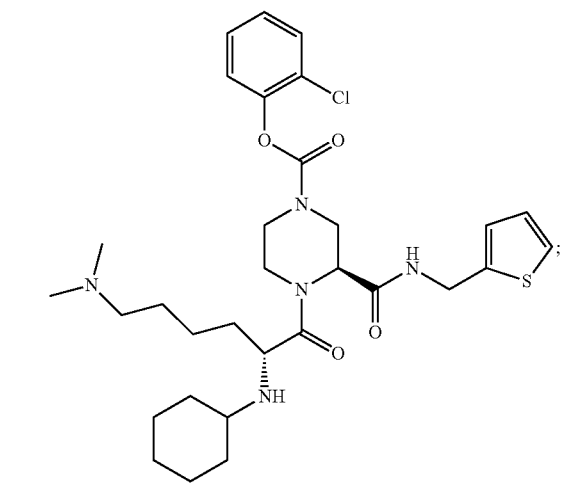
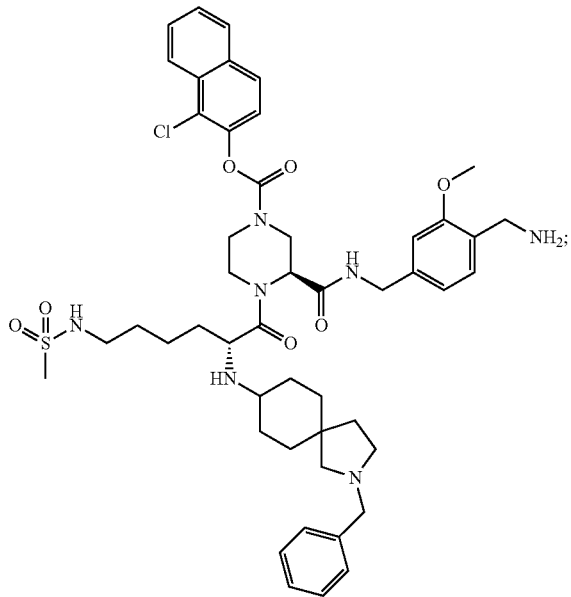
236
-continued
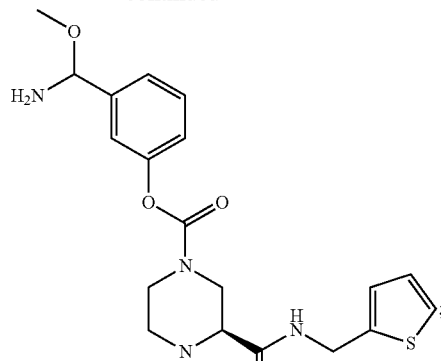
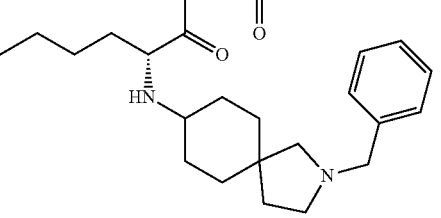
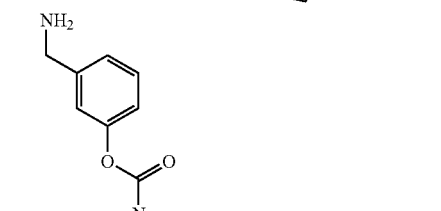
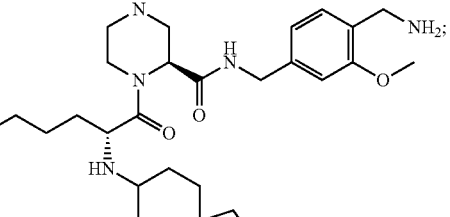

237
-continued
238
-continued
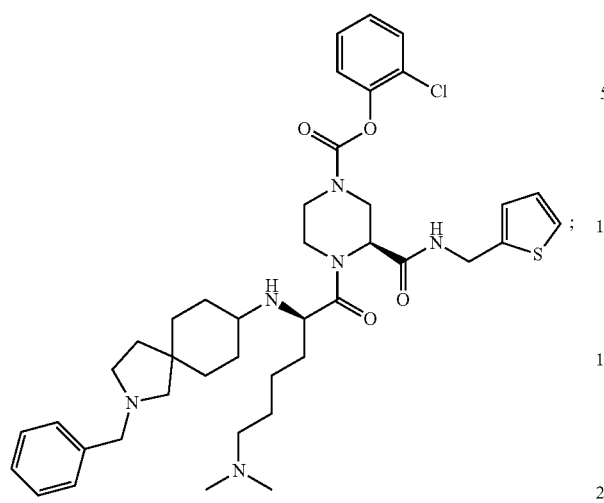
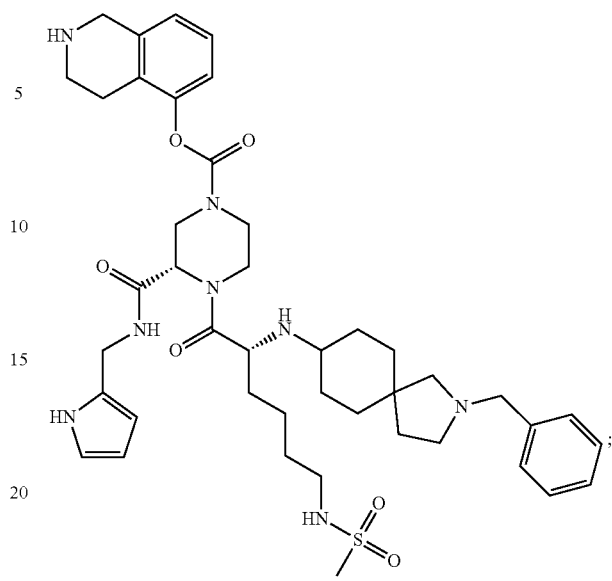
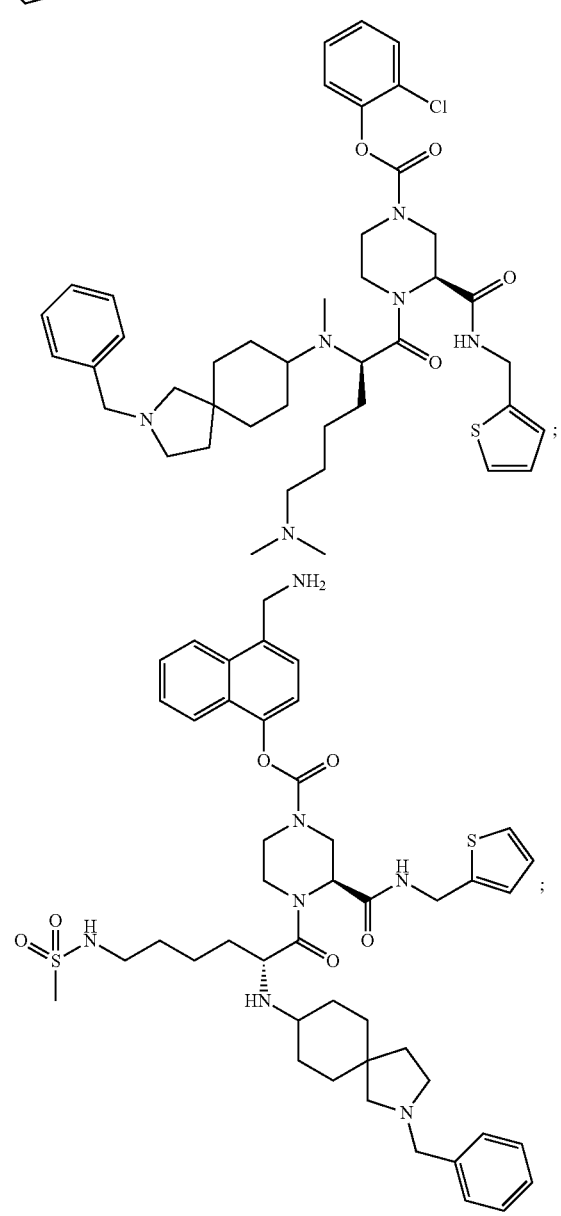
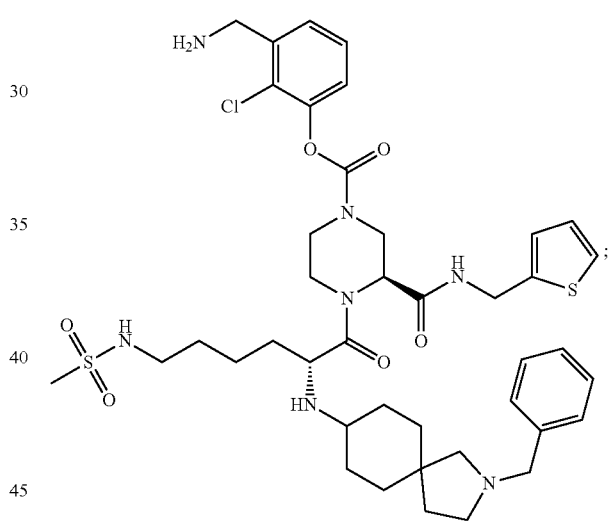
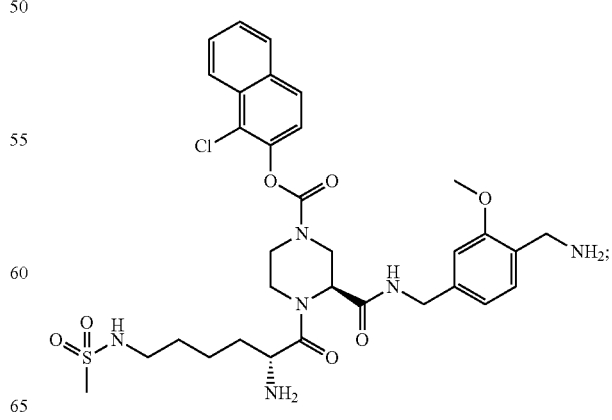

239
-continued
240
-continued
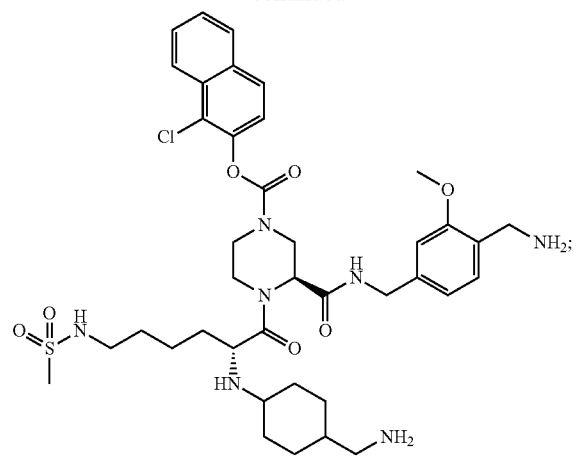
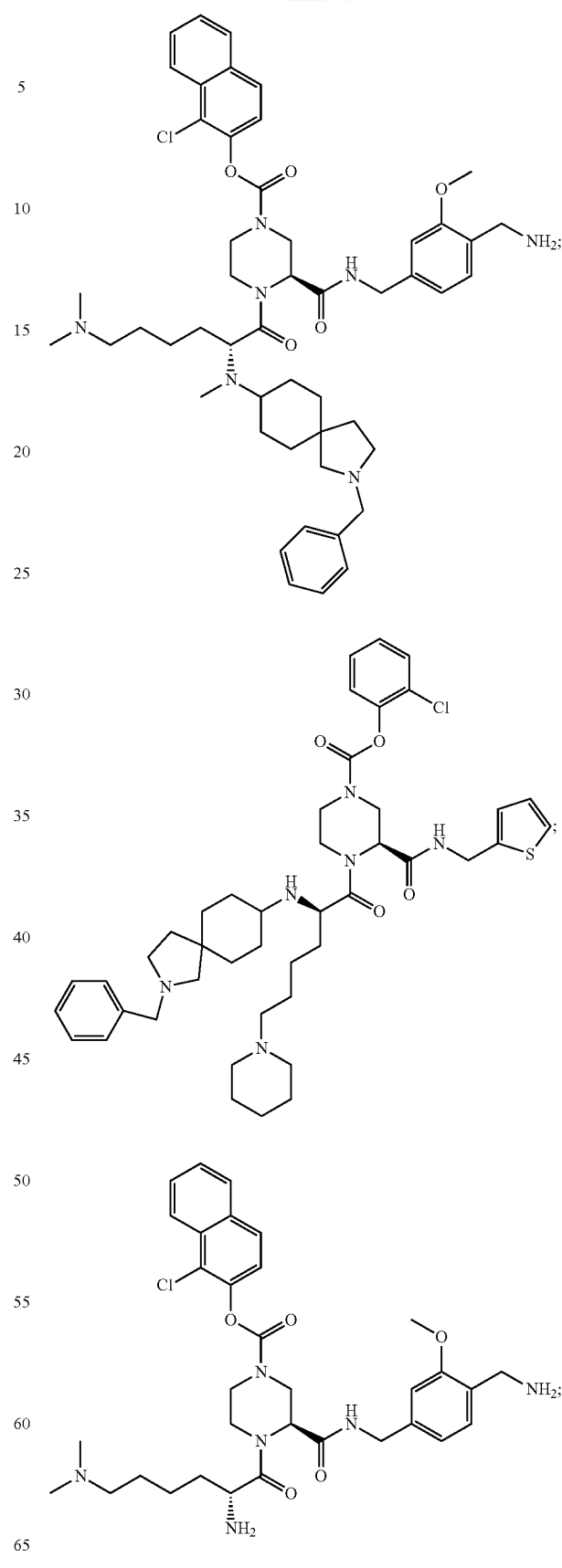

241
-continued
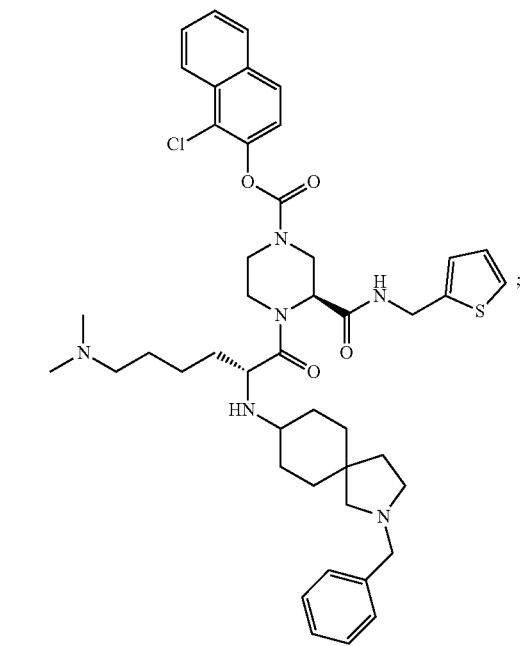
242
-continued
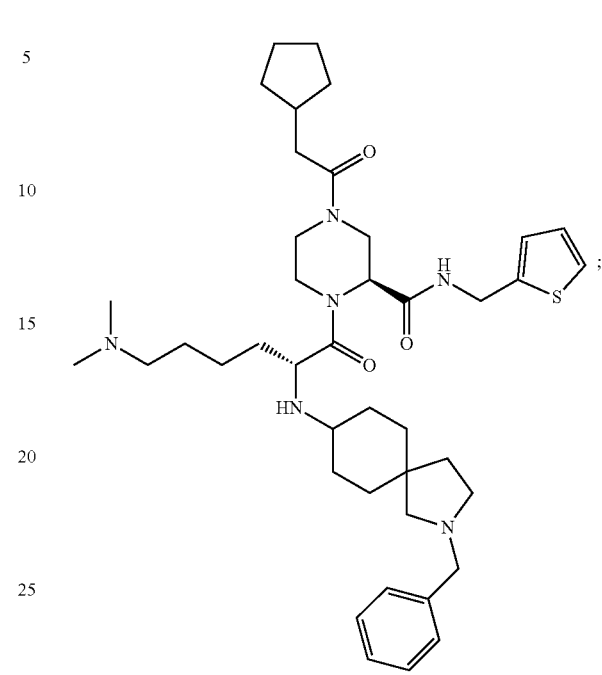
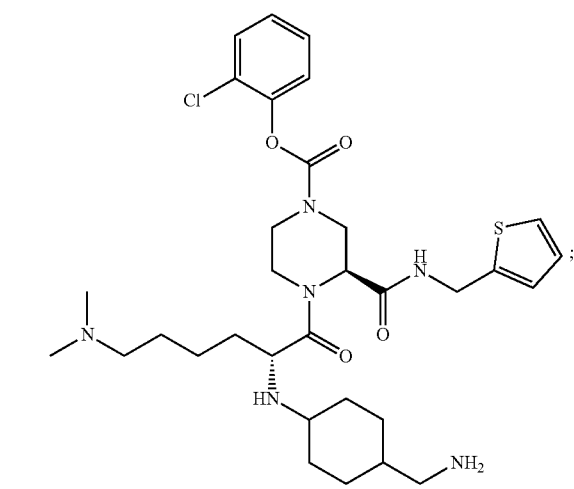
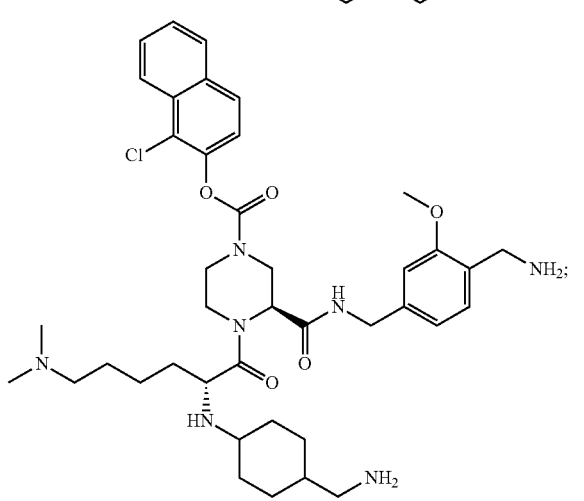
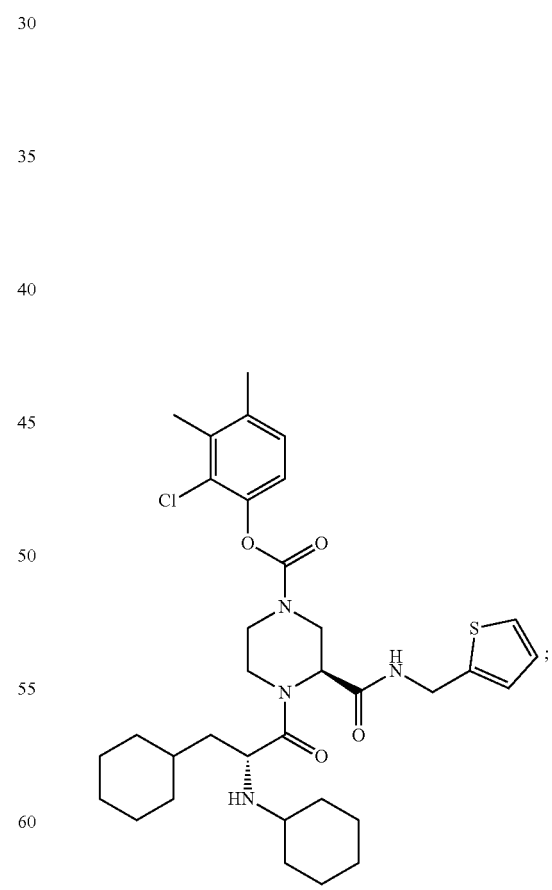

243
-continued
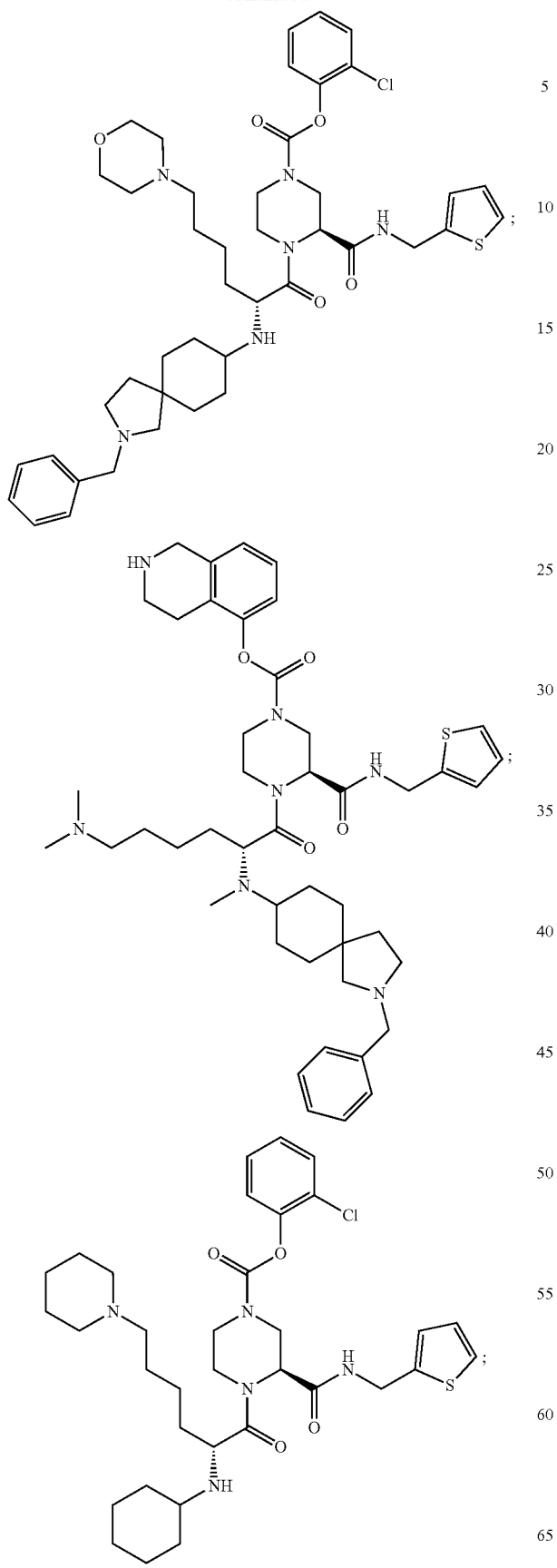
244
-continued
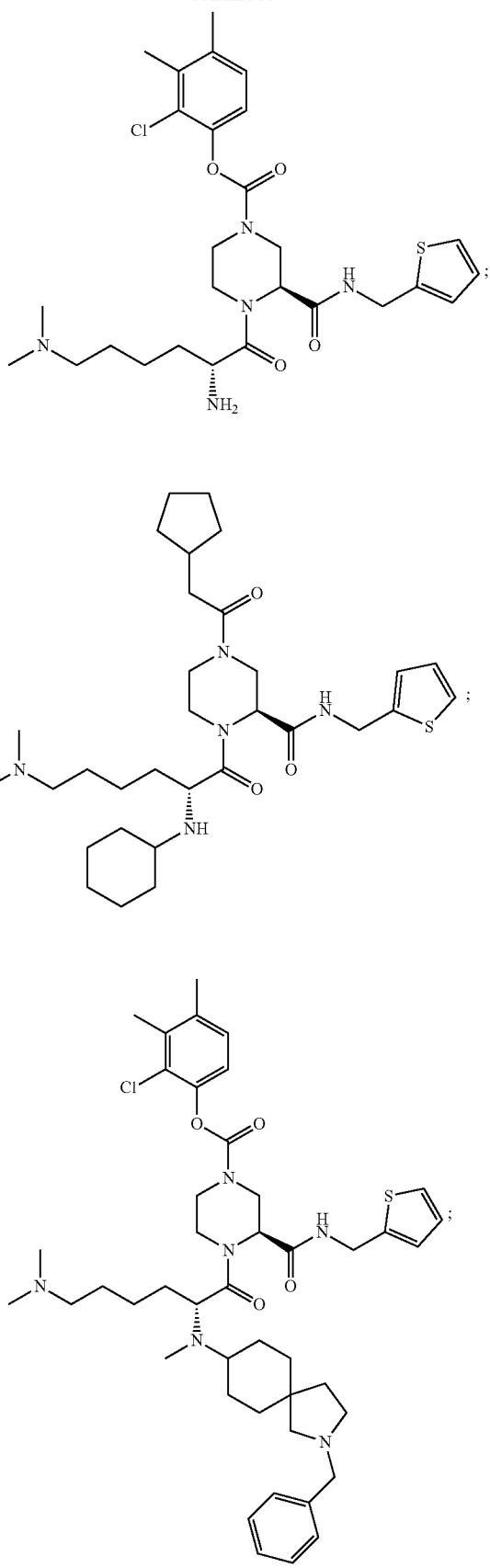

245
-continued
246
-continued
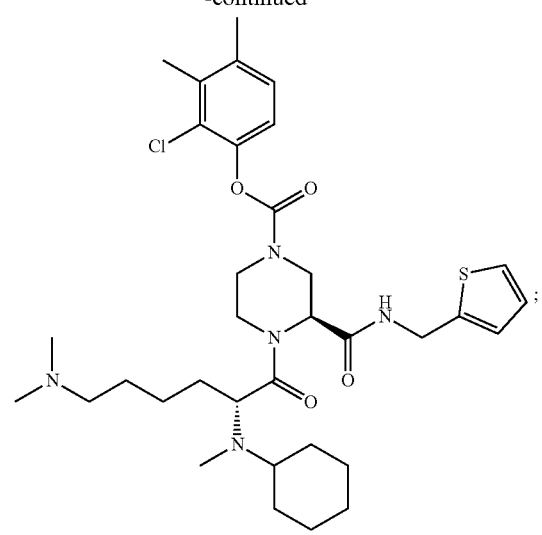
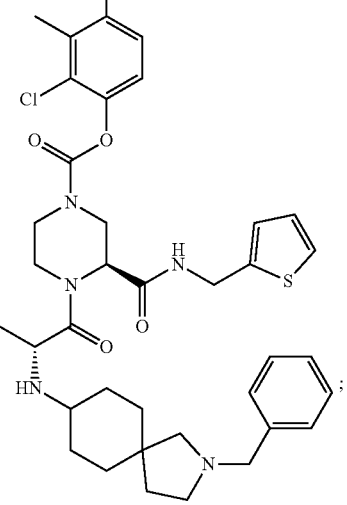
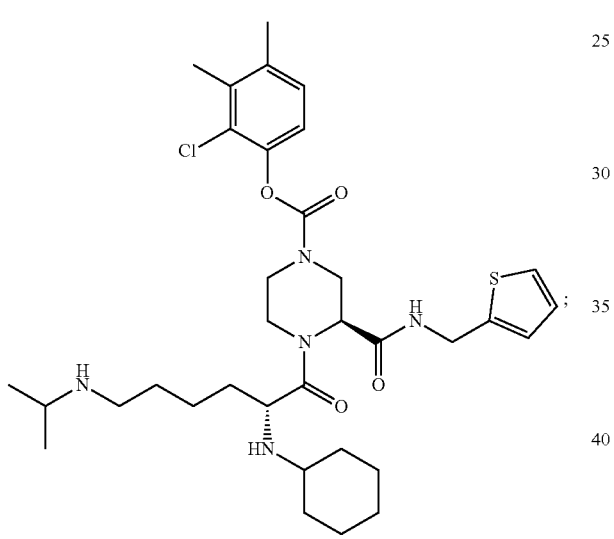
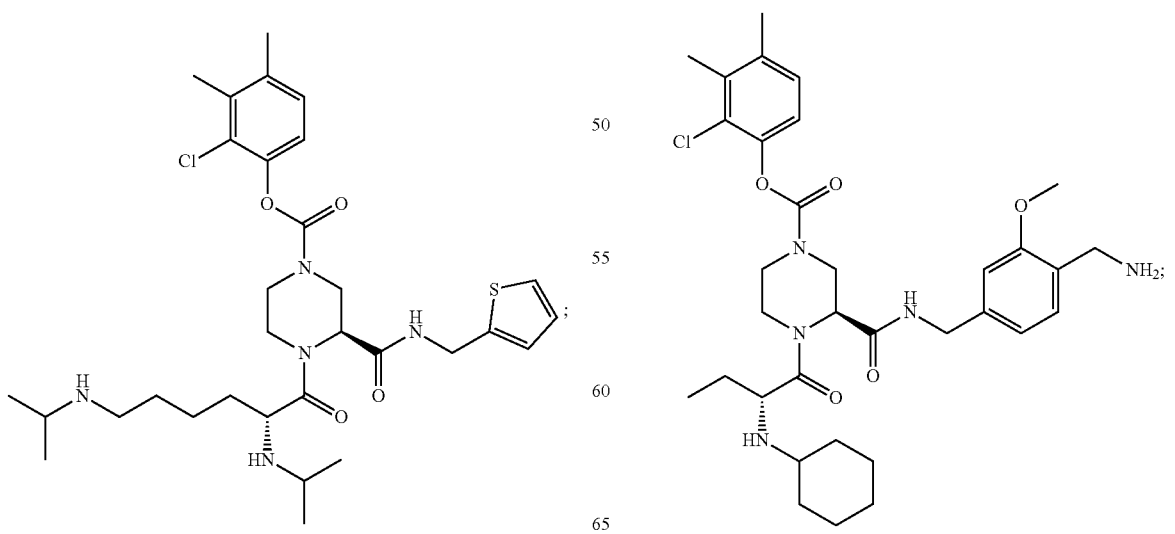

247
-continued
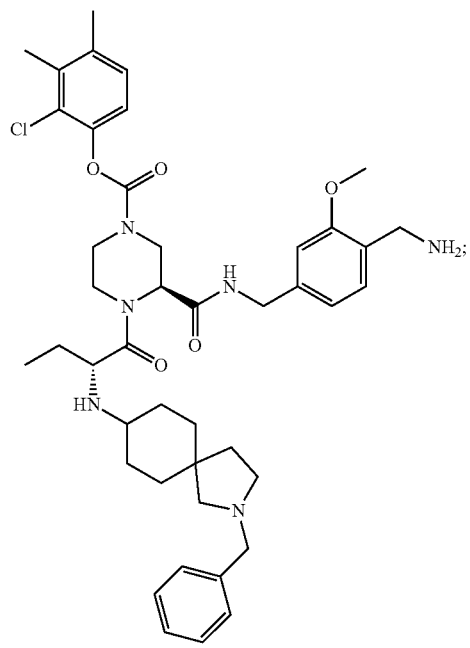
248
-continued
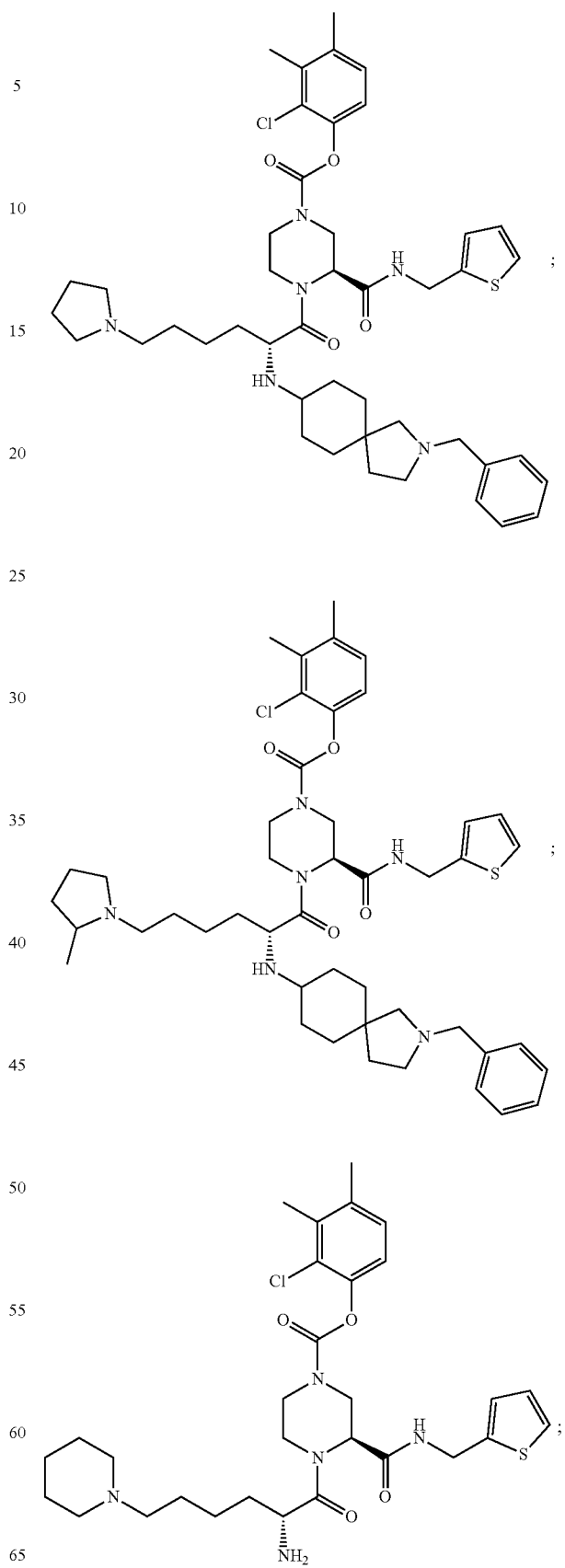

249
-continued
250
-continued
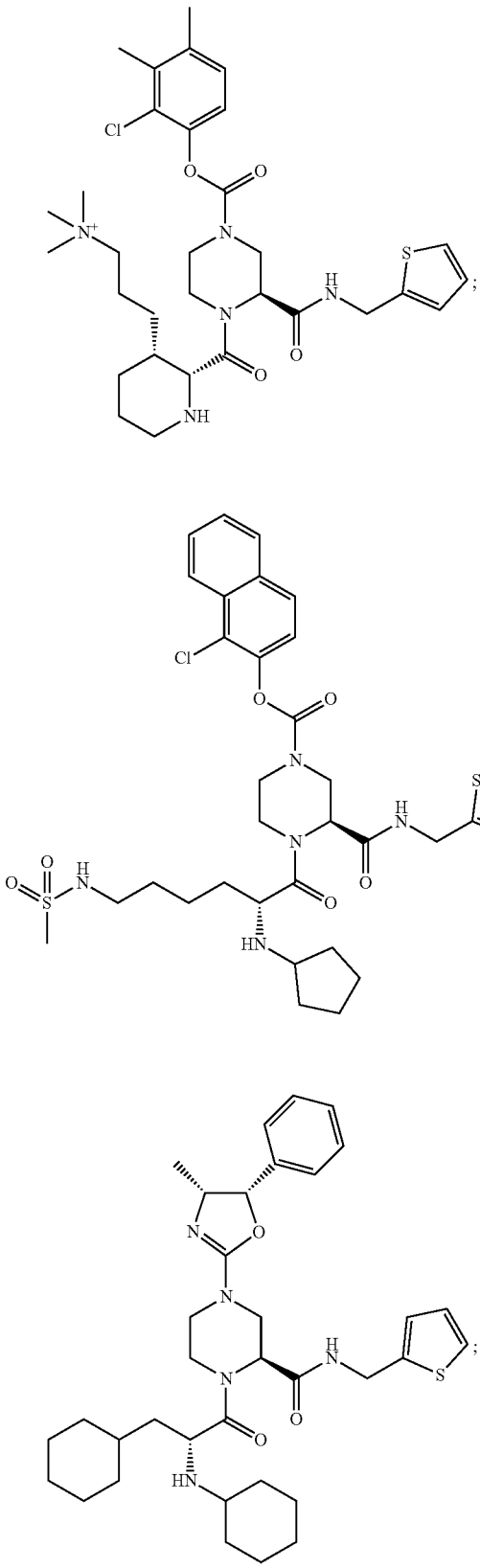
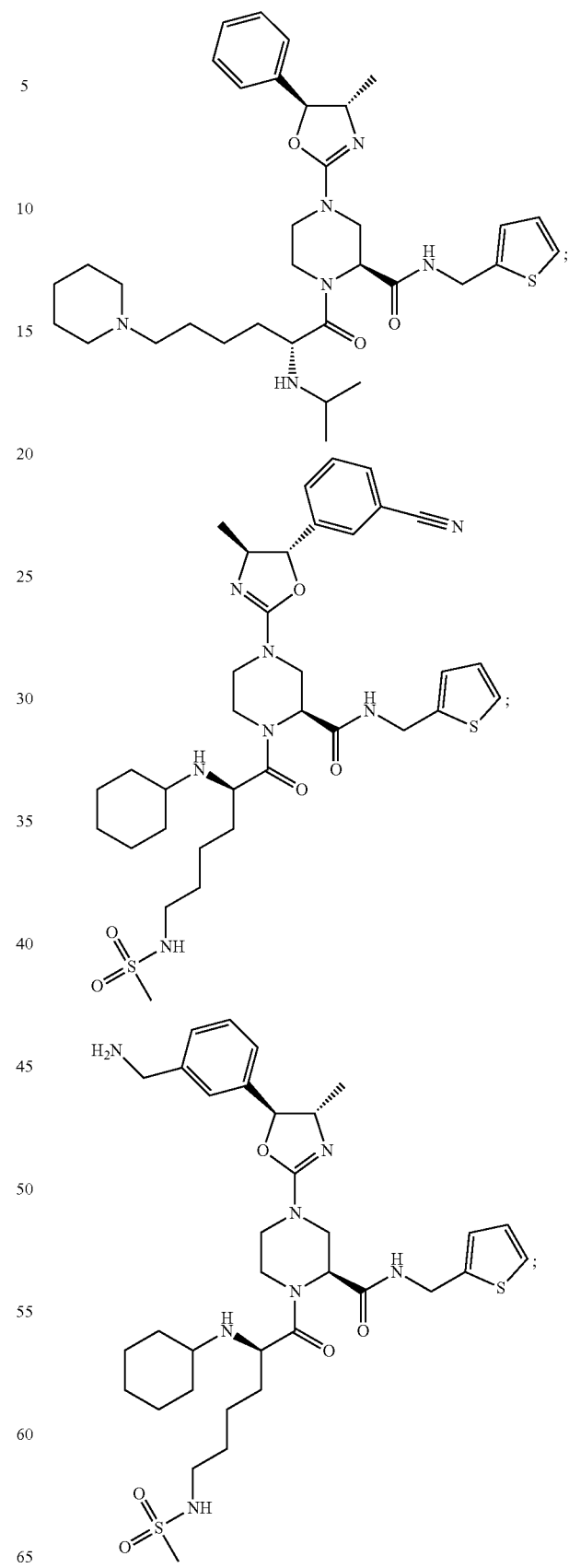

251
-continued
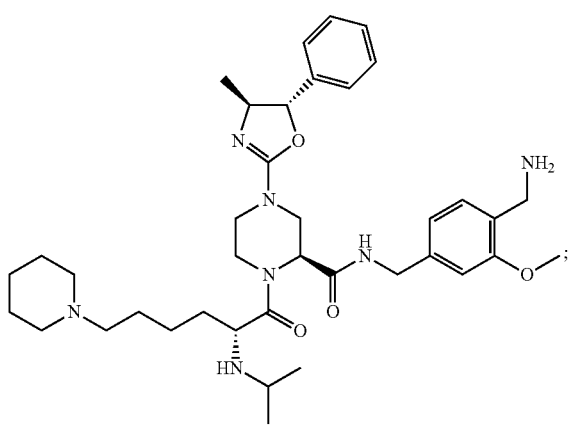
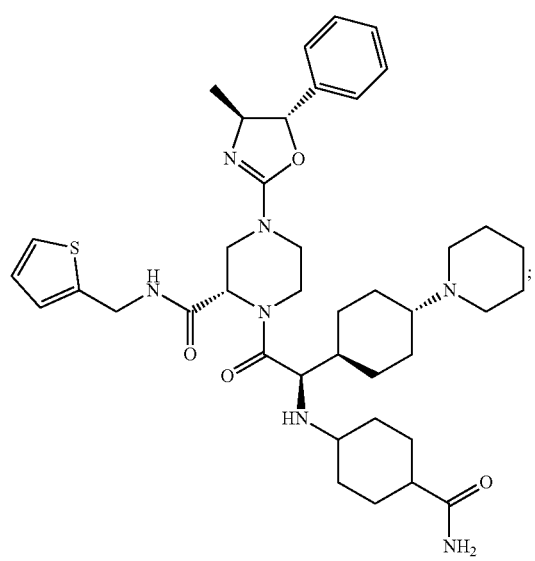
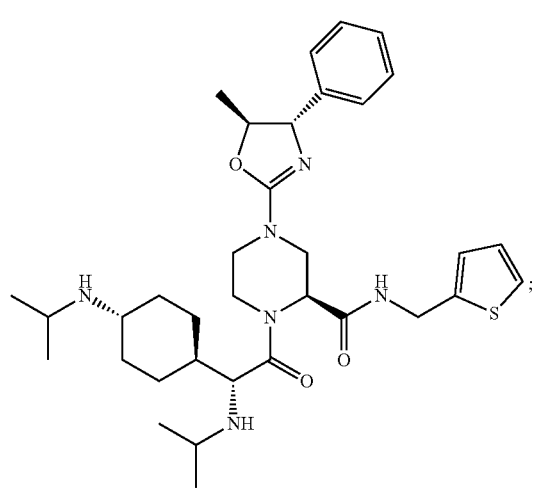
252
-continued
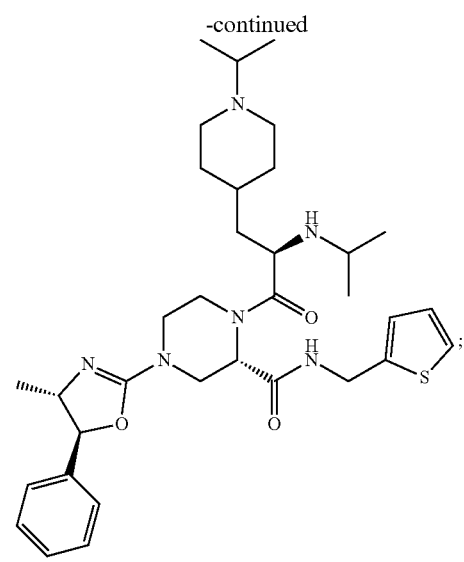
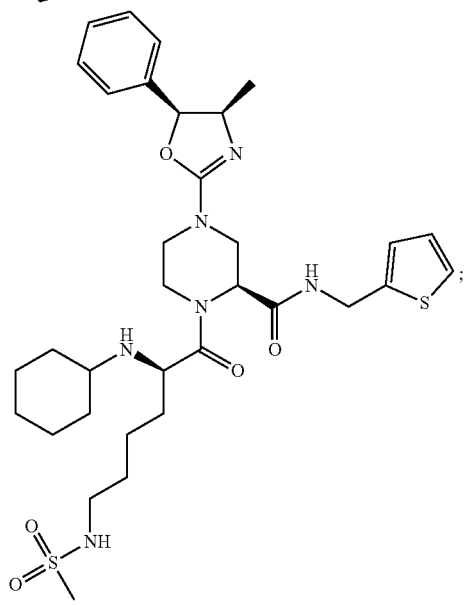
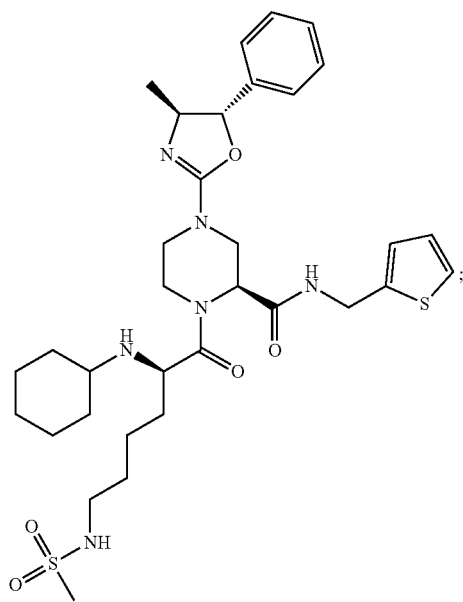

253
-continued
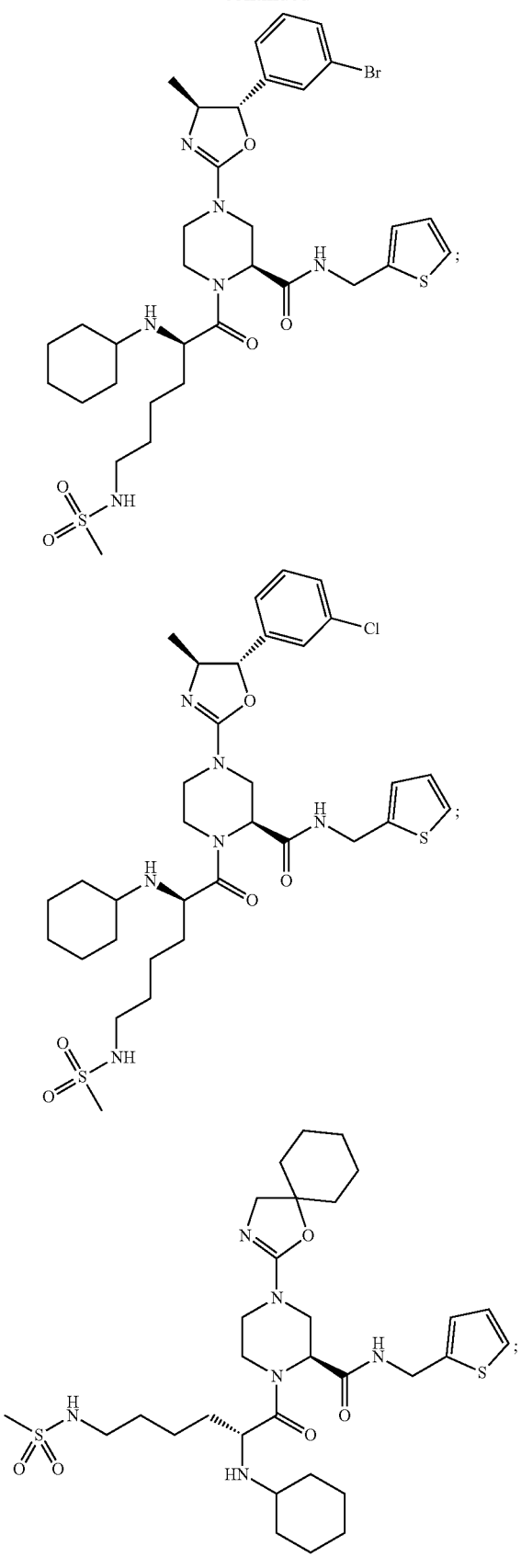
254
-continued
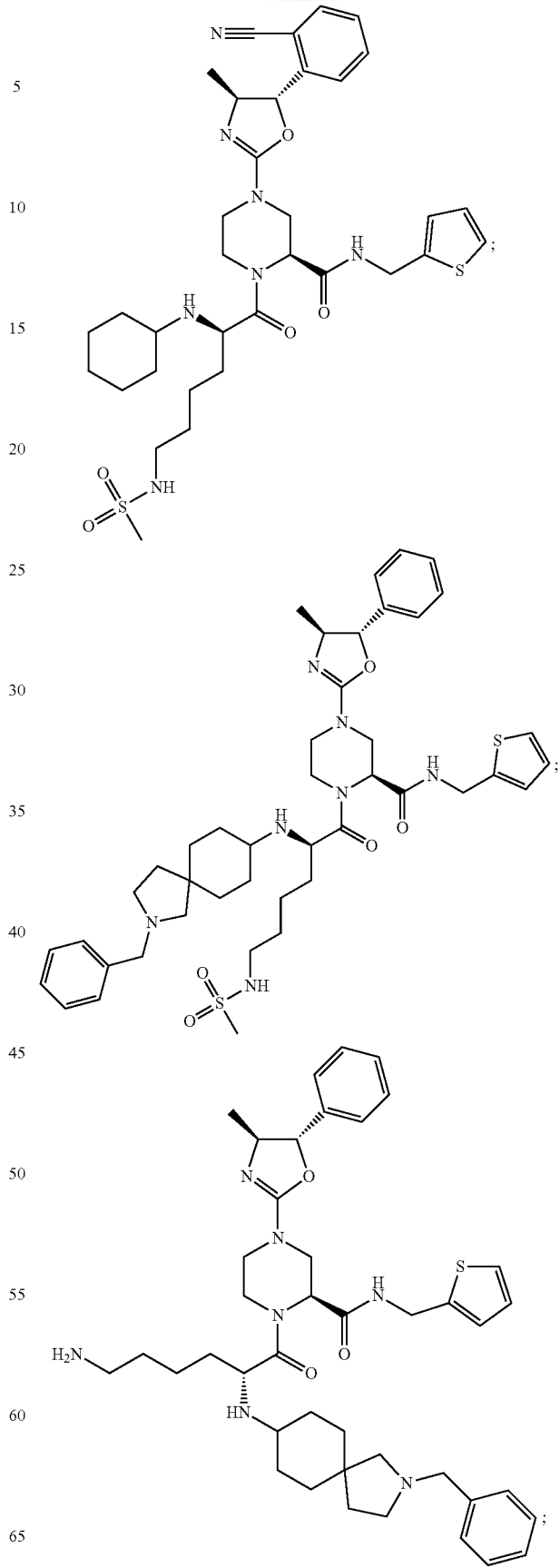

255
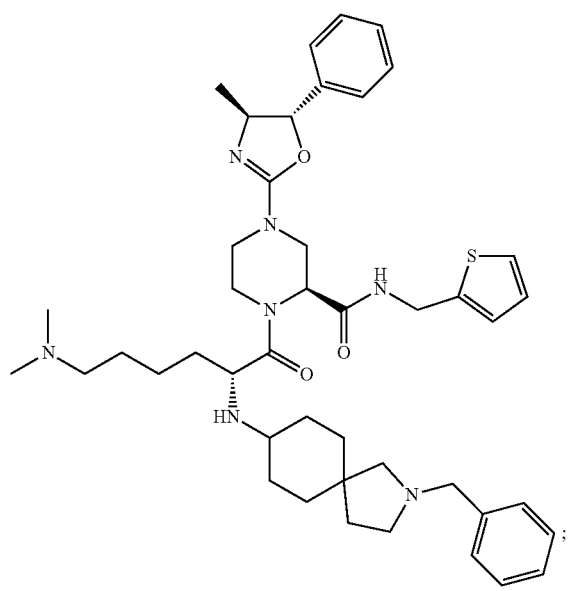
256
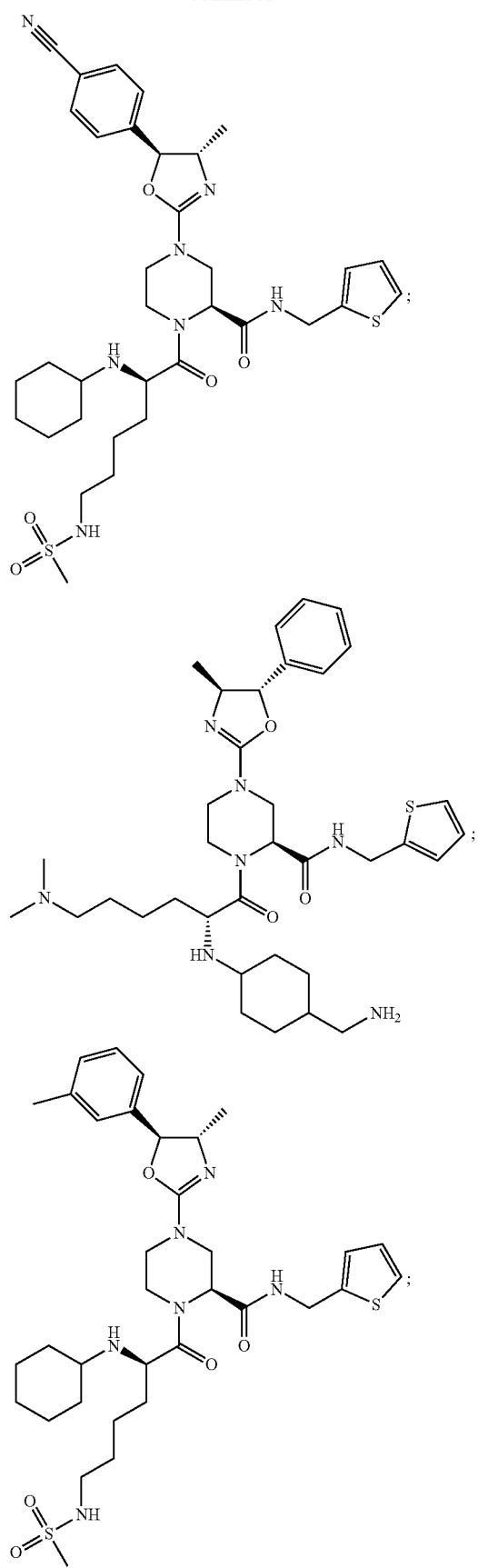 [SMILES: C[C@@H]1N=C(N2CCN(C(=O)[C@@H](CCCCNS(C)(=O)=O)NC3CCCCC3)[C@H](C(=O)NCc3cccs3)C2)O[C@H]1c1ccc(C#N)cc1 ; C[C@@H]1N=C(N2CCN(C(=O)[C@@H](CCCCN(C)C)NC3CCC(CN)CC3)[C@H](C(=O)NCc3cccs3)C2)O[C@H]1c1ccccc1 ; Cc1cccc([C@@H]2OC(N3CCN(C(=O)[C@@H](CCCCNS(C)(=O)=O)NC4CCCCC4)[C@H](C(=O)NCc4cccs4)C3)=N[C@H]2C)c1]
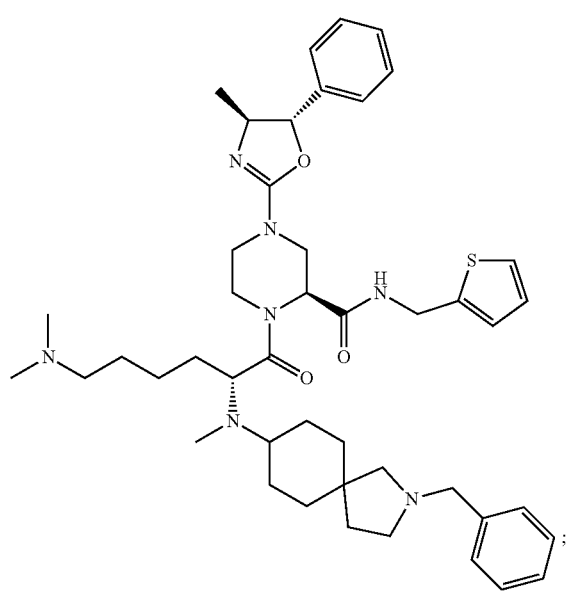

257
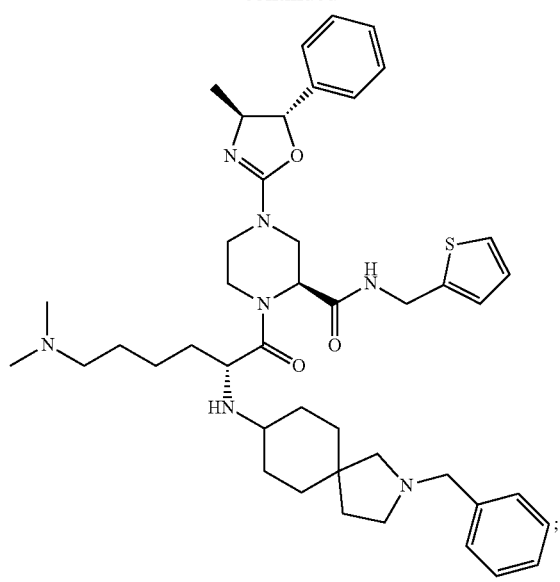
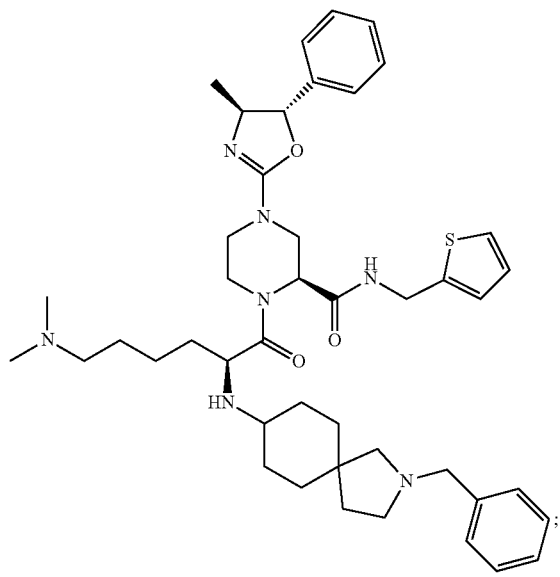
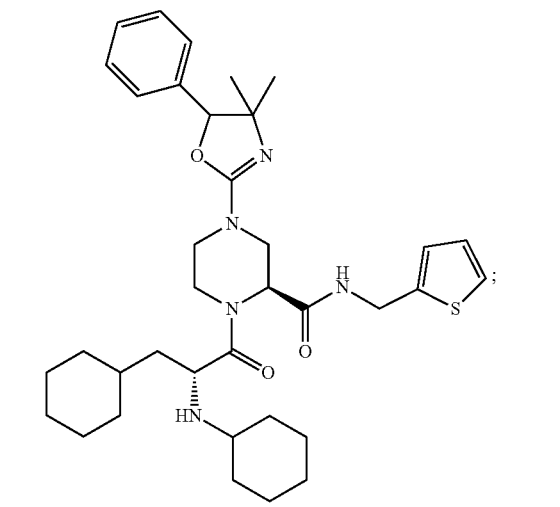
258
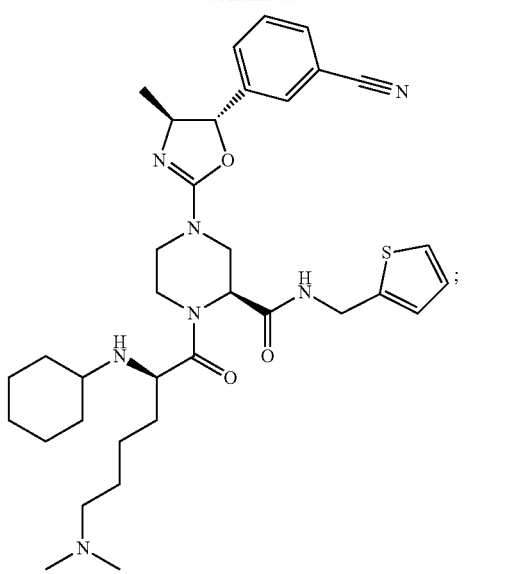
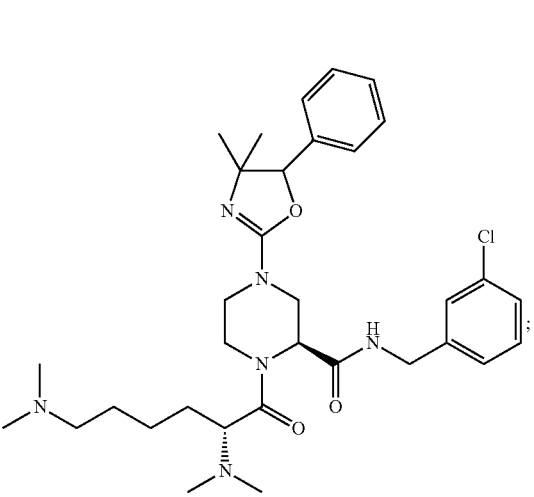
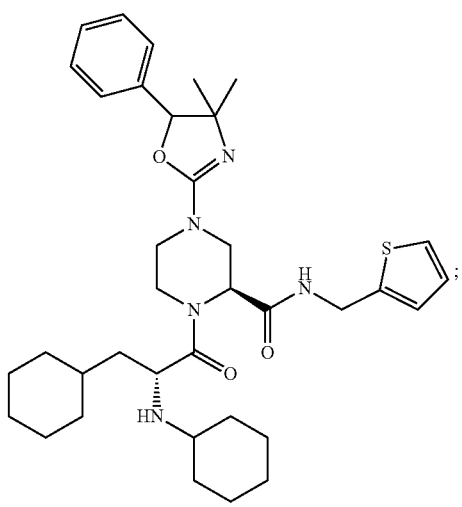

259
-continued
260
-continued
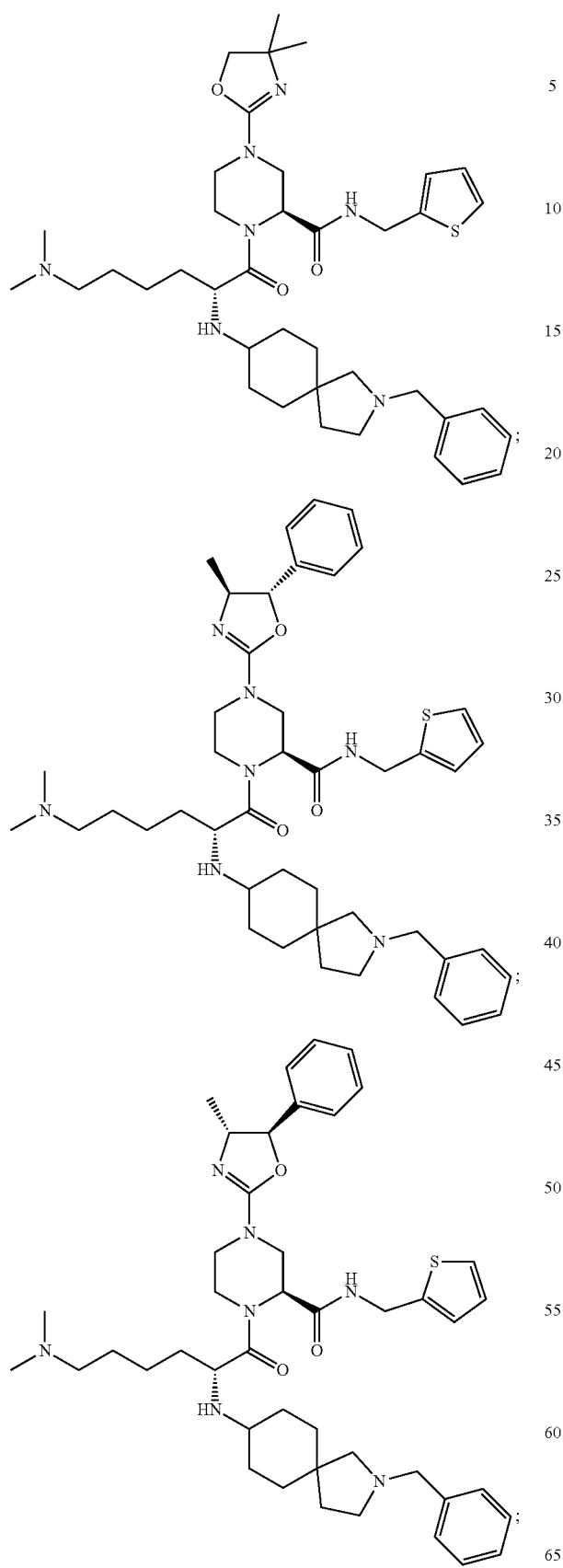
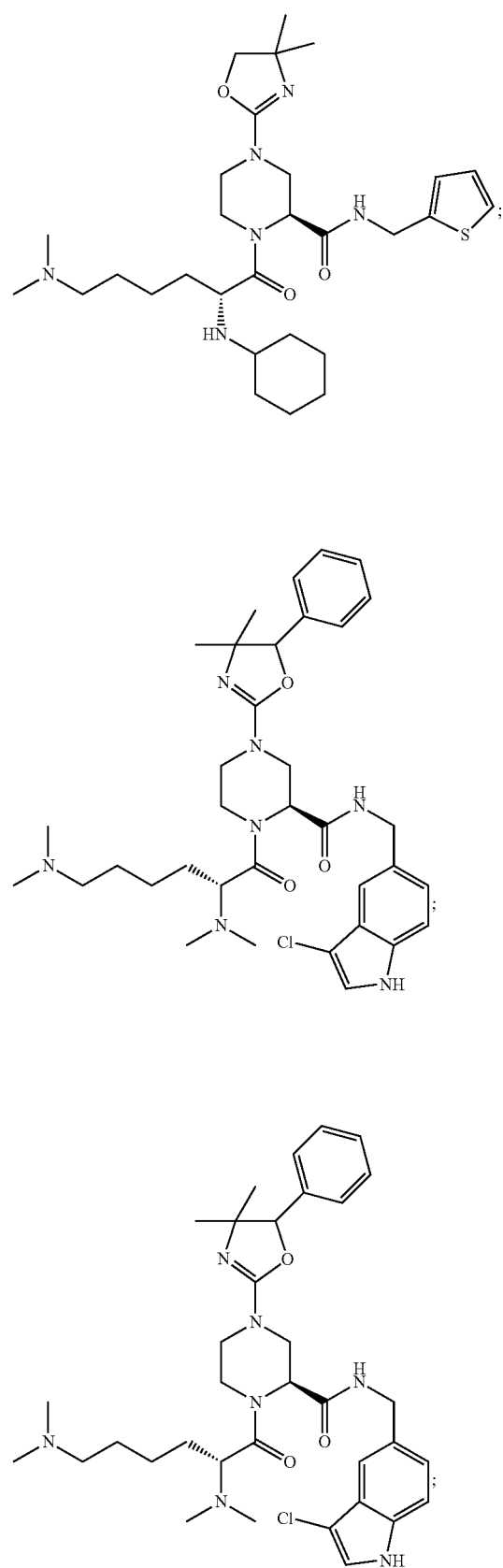

261
-continued
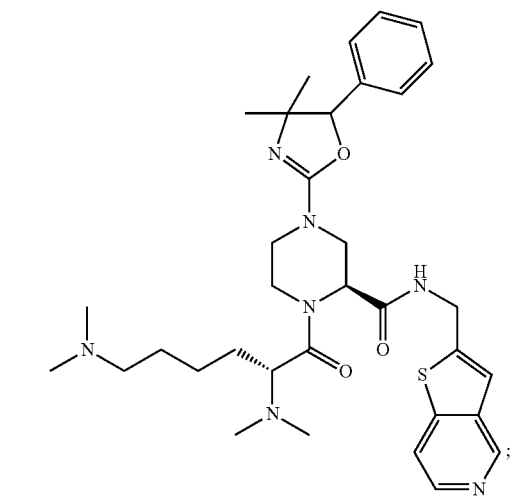
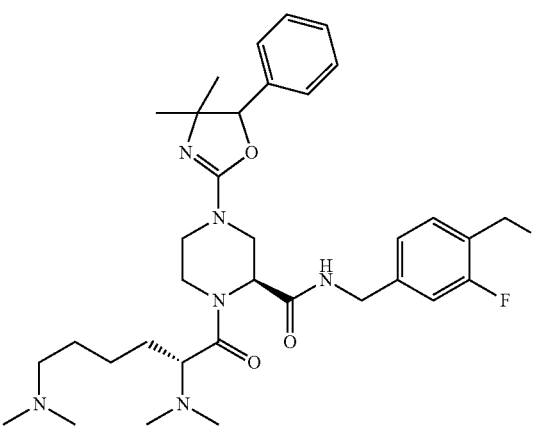
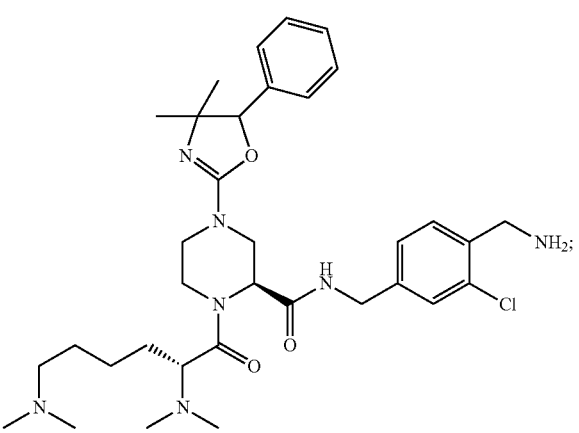
262
-continued
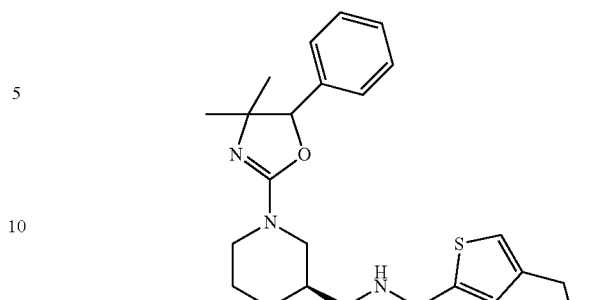
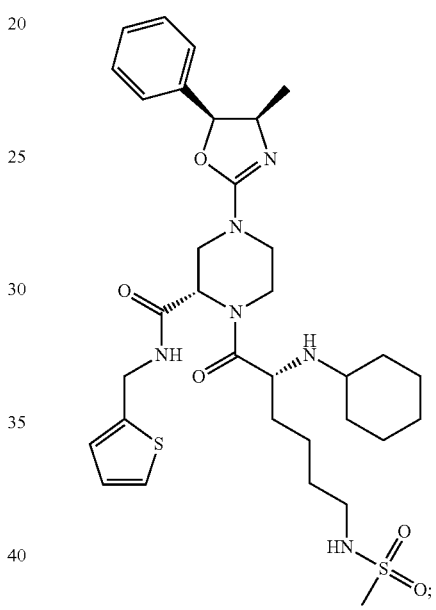
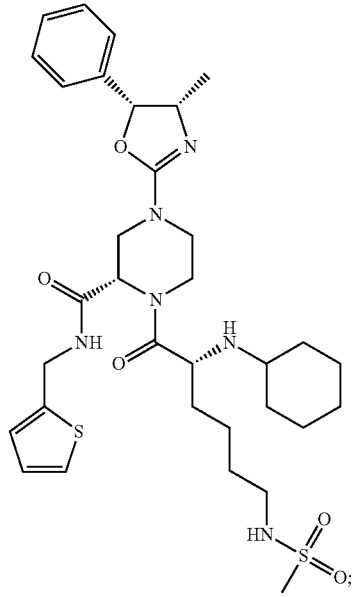

263
-continued
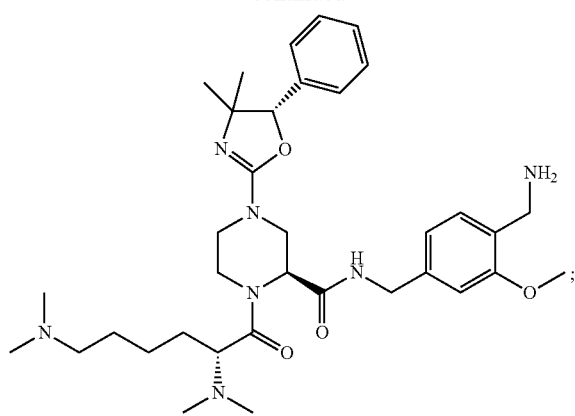
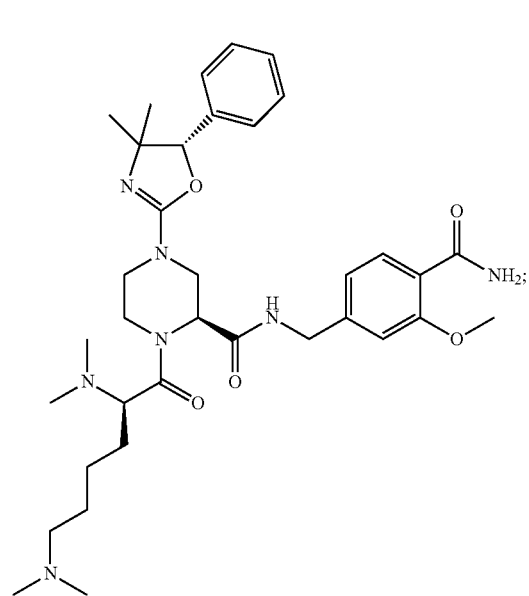
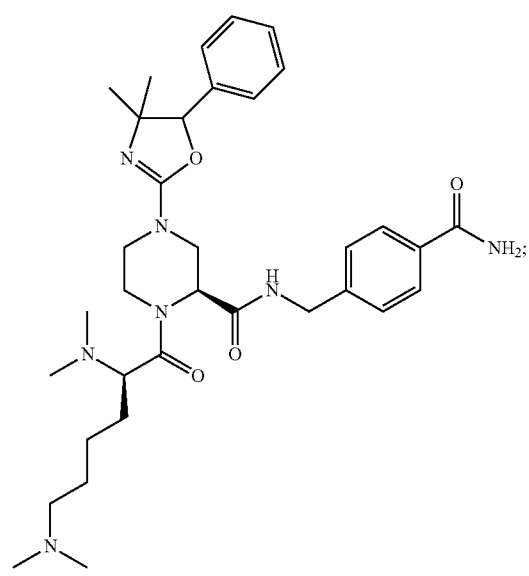
264
-continued
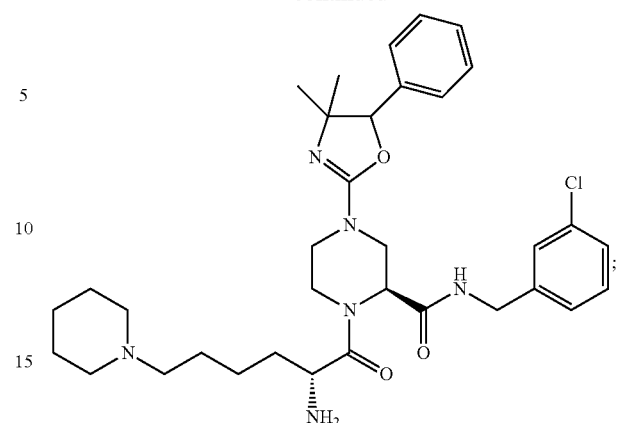
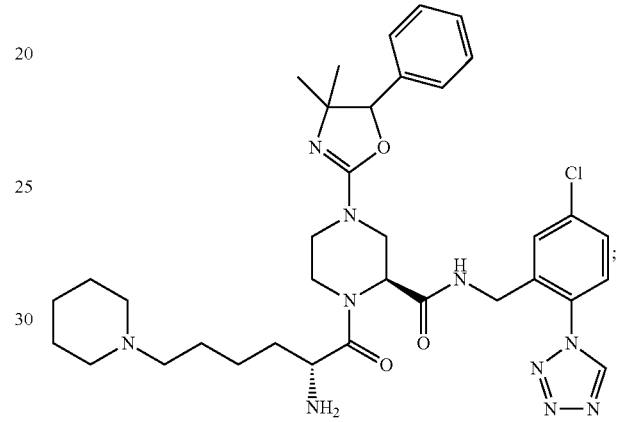
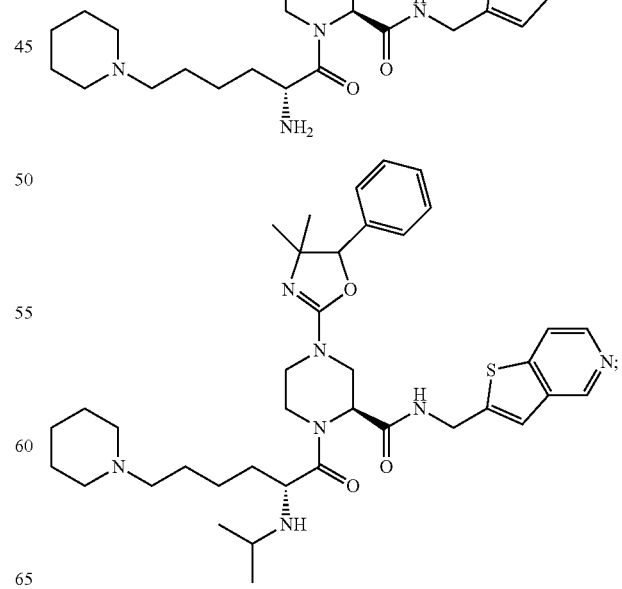

265
-continued
266
-continued
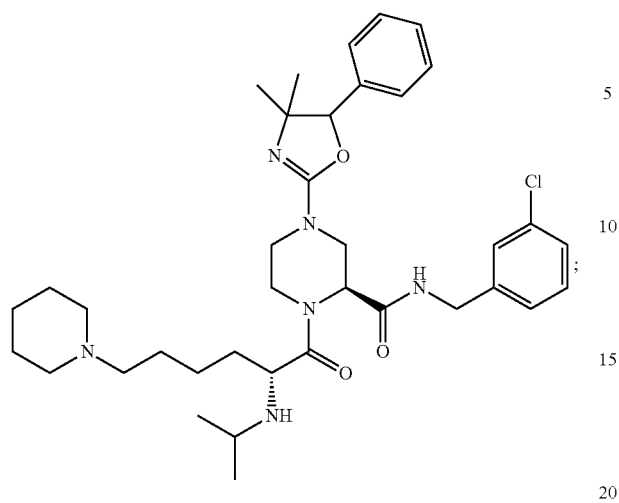
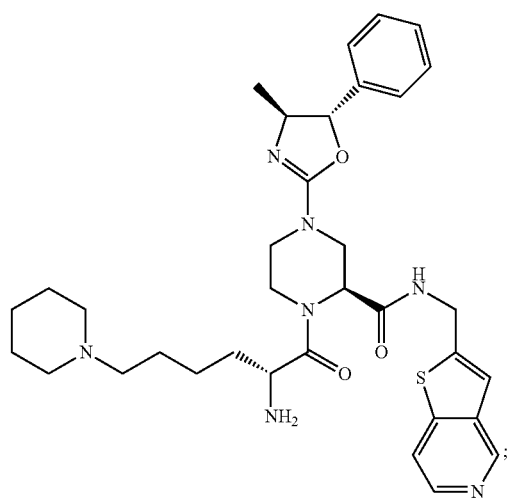
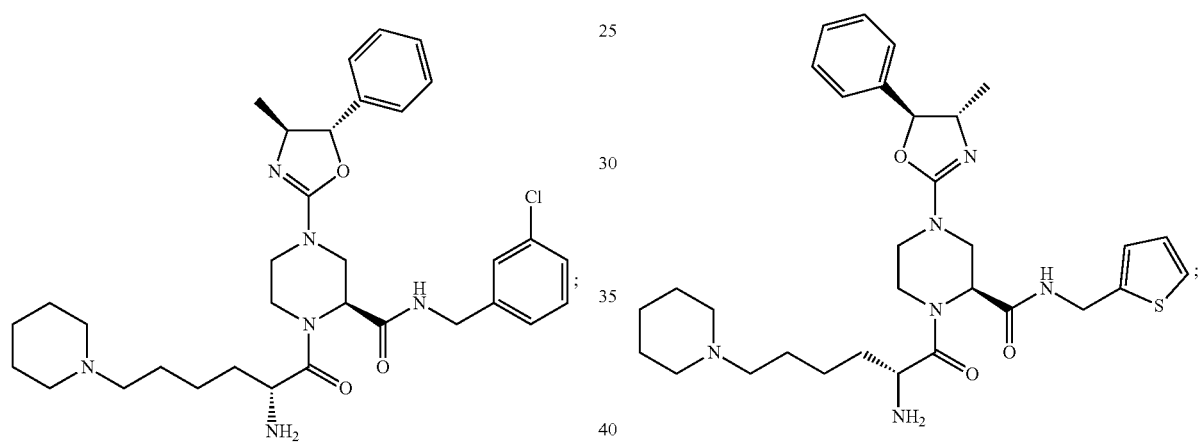
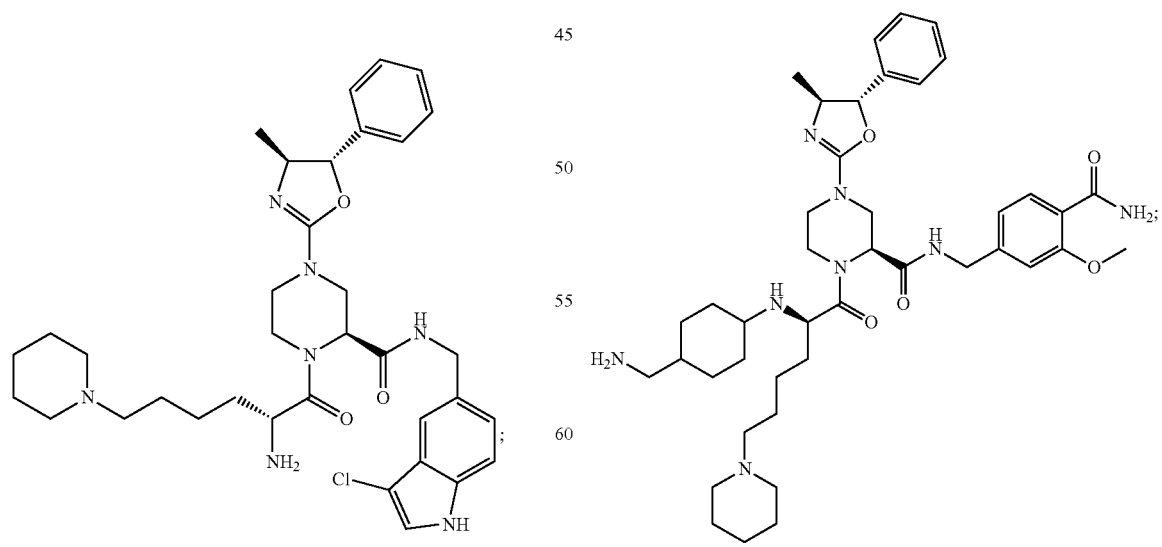

267 -continued
268 -continued
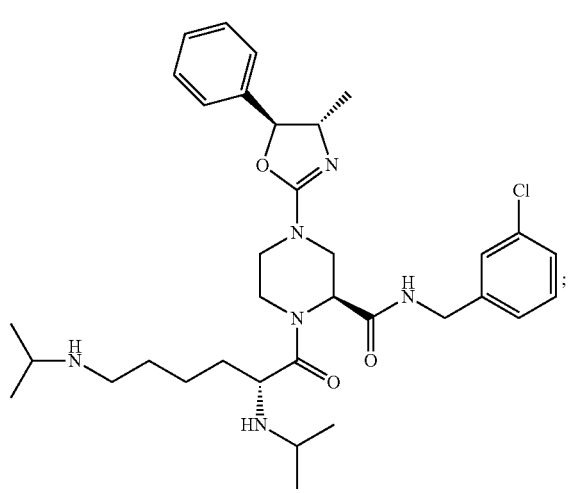
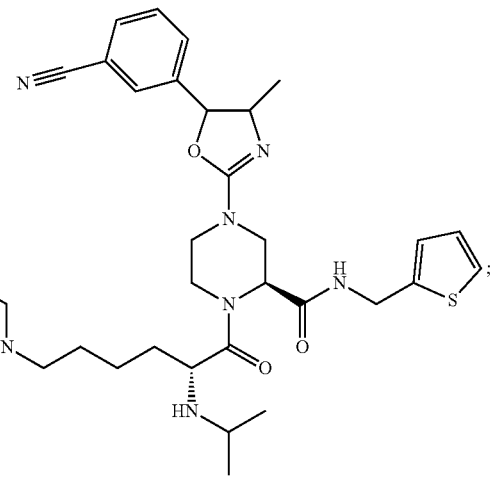
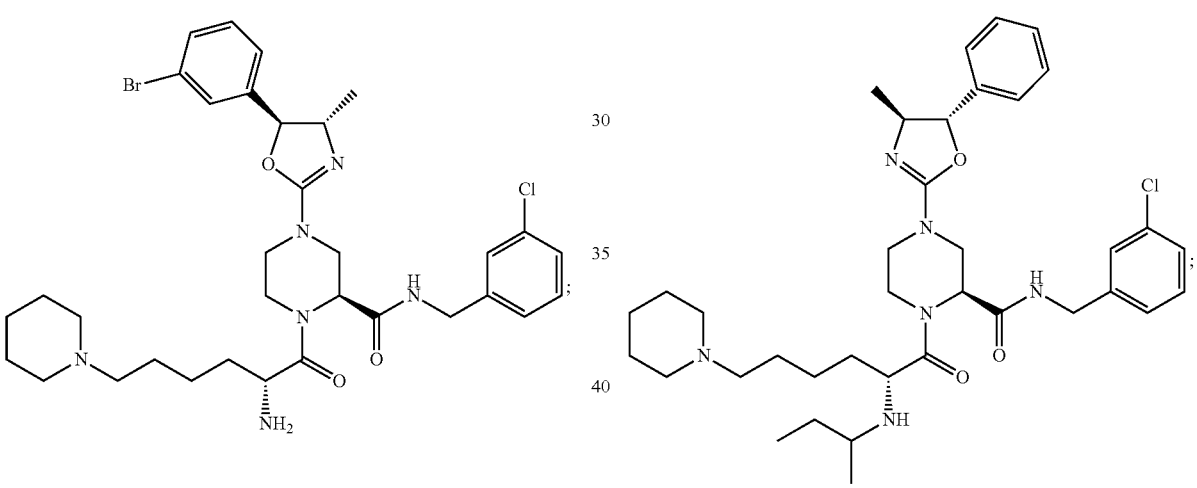
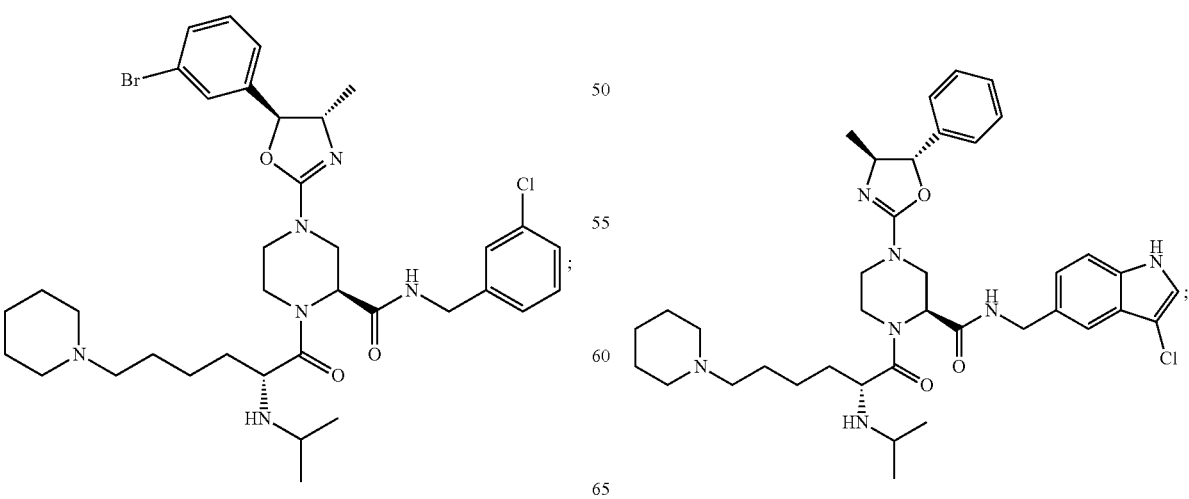

269
-continued
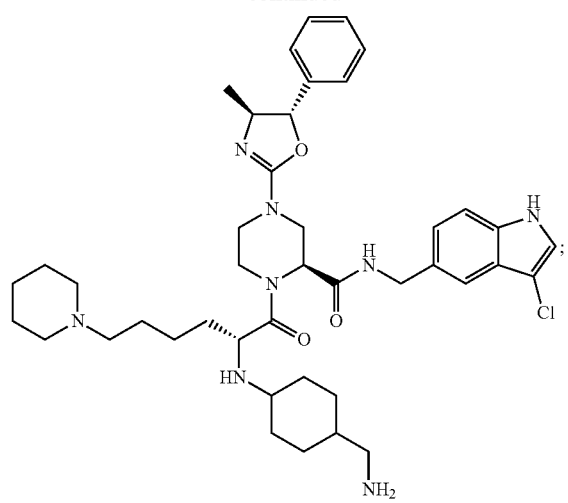
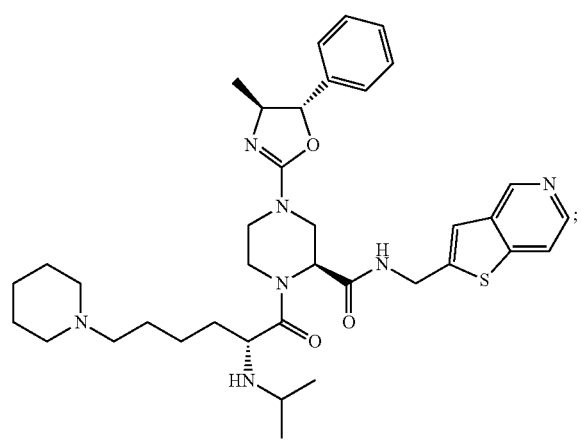
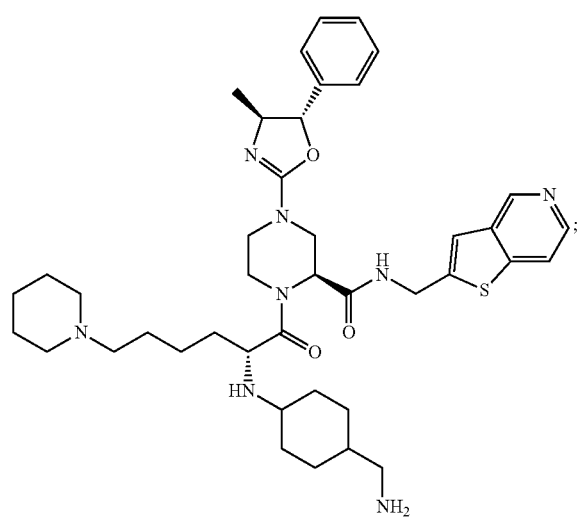
270
-continued
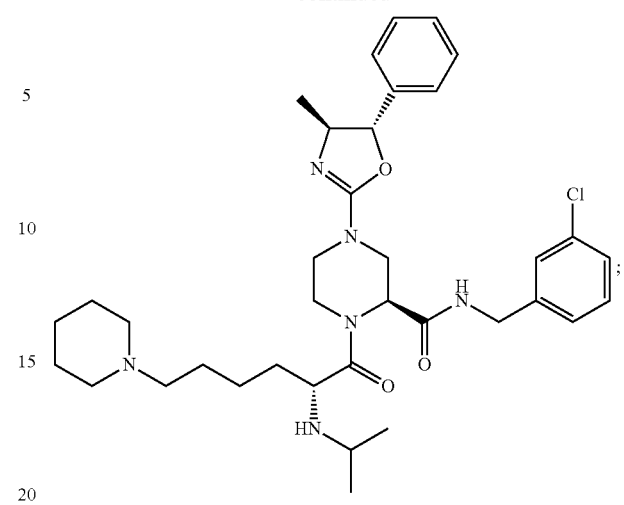
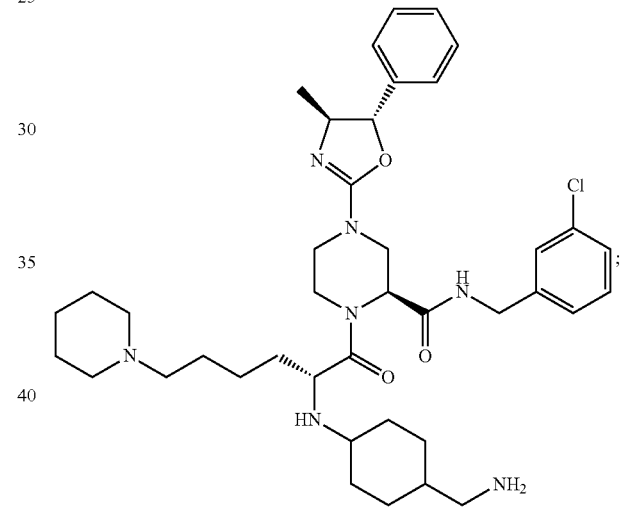
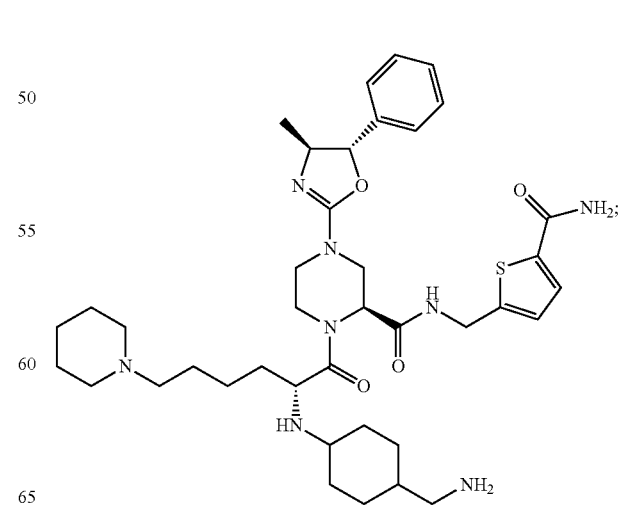

-continued

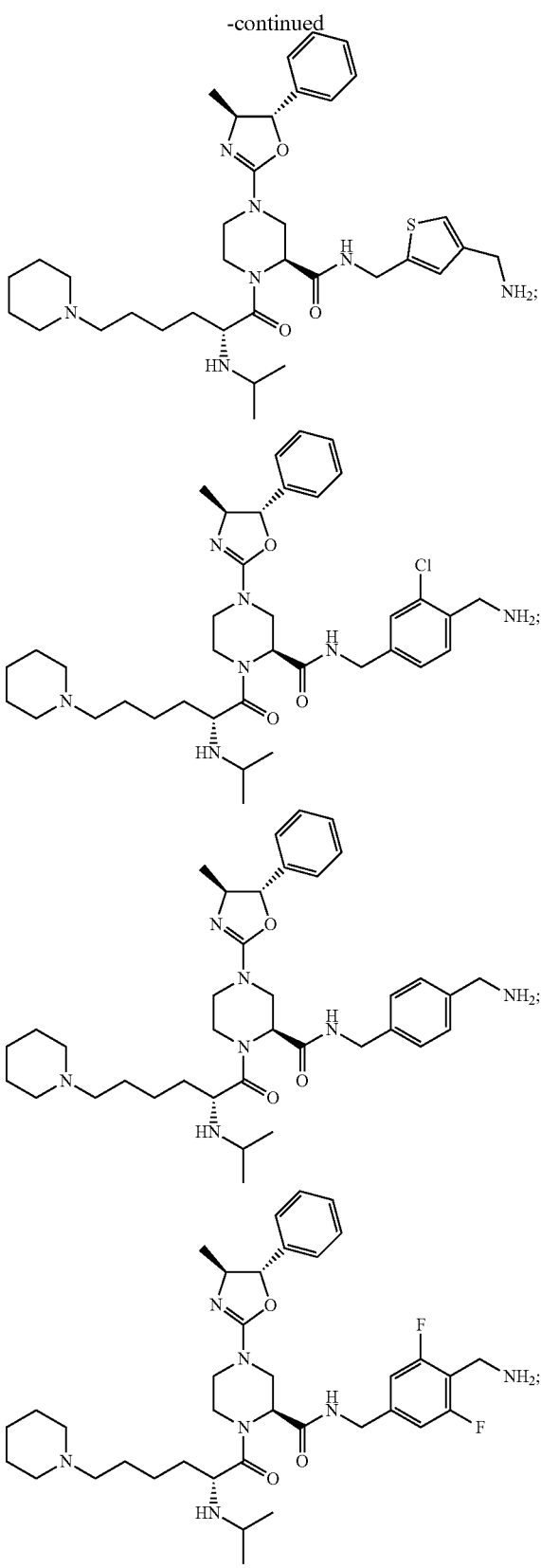

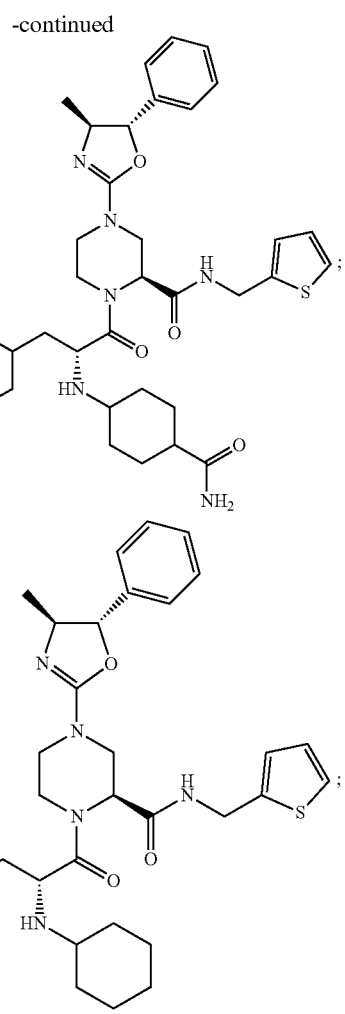

or a pharmaceutically acceptable salt thereof.

8. A pharmaceutical composition comprising a compound of claim 1 or a pharmaceutically acceptable salt thereof and a pharmaceutically acceptable carrier.

9. A method for inhibiting thrombus formation in blood or treating thrombus formation in blood comprising administering a composition of claim 8 to a mammal in need of thereof.

10. A method for preventing thrombus formation in blood comprising administering a composition of claim 8 to a mammal in need thereof.

11. A method of treating venous thromboembolism and pulmonary embolism in a mammal comprising administering a composition of claim 8 to a mammal in need thereof.

12. A method of treating deep vein thrombosis in a mammal comprising administering a composition of claim 8 to a mammal in need thereof.

13. A method of treating thromboembolic stroke in a human comprising administering a composition of claim 8 to a human in need thereof.

* * * * *